US010047096B2

(12) United States Patent
Schall et al.

(10) Patent No.: US 10,047,096 B2
(45) Date of Patent: Aug. 14, 2018

(54) SUBSTITUTED PYRIDOBENZODIAZEPINONE-DERIVATIVES AND USE THEREOF

(71) Applicants: Bayer Pharma Aktiengesellschaft, Berlin (DE); Petra Heinrich-Keldenich, Wuppertal (DE)

(72) Inventors: Andreas Schall, Wuppertal (DE); Jürgen Klar, Wuppertal (DE); Mario Lobell, Wuppertal (DE); Hartmut Schirok, Langenfeld (DE); Joachim Telser, Wuppertal (DE); Steffen Müller, Essen (DE); Dirk Brohm, Mettmann (DE); Hans Briem, Berlin (DE); Hannah Jörißen, Heiligenhaus (DE); Joerg Keldenich, Berlin (DE); Michael Böttger, Wuppertal (DE); Georges Von Degenfeld, Leverkusen (DE); Thomas Schlange, Haan (DE); Ulf Bömer, Glienicke (DE); Niels Lindner, Wuppertal (DE); Hanna Eilken, Wuppertal (DE); Dmitrij Hristodorov, Wuppertal (DE); Pierre Wasnaire, Düsseldorf (DE); Kersten Matthias Gericke, Wuppertal (DE); Lars Bärfacker, Düsseldorf (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/529,043

(22) PCT Filed: Nov. 23, 2015

(86) PCT No.: PCT/EP2015/077299
§ 371 (c)(1),
(2) Date: May 23, 2017

(87) PCT Pub. No.: WO2016/083276
PCT Pub. Date: Jun. 2, 2016

(65) Prior Publication Data
US 2017/0253602 A1  Sep. 7, 2017

(30) Foreign Application Priority Data
Nov. 25, 2014  (EP) .................................... 14194739

(51) Int. Cl.
*A61K 31/551* (2006.01)
*C07D 471/04* (2006.01)
*C07D 487/04* (2006.01)
*A61K 31/5513* (2006.01)
*A61K 39/395* (2006.01)

(52) U.S. Cl.
CPC ........ *C07D 487/04* (2013.01); *A61K 31/5513* (2013.01); *A61K 39/39558* (2013.01)

(58) Field of Classification Search
CPC .......................... A61K 31/551; C07D 471/04
USPC ........................................ 514/220; 540/495
See application file for complete search history.

(56) References Cited

U.S. PATENT DOCUMENTS 7,943,608 B2  5/2011  Schultz et al.

FOREIGN PATENT DOCUMENTS

| CN | 102690278 | 9/2012 |
| EP | 0393604 | 10/1990 |
| EP | 0410148 | 1/1991 |
| EP | 0429987 | 6/1991 |
| EP | 0767172 | 4/1997 |
| EP | 2199295 | 6/2010 |
| WO | WO-2003097644 | 11/2003 |
| WO | WO-2004076424 | 9/2004 |
| WO | WO-2004096795 | 11/2004 |
| WO | WO-2006097449 | 9/2006 |
| WO | WO-2007079826 | 7/2007 |
| WO | WO-2007095188 | 8/2007 |
| WO | WO-2008150364 | 12/2008 |
| WO | WO-2010077680 | 7/2010 |
| WO | WO-2010080712 | 7/2010 |
| WO | WO-2012045194 | 4/2012 |
| WO | WO-2013004551 | 1/2013 |

OTHER PUBLICATIONS

Anderson, R.J., et al. (2005). "Concise Total Synthesis of Variolin B and Deoxyvariolin B," *J. Org. Chem.* 70: 6204-6212.
Bressler, N.M. (Apr. 21, 2004). "Age-Related Macular Degeneration Is the Leading Cause of Blindness . . . ," *JAMA* 291(15): 1900-1901.
Brown, D.M. et al. (Jan. 2009). "Ranibizumab versus Verteporfin Photodynamic Therapy for Neovascular Age-Related Macular Degeneration: Two-Year Results of the Anchor Study," *Ophthalmology* 116(1): 57-65.
Carmeliet, P. et al (Sep. 14, 2000). "Angiogenesis in cancer and other diseases," *Nature* 407: 249-257.
Carmeliet, P. (Dec. 15, 2005). "Angiogenesis in life, disease and medicine," *Nature* 438: 932-936.
Chang, T.S. et al. (Nov. 2007). "Improved Vision-related Function After Ranibizumab Treatment of Neovascular Age-Related Macular Degeneration," *Arch. Ophthalmol* 125 (11): 1460-1469.

(Continued)

Primary Examiner — Brenda L Coleman
(74) Attorney, Agent, or Firm — Morrison & Foerster LLP

(57) ABSTRACT

The present application relates to novel (3-hydroxyphenyl) amino-substituted pyrido[2,3-b][1,5]benzodiazepin-5-one derivatives, to processes for preparation thereof, to the use thereof alone or in combination for treatment and/or prevention of diseases and to the use thereof for production of medicaments for treatment and/or prevention of diseases, especially of angiogenic disorders and hyperproliferative disorders in which neovascularization plays a role, for example ophthalmological disorders and cancers and tumours. Such treatments can be effected as monotherapy or else in combination with other medicaments or further therapeutic measures.

12 Claims, No Drawings

(56) References Cited

OTHER PUBLICATIONS

Connor, K.M. et al. (2009). "Quantification of oxygen-induced retinopathy in the mouse: a model of vessel loss, vessel regrowth and pathological angiogenesis," *Nature Protocols* 4(11): 1565-1573.

Ferrara, N. et al. (Dec. 15, 2005). "Angiogenesis as a therapeutic target," *Nature* 438: 967-974.

Goel, S. et al. (Jul. 2011). "Normalization of the Vasculature for Treatment of Cancer and Other Diseases," *Physiol. Rev.* 91: 1071-1121.

Hanahan, D. et al. (Jan. 7, 2000). "The Hallmarks of Cancer," *Cell* 100: 57-70.

Heldin, C.H. et al. (Oct. 1999). "Mechanism of Action and In Vivo Role of Platelet-Derived Growth Factor," *Physiological Reviews* 79(4): 1283-1316.

International Search Report dated Dec. 14, 2015 for PCT Application No. PCT/EP2015/077299, filed Nov. 23, 2015, 9 pages.

Jain, R.K. (Jun. 2003). "Molecular regulation of vessel maturation," *Nature Medicine* 9: 685-693.

Jo, N. et al. (Jun. 2006). "Inhibition of Platelet-Derived Growth Factor B Signaling Enhances the Efficacy of Anti-Vascular Endothelial Growth Factor Therapy in Multiple Models of Ocular Neovascularization," *Am. J. Pathol.* 168(6): 2036-2053.

Marzi, E. et al. (2001). "Strategies for the Selective Functionalization of Dichloropyridines at Various Sites," *Eur. J. Org. Chem.* 7: 1371-1376.

McGimpsey, S. J. Et al. (2010). "VEGF-targeted therapy and beyond: pharmacotherapy and emerging treatments in age-related macular degeneration," Expert Rev. Clin. Pharmacol. 3(2): 243-252.

Risau, W. (Apr. 17, 1997). "Mechanisms of angiogenesis," *Nature* 386: 671-674.

Rofagha, S. et al. (Nov. 2013). "Seven-Year Outcomes in Ranibizumab-Treated Patients in Anchor, Marina, and Horizon." *Ophthalmology* 120(11): 2292-2299.

Singer, M.A. et al. (2012). "Horizon: An Open-Label Extension Trial of Ranibizumab for Choroidal Neovascularization Secondary to Age-Related Macular Degeneration," *Ophthalmology* 119(6): 1175-1183.

Wilkinson-Berka, J.L. et al. (2004). "Inhibition of Platelet-Derived Growth Factor Promotes Pericyte Loss and Angiogenesis in Ischemic Retinopathy," *Am. J. Pathol.* 164(4): 1263-1273.

SUBSTITUTED PYRIDOBENZODIAZEPINONE-DERIVATIVES AND USE THEREOF

CROSS REFERENCE TO RELATED APPLICATIONS

This application is the national stage of International Application No. PCT/EP2015/077299, filed internationally on Nov. 23, 2015, which claims the benefit of European Application No. 14194739.0, filed Nov. 25, 2014, the disclosures of which are hereby incorporated by reference in their entireties for all purposes.

The present application relates to novel (3-hydroxyphenyl)amino-substituted pyrido[2,3-b][1,5]benzodiazepin-5-one derivatives, to processes for preparation thereof, to the use thereof alone or in combination for treatment and/or prevention of diseases and to the use thereof for production of medicaments for treatment and/or prevention of diseases, especially of angiogenic disorders and hyperproliferative disorders in which neovascularization plays a role, for example ophthalmological disorders and cancers and tumours. Such treatments can be effected as monotherapy or else in combination with other medicaments or further therapeutic measures.

The process of angiogenesis, i.e. the formation of new blood vessels from existing vessels, occurs in the fully grown organism both under physiological conditions, for example in wound healing or in the ovarian cycle, and in pathological processes, especially in the event of cancers and tumours and in the event of particular eye disorders, inflammation disorders, autoimmune disorders, cardiovascular disorders, renal disorders and endometriosis with dysregulated angiogenesis [Risau, *Nature* 386, 671 (1997); Jain, *Nat. Med.* 9, 685 (2003)]. Angiogenesis is a complex process which includes the proliferation and migration of endothelial cells, extracellular proteolysis and the modification of the vessel wall by coverage with pericytes and is affected in this context by various pro-angiogenic and anti-angiogenic factors [Carmeliet and Jain, *Nature* 407, 249-257 (2000)].

Cancers are the consequence of uncontrolled cell growth of the most diverse tissues. In many cases the new cells penetrate into existing tissue (invasive growth), or they metastasize into remote organs. Cancers occur in a wide variety of different organs and often have tissue-specific courses. The term "cancer" as a generic term therefore describes a large group of defined diseases of different organs, tissue and cell types.

Developing tumours are not vascularized at first. A prerequisite for further growth beyond a volume of a few mm$^3$ is the new formation of blood vessels in order to supply the tumour with oxygen and nutrients. This induction of angiogenesis, also called the angiogenic switch, is one of the characteristic features of cancer development [Hanahan and Weinberg, *Cell* 100, 57 (2000)]. Furthermore, intratumoral neovascularization increases the probability of tumour cells getting into the systemic circulation, and so significant vascularization leads to an increase in metastasis potential.

The dependence of the tumours on neovascularization caused inhibition of angiogenesis to become a novel treatment principle in cancer treatment [Ferrara et al., *Nature* 438, 967 (2005); Carmeliet, *Nature* 438, 932 (2005)]. At the same time, the supply of the growing tumour is worsened by inhibition of the even growth of the blood vessel system. This frequently leads to slowed growth, to stabilization of the existing state or even to regression of the tumour. One of the most important pro-angiogenic factors is vascular endothelial growth factor (VEGF). With a VEGF-neutralizing monoclonal antibody that inhibits blood vessel growth (bevacizumab), it has been possible to prolong the life expectancy of colorectal carcinoma patients. VEGFR kinase inhibitors such as sorafenib, sunitinib or pazopanib are successful in the treatment of renal cell carcinoma, liver carcinoma or advanced stages of gastrointestinal stromal tumours (GIST). It is often the case, however, that the efficacy of the currently available anti-angiogenic treatments does not meet expectations, and considerable side effects additionally have to be accepted. Therefore, there is still a great demand for novel compounds and methods having improved therapeutic efficacy.

Age-related macular degeneration (AMD) is one of the most common causes of blindness among the elderly. AMD is generally divided into two forms, non-vascular (dry) AMD and vascular (wet) AMD. Wet AMD affects only about 10% of all AMD patients, but is much more commonly responsible for a significant loss of sight. Wet macular degeneration is characterized by colloidal vascular growth; in the course of this, immature pathological vessels grow from the choroid into the retina. The permeability of these immature vessels leads to exudation and haemorrhage. If untreated, this leads to irreversible damage in the retina and to loss of central vision [Bressler, *JAMA* 291, 1900-1901 (2004)].

The treatment of wet macular degeneration has distinctly improved in the last few decades since anti-VEGF therapeutics, for example pegaptanib, ranibizumab, bevacizumab and aflibercept, have been brought onto the market and used in clinical practice [McGimpsey and Chakravarthy, *Expert Rev. Clin. Pharmacol.* 3 (2), 243-252 (2010)]. For instance, with various anti-VEGF treatment regimes for wet AMD, an improvement or stabilization of vision has been achieved in about 80% of patients, provided that treatment was commenced at an early stage after the occurrence of loss of vision [Chang et al., *Arch. Ophthalmol.* 125 (11), 1460-1469 (2007); Brown et al., *Ophthalmology* 116, 57-65 (2009)]. Only 30-40% of patients were able to gain more than three lines on the Snellen eye chart, and 15-20% of patients, in spite of treatment, actually lost up to 15 letters on this scale [Singer et al., *Ophthalmology* 119, 1175-1183 (2012); Rofagha et al., *Ophthalmology* 120, 2292-2299 (2013)].

Regulation of angiogenesis involves not only VEGF-mediated signal transduction but also numerous further signal transduction systems including the PDGF signalling pathway. PDGF (platelet-derived growth factor) is released by blood platelets in the event of injury, in order to stimulate the healing of the tissue, and plays an important role in embryogenesis, especially in the development of the kidneys, blood vessels, lungs and central nervous system. PDGF is formed by smooth muscle cells and endothelial cells among others and is involved in cell proliferation and cell migration [Heldin and Westermark, *Physiol. Rev.* 79 (4), 1283-1316 (1999)].

Against this background, many experts are of the view that a further increase in therapeutic efficiency is possible only through the introduction of a combination treatment including substances which also address the VEGF-independent signalling pathways, for example the PDGF signalling pathway [McGimpsey and Chakravarthy, *Expert Rev. Clin. Pharmacol.* 3 (2), 243-252 (2010)]. This is supported by numerous different preclinical trials in which the role of the VEGF and PDGF growth factors for ocular neovascularization was examined.

It has been shown that the PDGF growth factor plays an important role in maintaining vascular integrity [Goel et al.,

*Physiol. Rev.* 91, 1071-1121 (2011)]. Endothelial cells in newly formed vessels secrete PDGF in order to guide pericytes to the vessel walls. This process is called vessel maturation and leads to different degrees of coverage of the mature vessels by pericytes. It is important to mention in this connection that endothelial cells in mature vessels become mostly independent of VEGF signalling with regard to their survival.

A crucial function of PDGF signalling for retinal and choroidal neovascularization has also been shown in pre-clinical animal models and even in a clinical situation. In a rat model for retinopathy of prematurity, systematic treatment with a PDGFR inhibitor led to induced apoptosis in pericytes in the inner retina [Wilkinson-Berka et al., *Am. J. Pathol.* 164 (4), 1263-1273 (2004)]. The combination of a PDGFRβ antibody with a VEGF-A aptamer in a murine CNV model led to an additive reduction in neovascularization both in a preventative and in a therapeutic approach [Jo et al., *Am. J. Pathol.* 168 (6), 2036-2053 (2006)].

The clinical applicability of such an approach targeted at PDGF is supported by the results from a clinical phase II trial with a PDGF-B aptamer (Fovista®). The monthly combination of an anti-VEGF treatment (ranibizumab) with Fovista® over a period of 24 weeks led to a rise in visual acuity by 62% compared to anti-VEGF therapy alone [press release from Ophthotech Corp., 13 Jun. 2012]. This underlines the potential relevance of a therapeutic approach which, in the treatment of neovascular disorders such as wet AMD, addresses the PDGF signalling pathway in addition to the VEGF signalling.

It was thus an object of the present invention to identify and provide new compounds of low molecular weight which, in a potent and dual manner, inhibit both the VEGF and the PDGF signalling pathway and are thus suitable for treatment and/or prevention of angiogenic disorders, especially of ophthalmological disorders and cancers and tumours.

Bis-fused 1,4-diazepin-5-one derivatives suitable as inhibitors of various kinases, especially for treatment of cancers, are known from WO 2004/076424-A1, WO 2004/096795-A2, WO 2007/079826-A1, WO 2007/095188-A2, WO 2010/077680-A2, WO 2010/080712-A2 and WO 2012/045194-A1 inter alia. EP 2 199 295-A1 describes bis-fused 1,4-diazepinone derivatives for treatment of diabetes. EP 0 393 604-A2, EP 0 410 148-A1, EP 0 429 987-A2, EP 0 767 172-A1 and WO 03/097644-A2 disclose pyrido-fused 1,4-diazepinones for treatment of HIV infections. Application CN 102690278-A [*Chem. Abstr.* 157:577416; *DWPI* 2012-R67146] describes pyrimidobenzazepine derivatives for treatment of cytokine-induced disorders.

The present invention provides compounds of the general formula (I)

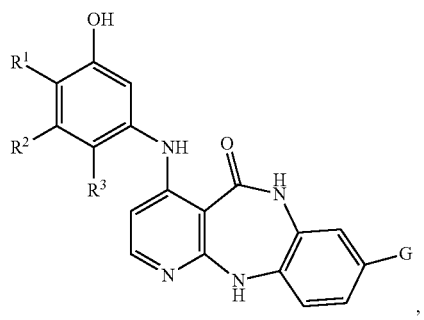

(I)

in which $R^1$ is hydrogen, halogen, hydroxyl or $(C_1-C_4)$-alkyl or a group of the formula —NH—C(=O)—$R^4$, —NH—C(=O)—O—$R^5$ or —NH—SO$_2$—$R^6$ in which $R^4$ is hydrogen or $(C_1-C_4)$-alkyl, $R^5$ is $(C_1-C_4)$-alkyl and $R^6$ is $(C_1-C_4)$-alkyl or phenyl, $R^2$ is hydrogen, fluorine, chlorine, methyl or methoxy, $R^3$ is hydrogen, fluorine, chlorine or methyl, and G is cyano, hydroxycarbonyl or a group of the formula —C(=O)—NR$^{7A}$R$^{7B}$ or —CH$_2$—NR$^{8A}$R$^{8B}$ in which $R^{7A}$ is hydrogen or $(C_1-C_4)$-alkyl which may be substituted by hydroxyl or $(C_1-C_4)$-alkoxy or up to trisubstituted by fluorine, $R^{7B}$ is hydrogen, $(C_1-C_6)$-alkyl, $(C_3-C_6)$-cycloalkyl, phenyl, 4- to 7-membered heterocyclyl or 5- to 10-membered heteroaryl, where $(C_1-C_6)$-alkyl may be up to hexasubstituted by fluorine and up to disubstituted, identically or differently, by a radical selected from the group of —OR$^9$, —O—(CH$_2$CH$_2$O)$_n$—R$^{10}$, —SR$^{11}$, —NR$^{12A}$R$^{12B}$, —C(=O)—NR$^{13A}$R$^{13B}$, $(C_3-C_6)$-cycloalkyl, $(C_4-C_6)$-cycloalkenyl, phenyl, 4- to 7-membered heterocyclyl and 5- or 6-membered heteroaryl, and where (i) the cycloalkyl groups mentioned may be up to disubstituted, identically or differently, by a radical selected from the group of fluorine, $(C_1-C_4)$-alkyl, hydroxyl, $(C_1-C_4)$-alkoxy, hydroxycarbonyl and $(C_1-C_4)$-alkoxycarbonyl, (ii) the phenyl groups mentioned may be up to disubstituted, identically or differently, by a radical selected from the group of fluorine, chlorine, $(C_1-C_4)$-alkyl and $(C_1-C_4)$-alkoxy, (iii) the heterocyclyl groups mentioned may be up to trisubstituted, identically or differently, by a radical selected from the group of fluorine, $(C_1-C_4)$-alkyl, hydroxyl, oxo, hydroxycarbonyl and $(C_1-C_4)$-alkoxycarbonyl, and (iv) the heteroaryl groups mentioned may be up to disubstituted, identically or differently, by a radical selected from the group of fluorine, chlorine, $(C_1-C_4)$-alkyl and $(C_1-C_4)$-alkoxy, and in which $R^9$ is hydrogen or $(C_1-C_4)$-alkyl which may be substituted by 4- to 6-membered heterocyclyl, $R^{10}$ is hydrogen or $(C_1-C_4)$-alkyl, $R^{11}$ is $(C_1-C_4)$-alkyl, $R^{12A}$, $R^{12B}$, $R^{13A}$ and $R^{13B}$ are each independently hydrogen or $(C_1-C_4)$-alkyl which may be substituted by hydroxyl and n is an integer in the range from 1 to 10 inclusive, or $R^{7A}$ and $R^{7B}$ are joined to one another and, together with the nitrogen atom to which they are bonded, form a 4- to 10-membered heterocycle which may contain up to 2 further ring heteroatoms from the group of N, O and S and which may be up to tetrasubstituted, identically or differently, by a radical selected from the group of fluorine, $(C_1-C_4)$-alkyl, oxo, —OR$^{14}$, —NR$^{15A}$R$^{15B}$, —C(=O)—NR$^{16A}$R$^{16B}$ and phenyl, where $(C_1-C_4)$-alkyl for its part may be substituted by hydroxy or up to three times by fluorine
and in which
$R^{14}$ is hydrogen, $(C_1-C_4)$-alkyl or phenyl,
where $(C_1-C_4)$-alkyl may be substituted by hydroxyl, —C(=O)—$NR^{17A}R^{17B}$ or $(C_3-C_6)$-cycloalkyl or up to trisubstituted by fluorine,
and
$R^{15A}$, $R^{15B}$, $R^{16A}$, $R^{16B}$, $R^{17A}$ and $R^{17B}$ are each independently hydrogen or $(C_1-C_4)$-alkyl which may be substituted by hydroxyl,
$R^{8A}$ is hydrogen or $(C_1-C_4)$-alkyl which may be substituted by hydroxyl or $(C_1-C_4)$-alkoxy or up to trisubstituted by fluorine,
and
$R^{8B}$ is hydrogen, $(C_1-C_6)$-alkyl, $(C_3-C_6)$-cycloalkyl, phenyl, 4- to 7-membered heterocyclyl or 5- to 10-membered heteroaryl,
where $(C_1-C_6)$-alkyl may be up to hexasubstituted by fluorine and up to disubstituted, identically or differently, by a radical selected from the group of —$OR^{18}$, —O—$(CH_2CH_2O)_p$—$R^{19}$, —$SR^{20}$, —$NR^{21A}R^{21B}$, —C(=O)—$NR^{22A}R^{22B}$, $(C_3-C_6)$-cycloalkyl, $(C_4-C_6)$-cycloalkenyl, phenyl, 4- to 7-membered heterocyclyl and 5- or 6-membered heteroaryl,
and where
(i) the cycloalkyl groups mentioned may be up to disubstituted, identically or differently, by a radical selected from the group of fluorine, $(C_1-C_4)$-alkyl, hydroxyl, $(C_1-C_4)$-alkoxy, hydroxycarbonyl and $(C_1-C_4)$-alkoxycarbonyl,
(ii) the phenyl groups mentioned may be up to disubstituted, identically or differently, by a radical selected from the group of fluorine, chlorine, $(C_1-C_4)$-alkyl and $(C_1-C_4)$-alkoxy,
(iii) the heterocyclyl groups mentioned may be up to trisubstituted, identically or differently, by a radical selected from the group of fluorine, $(C_1-C_4)$-alkyl, hydroxyl, oxo, hydroxycarbonyl and $(C_1-C_4)$-alkoxycarbonyl,
and
(iv) the heteroaryl groups mentioned may be up to disubstituted, identically or differently, by a radical selected from the group of fluorine, chlorine, $(C_1-C_4)$-alkyl and $(C_1-C_4)$-alkoxy,
and in which
$R^{18}$ is hydrogen or $(C_1-C_4)$-alkyl which may be substituted by 4- to 6-membered heterocyclyl,
$R^{19}$ is hydrogen or $(C_1-C_4)$-alkyl,
$R^{20}$ is $(C_1-C_4)$-alkyl,
$R^{21A}$, $R^{21B}$, $R^{22A}$ and $R^{22B}$ are each independently hydrogen or $(C_1-C_4)$-alkyl which may be substituted by hydroxyl
and
p is an integer in the range from 1 to 10 inclusive,
or
$R^{8A}$ and $R^{8B}$ are joined to one another and, together with the nitrogen atom to which they are bonded, form a 4- to 10-membered heterocycle which may contain up to 2 further ring heteroatoms from the group of N, O and S and which may be up to tetrasubstituted, identically or differently, by a radical selected from the group of fluorine, $(C_1-C_4)$-alkyl, oxo, —$OR^{23}$, —$NR^{24A}R^{24B}$, —C(=O)—$NR^{25A}R^{25B}$ and phenyl,
where $(C_1-C_4)$-alkyl for its part may be substituted by hydroxy or up to three times by fluorine
and in which
$R^{23}$ is hydrogen, $(C_1-C_4)$-alkyl or phenyl,
where $(C_1-C_4)$-alkyl may be substituted by hydroxyl, —C(=O)—$NR^{26A}R^{26B}$ or $(C_3-C_6)$-cycloalkyl or up to trisubstituted by fluorine,
and
$R^{24A}$, $R^{24B}$, $R^{25A}$, $R^{25B}$, $R^{26A}$ and $R^{26B}$ are each independently hydrogen or $(C_1-C_4)$-alkyl which may be substituted by hydroxyl,
and the salts, solvates and solvates of the salts thereof.

Inventive compounds are the compounds of the formula (I) and the salts, solvates and solvates of the salts thereof, the compounds of the formulae (I-A), (I-B), (I-C) and (I-D) below that are encompassed by formula (I) and the salts, solvates and solvates of the salts thereof, and the compounds cited hereinafter as working examples that are encompassed by formula (I) and the salts, solvates and solvates of the salts thereof, if the compounds cited hereinafter that are encompassed by formula (I) are not already salts, solvates and solvates of the salts.

Preferred salts in the context of the present invention are physiologically acceptable salts of the inventive compounds. Also encompassed are salts which are not themselves suitable for pharmaceutical applications but can be used, for example, for the isolation, purification or storage of the inventive compounds.

Physiologically acceptable salts of the inventive compounds especially include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

In addition, physiologically acceptable salts of the inventive compounds also include salts derived from conventional bases, by way of example and with preference alkali metal salts (e.g. sodium and potassium salts), alkaline earth metal salts (e.g. calcium and magnesium salts), zinc salts and ammonium salts derived from ammonia or organic amines having 1 to 20 carbon atoms, by way of example and with preference ethylamine, diethylamine, triethylamine, N,N-ethyldiisopropylamine, monoethanolamine, diethanolamine, triethanolamine, dimethylaminoethanol, diethylaminoethanol, tris(hydroxymethyl)aminomethane, choline, benzalkonium, procaine, dibenzylamine, dicyclohexylamine, N-methylmorpholine, N-methylpiperidine, arginine, lysine and 1,2-ethylenediamine.

Solvates in the context of the invention are described as those forms of the inventive compounds which form a complex in the solid or liquid state by coordination with solvent molecules. Hydrates are a specific form of the solvates in which the coordination is with water. Solvates preferred in the context of the present invention are hydrates.

The inventive compounds may, depending on their structure, exist in different stereoisomeric forms, i.e. in the form of configurational isomers or else, if appropriate, of conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for the purpose, especially HPLC chromatography on achiral or chiral separation phases. In the case of carboxylic acids as intermediates or end products, separation is alternatively also possible via diastereomeric salts using chiral amine bases.

If the inventive compounds can occur in tautomeric forms, the present invention encompasses all the tautomeric forms.

The present invention also encompasses all suitable isotopic variants of the inventive compounds. An isotopic variant of an inventive compound is understood here to mean a compound in which at least one atom within the inventive compound has been exchanged for another atom of the same atomic number, but with a different atomic mass than the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as $^2$H (deuterium), $^3$H (tritium), $^{13}$C $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of an inventive compound, especially those in which one or more radioactive isotopes have been incorporated, may be beneficial, for example, for the examination of the mechanism of action or of the active ingredient distribution in the body; due to comparatively easy preparability and detectability, particularly compounds labelled with $^3$H, $^{14}$C and/or $^{18}$F isotopes are suitable for the purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the inventive compounds may therefore possibly also constitute a preferred embodiment of the present invention. Isotopic variants of the inventive compounds can be prepared by commonly used processes known to those skilled in the art, for example by the methods described further down and the procedures described in the working examples, by using corresponding isotopic modifications of the respective reagents and/or starting compounds.

In addition, the present invention also encompasses prodrugs of the inventive compounds. The term "prodrugs" refers here to compounds which may themselves be biologically active or inactive, but are converted while present in the body, for example by a metabolic or hydrolytic route, to inventive compounds.

In the context of the present invention, unless specified otherwise, the substituents and radicals are defined as follows:

($C_1$-$C_6$)-Alkyl, ($C_1$-$C_4$)-alkyl and ($C_1$-$C_3$)-alkyl in the context of the invention represent a straight-chain or branched alkyl radical having 1 to 6, 1 to 4 and 1 to 3 carbon atoms respectively. Examples include: methyl, ethyl, n-propyl, isopropyl, n-butyl, isobutyl, sec-butyl, tert-butyl, n-pentyl, 2-pentyl, 3-pentyl, neopentyl, 3-methylbutyl, n-hexyl, 2-hexyl, 3-hexyl and 4-methylpentyl. Preference is given to a straight-chain or branched alkyl radical having 1 to 4 carbon atoms, such as methyl, ethyl, n-propyl, isopropyl, n-butyl, isobutyl, sec-butyl and tert-butyl. Particular preference is given to a straight-chain or branched alkyl radical having 1 to 3 carbon atoms, such as methyl, ethyl, n-propyl and isopropyl.

($C_1$-$C_4$)-Alkoxy and ($C_1$-$C_3$)-alkoxy in the context of the invention represent a straight-chain or branched alkoxy radical having 1 to 4 and 1 to 3 carbon atoms respectively. Examples include: methoxy, ethoxy, n-propoxy, isopropoxy, n-butoxy, isobutoxy, sec-butoxy and tert-butoxy. Preference is given to a straight-chain or branched alkoxy radical having 1 to 3 carbon atoms, such as methoxy, ethoxy, n-propoxy and isopropoxy.

($C_1$-$C_4$)-Alkoxycarbonyl in the context of the invention is a straight-chain or branched alkoxy radical which has 1 to 4 carbon atoms and is joined to the rest of the molecule via a carbonyl group [—C(=O)—] bonded to the oxygen atom. Examples include: methoxycarbonyl, ethoxycarbonyl, n-propoxycarbonyl, isopropoxycarbonyl, n-butoxycarbonyl and tert-butoxycarbonyl.

($C_3$-$C_6$)-Cycloalkyl in the context of the invention is a monocyclic saturated cycloalkyl group having 3 to 6 ring carbon atoms. Examples include: cyclopropyl, cyclobutyl, cyclopentyl and cyclohexyl.

($C_4$-$C_6$)-Cycloalkenyl in the context of the invention is a monocyclic cycloalkyl group which has 4 to 6 ring carbon atoms and contains one double bond in the ring. Examples include: cyclobutenyl, cyclopentenyl and cyclohexenyl.

4- to 7-membered heterocyclyl in the context of the invention is a monocyclic or optionally bicyclic saturated heterocycle which has a total of 4 to 7 ring atoms, contains one or two identical or different ring heteroatoms from the group of N, O and S and is joined via a ring carbon atom or optionally via a ring nitrogen atom. Examples include: azetidinyl, oxetanyl, thietanyl, pyrrolidinyl, pyrazolidinyl, tetrahydrofuranyl, thiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, azepanyl, 1,4-diazepanyl, 1,4-oxazepanyl and 7-azabicyclo[2.2.1]heptyl. Preference is given in the context of the invention to 4- to 6 membered heterocyclyl which is a monocyclic saturated heterocycle which has a total of 4 to 6 ring atoms, contains one or two identical or different ring heteroatoms from the group of N and O and is joined via a ring carbon atom or optionally via a ring nitrogen atom, for example azetidinyl, oxetanyl, pyrrolidinyl, pyrazolidinyl, tetrahydrofuranyl, 1,3-oxazolidinyl, piperidinyl, piperazinyl, tetrahydropyranyl, 1,4-dioxanyl, 1,2-oxazinanyl and morpholinyl. Particular preference is given to 5- or 6 membered heterocyclyl which is a monocyclic saturated heterocycle which has a total of 5 or 6 ring atoms, contains one or two identical or different ring heteroatoms from the group of N and O and is joined via a ring carbon atom or optionally via a ring nitrogen atom, for example pyrrolidinyl, pyrazolidinyl, tetrahydrofuranyl, 1,3-oxazolidinyl, piperidinyl, piperazinyl, tetrahydropyranyl, 1,4-dioxanyl, 1,2-oxazinanyl and morpholinyl.

5- to 10-membered heteroaryl in the context of the invention is a monocyclic or optionally bicyclic aromatic heterocycle (heteroaromatic) which has a total of 5 to 10 ring atoms, contains up to four identical or different ring heteroatoms from the group of N, O and S and is joined via a ring carbon atom or optionally via a ring nitrogen atom. Examples include: furyl, pyrrolyl, thienyl, pyrazolyl, imidazolyl, 1,2-oxazolyl (isoxazolyl), 1,3-oxazolyl, 1,2-thiazolyl (isothiazolyl), 1,3-thiazolyl, 1,2,3-triazolyl, 1,2,4-triazolyl, 1,2,4-oxadiazolyl, 1,3,4-oxadiazolyl, 1,2,4-thiadiazolyl, 1,3,4-thiadiazolyl, tetrazolyl, pyridyl, pyrimidinyl, pyridazinyl, pyrazinyl, 1,2,4-triazinyl, 1,3,5-triazinyl, benzofuranyl, benzothienyl, benzimidazolyl, benzoxazolyl, benzothiazolyl, benzotriazolyl, indolyl, indolizinyl, indazolyl, quinolinyl, isoquinolinyl, naphthyridinyl, quinazolinyl, quinoxalinyl, cinnolinyl, phthalazinyl, pyrazolo[3,4-b]pyridinyl, purinyl and pteridinyl. Preference is given in the context of the invention to 5- or 6 membered heteroaryl which is a monocyclic heteroaromatic system which has a total of 5 or 6 ring atoms, contains one or two identical or different ring heteroatoms from the group of N, O and S and is joined via a ring carbon atom or optionally via a ring nitrogen atom, for example furyl, pyrrolyl, thienyl, pyrazolyl, imidazolyl, 1,3-oxazolyl, 1,3-thiazolyl, pyridyl, pyrimidinyl, pyridazinyl and pyrazinyl.

In the definition of $R^{7A}$ and $R^{7B}$ or $R^{8A}$ and $R^{8B}$ radicals that are joined to one another and thus form a ring, the term 4- to 10-membered heterocycle means a mono- or optionally bicyclic saturated heterocycle which has a total of 4 to 10 ring atoms, contains one ring nitrogen atom, is joined via said atom and may contain up to two further, identical or different, ring heteroatoms from the group of N, O and S. Examples include: azetidinyl, pyrrolidinyl, pyrazolidinyl, 1,2-oxazolidinyl, imidazolidinyl, 1,3-oxazolidinyl, 1,3-thiazolidinyl, piperidinyl, piperazinyl, 1,2-oxazinanyl, morpholinyl, thiomorpholinyl, azepanyl, 1,4-diazepanyl, 1,4-oxazepanyl, azocanyl, 1,5-diazocanyl, 1,5-oxazocanyl, octahydropyrrolo[3,4-b]pyrrolyl, octahydropyrrolo[3,4-c]pyrrolyl, octahydroindolyl, octahydroisoindolyl, octahydropyrrolo[3,4-b]pyridyl, octahydropyrrolo[3,4-c]pyridyl, octahydropyrrolo[3,4-b]pyrazinyl, decahydroquinolinyl, decahydroisoquinolinyl, octahydropyrido[1,2-a]pyrazinyl, octahydropyrazino[1,2-a]pyrazinyl, 3-azabicyclo[3.1.0]hexyl, 7-azabicyclo[2.2.1]heptyl, 3-azabicyclo[3.2.0]heptyl, 2-oxa-6-azaspiro[3.3]heptyl, 2-azabicyclo[2.2.2]octyl, 2,5-diazabicyclo[2.2.2]octyl, 3-azabicyclo[3.2.1]octyl, 8-azabicyclo[3.2.1]octyl and 8-oxa-3-azabicyclo[3.2.1]octyl. Preference is given to a 5- to 7-membered heterocycle which is a monocyclic saturated heterocycle which has a total of 5 to 7 ring atoms, contains one ring nitrogen atom, is joined via said atom and may contain one further ring heteroatom from the group of N, O and S, for example pyrrolidinyl, pyrazolidinyl, imidazolidinyl, 1,3-oxazolidinyl, 1,3-thiazolidinyl, piperidinyl, piperazinyl, 1,2-oxazinanyl, morpholinyl, thiomorpholinyl, azepanyl, 1,4-diazepanyl and 1,4-oxazepanyl. Particular preference is given to a 5- to 7-membered heterocycle which is a monocyclic saturated heterocycle which has a total of 5 to 7 ring atoms, contains one ring nitrogen atom, is joined via said atom and may contain one further ring heteroatom from the group of N and O, for example pyrrolidinyl, pyrazolidinyl, imidazolidinyl, 1,3-oxazolidinyl, piperidinyl, piperazinyl, 1,2-oxazinanyl, morpholinyl, azepanyl, 1,4-diazepanyl and 1,4-oxazepanyl.

An oxo substituent in the context of the invention is an oxygen atom bonded to a carbon or sulphur atom via a double bond.

Halogen in the context of the invention includes fluorine, chlorine, bromine and iodine. Preference is given to chlorine, fluorine or bromine, particular preference to fluorine or chlorine.

In the context of the present invention, all radicals which occur more than once are defined independently of one another. When radicals in the inventive compounds are substituted, the radicals may be mono- or polysubstituted, unless specified otherwise. Substitution by one or two identical or different substituents is preferred. Particular preference is given to substitution by one substituent.

Preference is given in the context of the present invention to compounds of the formula (I) in which $R^1$ is hydrogen, fluorine, chlorine, $(C_1-C_4)$-alkyl or a group of the formula —NH—SO$_2$—R$^6$ in which
  $R^6$ is $(C_1-C_4)$-alkyl or phenyl,
$R^2$ is hydrogen, fluorine, chlorine or methyl,
$R^3$ is hydrogen, fluorine, chlorine or methyl,
and
G is cyano or a group of the formula —C(=O)—NR$^{7A}$R$^{7B}$ or —CH$_2$—NR$^{8A}$R$^{8B}$ in which
  $R^{7A}$ is hydrogen, methyl, ethyl, 2-hydroxyethyl, 2-methoxyethyl or 2-ethoxyethyl,
    where methyl and ethyl may be up to trisubstituted by fluorine,
  $R^{7B}$ is hydrogen, $(C_1-C_4)$-alkyl or $(C_3-C_6)$-cycloalkyl,
    where $(C_1-C_4)$-alkyl may be up to trisubstituted by fluorine and up to disubstituted, identically or differently, by a radical selected from the group of —OR$^9$, —SR$^{11}$, —NR$^{12A}$R$^{12B}$, $(C_3-C_6)$-cycloalkyl and phenyl,
    and where
    (i) the cycloalkyl groups mentioned may be up to disubstituted, identically or differently, by a radical selected from the group of fluorine, methyl, ethyl, hydroxyl, methoxy, ethoxy, hydroxycarbonyl, methoxycarbonyl and ethoxycarbonyl,
    and
    (ii) the phenyl groups mentioned may be up to disubstituted, identically or differently, by a radical selected from the group of fluorine, chlorine, methyl, ethyl, methoxy and ethoxy,
    and in which
    $R^9$ is hydrogen, methyl or ethyl,
    $R^{11}$ is methyl or ethyl
    and
    $R^{12A}$ and $R^{12B}$ are each independently hydrogen, methyl, ethyl or 2-hydroxyethyl,
or
  $R^{7A}$ and $R^{7B}$ are joined to one another and, together with the nitrogen atom to which they are bonded, form a 5- to 7-membered heterocycle which may contain one further ring heteroatom from the group of N, O and S and which may be up to tetrasubstituted, identically or differently, by a radical selected from the group of fluorine, $(C_1-C_3)$-alkyl, oxo, —OR$^{14}$, —NR$^{15A}$R$^{15B}$, —C(=O)—NR$^{16A}$R$^{16B}$ and phenyl,
    where $(C_1-C_3)$-alkyl for its part may be substituted by hydroxy or up to three times by fluorine
    and in which
    $R^{14}$ is hydrogen, methyl or ethyl
    and
    $R^{15A}$, $R^{15B}$, $R^{16A}$ and $R^{16B}$ are each independently hydrogen, methyl or ethyl,
  $R^{8A}$ is hydrogen or $(C_1-C_4)$-alkyl which may be substituted by hydroxyl, methoxy or ethoxy or up to trisubstituted by fluorine,
  and
  $R^{8B}$ is hydrogen, $(C_1-C_6)$-alkyl, $(C_3-C_6)$-cycloalkyl, phenyl, 5- or 6-membered heterocyclyl or 5- or 6-membered heteroaryl,
    where $(C_1-C_6)$-alkyl may be up to trisubstituted by fluorine and up to disubstituted, identically or differently, by a radical selected from the group of —OR$^{18}$, —SR$^{20}$, —NR$^{21A}$R$^{21B}$, —C(=O)—NR$^{22A}$R$^{22B}$, $(C_3-C_6)$-cycloalkyl, phenyl, 5- or 6-membered heterocyclyl and 5- or 6-membered heteroaryl,
    and where
    (i) the cycloalkyl groups mentioned may be up to disubstituted, identically or differently, by a radical selected from the group of fluorine, $(C_1-C_3)$-alkyl, hydroxyl, $(C_1-C_3)$-alkoxy, hydroxycarbonyl, methoxycarbonyl and ethoxycarbonyl, (ii) the phenyl groups mentioned may be up to disubstituted, identically or differently, by a radical selected from the group of fluorine, chlorine, methyl, ethyl, methoxy and ethoxy, (iii) the heterocyclyl groups mentioned may be up to trisubstituted, identically or differently, by a radical selected from the group of fluorine, $(C_1-C_3)$-alkyl, hydroxyl, oxo, hydroxycarbonyl, methoxycarbonyl and ethoxycarbonyl, and (iv) the heteroaryl groups mentioned may be up to disubstituted, identically or differently, by a radical selected from the group of fluorine, chlorine, $(C_1-C_3)$-alkyl and $(C_1-C_3)$-alkoxy, and in which $R^{18}$ is hydrogen or $(C_1-C_3)$-alkyl, $R^{20}$ is $(C_1-C_3)$-alkyl and $R^{21A}$, $R^{21B}$, $R^{22A}$ and $R^{22B}$ are each independently hydrogen or $(C_1-C_3)$-alkyl which may be substituted by hydroxyl, or $R^{8A}$ and $R^{8B}$ are joined to one another and, together with the nitrogen atom to which they are bonded, form a 5- to 7-membered heterocycle which may contain one further ring heteroatom from the group of N, O and S and which may be up to tetrasubstituted, identically or differently, by a radical selected from the group of fluorine, $(C_1-C_4)$-alkyl, oxo, —$OR^{23}$, —$NR^{24A}R^{24B}$, —C(=O)—$NR^{25A}R^{25B}$ and phenyl, where $(C_1-C_4)$-alkyl for its part may be substituted by hydroxy or up to three times by fluorine and in which $R^{23}$ is hydrogen or $(C_1-C_3)$-alkyl, where $(C_1-C_3)$-alkyl may be substituted by hydroxyl or $(C_3-C_6)$-cycloalkyl or up to trisubstituted by fluorine, and $R^{24A}$, $R^{24B}$, $R^{25A}$ and $R^{25B}$ are each independently hydrogen or $(C_1-C_3)$-alkyl which may be substituted by hydroxyl, and the salts, solvates and solvates of the salts thereof.

In the context of the present invention, particular preference is given to compounds of the formula (I) in which $R^1$ is hydrogen, fluorine, chlorine or $(C_1-C_4)$-alkyl, $R^2$ is hydrogen or fluorine, $R^3$ is hydrogen, fluorine, chlorine or methyl, and G is a group of the formula —C(=O)—$NR^{7A}R^{7B}$ or —$CH_2$—$NR^{8A}R^{8B}$ in which $R^{7A}$ is hydrogen, methyl or ethyl, $R^{7B}$ is methyl, ethyl, 2-hydroxyethyl or cyclohexyl, where cyclohexyl may be up to disubstituted by hydroxyl, or $R^{7A}$ and $R^{7B}$ are joined to one another and, together with the nitrogen atom to which they are bonded, form a 5- to 7-membered heterocycle which may contain one further ring heteroatom from the group of N and O and which may be up to disubstituted, identically or differently, by a radical selected from the group of methyl, ethyl, oxo and hydroxyl, where methyl and ethyl may in turn be substituted by hydroxyl, $R^{8A}$ is hydrogen or $(C_1-C_4)$-alkyl, and $R^{8B}$ is $(C_1-C_6)$-alkyl, $(C_3-C_6)$-cycloalkyl or 5- or 6-membered heterocyclyl, where $(C_1-C_6)$-alkyl may be up to trisubstituted by fluorine and up to disubstituted, identically or differently, by a radical selected from the group of —$OR^{18}$, —$SR^{20}$, —$NR^{21A}R^{21B}$, $(C_3-C_6)$-cycloalkyl, 5- or 6-membered heterocyclyl and 5- or 6-membered heteroaryl, and where (i) the cycloalkyl groups mentioned may be up to disubstituted, identically or differently, by a radical selected from the group of fluorine, $(C_1-C_3)$-alkyl, hydroxyl, $(C_1-C_3)$-alkoxy, hydroxycarbonyl, methoxycarbonyl and ethoxycarbonyl, (ii) the heterocyclyl groups mentioned may be up to trisubstituted, identically or differently, by a radical selected from the group of fluorine, $(C_1-C_3)$-alkyl, hydroxyl, oxo, hydroxycarbonyl, methoxycarbonyl and ethoxycarbonyl, and (iii) the heteroaryl group mentioned may be up to disubstituted, identically or differently, by a radical selected from the group of fluorine, chlorine, $(C_1-C_3)$-alkyl and $(C_1-C_3)$-alkoxy, and in which $R^{18}$ is hydrogen, methyl or ethyl, $R^{20}$ is methyl or ethyl and $R^{21A}$ and $R^{21B}$ are each independently hydrogen, methyl or ethyl, or $R^{8A}$ and $R^{8B}$ are joined to one another and, together with the nitrogen atom to which they are bonded, form a 5- to 7-membered heterocycle which may contain one further ring heteroatom from the group of N and O and which may be up to tetrasubstituted, identically or differently, by a radical selected from the group of fluorine, $(C_1-C_3)$-alkyl, oxo, —$OR^{23}$, —$NR^{24A}R^{24B}$ and —C(=O)—$NR^{25A}R^{25B}$, where $(C_1-C_3)$-alkyl for its part may be substituted by hydroxy or up to three times by fluorine and in which $R^{23}$ is hydrogen or $(C_1-C_3)$-alkyl, where $(C_1-C_3)$-alkyl may be substituted by hydroxyl or up to trisubstituted by fluorine, and $R^{24A}$, $R^{24B}$, $R^{25A}$ and $R^{25B}$ are each independently hydrogen, methyl or ethyl, and the salts, solvates and solvates of the salts thereof.

A particular embodiment of the present invention comprises compounds of the formula (I) in which $R^1$ is chlorine or methyl, $R^2$ is hydrogen and $R^3$ is fluorine, and the salts, solvates and solvates of the salts thereof.

A further particular embodiment of the present invention comprises compounds of the formula (I) in which $R^1$ and $R^2$ are each hydrogen and $R^3$ is methyl, and the salts, solvates and solvates of the salts thereof.

A further particular embodiment of the present invention comprises compounds of the formula (I) in which G is a group of the formula —C(=O)—$NR^{7A}R^{7B}$ in which $R^{7A}$ is hydrogen, methyl or ethyl, $R^{7B}$ is methyl, ethyl, 2-hydroxyethyl or cyclohexyl, where cyclohexyl may be up to disubstituted by hydroxyl, or $R^{7A}$ and $R^{7B}$ are joined to one another and, together with the nitrogen atom to which they are bonded, form a 5- to 7-membered heterocycle which may contain one further ring heteroatom from the group of N and O and which may be up to disubstituted, identically or differently, by a radical selected from the group of methyl, ethyl, oxo and hydroxyl, where methyl and ethyl may in turn be substituted by hydroxyl, and the salts, solvates and solvates of the salts thereof.

A further particular embodiment of the present invention comprises compounds of the formula (I) in which G is a group of the formula —$CH_2$—$NR^{8A}R^{8B}$ in which $R^{8A}$ is hydrogen or $(C_1$-$C_4)$-alkyl and $R^{8B}$ is $(C_1$-$C_6)$-alkyl, $(C_3$-$C_6)$-cycloalkyl or 5- or 6-membered heterocyclyl, where $(C_1$-$C_6)$-alkyl may be up to trisubstituted by fluorine and up to disubstituted, identically or differently, by a radical selected from the group of —$OR^{18}$, —$SR^{20}$, —$NR^{21A}R^{21B}$, $(C_3$-$C_6)$-cycloalkyl, 5- or 6-membered heterocyclyl and 5- or 6-membered heteroaryl, and where (i) the cycloalkyl groups mentioned may be up to disubstituted, identically or differently, by a radical selected from the group of fluorine, $(C_1$-$C_3)$-alkyl, hydroxyl, $(C_1$-$C_3)$-alkoxy, hydroxycarbonyl, methoxycarbonyl and ethoxycarbonyl, (ii) the heterocyclyl groups mentioned may be up to trisubstituted, identically or differently, by a radical selected from the group of fluorine, $(C_1$-$C_3)$-alkyl, hydroxyl, oxo, hydroxycarbonyl, methoxycarbonyl and ethoxycarbonyl, and (iii) the heteroaryl group mentioned may be up to disubstituted, identically or differently, by a radical selected from the group of fluorine, chlorine, $(C_1$-$C_3)$-alkyl and $(C_1$-$C_3)$-alkoxy, and in which $R^{18}$ is hydrogen, methyl or ethyl, $R^{20}$ is methyl or ethyl and $R^{21A}$ and $R^{21B}$ are each independently hydrogen, methyl or ethyl, and the salts, solvates and solvates of the salts thereof.

A further particular embodiment of the present invention comprises compounds of the formula (I) in which G is a group of the formula —$CH_2$—$NR^{8A}R^{8B}$ in which $R^{8A}$ and $R^{8B}$ are joined to one another and, together with the nitrogen atom to which they are bonded, form a 5- to 7-membered heterocycle which may contain one further ring heteroatom from the group of N and O and which may be up to tetrasubstituted, identically or differently, by a radical selected from the group of fluorine, $(C_1$-$C_3)$-alkyl, oxo, —$OR^{23}$, —$NR^{24A}R^{24B}$ and —$C(=O)$—$NR^{25A}R^{25B}$, where $(C_1$-$C_3)$-alkyl for its part may be substituted by hydroxy or up to three times by fluorine and in which $R^{23}$ is hydrogen or $(C_1$-$C_3)$-alkyl, where $(C_1$-$C_3)$-alkyl may be substituted by hydroxyl or up to trisubstituted by fluorine, and $R^{24A}$, $R^{24B}$, $R^{25A}$ and $R^{25B}$ are each independently hydrogen, methyl or ethyl, and the salts, solvates and solvates of the salts thereof.

In the context of the present invention, very particular preference is given to compounds of the formula (I) in which $R^1$ is methyl, $R^2$ is hydrogen, $R^3$ is fluorine and G is a group of the formula —$CH_2$—$NR^{8A}R^{8B}$ in which $R^{8A}$ is hydrogen, methyl or ethyl and $R^{8B}$ is $(C_1$-$C_6)$-alkyl or $(C_3$-$C_6)$-cycloalkyl, where $(C_1$-$C_6)$-alkyl may be up to disubstituted, identically or differently, by a radical selected from the group of hydroxyl, methoxy and ethoxy and $(C_3$-$C_6)$-cycloalkyl may be up to disubstituted, identically or differently, by a radical selected from the group of hydroxyl, methoxy, ethoxy, isopropoxy, hydroxycarbonyl, methoxycarbonyl and ethoxycarbonyl, or $R^{8A}$ and $R^{8B}$ are joined to one another and, together with the nitrogen atom to which they are bonded, form a 5- to 7-membered heterocycle which may contain one further ring heteroatom from the group of N and O and which may be up to disubstituted, identically or differently, by a radical selected from the group of methyl, ethyl, hydroxyl, methoxy, ethoxy and n-propoxy, where methyl and ethyl may in turn be substituted by hydroxyl, and the salts, solvates and solvates of the salts thereof.

Irrespective of the particular combinations of the radicals specified, the individual radical definitions specified in the particular combinations or preferred combinations of radicals are also replaced as desired by radical definitions from other combinations.

Very particular preference is given to combinations of two or more of the abovementioned preferred ranges.

The invention further provides a process for preparing the inventive compounds, characterized in that either

[A] a compound of the formula (II)

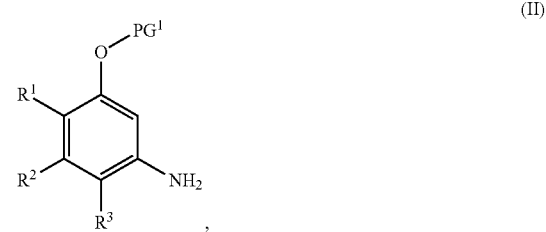

(II)

in which $R^1$, $R^2$ and $R^3$ are as defined above, and $PG^1$ is a suitable protecting group, for example benzyl, 4-methoxybenzyl or 2,4-dimethoxybenzyl, is reacted in the presence of a base with 2,4-dichloropyridine-3-carboxylic acid (III)

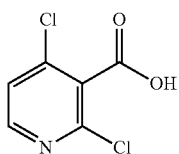

(III)

to give a compound of the formula (IV)

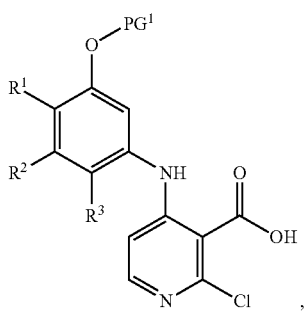

(IV)

in which $PG^1$, $R^1$, $R^2$ and $R^3$ are as defined above,
then coupled with 3,4-diaminobenzonitrile (V)

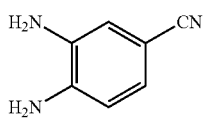

(V)

with activation of the carboxylic acid function in (IV) to give a compound of the formula (VI)

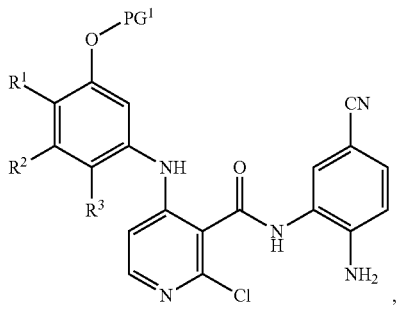

(VI)

in which $PG^1$, $R^1$, $R^2$ and $R^3$ are as defined above,
then this compound is cyclized by heating in an inert solvent to give a compound of the formula (VII)

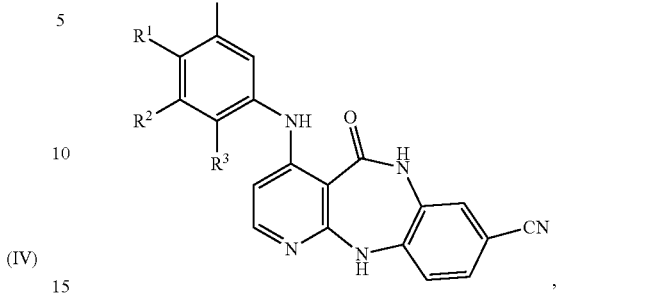

(VII)

in which $PG^1$, $R^1$, $R^2$ and $R^3$ are as defined above,
and then the protecting group $PG^1$ is detached to obtain an inventive compound of the formula (I-A)

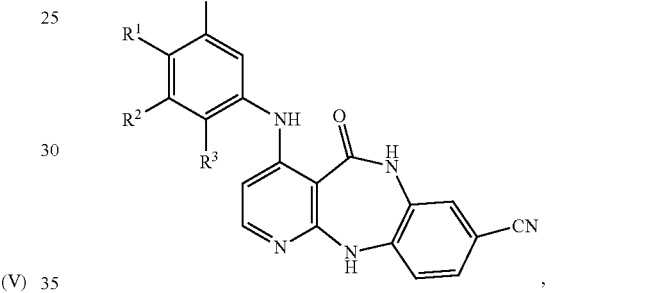

(I-A)

in which $R^1$, $R^2$ and $R^3$ are as defined above or

[B] a compound of the formula (VIII)

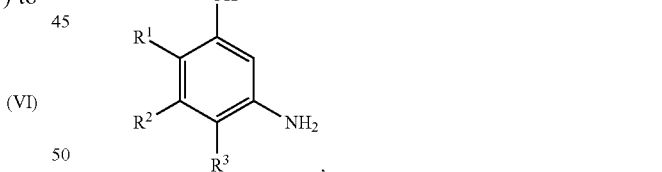

(VIII)

in which $R^1$, $R^2$ and $R^3$ are as defined above
is reacted in the presence of an acid while heating with a compound of the formula (IX)

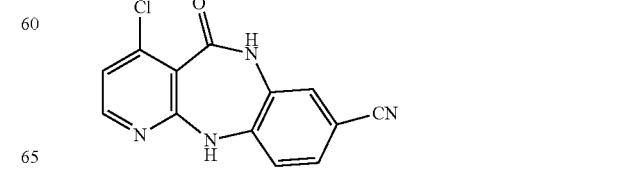

(IX)

to give the inventive compound of the formula (I-A)

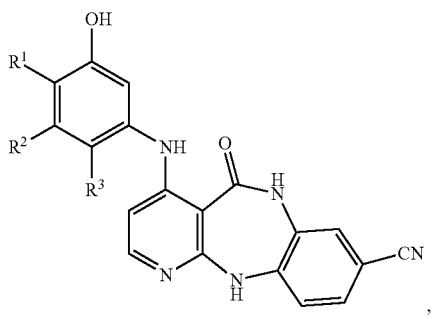

(I-A)

in which R¹, R² and R³ are as defined above
and optionally
[C] the compound of the formula (I-A) thus obtained is converted by treatment with an aqueous acid to an inventive compound of the formula (I-B)

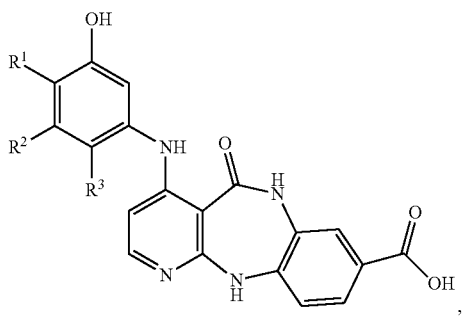

(I-B)

in which R¹, R² and R³ are as defined above
and the latter is optionally subsequently coupled with a compound of the formula (X)

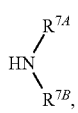

(X)

in which $R^{7A}$ and $R^{7B}$ are as defined above
with activation of the carboxylic acid function in (I-B) to give an inventive compound of the formula (I-C)

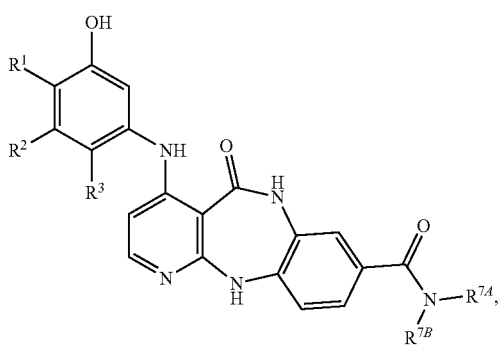

(I-C)

in which R¹, R², R³, $R^{7A}$ and $R^{7B}$ are as defined above, or optionally
[D] the compound of the formula (I-A) obtained above is converted by reaction with diisobutylaluminium hydride to a compound of the formula (XI)

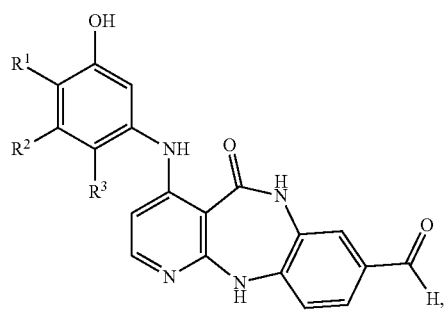

(XI)

in which R¹, R² and R³ are as defined above
and the latter is then reacted in the presence of a suitable reducing agent with a compound of the formula (XII)

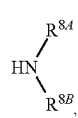

(XII)

in which $R^{8A}$ and $R^{8B}$ are as defined above
to give an inventive compound of the formula (I-D)

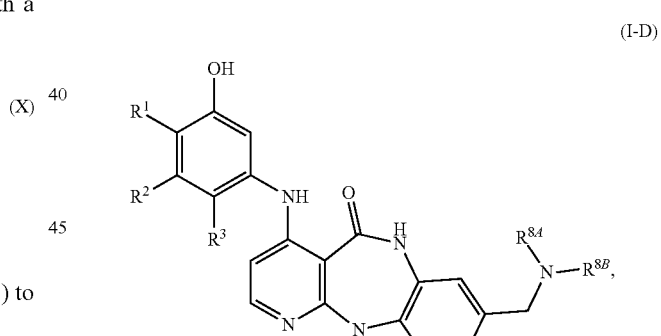

(I-D)

in which R¹, R², R³, $R^{8A}$ and $R^{8B}$ are as defined above, and the compounds of the formulae (I-A), (I-B), (I-C) and (I-D) thus obtained are optionally separated into their enantiomers and/or diastereomers and/or optionally converted with the appropriate (i) solvents and/or (ii) acids or bases to the solvates, salts and/or solvates of the salts thereof.

Suitable bases for the process step (II)+(III)→(IV) are strong non-nucleophilic bases such as sodium hydride or potassium hydride, lithium bis(trimethylsilyl)amide, sodium bis(trimethylsilyl)amide or potassium bis(trimethylsilyl)amide or lithium diisopropylamide; preference is given to using lithium bis(trimethylsilyl)amide. Useful inert solvents for this reaction especially include ethers such as diethyl ether, diisopropyl ether, methyl tert-butyl ether, tetrahydrofuran, 1,4-dioxane, 1,2-dimethoxymethane or bis(2-methoxyethyl) heater, hydrocarbons such as n-pentane, n-hexane, isohexane, n-heptane or cyclohexane, polar aprotic solvents such as N,N-dimethylformamide (DMF), N,N'-dimethylpropyleneurea (DMPU) or N-methylpyrrolidone (NMP) or mixtures of such solvents; preference is given to using a mixture of tetrahydrofuran and n-hexane. The reaction is generally effected within a temperature range of −78° C. to +25° C.

Instead of the carboxylic acid (III), in this process step—under otherwise identical reaction conditions—it is also possible to use an ester derivative of the formula (XIII)

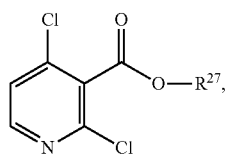

(XIII)

in which R$^{27}$ is methyl or ethyl;
the resulting product of the formula (XIV)

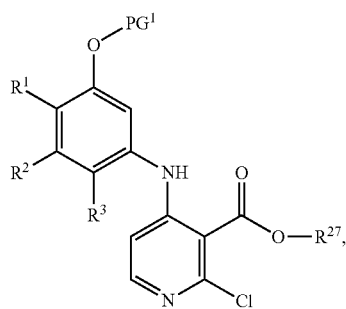

(XIV)

in which PG$^1$, R$^1$, R$^2$, R$^3$ and R$^{27}$ are as defined above is then converted in a customary manner by alkaline hydrolysis to the carboxylic acid of the formula (IV).

The coupling reaction (IV)+(V)→(VI) [amide formation] can be conducted with the aid of a condensing or activating agent or can be effected via the intermediate of the corresponding carbonyl chloride formed from (IV).

Suitable condensing or activating agents of this kind are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, α-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl) phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate, or tertiary amine bases such as triethylamine, N-methylmorpholine (NMM), N-methylpiperidine, N,N-diisopropylethylamine, pyridine or 4-N,N-dimethylaminopyridine (DMAP). Preference is given to using O-(benzotriazol-1-yl)-N,N,N',N'-tetramethyluronium tetrafluoroborate (TBTU) or O-(7-azabenzotriazol-1-yl)-N,N,N',N'-tetramethyluronium hexafluorophosphate (HATU), in each case in combination with N,N-diisopropylethylamine as base.

In the case of a two-stage reaction regime via the carbonyl chloride formed from (IV), the coupling with the amine component (V) is conducted in the presence of a customary auxiliary base such as sodium carbonate, potassium carbonate, sodium hydride, triethylamine, N-methylmorpholine (NMM), N-methylpiperidine, N,N-diisopropylethylamine, pyridine, 2,6-dimethylpyridine, 4-N,N-dimethylaminopyridine (DMAP), 1,8-diazabicyclo[5.4.0]undec-7-ene (DBU) or 1,5-diazabicyclo[4.3.0]non-5-ene (DBN); preference is given to using N,N-diisopropylethylamine. The preparation of the carbonyl chloride itself is accomplished in a customary manner by treatment of the carboxylic acid (IV) with thionyl chloride, phosphoryl chloride or oxalyl chloride, optionally under the catalytic action of N,N-dimethylformamide (DMF), in an inert solvent such as dichloromethane.

Inert solvents for the coupling reactions mentioned are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, acetonitrile, butyronitrile, ethyl acetate, pyridine, dimethyl sulphoxide (DMSO), N,N-dimethylformamide (DMF), N,N'-dimethylpropyleneurea (DMPU) or N-methylpyrrolidinone (NMP). It is also possible to use mixtures of such solvents. Preference is given to using dichloromethane, tetrahydrofuran, N,N-dimethylformamide or mixtures of these solvents. The reactions are generally effected within a temperature range of −20° C. to +40° C., preferably at 0° C. to +30° C.

The cyclization reaction (VI)→(VII) is advantageously conducted using a microwave apparatus within a temperature range of +60° C. to +200° C., preferably at +100° C. to +180° C. The addition of an acid, for example trifluoroacetic acid, hydrogen chloride, p-toluenesulphonic acid or pyridinium chloride, may possibly be beneficial.

Suitable inert solvents for the cyclization reaction are relatively high-boiling alcohols such as ethanol, n-propanol, isopropanol, n-butanol, tert-butanol, ethylene glycol, 2-methoxyethanol or 2-ethoxyethanol, relatively high-boiling ethers such as 1,4-dioxane, 1,2-dimethoxyethane, bis(2-methoxyethyl) ether or bis(2-ethoxyethyl) ether, relatively high-boiling hydrocarbons or chlorohydrocarbons such as benzene, toluene, xylene, chlorobenzene or 1,2-dichlorobenzene, or such solvents as acetonitrile, butyronitrile, dimethyl sulphoxide (DMSO), N,N-dimethylformamide (DMF), N,N-dimethylacetamide (DMA), N-methylpyrrolidinone (NMP) or N,N'-dimethylpropyleneurea (DMPU). Preference is given to using isopropanol, 2-ethoxyethanol, acetonitrile or 1,2-dichlorobenzene.

The removal of the protecting group $PG^1$ in process step (VII)→(I-A) is effected by customary methodology by treatment with trifluoroacetic acid in the presence of thioanisole, optionally with addition of an inert solvent, for example dichloromethane or 1,2-dichloroethane, or by hydrogenation (hydrogenolysis) in the presence of a suitable catalyst, for example palladium on activated carbon, in an alcohol such as methanol, ethanol or isopropanol or an ether such as diethyl ether, diisopropyl ether, methyl tert-butyl ether, tetrahydrofuran, 1,4-dioxane or 1,2-dimethoxymethane as solvent [cf. T. W. Greene and P. G. M. Wuts, *Protective Groups in Organic Synthesis*, Wiley, New York, 1999]. The reactions are generally conducted within a temperature range of −20° C. to +40° C.

The process step (VIII)+(IX)→(I-A) is conducted in the presence of an acid, for example hydrogen chloride, p-toluenesulphonic acid or pyridinium chloride, within a temperature range of +50° C. to +200° C., preferably at +100° C. to +180° C., and the use of a microwave apparatus may be advantageous here too. Preference is given to using hydrogen chloride, in the form of an anhydrous solution in 1,4-dioxane, or pyridinium chloride as acid addition.

Inert solvents used for this reaction are relatively high-boiling alcohols such as ethanol, n-propanol, isopropanol, n-butanol, tert-butanol, ethylene glycol, 2-methoxyethanol or 2-ethoxyethanol, relatively high-boiling ethers such as 1,4-dioxane, 1,2-dimethoxyethane, bis(2-methoxyethyl) ether or bis(2-ethoxyethyl) ether, relatively high-boiling hydrocarbons or chlorohydrocarbons such as benzene, toluene, xylene, chlorobenzene or 1,2-dichlorobenzene, or such solvents as acetonitrile, butyronitrile, dimethyl sulphoxide (DMSO), N,N-dimethylformamide (DMF), N,N-dimethylacetamide (DMA), N-methylpyrrolidinone (NMP) or N,N'-dimethylpropyleneurea (DMPU). Preference is given to using isopropanol, 2-ethoxyethanol or N,N-dimethylformamide.

Since the target compounds of the formula (I-A) often have inadequate solubility for chromatographic purification, it may be helpful to facilitate and improve such a purification by first converting the crude product obtained from the reaction (VIII)+(IX)→(I-A) by a standard method to a silyl ether derivative, for example to a compound of the formula (XV)

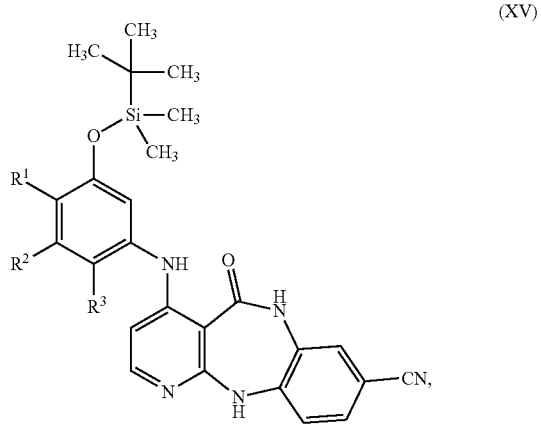

(XV)

in which $R^1$, $R^2$ and $R^3$ are as defined above, then undertaking the purification at this stage and subsequently detaching the silyl group again by known methodology, for example by treatment with tetra-n-butylammonium fluoride (TBAF), aqueous trifluoroacetic acid (TFA) or hydrochloric acid.

The silyl ether derivative (XV) may also, if desired, be converted in analogy to the above-described process [D] to the protected target compound (XX)

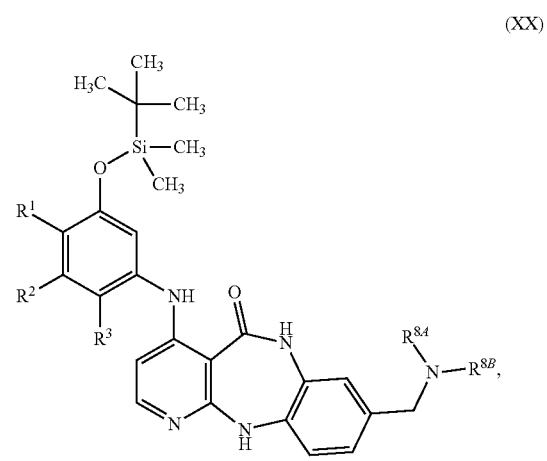

(XX)

in which $R^1$, $R^2$, $R^3$, $R^{8A}$ and $R^{8B}$ are as defined above, in order to utilize the better purification options here too; the detachment of the silyl group to give the inventive compound (I-D) is accomplished in the same way as outlined above.

The transformation (I-A)→(I-B) is effected by a familiar method by hydrolysis of the nitrile group with an aqueous acid, for example hydrochloric acid, at a reaction temperature in the range of +50° C. to +120° C.

The coupling reaction (I-B)+(X)→(I-C) [amide formation] is generally conducted with the aid of a condensing or activating agent, but can also be effected via the intermediate of the corresponding carbonyl chloride formed from (I-B). These reactions are conducted under analogous conditions to those described specifically above for the related coupling reaction (IV)+(V)→(VI).

The reduction reaction (I-A)→(XI) is effected by a known method with the aid of diisobutylaluminium hydride (DIBAL-H). The reaction is preferably conducted in a solvent mixture of dichloromethane and tetrahydrofuran or toluene and generally takes place within a temperature range of −78° C. to +25° C.

Suitable reducing agents for the process step (XI)+(XII)→(I-D) [reductive amination] for such purposes are customary alkali metal borohydrides such as lithium borohydride, sodium borohydride, potassium borohydride, sodium cyanoborohydride or sodium triacetoxyborohydride; preference is given to using sodium cyanoborohydride or sodium triacetoxyborohydride. The addition of an acid, such as acetic acid in particular, and/or of a dehydrating agent, for example molecular sieve or trimethyl or triethyl orthoformate, may be beneficial in these reactions.

Suitable solvents for these reactions are especially alcohols such as methanol, ethanol, n-propanol or isopropanol, ethers such as diisopropyl ether, methyl tert-butyl ether, tetrahydrofuran, 1,4-dioxane or 1,2-dimethoxymethane, polar aprotic solvents such as acetonitrile or N,N-dimethylformamide (DMF) or mixtures of such solvents. Preference is given to using ethanol, tetrahydrofuran, 1,4-dioxane or N,N-dimethylformamide. The reactions are effected generally within a temperature range from −20° C. to +50° C., depending on the reactivity of the amine component (XII) used.

The above-detailed compound of the formula (IX) can be prepared by coupling a compound of the formula (XVI)

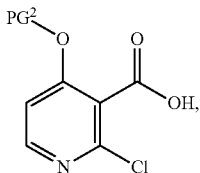
(XVI)

in which

PG² is a suitable protecting group, for example allyl or methyl, with 3,4-diaminobenzonitrile (V)

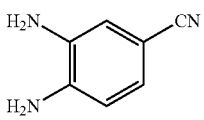
(V)

with activation of the carboxylic acid function in (XVI) to give a compound of the formula (XVII)

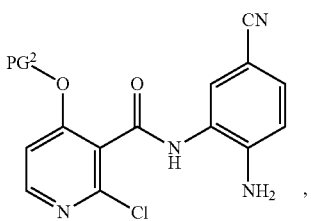
(XVII)

in which PG² is as defined above, then cyclizing it by heating in the presence of an acid with detachment of the protecting group PG² to give a compound of the formula (XVIII)

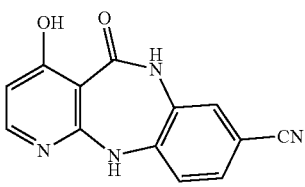
(XVIII)

and subsequently chlorinating the latter with phosphorus oxychloride in the presence of a base to give the compound of the formula (IX)

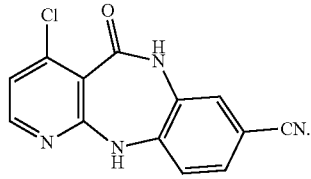
(IX)

The coupling (XVI)+(V)→(XVII) is effected in the same way as described specifically above for the related amide formation (IV)+(V)→(VI). The two-stage reaction variant via the carbonyl chloride formed from (XVI) is preferred in this case.

The transformation (XVII)→(XVIII) [cyclization with simultaneous protecting group detachment] is accomplished by heating (XVII) in the presence of an acid. The reaction is generally effected within a temperature range of +60° C. to +200° C., especially at temperatures of +100° C. to +180° C., and the use of a microwave apparatus may be beneficial. Suitable acid additions are especially trifluoroacetic acid, p-toluenesulphonic acid, pyridinium chloride, hydrogen chloride in anhydrous form or else hydrochloric acid.

Suitable inert solvents for this reaction are relatively high-boiling alcohols such as ethanol, n-propanol, isopropanol, n-butanol, tert-butanol, ethylene glycol, 2-methoxyethanol or 2-ethoxyethanol, relatively high-boiling ethers such as 1,4-dioxane, 1,2-dimethoxyethane, bis(2-methoxyethyl) ether or bis(2-ethoxyethyl) ether, relatively high-boiling hydrocarbons or chlorohydrocarbons such as benzene, toluene, xylene, chlorobenzene or 1,2-dichlorobenzene, or such solvents as acetonitrile, butyronitrile, dimethyl sulphoxide (DMSO), N,N-dimethylformamide (DMF), N,N-dimethylacetamide (DMA), N-methylpyrrolidinone (NMP) or N,N'-dimethylpropyleneurea (DMPU). Preference is given to using 2-ethoxyethanol, acetonitrile or 1,2-dichlorobenzene.

The subsequent transformation (XVIII)→(IX) is effected by treatment of (XVIII) with excess phosphorus oxychloride (phosphoryl chloride), optionally in the presence of a tertiary amine base such as triethylamine, N,N-diisopropylethylamine, pyridine or 2,6-dimethylpyridine; preference is given to using triethylamine. The reaction—in the case of employment of a correspondingly large excess of phosphorus oxychloride—can be executed without further additional solvent; alternatively, it is also possible to add an inert solvent, for example acetonitrile, sulpholane, chlorobenzene or 1,2-dichlorobenzene. The reaction is typically effected within a temperature range of 0° C. to +100° C.

The reaction of (XVIII) with phosphorus oxychloride under the reaction conditions described generally gives rise to a mixture of varying proportions of the monochlorinated target compound (IX) and the dichlorinated compound (XIX)

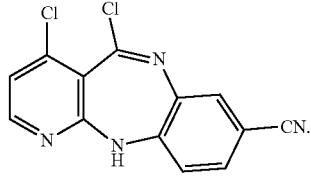
(XIX)

Because of its sparing solubility, this mixture of (IX) and (XIX) is appropriately used as such, i.e. without further separation, in subsequent reactions with the compounds (VIII). Unwanted by-products of the reaction with (VIII) that result from (XIX) are then removed in the course of the aqueous reaction workup and the further purification of the target compound (I-A) [see also the above-described further purification option via silyl ether derivatives, for example (XV)].

An alternative process for preparing compounds of the formula (I-D) involves coupling the above-described compound (XVI)

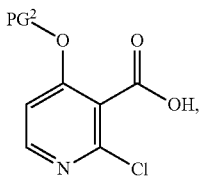
(XVI)

in which

PG$^2$ is a suitable protecting group, for example allyl or methyl, with a 2-nitroaniline derivative of the formula (XXI)

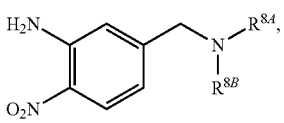
(XXI)

in which R$^{8A}$ and R$^{8B}$ are as defined above with activation of the carboxylic acid function in (XVI) to give a compound of the formula (XXII)

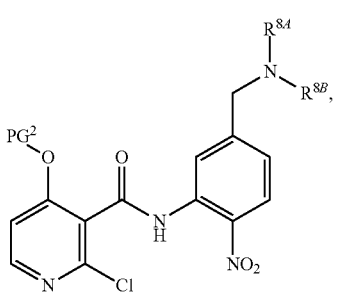
(XXII)

in which R$^{8A}$, R$^{8B}$ and PG$^2$ are as defined above, then reducing the latter to the aniline derivative of the formula (XXIII)

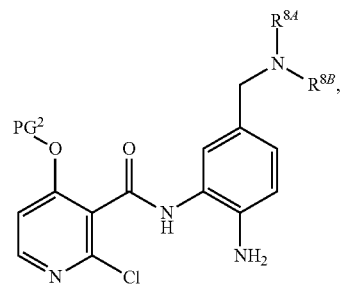
(XXIII)

in which R$^{8A}$, R$^{8B}$ and PG$^2$ are as defined above, then cyclizing the latter by heating in the presence of an acid with simultaneous detachment of the protecting group PG$^2$ to give a compound of the formula (XXIV)

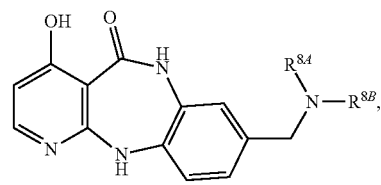
(XXIV)

in which R$^{8A}$ and R$^{8B}$ are as defined above then chlorinating the latter with phosphorus oxychloride to give a compound of the formula (XXV)

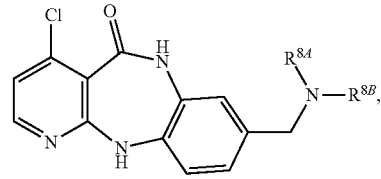
(XXV)

in which R$^{8A}$ and R$^{8B}$ are as defined above, and finally reacting the latter by heating with a compound of the formula (VIII)

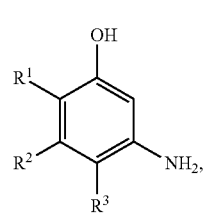
(VIII)

in which R$^1$, R$^2$ and R$^3$ are as defined above, in the presence of an acid, to give the target compound of the formula (I-D)

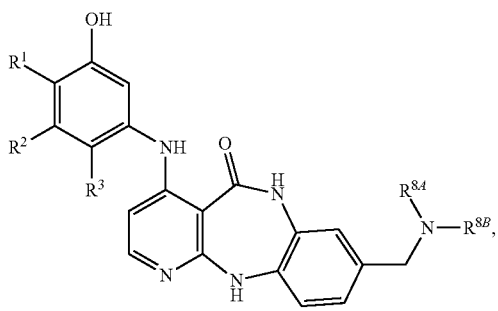

(I-D)

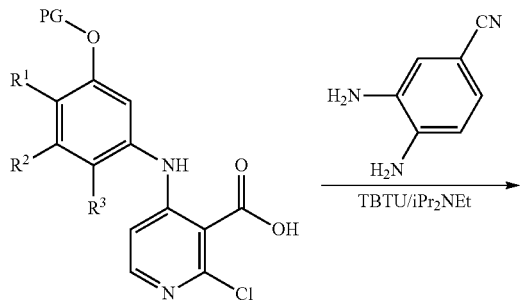

in which $R^1$, $R^2$, $R^3$, $R^{8A}$ and $R^{8B}$ are as defined above.

The coupling (XVI)+(XXI)→(XXII) is effected in the same way as elucidated specifically above for the related amide formation (IV)+(V)→(VI). The two-stage reaction variant via the carbonyl chloride formed from (XVI) is preferred here, and a suitable auxiliary base is especially a strong base such as sodium hydride.

The reduction of the nitro compound (XXII) to the aniline derivative (XXIII) is accomplished by a method customary for such purposes, for example with the aid of tin(II) chloride, by treatment with iron powder in hydrochloric acid or zinc powder in acetic acid or by hydrogenation in the presence of a catalyst such as palladium on charcoal or Raney nickel, preference being given to using tin(II) chloride as reducing agent.

The subsequent transformation (XXIII)→(XXIV)→(XXV) is conducted in a similar manner to that described above for the sequence (XVII)→(XVIII)→(IX); however, it is possible to dispense with the addition of a tertiary amine base in the reaction of (XXIV) with phosphorus oxychloride.

Finally, the reaction (XXV)+(VIII)→(I-D) is effected under the same conditions as described above for the related reaction (VIII)+(IX)→(I-A).

The compounds of the formulae (II), (III), (V), (VIII), (X), (XII), (XVI) and (XXI) are either commercially available or described as such in the literature, or they can be prepared from other commercially available compounds by literature methods familiar to those skilled in the art. Numerous detailed procedures and further literature references can also be found in the Experimental Part, in the section on the preparation of the starting compounds and intermediates. The preparation of the inventive compounds can be illustrated by way of example by the following reaction schemes:

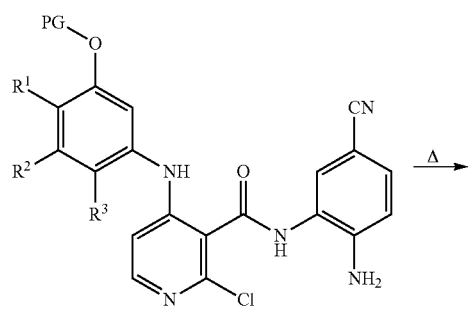

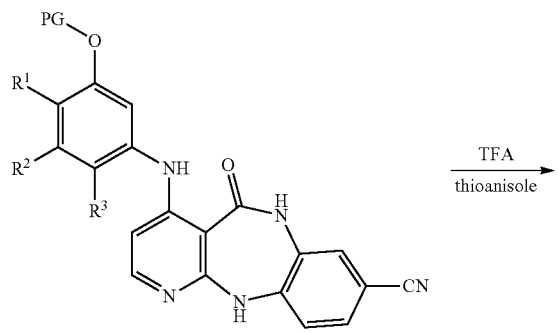

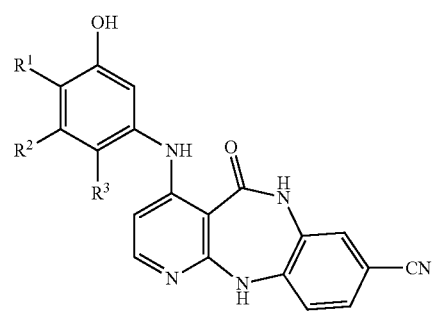

[PG = benzyl].

Scheme 1

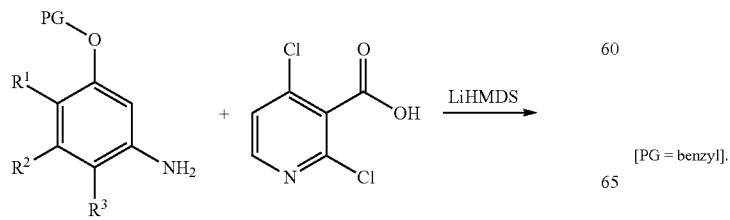

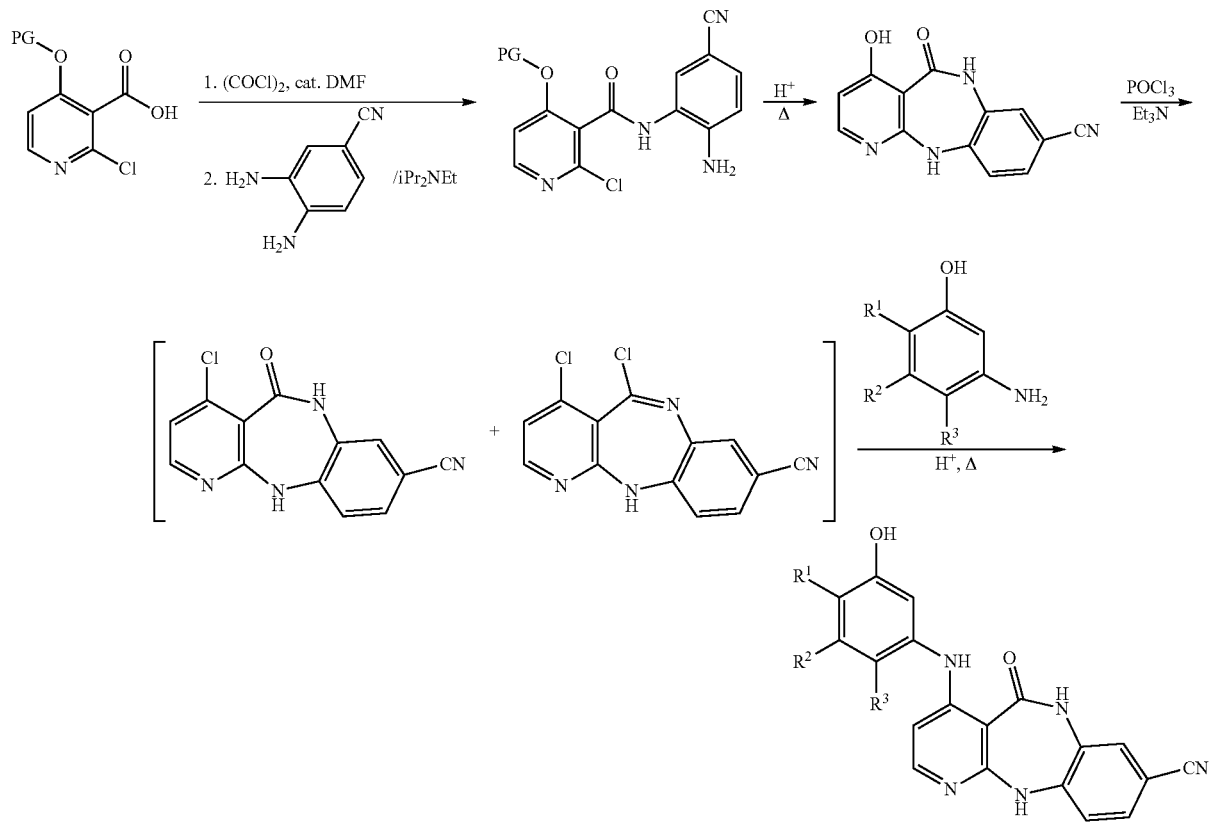
[PG = allyl or methyl].
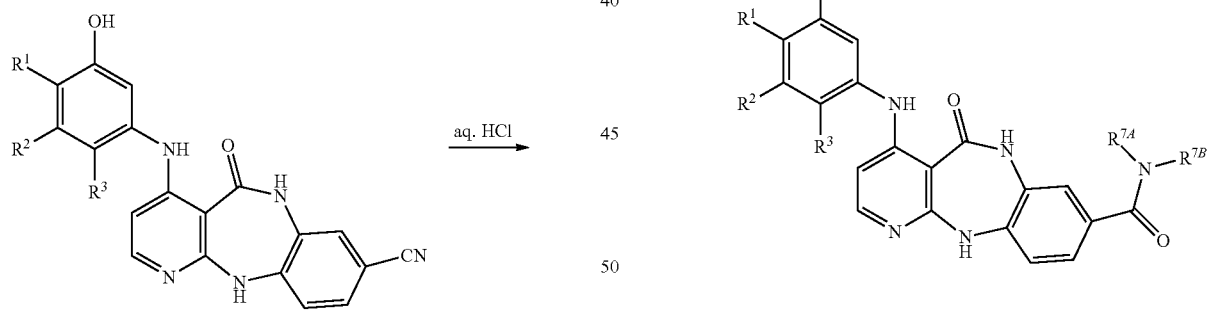
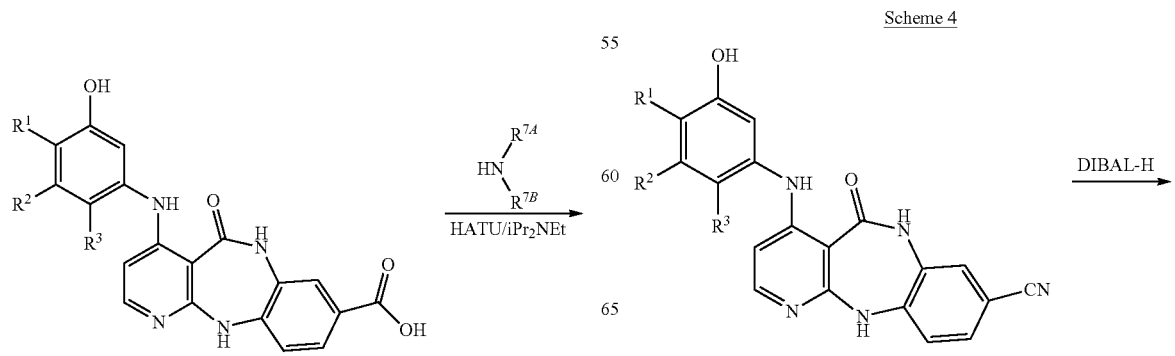

-continued

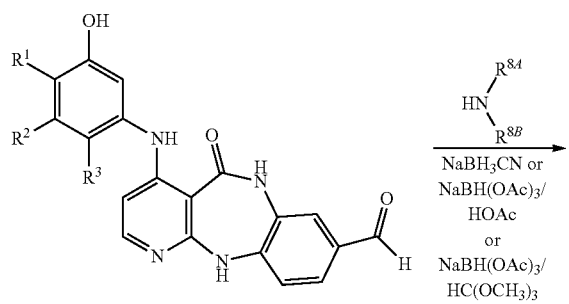

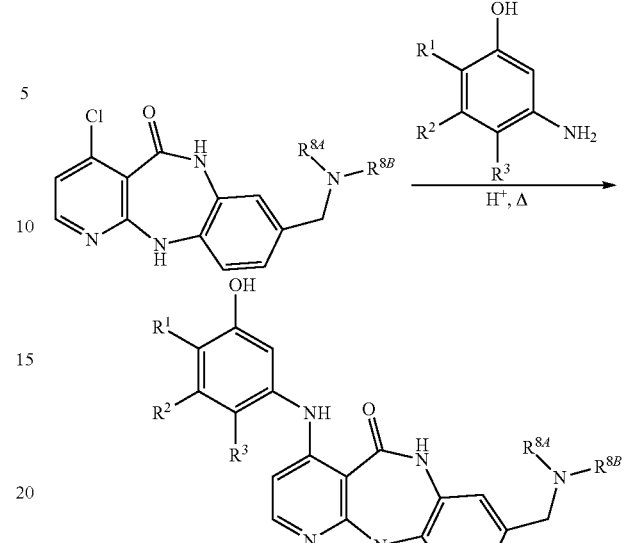

[PG = allyl or methyl].

Scheme 5

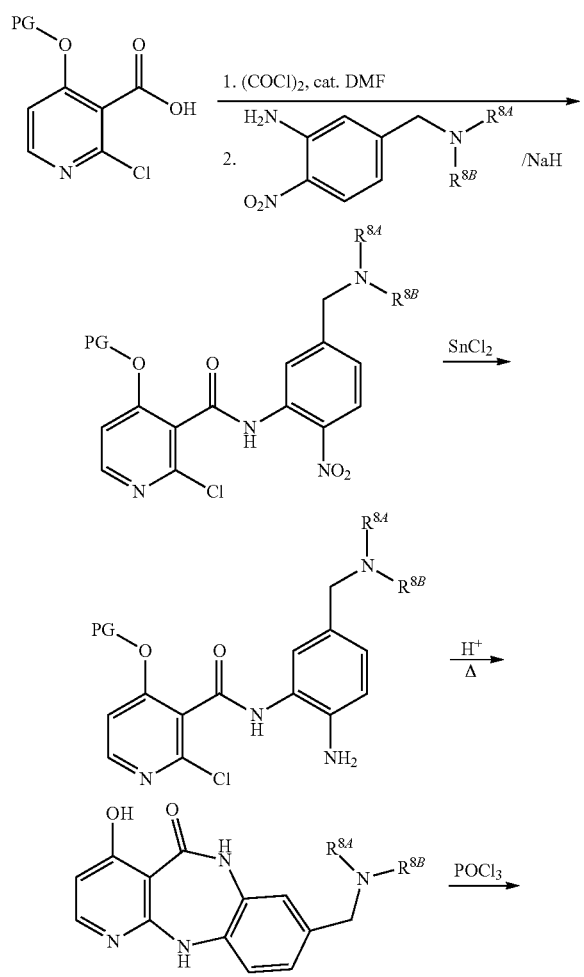

The inventive compounds have valuable pharmacological properties and can be used for prevention and treatment of diseases in humans and animals.

The inventive compounds are low molecular weight, potent and dual-action inhibitors of the VEGF and PDGF signalling pathway and are therefore suitable for treatment and/or prevention of angiogenic disorders, especially of ophthalmological disorders, of cancers and tumours and other disorders and pathological processes in which neovascularization/neoangiogenesis plays a role.

The ophthalmological disorders which can be treated and prevented using the inventive compounds, in the context of the invention, should be understood, for example, to mean the following disorders: age-related macular degeneration (AMD) including dry (non-exudative) and wet (exudative, neovascular) AMD, choroidal neovascularization (CNV), choroidal neovascular membranes (CNVM), cystoid macular oedema (CME), epiretinal membranes (ERM) and macular perforations, myopia-associated choroidal neovascularization, angioid and vascular streaks, retinal detachment, diabetic retinopathy, diabetic macular oedema (DME), atrophic and hypertrophic lesions in the retinal pigment epithelium, retinal vein occlusion, choroidal retinal vein occlusion, macular oedema, macular oedema associated with renal vein occlusion, Retinitis pigmentosa, Stargardt disease, retinopathy of prematurity, glaucoma, inflammation disorders of the eye, for example uveitis, scleritis or endocarditis, cataract, refraction anomalies, for example myopia, hyperopia, astigmatism or keratoconus, corneal angiogenesis resulting, for example, from keratitis, corneal transplant or keratoplasty, corneal angiogenesis resulting from hypoxia (for example through extensive wearing of contact lenses), conjunctival pterygium, subcorneal oedema and intracorneal oedema.

Because of their profile of activity, the inventive compounds are especially suitable for treatment and/or prevention of age-related macular degeneration (AMD), choroidal neovascularization (CMV), myopia-associated choroidal neovascularization, diabetic retinopathy, macular oedema and retinal vein occlusion.

The cancers and tumours which can be treated and/or prevented using the inventive compounds, in the context of the invention, include, for example, the following disorders: mammary carcinomas and mammary tumours (mammary carcinomas including ductal and lobular forms, also in situ), tumours of the respiratory tract (small-cell and non-small-cell pulmonary carcinoma, bronchial carcinoma), cerebral tumours (e.g. of the brain stem and of the hypothalamus, astrocytoma, ependymoma, glioblastoma, glioma, medulloblastoma, meningioma and neuro-ectodermal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of the stroma and connective tissue (inter alia soft tissue sarcomas, osteosarcomas, malignant fibrous histiocytomas, chondrosarcomas, fibrosarcomas, haemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative diseases of the blood, the lymph system and the spinal cord, in solid form and as circulating cells, such as leukaemias, lymphomas and myeloproliferative diseases, for example acute myeloid, acute lymphoblastic, chronic myeloid, chronic lymphocytic and hairy cell leukaemia, multiple myeloma (plasmacytoma) and AIDS-correlated lymphomas, Hodgkin's lymphomas, non-Hodgkin's lymphomas, cutaneous T cell lymphomas, Burkitt's lymphomas and lymphomas in the central nervous system.

The treatment of the aforementioned cancers in the context of the present invention may include both a treatment of the solid tumours and a treatment of metastasizing or circulating forms thereof.

Because of their profile of activity, the inventive compounds are especially suitable for treatment and/or prevention of mammary, colorectal, hepatic, renal and ovarian carcinomas, glioblastomas, acute myeloid leukaemia (AML), chronic myeloid leukaemia (CML) and multiple myeloma.

The compounds of the present invention can also be used for treatment of vascular malformation, such as haemangiomas, haemangioblastomas, cavernomas and lymphangiomas, and further disorders associated with excessive or abnormal angiogenesis. These include psoriasis, rosacea, retrolental fibroplasia, angiofibroma, inflammation, rheumatoid arthritis, restenosis, in-stent restenosis and restenosis after vascular implantation, microangiopathy, glomerulopathy, endometriosis, renal disorders (for example glomerulonephritis, diabetic nephropathy, malignant nephrosclerosis) and fibrotic disorders (for example renal cirrhosis, mesangiosis, arteriosclerosis).

The aforementioned well-characterized diseases in humans can also occur with comparable aetiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the inventive compounds for the treatment and/or prevention of disorders, especially of the aforementioned disorders.

The present invention further provides for the use of the inventive compounds for production of a medicament for treatment and/or prevention of disorders, especially of the aforementioned disorders.

The present invention further provides a medicament comprising at least one of the inventive compounds for treatment and/or prevention of disorders, especially of the aforementioned disorders.

The present invention further provides for the use of the inventive compounds in a method for treatment and/or prevention of disorders, especially of the aforementioned disorders.

The present invention further provides a process for treatment and/or prevention of disorders, especially of the aforementioned disorders, using an effective amount of at least one of the inventive compounds.

The inventive compounds can be used alone or, if required, in combination with one or more other pharmacologically active substances, provided that this combination does not lead to undesirable and unacceptable side effects. The present invention therefore further provides medicaments comprising at least one of the inventive compounds and one or more further active ingredients, especially for treatment and/or prevention of the aforementioned disorders. Preferred examples of combination active ingredients suitable for the purpose include:

active ingredients which inhibit neoangiogenesis, by way of example and with preference inhibitors of the VEGF and/or PDGF signalling pathways, inhibitors of the integrin signalling pathways, inhibitors of the angiopoietin-Tie signalling pathways, inhibitors of the PI3K-Akt-mTor signalling pathways, inhibitors of the Ras-Raf-Mek-Erk signalling pathway, inhibitors of the MAPK signalling pathways, inhibitors of the FGF signalling pathways, inhibitors of the sphingosine-1-phosphate signalling pathways, inhibitors of endothelial cell proliferation or apoptosis-inducing active ingredients;

active ingredients which reduce vascular wall permeability (oedema formation), by way of example and with preference corticosteroids, inhibitors of the ALK1-Smad1/5 signalling pathway, inhibitors of the VEGF and/or PDGF signalling pathways, cyclooxygenase inhibitors, inhibitors of the kallikrein-kinin system or inhibitors of the sphingosine-1-phosphate signalling pathways; and/or active ingredients which reduce damage to the retina under oxidative stress, by way of example and with preference inhibitors of the complement system, especially antagonists of the complement C5a receptor, or agonists of the 5-HT$_{1A}$ receptor.

In a preferred embodiment of the invention, the inventive compounds are administered in combination with an inhibitor of the VEGF and/or PDGF signalling pathways, by way of example and with preference aflibercept, ranibizumab, bevacizumab, KH902, pegaptanib, ramucirumab, squalamin, bevasiranib, apatinib, axitinib, brivanib, cediranib, dovitinib, lenvatinib, linifanib, motesanib, pazopanib, regorafenib, sorafenib, sunitinib, tivozanib, vandetanib, vatalanib, vargatef or E-10030.

In a preferred embodiment of the invention, the inventive compounds are administered in combination with an inhibitor of the angiopoietin-Tie signalling pathways, by way of example and with preference AMG 386, and/or with a modulator of Tie2 receptor tyrosine kinase.

In a preferred embodiment of the invention, the inventive compounds are administered in combination with an inhibitor of the integrin signalling pathways, by way of example and with preference volociximab, cilengitid or ALG-1001.

In a preferred embodiment of the invention, the inventive compounds are administered in combination with an inhibitor of the PI3K-Akt-mTor signalling pathways, by way of example and with preference XL 147, perifosin, MK-2206, sirolimus, temsirolimus or everolimus.

In a preferred embodiment of the invention, the inventive compounds are administered in combination with a corticosteroid, by way of example and with preference anecortave, betamethasone, dexamethasone, triamcinolone or fluocinolone.

In a preferred embodiment of the invention, the inventive compounds are administered in combination with an inhibitor of the ALK1-Smad1/5 signalling pathway, by way of example and with preference ACE-041 or one of the compounds described in WO 2013/004551-A1.

In a preferred embodiment of the invention, the inventive compounds are administered in combination with a cyclooxygenase inhibitor, by way of example and with preference bromfenac or nepafenac.

In a preferred embodiment of the invention, the inventive compounds are administered in combination with an inhibitor of the kallikrein-kinin system, by way of example and with preference safotibant or ecallantide.

In a preferred embodiment of the invention, the inventive compounds are administered in combination with an inhibitor of the sphingosine-1-phosphate signalling pathways, by way of example and with preference sonepcizumab.

In a preferred embodiment of the invention, the inventive compounds are administered in combination with an antagonist of the complement C5a receptor, by way of example and with preference eculizumab.

In a preferred embodiment of the invention, the inventive compounds are administered in combination with an agonist of the 5-HT$_{1A}$ receptor, by way of example and with preference tandospirone.

The inventive compounds can also be administered in conjunction with photodynamic therapy, consisting of an active ingredient such as verteporfin, for example, and the action of light.

In addition, the inventive compounds can also be combined with one or more active ingredients from the following classes:

antioxidants and free-radical scavengers;
active hypotensive ingredients, by way of example and with preference from the group of the calcium antagonists, angiotensin AII antagonists, ACE inhibitors, beta-receptor blockers, alpha-receptor blockers, diuretics, phosphodiesterase inhibitors, sGC stimulators, cGMP elevators, aldosterone antagonists, mineralocorticoid receptor antagonists, ECE inhibitors and vasopeptidase inhibitors;
antidiabetics, by way of example and with preference from the group of the insulins and insulin derivatives, sulphonylureas, biguanides, meglitinide derivatives, glucosidase inhibitors, PPAR-gamma agonists, GLP 1 receptor agonists, glucagon antagonists, insulin sensitizers, CCK1 receptor agonists, leptin receptor agonists, potassium channel antagonists and the inhibitors of hepatic enzymes that are involved in the stimulation of gluconeogenesis and/or glycogenolysis;
antiinfectives, by way of example and with preference from the group of the antibacterial, antifungal and/or antiviral substances; and/or
substances for treatment of glaucoma, by way of example and with preference from the group of the adrenergics, beta-blockers, carbonic anhydrase inhibitors, parasympathomimetics and prostaglandins.

In a preferred embodiment of the invention, the inventive compounds are administered in combination with an antioxidant/free-radical scavenger, by way of example and with preference probucol.

Hypotensive agents are preferably understood to mean compounds from the group of the calcium antagonists, angiotensin AII antagonists, ACE inhibitors, beta-receptor blockers, alpha-receptor blockers and diuretics.

In a preferred embodiment of the invention, the inventive compounds are administered in combination with a calcium antagonist, by way of example and with preference nifedipine, amlodipine, verapamil or diltiazem.

In a preferred embodiment of the invention, the inventive compounds are administered in combination with an angiotensin AII antagonist, by way of example and with preference losartan, valsartan, candesartan, irbesartan, olmesartan or telmisartan.

In a preferred embodiment of the invention, the inventive compounds are administered in combination with an ACE inhibitor, by way of example and with preference enalapril, captopril, lisinopril, ramipril, delapril, fosinopril, quinopril, perindopril or trandopril.

In a preferred embodiment of the invention, the inventive compounds are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with a diuretic, by way of example and with preference furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Antidiabetics are preferably understood to mean insulin and insulin derivatives and orally active hypoglycaemic ingredients. Insulin and insulin derivatives here include both insulins of animal, human or biotechnological origin and mixtures thereof. Orally active hypoglycaemic ingredients preferably include compounds from the group of the sulphonylureas, biguanides, meglitinide derivatives, glucosidase inhibitors and PPAR-gamma agonists.

In a preferred embodiment of the invention, the inventive compounds are administered in combination with insulin.

In a preferred embodiment of the invention, the inventive compounds are administered in combination with a sulphonylurea, by way of example and with preference tolbutamide, glibenclamide, glimepiride, glipizide or gliclazide.

In a preferred embodiment of the invention, the inventive compounds are administered in combination with a biguanide, by way of example and with preference metformin.

In a preferred embodiment of the invention, the inventive compounds are administered in combination with a meglitinide derivative, by way of example and with preference repaglinide or nateglinide.

In a preferred embodiment of the invention, the inventive compounds are administered in combination with a glucosidase inhibitor, by way of example and with preference miglitol or acarbose.

In a preferred embodiment of the invention, the inventive compounds are administered in combination with a PPAR-gamma agonist, by way of example and with preference pioglitazone or rosiglitazone.

In a preferred embodiment of the invention, the inventive compounds are administered in combination with an active antibacterial ingredient, by way of example and with preference amikacin, ampicillin, bacitracin, cefazolin, ceftazidim, ceftriaxon, ciprofloxacin, clindamycin, colistimethat, erythromycin, gentamicin, moxifloxacin, penicillin G, tobramycin or vancomycin.

In a preferred embodiment of the invention, the inventive compounds are administered in combination with an active antifungal ingredient, by way of example and with preference amphotericin B.

In a preferred embodiment of the invention, the inventive compounds are administered in combination with an active antiviral ingredient, by way of example and with preference fomivirsen or ganciclovir.

In a preferred embodiment of the invention, the inventive compounds are administered in combination with an adrenergic, by way of example and with preference dipivefrin, epinephrine, aproclonidine, brimonidine or clonidine.

In a preferred embodiment of the invention, the inventive compounds are administered in combination with a beta-blocker, by way of example and with preference betaxolol, befunolol, levobunolol, metipranolol, timolol, carteolol or pindolol.

In a preferred embodiment of the invention, the inventive compounds are administered in combination with a carboanhydrase inhibitor, by way of example and with preference brinzolamide, dorzolamide, acetazolamide, dichlorphenamide or methazolamide.

In a preferred embodiment of the invention, the inventive compounds are administered in combination with a parasympathomimetic, by way of example and with preference pilocarpine, aceclidine, carbachol, acetylcholine, demecarium bromide, ecothiophate iodide or physostigmine.

In a preferred embodiment of the invention, the inventive compounds are administered in combination with a prostaglandin or prostaglandin derivative, by way of example and with preference bimatoprost, latanoprost, tafluprost, travoprost or unoprostone.

In addition, the inventive compounds can also be used in conjunction with other therapeutic measures such as radiotherapy and/or surgical intervention.

Particular preference is given to combinations of the inventive compounds with one or more active ingredients selected from the class of the anti-VEGF therapeutics (VEGF signalling pathway inhibitors) such as aflibercept, ranibizumab, bevacizumab or pegaptanib.

The present invention further provides medicaments which comprise at least one inventive compound, typically together with one or more inert, nontoxic, pharmaceutically suitable excipients, and for the use thereof for the aforementioned purposes.

The inventive compounds can act systemically and/or locally. For this purpose, they can be administered in a suitable manner, for example by the oral, parenteral, pulmonal, nasal, sublingual, lingual, buccal, rectal, dermal, transdermal, extraocular, intraocular or otic route, or as an implant or stent.

The inventive compounds can be administered in suitable administration forms for these administration routes.

Suitable administration forms for oral administration are those which work according to the prior art and release the inventive compounds rapidly and/or in a modified manner and which contain the inventive compounds in crystalline and/or amorphized and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

Suitable administration forms for extraocular (topical) administration are those which operate in accordance with the prior art, which release the inventive compounds rapidly and/or in a modified or controlled manner and which contain the inventive compounds in crystalline and/or amorphized and/or dissolved form, for example eye drops, sprays or lotions (e.g. solutions, suspensions, vesicular/colloidal systems, emulsions, aerosols), powders for eye drops, sprays or lotions (e.g. ground active ingredient, mixtures, lyophilizates, precipitated active ingredient), semisolid eye preparations (e.g. hydrogels, in-situ hydrogels, creams or ointments) or eye inserts (solid or semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable administration forms for intraocular administration are those which operate in accordance with the prior art, which release the inventive compounds rapidly and/or in a modified or controlled manner and which contain the inventive compounds in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active ingredient, mixtures, lyophilizates, precipitated active ingredient), gels for injection (semisolid preparations, e.g. hydrogels, in-situ hydrogels) or implants (solid preparations, e.g. biodegradable and nonbiodegradable implants, implantable pumps).

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

For the treatment of ophthalmological disorders, preference is given to extraocular topical and intraocular administration and, for the treatment of other disorders, to oral and intravenous administration.

The inventive compounds can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight. In the case of extraocular administration, the dosage is about 1 to 50 mg/ml with an application volume of 10 to 100 µl.

It may nevertheless be necessary in some cases to deviate from the stated amounts, specifically as a function of the body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms
abs. absolute
Ac acetyl
aq. aqueous, aqueous solution
Boc tert-butoxycarbonyl
br. broad (in NMR signal)
Ex. Example
Bu butyl
c concentration
ca. circa, about
cat. catalytic
CI chemical ionization (in MS)
CV column volume
Δ temperature increase, heating (of a reaction mixture)
d doublet (in NMR)
d day(s)
TLC thin-layer chromatography
DCC N,N'-dicyclohexylcarbodiimide
DCI direct chemical ionization (in MS)
dd doublet of doublets (in NMR)
DIBAL-H diisobutylaluminium hydride
DMAP 4-(dimethylamino)pyridine
DMF N,N-dimethylformamide
DMSO dimethyl sulphoxide
dt doublet of triplets (in NMR)
of theory of theory (in chemical yield)
ee enantiomeric excess
EI electron impact ionization (in MS)
ent enantiomerically pure, enantiomer
eq. equivalent(s)
ESI electrospray ionization (in MS)
Et ethyl
GC gas chromatography
GC/MS gas chromatography-coupled mass spectrometry
h hour(s)
HATU O-(7-azabenzotriazol-1-yl)-N,N,N',N'-tetramethyluronium hexafluorophosphate
HPLC high-pressure, high-performance liquid chromatography
iPr isopropyl
conc. concentrated (in the case of a solution)
LC liquid chromatography
LC/MS liquid chromatography-coupled mass spectrometry
LiHMDS lithium hexamethyldisilazide
Lit. literature (reference)
m multiplet (in NMR)
Me methyl
min minute(s)
MS mass spectrometry
MTBE methyl tert-butyl ether
NMP N-methylpyrrolidin-2-one
NMR nuclear magnetic resonance spectrometry
Pr propyl
q (or quart) quartet (in NMR)
qd quartet of doublets (in NMR)
quant. quantitative (in chemical yield)
quint quintet (in NMR)
rac racemic, racemate
$R_f$ retention index (in TLC)
RP reverse phase (in HPLC)
RT room temperature
$R_t$ retention time (in HPLC, LC/MS)
s singlet (in NMR)
sept septet (in NMR)
t triplet (in NMR)
TBTU O-(benzotriazol-1-yl)-N,N,N',N'-tetramethyluronium tetrafluoroborate
tBu tert-butyl
td triplet of doublets (in NMR)
TFA trifluoroacetic acid
THF tetrahydrofuran
UV ultraviolet spectrometry
v/v ratio by volume (of a solution)
tog. together
HPLC, LC/MS and GC/MS Methods:
Method 1 (LC/MS):
  MS instrument type: Waters (Micromass) Quattro Micro; HPLC instrument type: Agilent 1100 Series; column: Thermo Hypersil GOLD 3µ 20×4 mm; eluent A: 1 l water+ 0.5 ml 50% formic acid, eluent B: 1 l acetonitrile+0.5 ml 50% formic acid; gradient: 0.0 min 100% A→3.0 min 10% A→4.0 min 10% A; oven: 50° C.; flow rate: 2 ml/min; UV detection: 210 nm Method 2 (LC/MS):
MS instrument: Waters ZQ; HPLC instrument: Agilent 1100 Series; UV DAD; column: Thermo Hypersil GOLD 3μ 20 mm×4 mm; eluent A: 1 l water+0.5 ml 50% formic acid, eluent B: 1 l acetonitrile+0.5 ml 50% formic acid; gradient: 0.0 min 100% A→3.0 min 10% A→4.0 min 10% A; oven: 55° C.; flow rate: 2 ml/min; UV detection: 210 nm.

Method 3 (LC/MS):
Instrument: Waters Acquity SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 210-400 nm.

Method 4 (GC-MS):
Instrument: Micromass GCT, GC6890; column: Restek RTX-35, 15 m×200 μm×0.33 μm; constant flow rate of helium: 0.88 ml/min; oven: 70° C.; inlet: 250° C.; gradient: 70° C., 30° C./min→310° C. (hold for 3 min).

Method 5 (LC/MS):
Instrument: Waters Acquity SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 6 (LC/MS):
MS instrument: Waters (Micromass) QM; HPLC instrument: Agilent 1100 series; column: Agilent ZORBAX Extend-C18 3.0 mm×50 mm 3.5μ; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 7 (LC/MS):
Instrument: Agilent MS Quad 6150; HPLC: Agilent 1290; column: Waters Acquity UPLC HSS T3 1.8μ 50×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 8 (LC/MS):
Instrument: Waters Acquity SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 9 (LC/MS):
Instrument: Micromass Quattro Premier with Waters UPLC Acquity; column: Thermo Hypersil GOLD 1.9μ 50×1 mm; eluent A: 1 l water+0.5 ml 50% formic acid, eluent B: 1 l acetonitrile+0.5 ml 50% formic acid; gradient: 0.0 min 90% A→0.1 min 90% A→1.5 min 10% A→2.2 min 10% A; oven: 50° C.; flow rate: 0.33 ml/min; UV detection: 210 nm.

Method 10 (LC/MS):
MS instrument: Waters ZQ 2000; HPLC instrument: Agilent 1100, 2-column combination; Autosampler: HTC PAL; column: YMC-ODS-AQ, 50×4.6 mm, 3.0 μm; eluent A: water+0.1% formic acid, eluent B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm Method 11 (Preparative HPLC):
System: Gilson Abimed HPLC, binary pump system; column: Reprosil C-18 10 μm, 250×30 mm; eluent A: water, eluent B: acetonitrile; gradient: 0-3 min 10% B, 3.01-31 min 90% B, 31 min 90% B; flow rate: 50 ml/min; UV detection: 210 nm.

Method 12 (Preparative HPLC):
System: Gilson Abimed HPLC, binary pump system; column: Reprosil C-18 10 μm, 250×30 mm; eluent A: water+0.01% ammonia, eluent B: acetonitrile; gradient: 0-3 min 10% B, 3.01-31 min 90% B, 31 min 90% B; flow rate: 50 ml/min; UV detection: 210 nm.

Method 13 (Preparative HPLC):
System: Gilson Abimed HPLC, binary pump system; column: Reprosil C-18 10 μm, 250×30 mm; eluent A: water+0.1% ammonia, eluent B: methanol; gradient: 0-3 min 10% B, 3.01-31 min 90% B, 31 min 90% B; UV detection: 210 nm.

Method 14 (Preparative HPLC):
System: Gilson Abimed HPLC, binary pump system; column: Reprosil C-18 10 μm, 250×30 mm; eluent A: water+0.01% ammonia, eluent B: acetonitrile; gradient: 0-3 min 35% B, 3.01-31 min 80% B, 31 min 80% B; flow rate: 50 ml/min; UV detection: 210 nm.

Method 15 (Preparative HPLC):
System: Gilson Abimed HPLC, binary pump system; column: Chromatorex 125×30 mm, 10 μm; eluent A: water+0.1% formic acid, eluent B: acetonitrile+0.1% formic acid; gradient: 0-3 min 90% A, 3.01-31 min 10% A.

Method 16 (Preparative HPLC):
System: Gilson Abimed HPLC, binary pump system; column: Chromatorex 125×30 mm, 10 μm; eluent A: water, eluent B: acetonitrile; gradient: 0-3 min 90% A, 3.01-31 min 5% A.

Method 17 (Preparative HPLC):
Column: Kinetex C18 5 μm, 100×30 mm; flow rate: 60 ml/min; eluent A: water, eluent B: acetonitrile, eluent C: 1% formic acid in water; gradient: 0-1 min 90% A, 5% B, 5% C, 9.5 min 45% A, 50% B, 5% C.

Method 18 (Preparative Chiral HPLC):
Column: Daicel Chiralpak IF 250×20 mm, 5 μm; eluent: 60% isohexane/40% ethanol with 0.2% diethylamine; flow rate: 15 ml/min; temperature: 30° C.

Method 19 (Analytical Chiral HPLC):
Column: Daicel Chiralpak AZ-H 250×4.6 mm, 5 μm; eluent: 50% isohexane/50% ethanol with 0.2% diethylamine; flow rate: 1.0 ml/min; temperature: 35° C.

Method 20 (Preparative HPLC):
Column: Kinetex 100×30 mm, 5 μm; eluent A: water, eluent B: acetonitrile, eluent C: 1% formic acid in water; gradient: 0-1.00 min 90% A, 5% B, 5% C, 1.01-6.66 min 60% A, 35% B, 5% C.

Method 21 (Preparative Chiral HPLC):
Column: Daicel Chiralpak IF 250×20 mm, 5 μm; eluent: 75% isohexane/25% ethanol with 0.2% diethylamine; flow rate: 15 ml/min; temperature: 25° C.

Method 22 (Analytical Chiral HPLC):
Column: Daicel Chiralpak IA 250×4.6 mm, 5 μm; eluent: ethanol with 0.2% diethylamine; flow rate: 1.0 ml/min; temperature: 50° C.

Method 23 (Preparative HPLC):
System: Gilson Abimed HPLC, binary pump system; column: Chromatorex 125×30 mm, 10 μm; eluent A: water+0.01% trifluoroacetic acid, eluent B: acetonitrile; gradient: 0-3 min 90% A, 3.01-31 min 5% A.

Method 24 (Quantitative Ion Chromatography):
Quantitative determination of cations and anions with external standards. Instrument: Thermo Scientific ICS 5000+; capillary IC columns: IonPac AS11-HC and IonPac CS16; eluent: [OH]⁻ 60 mM; gradient: 0-3 min 1 mM, 30 min 25 mM, 35-38 min 60 mM, 38.1 min 1 mM; detection: conductivity detector.

Method 25 (LC/MS):

MS instrument type: Thermo Scientific FT-MS; HPLC instrument type: Thermo Scientific UltiMate 3000; column: Waters HSS T3, 2.1 mm×75 mm, C18 1.8 µm; eluent A: 1 l water+0.01% formic acid, eluent B: 1 l acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method 26 (LC/MS):

MS instrument: Waters (Micromass) Quattro Micro; HPLC instrument: Waters UPLC Acquity; column: Waters BEH C18 1.7µ, 50 mm×2.1 mm; eluent A: 1 l water+0.01 mol ammonium formate, eluent B: 1 l acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm.

Method 27 (Preparative HPLC):

System: Gilson Abimed HPLC, binary pump system; column: Sunfire C-18 5 µm, 125×20 mm; eluent A: water+0.05% TFA, eluent B: acetonitrile+0.05% TFA; gradient: 15% B isocratic, 15% B→50% B, 50% B isocratic, 50% B→90% B; flow rate: 20 ml/min; UV detection: 210 nm.

Method 28 (Preparative HPLC):

System: Gilson Abimed HPLC, binary pump system; column: Kromasil C-18 10 µm, 125×30 mm; eluent A: water+0.05% TFA, eluent B: acetonitrile+0.05% TFA; gradient: 15% B isocratic, 15% B→50% B, 50% B isocratic, 50% B→90% B; flow rate: 20 ml/min; UV detection: 210 nm.

Method 29 (Preparative HPLC):

System: Gilson Abimed HPLC, binary pump system; column: Sunfire C-18 5 Ξm, 125×20 mm; eluent A: water+0.05% TFA, eluent B: acetonitrile+0.05% TFA; gradient: 5% B isocratic, 5% B→25% B, 25% B isocratic, 25% B→50% B; flow rate: 20 ml/min; UV detection: 210 nm.

Method 30 (Preparative HPLC):

System: Gilson Abimed HPLC, binary pump system; column: Kromasil C-18 10 µm, 125×30 mm; eluent A: water+0.05% TFA, eluent B: acetonitrile+0.05% TFA; gradient: 5% B isocratic, 5% B→25% B, 25% B isocratic, 25% B→50% B; flow rate: 20 ml/min; UV detection: 210 nm.

Method 31 (Preparative Chiral HPLC):

Column: Daicel Chiralpak AY-H 250×20 mm, 5 µm; eluent: 25% isohexane/75% isopropanol with 0.2% diethylamine; flow rate: 15 ml/min; temperature: 55° C.

Method 32 (Analytical Chiral HPLC):

Column: Daicel Chiralpak IF 250×4.6 mm, 5 µm; eluent: 50% isohexane/50% isopropanol with 0.2% diethylamine; flow rate: 1.0 ml/min; temperature: 40° C.

Method 33 (Preparative Chiral HPLC):

Column: Daicel Chiralcel OX-H 250×20 mm, 5 µm; eluent: 70% isohexane/30% ethanol with 0.2% diethylamine; flow rate: 15 ml/min; temperature: 50° C.

Method 34 (Analytical Chiral HPLC):

Column: Daicel Chiralcel OX-H 250×4.6 mm, 5 µm; eluent: 70% isohexane/30% ethanol with 0.2% diethylamine; flow rate: 1.0 ml/min; temperature: 50° C.

Further Details:

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "×HCl", "×CF₃COOH", "×Na⁺" should not be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

The percentages in the example and test descriptions which follow are, unless indicated otherwise, percentages by weight; parts are parts by weight. Solvent ratios, dilution ratios and concentration data for the liquid/liquid solutions are based in each case on volume.

Purity figures are generally based on corresponding peak integrations in the LC/MS chromatogram, but may additionally also have been determined with the aid of the $^1$H NMR spectrum. If no purity is stated, the purity is generally >95% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of $^1$H NMR signals that follow have in some cases been taken directly from the suggestions of the ACD SpecManager (ACD/Labs Release 12.00, Product version 12.5) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the centre of the signal in question. In the case of broad multiplets, an interval is given. Signals obscured by solvent or water were either tentatively assigned or have not been listed.

Melting points and melting-point ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Materials and Intermediates:

Intermediate 1A 4-(Benzyloxy)-1-methyl-2-nitrobenzene

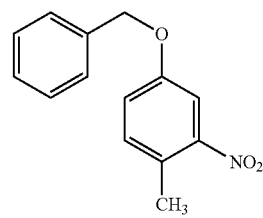

To a solution of 4-methyl-3-nitrophenol (5.00 g, 32.7 mmol) in acetone (100 ml) were added benzyl bromide (6.14 g, 35.9 mmol) and potassium carbonate (9.03 g, 65.3 mmol) and the mixture was stirred at 60° C. overnight. After cooling to RT, water was added and the mixture was extracted with ethyl acetate. The organic phase was washed with saturated aqueous sodium chloride solution, dried over sodium sulphate and concentrated under reduced pressure. 8.40 g (95% of theory) of the desired product were obtained with a purity of 90%, which were converted further without purification.

GC/MS (Method 4): $R_t$=7.16 min, m/z=243 $[M]^+$.

Intermediate 2A 5-(Benzyloxy)-2-methylaniline

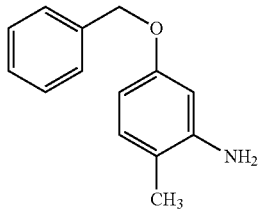 [SMILES: Cc1ccc(OCc2ccccc2)cc1N]

Zinc powder (6.72 g, 103 mmol) was initially charged in ethanol (300 ml), and 2 M hydrochloric acid (103 ml) was added. Directly thereafter, a solution of 4-(benzyloxy)-1-methyl-2-nitrobenzene (5.00 g, 20.6 mmol) from Intermediate 1A in ethanol (100 ml) was added dropwise. The mixture was left to stir at RT for another 1 h, then filtered with suction, and the filtrate was concentrated under reduced pressure. This residue was neutralized with saturated aqueous sodium hydrogencarbonate solution (about 200 ml) until a pH of 7 had been attained. The precipitate was filtered off with suction and washed with cyclohexane. The solid was then heated to boiling in methanol for 45 min, filtered off with suction while hot and washed thoroughly with methanol. The filtrate was concentrated under reduced pressure. After the residue had been dried, 3.66 g of the title compound (84% of theory) were obtained as a white solid.

LC/MS (Method 1, ESIpos): $R_t$=1.88 min, m/z=214 $[M+H]^+$.

$^1$H-NMR (400 MHz, DMSO-$d_6$): δ [ppm]=1.96 (s, 3H), 4.80 (br. s, 2H), 4.96 (s, 2H), 6.12 (dd, 1H), 6.27 (d, 1H), 6.78 (d, 1H), 7.27-7.43 (m, 5H).

Intermediate 3A

4-{[5-(Benzyloxy)-2-methylphenyl]amino}-2-chloropyridine-3-carboxylic acid

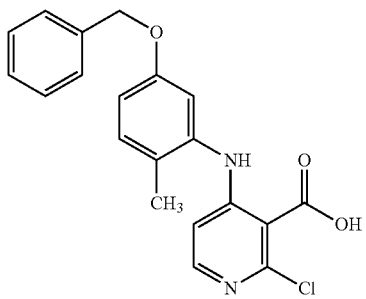 [SMILES: Cc1ccc(OCc2ccccc2)cc1Nc1ccnc(Cl)c1C(=O)O]

A solution of 5-(benzyloxy)-2-methylaniline (533 mg, 2.50 mmol) from Intermediate 2A in 8 ml of a 1:3 mixture of THF and hexane was initially charged at −78° C. Added dropwise at this temperature were 3.30 ml of a 1 M solution of LiHMDS in THF, and the mixture was left to stir at −78° C. for 1 h. Then a solution of 2,4-dichloropyridine-3-carboxylic acid (200 mg, 1.04 mmol) [E. Marzi, A. Bigi, M. Schlosser, Eur. J. Org. Chem. 2001, 7, 1371-1376] in THF (4 ml) was added dropwise. The reaction mixture then was allowed to warm to RT and stirring was continued overnight. Thereafter, 1 M hydrochloric acid and ethyl acetate were added. After phase separation, the aqueous phase was extracted twice with ethyl acetate, and the combined organic phases were washed with saturated aqueous sodium chloride solution, dried over sodium sulphate and concentrated under reduced pressure. The residue was stirred with dichloromethane, and the solid was filtered off with suction and washed with dichloromethane. This gave 289 mg (73% of theory) of the title compound as a white solid.

LC/MS (Method 1, ESIpos): $R_t$=2.04 min, m/z=369 $[M+H]^+$.

$^1$H-NMR (400 MHz, DMSO-$d_6$): δ [ppm]=2.05 (s, 3H), 5.09 (s, 2H), 6.28 (m, 1H), 6.85 (m, 1H), 6.89 (dd, 1H), 7.23 (d, 1H), 7.30-7.44 (m, 5H), 7.86 (dd, 1H), 8.46 (s, 1H), 13.3 (br. s, 1H).

Intermediate 4A

N-(2-Amino-5-cyanophenyl)-4-{[5-(benzyloxy)-2-methylphenyl]amino}-2-chloronicotinamide

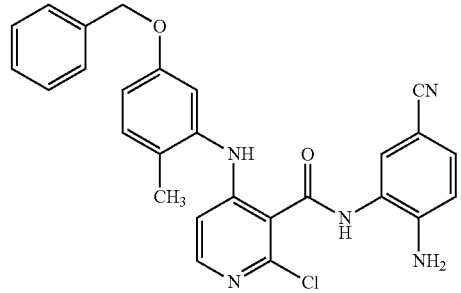 [SMILES: Cc1ccc(OCc2ccccc2)cc1Nc1ccnc(Cl)c1C(=O)Nc1cc(C#N)ccc1N]

4-{[5-(Benzyloxy)-2-methylphenyl]amino}-2-chloropyridine-3-carboxylic acid (200 mg, 0.542 mmol) from Intermediate 3A was dissolved in 2 ml of DMF. TBTU (192 mg, 0.596 mmol) and N,N-diisopropylethylamine (142 µl, 0.813 mmol) were added and the mixture was left to stir at RT for 30 min. Subsequently, 3,4-diaminobenzonitrile (108 mg, 0.813 mmol) was added and stirring of the mixture continued overnight. Thereafter, saturated aqueous ammonium chloride solution was added to the reaction mixture. It was extracted with ethyl acetate. The organic phase was washed with saturated aqueous sodium chloride solution and dried over sodium sulphate. The solvent was removed under reduced pressure and the residue was purified by means of column chromatography on silica gel (eluent: dichloromethane/7 M ammonia in methanol 30:1). This was followed by further purification, again by chromatography on silica gel (eluent: cyclohexane/ethyl acetate 5:1→2:1→1:1). In this way, 96 g (23% of theory) of the title compound were obtained in 64% purity.

LC/MS (Method 3, ESIpos): $R_t$=1.12 min, m/z=484 $[M+H]^+$.

Intermediate 5A

4-{[5-(Benzyloxy)-2-methylphenyl]amino}-5-oxo-6,11-dihydro-5H-pyrido[2,3-b][1,5]benzodiazepine-8-carbonitrile

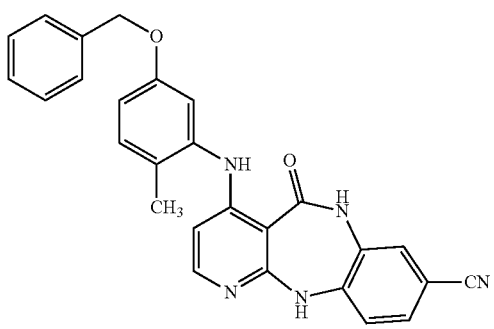 [SMILES: Cc1ccc(OCc2ccccc2)cc1Nc1ccnc2c1C(=O)Nc1cc(C#N)ccc1N2]

N-(2-Amino-5-cyanophenyl)-4-{[5-(benzyloxy)-2-methylphenyl]amino}-2-chloronicotinamide (96 mg, 0.127 mmol, 64% purity) from Intermediate 4A was dissolved in 4 ml of isopropanol. The mixture was heated to 180° C. in a microwave apparatus first for 20 min, then for a further 40 min. After cooling, the reaction mixture was concentrated under reduced pressure. In this way, 94 g (quant.) of the title compound were obtained in 64% purity.

LC/MS (Method 3, ESIpos): $R_t$=1.13 min, m/z=448 [M+H]$^+$.

Intermediate 6A

4-[(5-Hydroxy-2-methylphenyl)amino]-5-oxo-6,11-dihydro-5H-pyrido[2,3-b][1,5]benzodiazepine-8-carbaldehyde

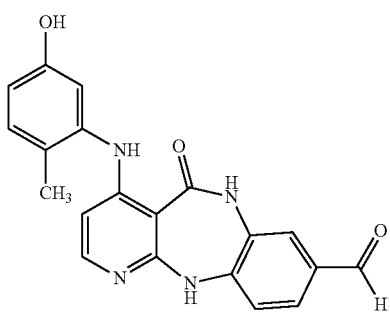 [SMILES: Cc1ccc(O)cc1Nc1ccnc2c1C(=O)Nc1cc(C=O)ccc1N2]

4-[(5-Hydroxy-2-methylphenyl)amino]-5-oxo-6,11-dihydro-5H-pyrido[2,3-b][1,5]benzodiazepine-8-carbonitrile (1.69 g, 4.16 mmol, 88% purity) from Example 1 was initially charged in 80 ml of THF and cooled to −70° C. with an acetone/dry ice bath. A 1 M solution of diisobutylaluminium hydride in dichloromethane (41.6 ml, 41.6 mmol) was slowly added dropwise, in the course of which the internal temperature was kept at −60° C. The mixture was then left to stir for a further 4 h, in the course of which the temperature was increased to 0° C. While cooling with an ice bath, 1 M hydrochloric acid was then slowly added dropwise until the dark red solution had lost its colour. The mixture was left to stir for a further hour, then diluted further with water and extracted with ethyl acetate. The organic phase was washed with saturated aqueous sodium chloride solution, dried over sodium sulphate and concentrated under reduced pressure. The crude product was combined with the crude product from a further batch (300 mg, 0.74 mmol of 4-[(5-hydroxy-2-methylphenyl)amino]-5-oxo-6,11-dihydro-5H-pyrido[2,3-b][1,5]benzodiazepine-8-carbonitrile in 88% purity) and they were purified together by chromatography on silica gel (eluent: tetrahydrofuran/petroleum ether 25:75→65:35). In this way, 685 g (34% of theory) of the title compound were obtained in 88% purity.

LC/MS (Method 5, ESIpos): $R_t$=0.68 min, m/z=361 [M+H]$^+$.

$^1$H-NMR (400 MHz, DMSO-d$_6$): δ [ppm]=2.07 (s, 3H), 6.31 (d, 1H), 6.56 (dd, 1H), 6.61 (d, 1H), 7.09 (d, 1H), 7.30 (d, 1H), 7.49 (d, 1H), 7.58 (dd, 1H), 7.78 (d, 1H), 8.80 (s, 1H), 9.36 (s, 1H), 9.81 (s, 1H), 9.95 (s, 1H), 10.27 (s, 1H).

Intermediate 7A 4-(Allyloxy)-2-chloronicotinic acid

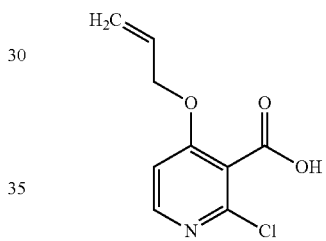

Under a nitrogen atmosphere, sodium hydride (60% in paraffin, 115 g, 2.87 mol) was initially charged in dioxane (448 ml) at RT. Allyl alcohol (1.99 kg, 2.33 litres, 34.3 mol) was slowly added dropwise at room temperature, and the mixture was stirred at RT for a further 30 min until a clear solution was obtained. 2,4-Dichloropyridine-3-carboxylic acid (269 g, 1.40 mol) [E. Marzi, A. Bigi, M. Schlosser, *Eur. J. Org. Chem.* 2001, 7, 1371-1376] was then added in four portions, and the reaction mixture was stirred at 100° C. overnight. The reaction solution was then concentrated and the residue was stirred with water (1.46 litres) and petroleum ether (1.61 litres). The organic phase was removed and discarded. The aqueous phase was admixed with ethyl acetate (1.61 litres) and acidified with semiconcentrated hydrochloric acid. The organic phase was removed, dried and concentrated. The crude product was combined with the crude product from a further batch (30 g, 156.3 mmol of 2,4-dichloropyridine-3-carboxylic acid) and they were purified together by chromatography on silica gel (eluent: dichloromethane/methanol 95:5→90:10). 131 g (40% of theory) of the title compound were obtained.

LC/MS (Method 5, ESIpos): $R_t$=0.73 min, m/z=214 [M+H]$^+$.

$^1$H-NMR (400 MHz, DMSO-d$_6$): δ [ppm]=4.75-4.80 (m, 2H), 5.25-5.45 (m, 2H), 5.93-6.06 (m, 1H), 7.23 (d, 1H), 9.32 (d, 1H).

Intermediate 8A

4-(Allyloxy)-N-(2-amino-5-cyanophenyl)-2-chloronicotinamide

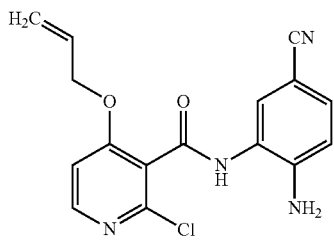 [SMILES: C=CCOc1ccnc(Cl)c1C(=O)Nc1cc(C#N)ccc1N]

4-(Allyloxy)-2-chloronicotinic acid from Intermediate 7A (100 g, 468 mmol) was initially charged in 1000 ml of dichloromethane. One drop of DMF was added thereto and the mixture was cooled to 0° C. Oxalyl chloride (119 g, 936 mmol) was added gradually. The mixture was allowed to warm to RT and left to stir until no further evolution of gas was observed. The reaction mixture was then concentrated under reduced pressure. Dichloromethane was again added, the mixture was again concentrated and this operation was repeated once again. The residue was then dissolved in 200 ml of DMF and added gradually to a solution, cooled to 0° C., of 3,4-diaminobenzonitrile (62.3 g, 468 mmol) in 800 ml of DMF. The mixture was left to stir at RT overnight. Thereafter, the reaction mixture was stirred into 4 litres of water and 1 litre of ethyl acetate, in the course of which a solid precipitated out. This precipitate was filtered off with suction, washed twice with ethyl acetate and dried under reduced pressure. 123 g (80% of theory) of the title compound were obtained.

LC/MS (Method 5, ESIpos): $R_t$=0.73 min, m/z=329 [M+H]$^+$.

$^1$H-NMR (400 MHz, DMSO-d$_6$): δ [ppm]=4.80 (d, 2H), 5.30 (dd, 1H), 5.42 (dd, 1H), 5.87 (s, 2H), 5.96-6.07 (m, 1H), 6.84 (d, 1H), 7.28 (d, 1H), 7.38 (dd, 1H), 7.74 (d, 1H), 8.37 (d, 1H), 10.0 (s, 1H).

Intermediate 9A

4-Hydroxy-5-oxo-6,11-dihydro-5H-pyrido[2,3-b][1,5]benzodiazepine-8-carbonitrile

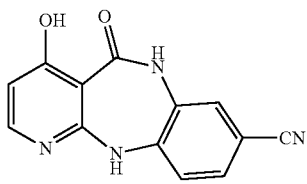 [SMILES: N#Cc1ccc2c(c1)NC(=O)c1c(O)ccnc1N2]

Method A:

4-(Allyloxy)-N-(2-amino-5-cyanophenyl)-2-chloronicotinamide (5.00 g, 15.2 mmol) from Intermediate 8A was initially charged in 1,2-dichlorobenzene (50 ml). The suspension was admixed with p-toluenesulphonic acid (3.04 g, 16.0 mmol) and heated to 145° C. (internal temperature) for 2 h. The mixture was then poured onto 50 ml of water and the pH was adjusted to 8-9 by adding saturated aqueous sodium hydrogencarbonate solution. The mixture was extracted three times with ethyl acetate and the combined organic phases were washed with saturated aqueous sodium chloride solution, dried over sodium sulphate and concentrated under reduced pressure. The residue was stirred with methanol, and the solid was filtered off with suction and washed twice with methanol. Drying under reduced pressure gave 2.83 g (74% of theory) of the title compound.

Method B:

N-(2-Amino-5-cyanophenyl)-2-chloro-4-methoxynicotinamide (1.10 g, 3.63 mmol) from Intermediate 12A was suspended in acetonitrile (15 ml), and 0.9 ml of 4 N hydrochloric acid was added. The mixture was heated to 160° C. in a microwave apparatus for 2.5 h. Thereafter, the mixture was concentrated under reduced pressure, and twice taken up in methanol and concentrated again each time. This residue was then stirred with methanol, and the solid was filtered off with suction and dried under reduced pressure. 0.57 g (62% of theory) of the title compound were obtained.

Method C:

N-(2-Amino-5-cyanophenyl)-2-chloro-4-methoxynicotinamide (6.0 g, 19.8 mmol) from Intermediate 12A was taken up in acetic acid (72 ml), benzenesulphonic acid (3.44 g, 21.7 mmol) was added and the mixture was heated to boiling for about 12 h. After cooling, the solvent was drawn off under reduced pressure and the residue was admixed with water (80 ml) and stirred for a few hours. This was followed by filtration. The filter residue was washed with water and dried under nitrogen at 35° C. The resultant solid (2.90 g) was then dissolved in DMF (120 ml), pyridinium hydrochloride (22.9 g, 142 mmol) was added and the mixture was heated to 85° C. for 12 h. Then the solvent was distilled off under reduced pressure and the residue was admixed with water. The precipitate formed was filtered off with suction and washed with water. The product was dried to constant weight at 35° C. under nitrogen. Yield: 2.71 g (54% of theory).

LC/MS (Method 5, ESIpos): $R_t$=0.67 min, m/z=253 [M+H]$^+$.

$^1$H-NMR (400 MHz, DMSO-d$_6$): δ [ppm]=6.43 (d, 1H), 7.19 (d, 1H), 7.28 (d, 1H), 7.42 (dd, 1H), 7.97 (d, 1H), 9.23 (s, 1H), 10.42 (s, 1H), 13.57 (s, 1H).

Intermediate 10A

4-Chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile

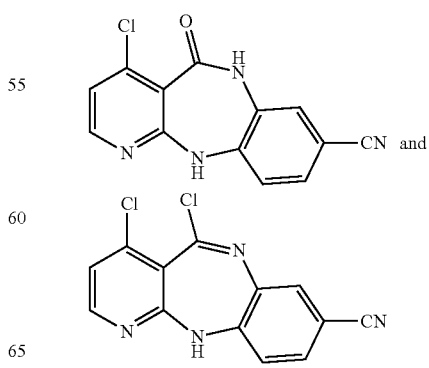

To an initial charge of 150 ml of sulpholane were successively added dropwise phosphoryl chloride (13.0 ml, 139 mmol) and triethylamine (19.4 ml, 139 mmol), in the course of which the temperature was kept at RT. Subsequently, the mixture was stirred at RT for a further 30 min. Then 4-hydroxy-5-oxo-6,11-dihydro-5H-pyrido[2,3-b][1,5]benzodiazepine-8-carbonitrile (14.1 g, 55.8 mmol) from Intermediate 9A was added and the mixture was heated to 70° C. for 5 h. Thereafter, the mixture was poured onto 1 litre of aqueous sodium hydrogencarbonate solution and stirred for 10 min. The precipitate was filtered off with suction, washed twice with water and dried under reduced pressure. 12.8 g of a 1:2 mixture of mono- and dichlorinated compound were obtained, which was used without further purification in subsequent reactions.

LC/MS (Method 5, ESIpos): $R_t$=0.75 min, m/z=271 [M+H]$^+$ und $R_t$=1.03 min, m/z=289 [M+H]$^+$.

$^1$H-NMR (400 MHz, DMSO-d$_6$): δ [ppm]=7.19 (d, 1H), 7.32 (d, 1H), 7.40 (d, 1H), 7.51 (dd, 1H), 8.20 (d, 1H), 9.27 (s, 1H), 10.51 (s, 1H) and δ [ppm]=7.20 (d, 1H), 7.29 (d, 1H), 7.63 (dd, 1H), 7.67 (d, 1H), 8.25 (d, 1H), 9.12 (s, 1H).

Intermediate 11A

4-[(2-Fluoro-5-hydroxy-4-methylphenyl)amino]-5-oxo-6,11-dihydro-5H-pyrido[2,3-b][1,5]benzodiazepine-8-carbaldehyde

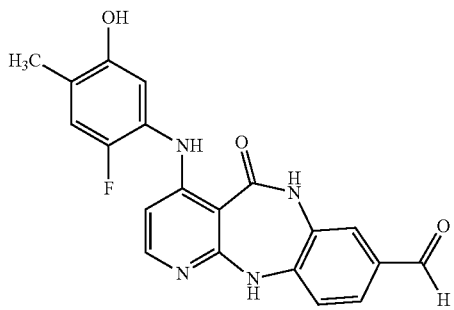 [SMILES: Cc1cc(F)c(Nc2ccnc3c2C(=O)Nc2cc(C=O)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbonitrile (5.87 g, 12.5 mmol, 80% purity) from Example 27 was initially charged in 240 ml of THF and cooled to −70° C. with acetone/dry ice bath. A 1 M solution of diisobutylaluminium hydride in dichloromethane (125 ml, 125 mmol) was slowly added dropwise, in the course of which the internal temperature was kept at −60° C. The mixture was then left to stir for a further 4 h, in the course of which the temperature was increased to 0° C. While cooling with an ice bath, 1 M hydrochloric acid was then slowly added dropwise until the dark red solution had lost its colour. The mixture was left to stir for a further hour, then diluted further with water and extracted with ethyl acetate. The organic phase was washed with saturated aqueous sodium chloride solution, dried over sodium sulphate and concentrated under reduced pressure. The residue was stirred with acetonitrile and filtered off with suction. Drying under reduced pressure gave 3.61 g (66% of theory) of the title compound in 86% purity.

LC/MS (Method 5, ESIpos): $R_t$=0.78 min, m/z=379 [M+H]$^+$.

$^1$H-NMR (400 MHz, DMSO-d$_6$): δ [ppm]=2.11 (s, 3H), 6.39 (dd, 1H), 6.72 (d, 1H), 7.05 (d, 1H), 7.29 (d, 1H), 7.48 (d, 1H), 7.58 (dd, 1H), 7.82 (d, 1H), 8.83 (s, 1H), 9.46 (s, 1H), 9.81 (s, 1H), 9.93 (s, 1H), 10.30 (s, 1H).

Intermediate 12A

N-(2-Amino-5-cyanophenyl)-2-chloro-4-methoxynicotinamide

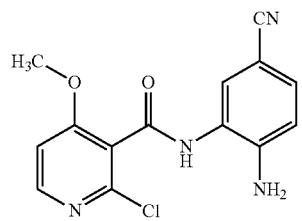 [SMILES: COc1ccnc(Cl)c1C(=O)Nc1cc(C#N)ccc1N]

Method A:

2-Chloro-4-methoxynicotinic acid (1.00 g, 5.33 mmol) [R. J. Anderson, J. B. Hill, J. C. Morris, *J. Org. Chem.* 2005, 70, 6204-6212] was suspended in 12 ml of dichloromethane, and one drop of DMF was added. The mixture was cooled to 0° C. and then oxalyl chloride (0.93 ml, 10.7 mmol) was added. The ice bath was removed again and stirring of the mixture continued until the evolution of gas had ended. Thereafter, the volatile constituents were removed under reduced pressure. Dichloromethane was added twice and the mixture was concentrated again each time. The residue was dissolved in 5 ml of DMF and added dropwise to a solution, cooled to 0° C., of 3,4-diaminobenzonitrile (710 mg, 5.33 mmol) and N,N-diisopropylethylamine (1.86 g, 10.7 mmol) in 10 ml of DMF. The reaction mixture was stirred at RT for 3 h, then added to 100 ml of water, and 10 ml of tert-butyl methyl ether were added. The mixture was stirred for a further 20 min and the solid was then filtered off under high suction and dried under reduced pressure. This gave 1.15 g (71% of theory) of the title compound.

Method B:

Solution A:

2-Chloro-4-methoxynicotinic acid (5.0 g, 26.7 mmol) was suspended in acetonitrile (50 ml), 1 drop of DMF was added and the mixture was cooled to 0° C. Thionyl chloride (3.90 ml, 53.3 mmol) was slowly added dropwise, then the mixture was stirred at 80° C. for a further 2 h. The solvent was then distilled off under reduced pressure and the residue, without further workup, was dissolved in 50 ml of DMF.

Solution B:

3,4-Diaminobenzonitrile (3.55 g, 26.7 mmol) was dissolved in DMF (50 ml), and N,N-diisopropylethylamine (9.3 ml, 53.3 mmol) was added.

Preparation of the Title Compound:

Solution B was cooled to 0° C., then solution A was slowly added dropwise while stirring. Thereafter, the mixture was stirred at room temperature for 2 h. For workup, the mixture was poured onto 500 ml of water, about 50 ml of tert-butyl methyl ether were added and the mixture was stirred. The solids were filtered off with suction and dried. Yield: 6.0 g (74% of theory).

LC/MS (Method 5, ESIpos): $R_t$=0.56 min, m/z=303 [M+H]$^+$.

$^1$H-NMR (400 MHz, DMSO-d$_6$): δ [ppm]=3.94 (s, 3H), 5.88 (br. s, 2H), 6.84 (d, 1H), 7.30 (d, 1H), 7.37 (dd, 1H), 7.80 (d, 1H), 8.39 (d, 1H), 9.94 (br. s, 1H).

Intermediate 13A

4-[(4-Chloro-2-fluoro-5-hydroxyphenyl)amino]-5-oxo-6,11-dihydro-5H-pyrido[2,3-b][1,5]benzodiazepine-8-carbaldehyde

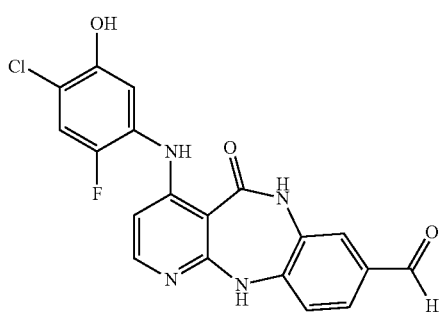 [SMILES: O=Cc1ccc2c(c1)NC(=O)c1c(Nc3cc(O)c(Cl)cc3F)ccnc1N2]

To a solution of 4-[(4-chloro-2-fluoro-5-hydroxyphenyl)amino]-5-oxo-6,11-dihydro-5H-pyrido[2,3-b][1,5]benzodiazepine-8-carbonitrile (439 mg, 91% pure, 1.01 mmol) from Example 37 in THF (20.0 ml) was slowly added dropwise, at −78° C., DIBAL-H (10.1 ml, 10.1 mmol, 1 M solution in dichloromethane). After the addition had ended, the mixture was stirred at −78° C. for another 30 min, then the cooling bath was removed and the reaction mixture was allowed to warm to RT. After 4 h, the mixture was cautiously added dropwise to water while stirring. Subsequently, ethyl acetate was added and the insoluble constituents were filtered off. The phases were separated and the aqueous phase was extracted twice more with ethyl acetate. The combined organic phases were washed with saturated aqueous sodium chloride solution and dried over sodium sulphate. Removal of the solvent gave the title compound (170 mg, 88% purity, 37% of theory) as a pale brown solid which was converted further in this form.

LC/MS (Method 5, ESIpos): $R_t$=0.82 min, m/z=399 [M+H]$^+$.

Intermediate 14A

5-Amino-2-propylphenol

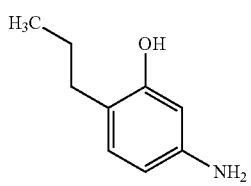

N-(3-Hydroxy-4-propylphenyl)acetamide (110 mg, 0.57 mmol) was heated under reflux in conc. hydrochloric acid (37%, 224 mg) and THF (2 ml) overnight. The reaction mixture was then concentrated. 109 g of the title compound were obtained, which were converted further without further purification.

LC/MS (Method 6, ESIpos): $R_t$=1.88 min, m/z=152 [M+H]$^+$.

$^1$H-NMR (400 MHz, DMSO-d$_6$): δ [ppm]=0.88 (t, 3H), 1.45-1.60 (m, 2H), 2.51-2.60 (m, 2H), 6.65-6.75 (m, 1H), 6.82-6.90 (m, 1H), 7.06-7.16 (m, 1H), 9.91 (s, 1H).

Intermediate 15A

5-Amino-2-bromophenol

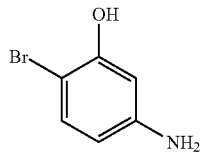

2-Bromo-5-nitrophenol (450 mg, 2.06 mmol) was initially charged in water (13.5 ml) and ethanol (13.5 ml). Ammonium chloride (596 mg, 11.15 mmol) and iron filings (691 mg, 12.39 mmol) were added and the mixture was stirred at 80° C. for 5 h. The reaction mixture was then cooled to RT and filtered through kieselguhr, and the filtrate was concentrated. Subsequent workup by means of column chromatography on silica gel (eluent: cyclohexane/ethyl acetate 1:1) gave 359 mg (93% of theory) of the title compound.

LC/MS (Method 3, ESIpos): $R_t$=0.41 min, m/z=188 [M+H]$^+$.

Intermediate 16A

5-Amino-2,3-difluorophenol

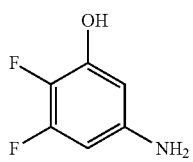

2,3-Difluoro-5-nitrophenol (300 mg, 1.71 mmol) was initially charged in water (11 ml) and ethanol (11 ml). Ammonium chloride (495 mg, 9.25 mmol) and iron filings (574 mg, 10.28 mmol) were added and the mixture was stirred at 80° C. for 4 h. The reaction mixture was then cooled to RT and filtered through kieselguhr, the filter residue was washed with ethyl acetate and the filtrate was concentrated. 265 g (96% of theory) of the title compound were obtained, which were converted further without purification.

LC/MS (Method 7, ESIpos): $R_t$=0.41 min, m/z=146 [M+H]$^+$.

$^1$H-NMR (400 MHz, DMSO-d$_6$): δ [ppm]=5.07 (s, 2H), 5.86-5.93 (m, 1H), 5.93-5.98 (m, 1H), 9.79 (s, 1H).

Intermediate 17A

3-Amino-4-fluorophenol

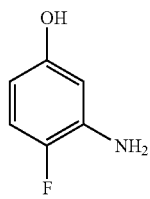

4-Fluoro-3-nitrophenol (300 mg, 1.91 mmol) was initially charged in water (12.5 ml) and ethanol (12.5 ml). Ammonium chloride (552 mg, 10.31 mmol) and iron filings (640 mg, 11.46 mmol) were added and the mixture was stirred at 80° C. for 4 h. The reaction mixture was then cooled to RT and filtered through kieselguhr, and the filtrate was extracted with ethyl acetate. The organic phase was dried, filtered and concentrated. 126 mg (39% of theory) of the title compound were obtained.

LC/MS (Method 6, ESIpos): $R_t$=0.99 min, m/z=128 [M+H]$^+$.

Intermediate 18A

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbonitrile

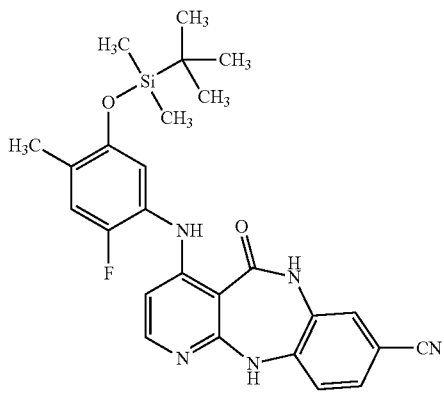 [SMILES: Cc1cc(F)c(Nc2ccnc3c2C(=O)Nc2cc(C#N)ccc2N3)cc1O[Si](C)(C)C(C)(C)C]

4-[(2-Fluoro-5-hydroxy-4-methylphenyl)amino]-5-oxo-6,11-dihydro-5H-pyrido[2,3-b][1,5]benzodiazepine-8-carbonitrile (8.50 g, 22.6 mmol, 81% purity) from Example 27 was initially charged in DMF (170 ml), and 1H-imidazole (9.25 g, 136 mmol), tert-butyl(chloro)dimethylsilane (18.4 g, 122 mmol) and DMAP (691 mg, 5.66 mmol) were added. The resulting mixture was stirred at room temperature overnight. Thereafter, water (800 ml) was added. The suspension was stirred for a further 30 min, then filtered with suction, and the resulting solid was dried. The aqueous phase was extracted with 4 portions each of 75 ml of MTBE, and the organic phase was washed with 50 ml of saturated aqueous sodium chloride solution, dried over sodium sulphate and concentrated. Both fractions of the crude product thus obtained were chromatographed using silica gel with cyclohexane/ethyl acetate as eluent. Yield: 4.60 g (96% purity, 40% of theory).

LC/MS (Method 25): $R_t$=2.66 min; MS (ESIpos): m/z=490 [M+H]$^+$ $^1$H-NMR (400 MHz, DMSO-d$_6$): δ [ppm]=−0.18 (s, 3H), 0.00 (s, 3H), 0.78 (s, 9H), 1.97 (s, 3H), 6.15 (d, 1H), 6.55 (d, 1H), 6.98 (d, 1H), 7.09 (d, 1H), 7.15 (s, 1H), 7.28 (d, 1H), 7.64 (d, 2H), 8.65 (s, 1H), 9.67 (s, 1H), 10.25 (s, 1H).

Intermediate 19A

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde

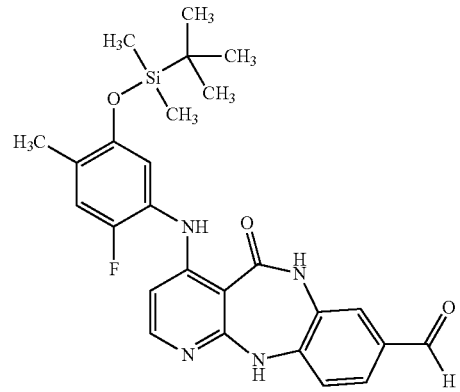 [SMILES: Cc1cc(F)c(Nc2ccnc3c2C(=O)Nc2cc(C=O)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbonitrile (10.20 g, 20.83 mmol) from Intermediate 18A was initially charged in THF (600 ml) and cooled to −70° C. in an acetone/dry ice bath. Diisobutylaluminium hydride (1 M in THF, 94 ml, 94 mmol) was slowly added dropwise, in the course of which the temperature was kept below −60° C. The mixture was stirred first at −78° C. for 30 min and then at room temperature for 5 h. Thereafter, the reaction mixture was stirred into 750 ml of 5% citric acid solution, and 375 ml of ethyl acetate and 245 ml of saturated aqueous sodium chloride solution were added. Then the organic solvents were distilled off under reduced pressure, in the course of which the title compound precipitated out. The solids were filtered off with suction and dried. Yield: 8.70 g (92% purity, 80% of theory).

LC/MS (Method 25): $R_t$=2.59 min; MS (ESIpos): m/z=493 [M+H]$^+$ $^1$H-NMR (400 MHz, DMSO-d$_6$): δ [ppm]=0.00 (s, 3H), 0.19 (s, 3H), 0.96 (s, 9H), 2.15 (s, 3H), 6.37 (d, 1H), 6.72 (d, 1H), 7.17 (d, 1H), 7.30 (d, 1H), 7.49 (s, 1H), 7.84 (d, 1H), 8.85 (s, 1H), 9.82 (s, 1H), 9.90 (s, 1H), 10.30 (s, 1H).

Intermediate 20A

8-{[(2-{[tert-Butyl(dimethyl)silyl]oxy}ethyl)(ethyl)amino]methyl}-4-[(5-{[tert-butyl(dimethyl)silyl]oxy}-2-fluoro-4-methylphenyl)amino]-6,11-dihydro-5H-pyrido[2,3-b][1,5]benzodiazepin-5-one

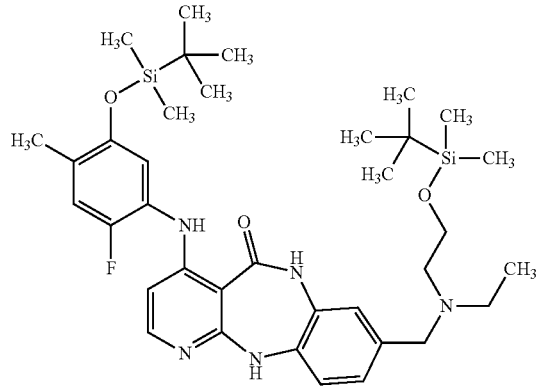 [SMILES: CCN(CCO[Si](C)(C)C(C)(C)C)Cc1ccc2c(c1)NC(=O)c1c(Nc3cc(O[Si](C)(C)C(C)(C)C)c(C)cc3F)ccnc1N2]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (8.45 g, 17.2 mmol; Intermediate 19A) was dissolved in THF (210 ml). Trimethyl orthoformate (38 ml, 340 mmol), 2-{[tert-butyl(dimethyl)silyl]oxy}-N-ethylethanamine (20.9 g, 103 mmol) and finally sodium triacetoxyborohydride (21.8 g, 103 mmol) were added. The mixture was stirred at room temperature for 1 h. The reaction mixture was then added to 1.5 litres of conc. aqueous sodium hydrogencarbonate solution and extracted four times with about 200 ml each time of ethyl acetate. The organic phases were combined, dried over sodium sulphate, filtered and concentrated. The residue was chromatographed using silica gel with dichloromethane/methanol 20:1 as eluent. The product-containing fractions were combined and concentrated. The residue was washed with 50 ml of n-hexane and dried. Yield: 10.2 g (87% of theory).

LC/MS (Method 25): $R_t$=2.10 min; MS (ESIneg): m/z=678 [M−H]⁻

¹H-NMR (400 MHz, DMSO-d₆): δ [ppm]=−0.40 (s, 6H), 0.17 (s, 6H), 0.78 (s, 9H), 0.96 (s, 9H), 0.97 (t, 3H), 2.13 (s, 3H), 3.29 (d, 2H), 3.47 (m, 2H), 3.55 (m, 2H), 6.36 (d, 1H), 6.70 (d, 1H), 6.95 (m, 2H), 7.04 (d, 1H), 7.15 (d, 1H), 7.79 (d, 1H), 8.11 (br. s, 1H), 9.86 (br. s, 1H), 10.89 (br. s, 1H).

Intermediate 21A tert-Butyl 4-({4-[(5-{[tert-butyl(dimethyl) silyl]oxy}-2-fluoro-4-methylphenyl)amino]-5-oxo-6,11-dihydro-5H-pyrido[2,3-b][1,5]benzodiazepin-8-yl}methyl)piperazine-1-carboxylate

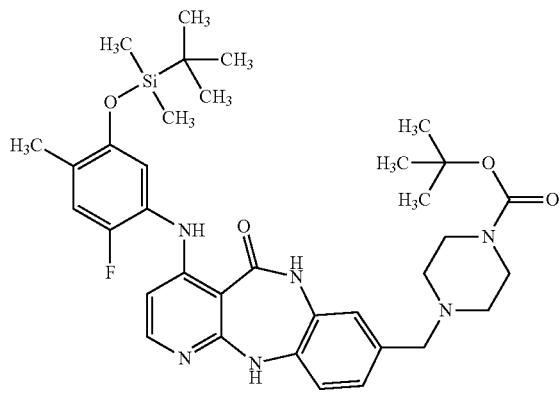 [SMILES: Cc1cc(F)c(Nc2ccnc3c2C(=O)Nc2cc(CN4CCN(C(=O)OC(C)(C)C)CC4)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (35 mg, 0.071 mmol; Intermediate 19A) was dissolved in THF (3.5 ml), and tert-butyl piperazine-1-carboxylate (52.9 mg, 0.284 mmol) and acetic acid (0.033 ml, 0.57 mmol) were added. The mixture was stirred at room temperature for 45 min. Subsequently, sodium cyanoborohydride (22.32 mg, 0.36 mmol) was added in three portions at room temperature over 4.5 h. Monitoring by HPLC-LC/MS indicated conversion. Saturated aqueous sodium bicarbonate solution was then added, and the reaction mixture was extracted three times with ethyl acetate. The organic phases were combined, dried over sodium sulphate, filtered and concentrated. The residue (46 mg) was used without further purification in subsequent reactions.

LC/MS (Method 8): $R_t$=3.61 min; MS (ESIneg): m/z=661 [M−H]⁻.

Intermediate 22A

4-[(5-{[tert-Butyl(dimethyl)silyl]oxy}-2-fluoro-4-methylphenyl)amino]-8-{[(2-hydroxyethyl)(methyl)amino]methyl}-6,11-dihydro-5H-pyrido[2,3-b][1,5]benzodiazepin-5-one

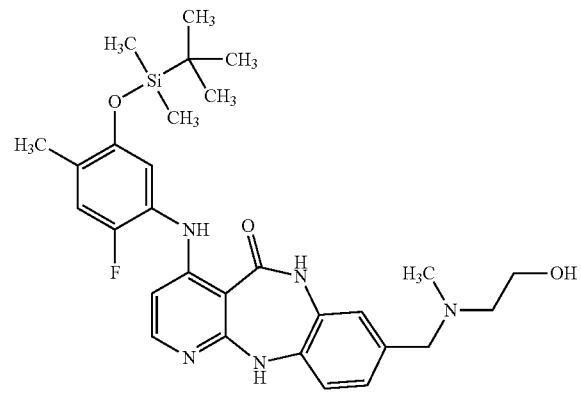 [SMILES: Cc1cc(F)c(Nc2ccnc3c2C(=O)Nc2cc(CN(C)CCO)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (30 mg, 0.061 mmol; Intermediate 19A) was dissolved in THF (3 ml), and N-methyl-2-[(trimethylsilyl)oxy]ethanamine (35.88 mg, 0.244 mmol) and acetic acid (0.028 ml, 0.487 mmol) were added. The mixture was stirred at room temperature for 2 h. Subsequently, sodium cyanoborohydride (19.14 mg, 0.304 mmol) was added in portions and stirring of the mixture continued at room temperature overnight. Saturated aqueous sodium bicarbonate solution was then added, and the reaction mixture was extracted three times with ethyl acetate. The organic phases were combined, dried over sodium sulphate, filtered and concentrated. The residue (50 mg) was used without further purification in subsequent reactions.

LC/MS (Method 7): $R_t$=1.19 min; MS (ESIneg): m/z=550 [M−H]⁻.

Intermediate 23A

4-[(5-{[tert-Butyl(dimethyl)silyl]oxy}-2-fluoro-4-methylphenyl)amino]-8-({[2-(dimethylamino)ethyl](ethyl)amino}methyl)-6,11-dihydro-5H-pyrido[2,3-b][1,5]benzodiazepin-5-one trifluoroacetic acid salt

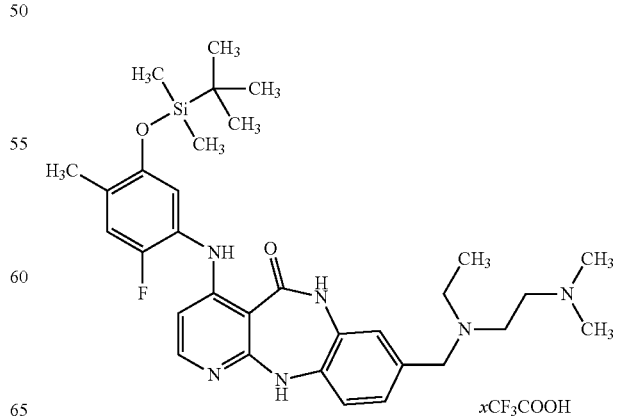

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and N,N-dimethyl-N'-ethyl-1,2-ethylenediamine (0.064 ml, 0.406 mmol) and acetic acid (0.046 ml, 0.812 mmol) were added. The mixture was stirred at room temperature for 45 min. Subsequently, sodium cyanoborohydride (9.56 mg, 0.152 mmol) was added in portions and stirring of the mixture continued at room temperature overnight. Monitoring by HPLC-LC/MS indicated incomplete conversion. Therefore, sodium cyanoborohydride (9.56 mg, 0.152 mmol) was added once again and the mixture was stirred at room temperature over a further 6 h. The reaction mixture was then concentrated, and the residue was dissolved in a mixture of acetonitrile and water with addition of one drop of TFA and purified by preparative HPLC (Method 27). The product-containing fractions were combined and concentrated. The residue (57 mg) was used as such in subsequent reactions.

Intermediate 24A tert-Butyl-{2-[({4-[(5-{[tert-butyl(dimethyl) silyl]oxy}-2-fluoro-4-methylphenyl)amino]-5-oxo-6,11-dihydro-5H-pyrido[2,3-b][1,5]benzodiazepin-8-yl}methyl)(ethyl)amino]ethyl}carbamate trifluoroacetic acid salt

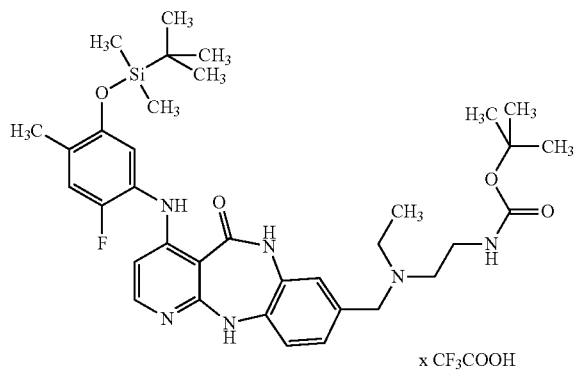 [SMILES: CCN(CCNC(=O)OC(C)(C)C)Cc1ccc2c(c1)NC(=O)c1c(Nc3cc(O[Si](C)(C)C(C)(C)C)c(C)cc3F)ccnc1N2]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and N-Boc-N'-ethyl-1,2-ethylenediamine hydrochloride (91.2 mg, 0.406 mmol), acetic acid (0.07 ml, 1.218 mmol) and N,N-diisopropylethylamine (45.9 mg, 0.355 mmol) were added. The mixture was stirred at room temperature for 45 min. Subsequently, sodium cyanoborohydride (9.56 mg, 0.152 mmol) was added in portions and stirring of the reaction mixture continued at room temperature overnight. Monitoring by HPLC-LC/MS indicated incomplete conversion. Therefore, sodium cyanoborohydride (9.56 mg, 0.152 mmol) was added once again and the mixture was stirred at room temperature over a further 6 h. The reaction mixture was then concentrated, and the residue was dissolved in a mixture of acetonitrile and water with addition of one drop of TFA and purified by preparative HPLC (Method 27). The product-containing fractions were combined and concentrated. The residue (59 mg) was used as such in subsequent reactions.

Intermediate 25A

8-{[(2-Aminoethyl)(ethyl)amino]methyl}-4-[(5-{[tert-butyl(dimethyl)silyl]oxy}-2-fluoro-4-methylphenyl)amino]-6,11-dihydro-5H-pyrido[2,3-b][1,5]benzodiazepin-5-one

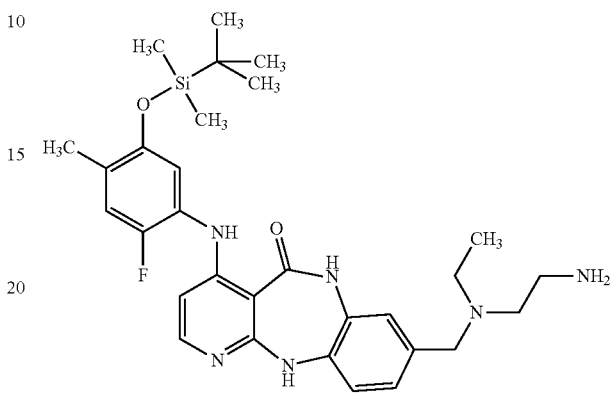

tert-Butyl-{2-[({4-[(5-{[tert-butyl(dimethyl) silyl]oxy}-2-fluoro-4-methylphenyl)amino]-5-oxo-6,11-dihydro-5H-pyrido[2,3-b][1,5]benzodiazepin-8-yl}methyl)(ethyl)amino]ethyl}carbamate (trifluoroacetic acid salt, Intermediate 24A; 59 mg, 0.076 mmol) was taken up in dichloromethane (10.8 ml), and trifluoroacetic acid (5.4 ml) was added. The mixture was stirred at room temperature for 30 min. Saturated aqueous sodium bicarbonate solution was then added, and the reaction mixture was extracted three times with ethyl acetate. The organic phases were combined, dried over sodium sulphate, filtered and concentrated. The residue (42 mg) was used without further purification in subsequent reactions.

Intermediate 26A

4-[(5-{[tert-Butyl(dimethyl)silyl]oxy}-2-fluoro-4-methylphenyl)amino]-8-({[(2R)-2-hydroxypropyl](methyl)amino}methyl)-6,11-dihydro-5H-pyrido[2,3-b][1,5]benzodiazepin-5-one

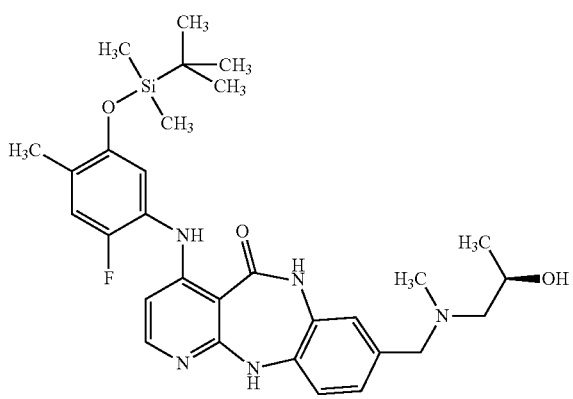 [SMILES: Cc1cc(F)c(Nc2ccnc3c2C(=O)Nc2cc(CN(C)C[C@@H](C)O)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and (2R)-1-(methylamino)propan-2-ol hydrochloride (51 mg, 0.406 mmol), acetic acid (0.046 ml, 0.812 mmol) and N,N-diisopropylethylamine (0.071 ml, 0.406 mmol) were added. The mixture was stirred at room temperature for 45 min. Subsequently, sodium cyanoborohydride (9.56 mg, 0.152 mmol) was added in portions and stirring of the mixture continued at room temperature overnight. Saturated aqueous sodium bicarbonate solution was then added, and the reaction mixture was extracted three times with ethyl acetate. The organic phases were combined, dried over sodium sulphate, filtered and concentrated. The residue (73 mg) was used without further purification in subsequent reactions.

LC/MS (Method 7): $R_t$=1.22 min; MS (ESIneg): m/z=564 [M−H]⁻.

Intermediate 27A

4-[(5-{[tert-Butyl(dimethyl)silyl]oxy}-2-fluoro-4-methylphenyl)amino]-8-({[(2S)-2-hydroxypropyl](methyl)amino}methyl)-6,11-dihydro-5H-pyrido[2,3-b][1,5]benzodiazepin-5-one

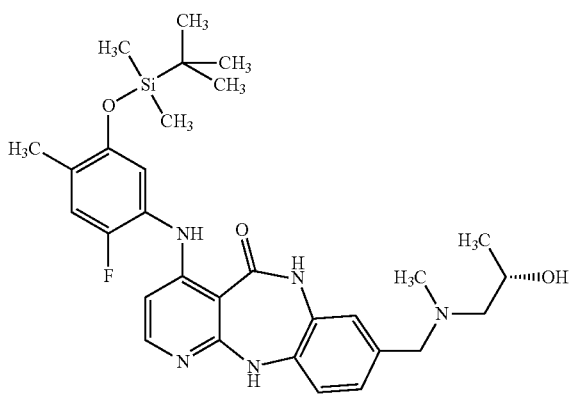 [SMILES: Cc1cc(F)c(Nc2ccnc3c2C(=O)Nc2cc(CN(C)C[C@H](C)O)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and (2S)-1-(methylamino)propan-2-ol (36.19 mg, 0.406 mmol) and acetic acid (0.046 ml, 0.812 mmol) were added. The mixture was stirred at room temperature for 45 min. Subsequently, sodium cyanoborohydride (9.56 mg, 0.152 mmol) was added in portions and stirring of the mixture continued at room temperature overnight. Saturated aqueous sodium bicarbonate solution was then added, and the reaction mixture was extracted three times with ethyl acetate. The organic phases were combined, dried over sodium sulphate, filtered and concentrated. The residue (74.8 mg) was used without further purification in subsequent reactions.

LC/MS (Method 7): $R_t$=1.22 min; MS (ESIneg): m/z=564 [M−H]⁻.

Intermediate 28A

4-[(5-{[tert-Butyl(dimethyl)silyl]oxy}-2-fluoro-4-methylphenyl)amino]-8-({[2-(dimethylamino)ethyl](methyl)amino}methyl)-6,11-dihydro-5H-pyrido[2,3-b][1,5]benzodiazepin-5-one trifluoroacetic acid salt

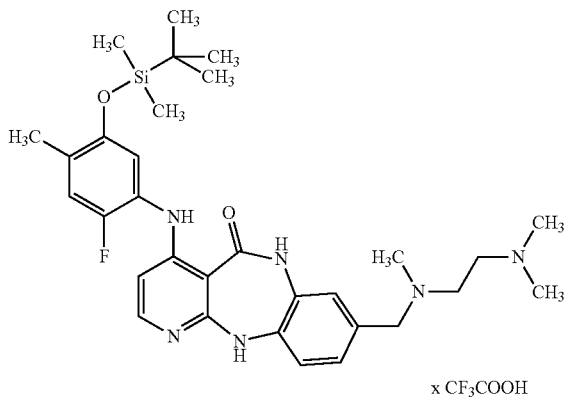

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (40 mg, 0.081 mmol; Intermediate 19A) was dissolved in THF (4 ml), and N,N,N'-trimethylethane-1,2-diamine (33.19 mg, 0.325 mmol) and acetic acid (0.037 ml, 0.65 mmol) were added. The mixture was stirred at room temperature for 45 min. Subsequently, sodium cyanoborohydride (7.65 mg, 0.122 mmol) was added in portions and stirring of the mixture continued at room temperature overnight. The reaction mixture was then concentrated, and the residue was dissolved in a mixture of acetonitrile and water with addition of one drop of TFA and purified by preparative HPLC (Method 27). The product-containing fractions were combined and concentrated. The residue (54 mg) was used as such in subsequent reactions.

LC/MS (Method 5): $R_t$=0.92 min; MS (ESIpos): m/z=579 [M+H]⁺.

Intermediate 29A

4-[(5-{[tert-Butyl(dimethyl)silyl]oxy}-2-fluoro-4-methylphenyl)amino]-8-{[ethyl(2-hydroxypropyl)amino]methyl}-6,11-dihydro-5H-pyrido[2,3-b][1,5]benzodiazepin-5-one trifluoroacetic acid salt

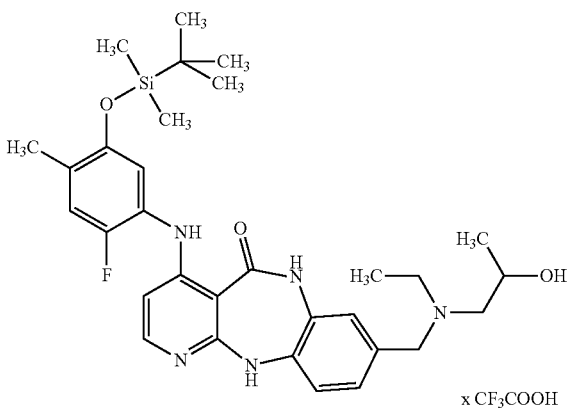 [SMILES: CCN(Cc1ccc2c(c1)NC(=O)c1c(Nc3cc(O[Si](C)(C)C(C)(C)C)c(C)cc3F)ccnc1N2)CC(C)O]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (40 mg, 0.081 mmol; Intermediate 19A) was dissolved in THF (4 ml), and 1-(ethylamino)propan-2-ol (33.51 mg, 0.325 mmol) and acetic acid (0.037 ml, 0.65 mmol) were added. The mixture was stirred at room temperature for 45 min. Subsequently, sodium cyanoborohydride (7.65 mg, 0.122 mmol) was added in portions and stirring of the mixture continued at room temperature overnight. The reaction mixture was then concentrated, and the residue was dissolved in a mixture of acetonitrile and water with addition of one drop of TFA and purified by preparative HPLC (Method 27). The product-containing fractions were combined and concentrated. The residue (40 mg) was used as such in subsequent reactions.

LC/MS (Method 5): $R_t$=0.97 min; MS (ESIpos): m/z=580 [M+H]$^+$.

Intermediate 30A

4-[(5-{[tert-Butyl(dimethyl)silyl]oxy}-2-fluoro-4-methylphenyl)amino]-8-{[(3S)-3-hydroxypyrrolidin-1-yl]methyl}-6,11-dihydro-5H-pyrido[2,3-b][1,5]benzodiazepin-5-one trifluoroacetic acid salt

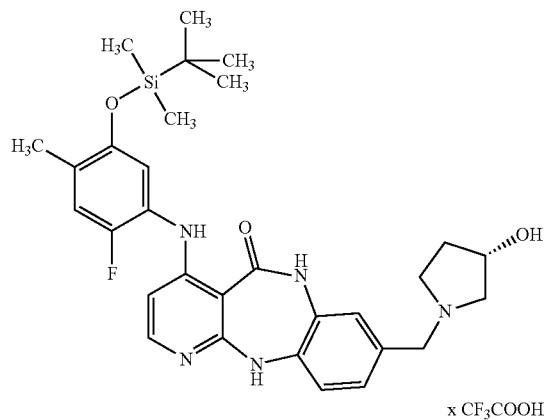 [SMILES: Cc1cc(F)c(Nc2ccnc3c2C(=O)Nc2cc(CN4CC[C@H](O)C4)ccc2N3)cc1O[Si](C)(C)C(C)(C)C]

x CF$_3$COOH

In analogy to Intermediate 29A, 4-[(5-{[tert-butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (40 mg, 0.081 mmol; Intermediate 19A) was reacted with (3S)-pyrrolidin-3-ol (28.30 mg, 0.325 mmol). This gave 50 mg of the title compound.

LC/MS (Method 5): $R_t$=0.93 min; MS (ESIpos): m/z=564 [M+H]$^+$.

Intermediate 31A

4-[(5-{[tert-Butyl(dimethyl)silyl]oxy}-2-fluoro-4-methylphenyl)amino]-8-{[(3R)-3-hydroxypyrrolidin-1-yl]methyl}-6,11-dihydro-5H-pyrido[2,3-b][1,5]benzodiazepin-5-one trifluoroacetic acid salt

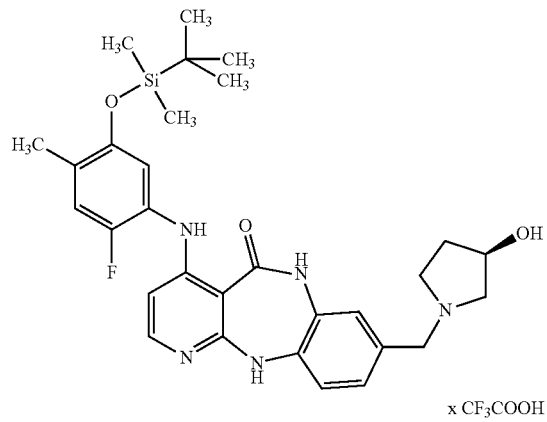 [SMILES: Cc1cc(F)c(Nc2ccnc3c2C(=O)Nc2cc(CN4CC[C@@H](O)C4)ccc2N3)cc1O[Si](C)(C)C(C)(C)C]

x CF$_3$COOH

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (40 mg, 0.081 mmol; Intermediate 19A) was dissolved in THF (4 ml), and (3R)-pyrrolidin-3-ol hydrochloride (40.14 mg, 0.325 mmol), acetic acid (0.056 ml, 0.974 mmol) and N,N-diisopropylethylamine (0.057 ml, 0.325 mmol) were added. The mixture was stirred at room temperature for 45 min. Subsequently, sodium cyanoborohydride (7.65 mg, 0.122 mmol) was added in portions and stirring of the mixture continued at room temperature overnight. The reaction mixture was then concentrated, and the residue was dissolved in a mixture of acetonitrile and water with addition of one drop of TFA and purified by preparative HPLC (Method 27). The product-containing fractions were combined and concentrated. The residue (47 mg) was used as such in subsequent reactions.

LC/MS (Method 5): $R_t$=0.92 min; MS (ESIpos): m/z=564 [M+H]$^+$.

Intermediate 32A tert-Butyl-{2-[({4-[(5-{[tert-butyl(dimethyl) silyl]oxy}-2-fluoro-4-methylphenyl)amino]-5-oxo-6,11-dihydro-5H-pyrido[2,3-b][1,5]benzodiazepin-8-yl}methyl)(methyl)amino]ethyl}carbamate trifluoroacetic acid salt

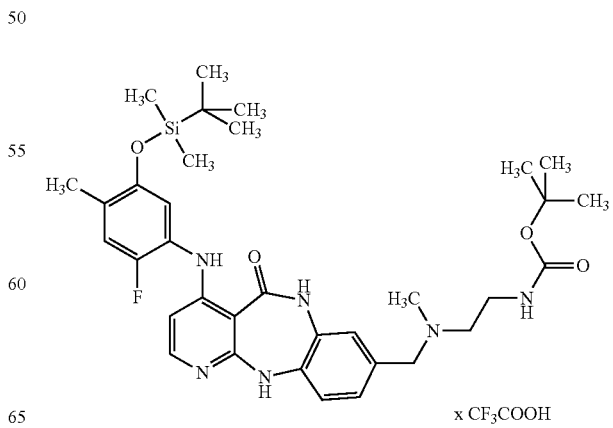

x CF$_3$COOH

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and tert-butyl [2-(methylamino)ethyl]carbamate hydrochloride (85.44 mg, 0.406 mmol), acetic acid (0.046 ml, 0.812 mmol) and N,N-diisopropylethylamine (0.071 ml, 0.406 mmol) were added. The mixture was stirred at room temperature for 45 min. Subsequently, sodium cyanoborohydride (9.57 mg, 0.152 mmol) was added in portions and stirring of the mixture continued at room temperature for 5 h. The reaction mixture was then concentrated, and the residue was dissolved in a mixture of acetonitrile and water with addition of one drop of TFA and purified by preparative HPLC (Method 28). The product-containing fractions were combined and concentrated. The residue (26 mg) was used as such in subsequent reactions.

LC/MS (Method 7): $R_t$=1.29 min; MS (ESIneg): m/z=649 [M−H]⁻.

Intermediate 33A

4-[(5-{[tert-Butyl(dimethyl)silyl]oxy}-2-fluoro-4-methylphenyl)amino]-8-{[3,4-cis-dihydroxypyrrolidin-1-yl]methyl}-6,11-dihydro-5H-pyrido[2,3-b][1,5]benzodiazepin-5-one

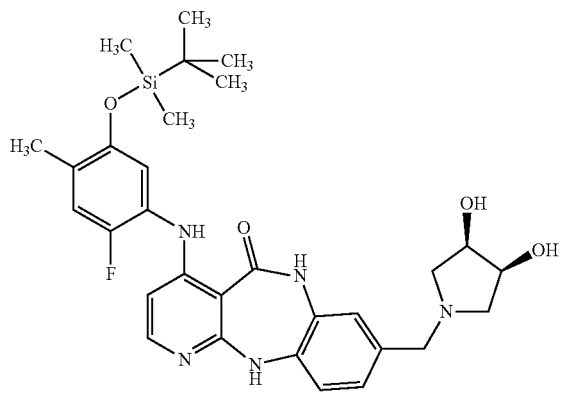 [SMILES: Cc1cc(F)c(Nc2ccnc3c2C(=O)Nc2cc(CN4C[C@@H](O)[C@@H](O)C4)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and cis-pyrrolidine-3,4-diol hydrochloride (56.66 mg, 0.406 mmol), acetic acid (0.046 ml, 0.812 mmol) and N,N-diisopropylethylamine (0.071 ml, 0.406 mmol) were added. The mixture was stirred at room temperature overnight. Subsequently, sodium cyanoborohydride (9.57 mg, 0.152 mmol) was added in portions and stirring of the mixture continued at room temperature for 5 h. Monitoring by HPLC-LC/MS indicated incomplete conversion. Therefore, sodium cyanoborohydride (9.57 mg, 0.152 mmol) was once again added in portions and stirring of the mixture continued at room temperature overnight. The reaction mixture was then concentrated, and the residue was dissolved in a mixture of acetonitrile and water with addition of one drop of TFA and purified by preparative HPLC (Method 28). The product-containing fractions were combined and concentrated. The residue obtained was admixed with saturated aqueous sodium hydrogencarbonate solution and extracted three times with ethyl acetate. The organic phases were combined, dried over sodium sulphate, filtered and concentrated. The residue (22.8 mg) was used as such in subsequent reactions.

LC/MS (Method 7): $R_t$=1.17 min; MS (ESIneg): m/z=578 [M−H]⁻.

Intermediate 34A

4-[(5-{[tert-Butyl(dimethyl)silyl]oxy}-2-fluoro-4-methylphenyl)amino]-8-{[4-(dimethylamino)piperidin-1-yl]methyl}-6,11-dihydro-5H-pyrido[2,3-b][1,5]benzodiazepin-5-one trifluoroacetic acid salt

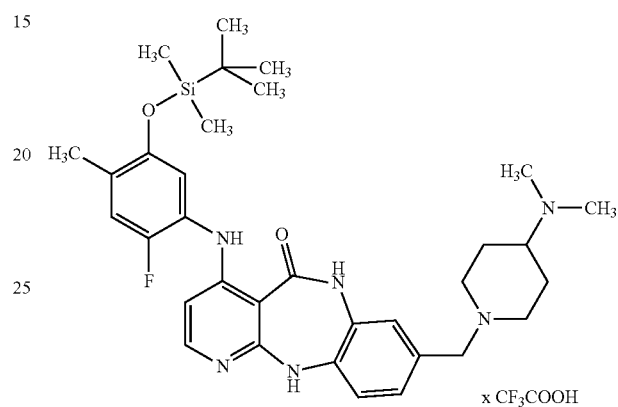

In analogy to Intermediate 29A, 4-[(5-{[tert-butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was reacted with 4-(dimethylamino)piperidine (52.1 mg, 0.406 mmol). 63.5 mg of the title compound were obtained.

LC/MS (Method 7): $R_t$=1.05 min; MS (ESIneg): m/z=603 [M−H]⁻.

Intermediate 35A tert-Butyl [(3R)-1-({4-[(5-{[tert-butyl(dimethyl)silyl]oxy}-2-fluoro-4-methylphenyl)amino]-5-oxo-6,11-dihydro-5H-pyrido[2,3-b][1,5]benzodiazepin-8-yl}methyl)piperidin-3-yl]carbamate trifluoroacetic acid salt

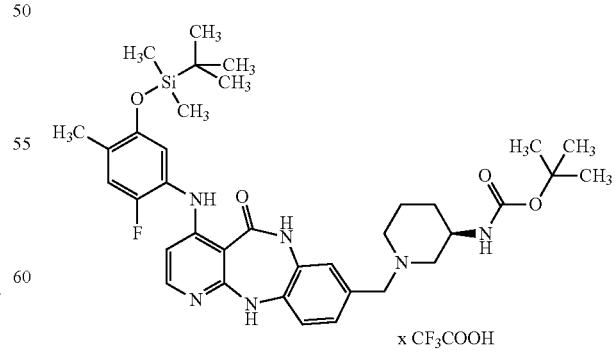

In analogy to Intermediate 29A, 4-[(5-{[tert-butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was reacted with tert-butyl (3R)-piperidin-3-ylcarbamate (81.3 mg, 0.406 mmol). 71.5 mg of the title compound were obtained.

LC/MS (Method 7): R$_t$=1.31 min; MS (ESIneg): m/z=675 [M–H]$^-$.

Intermediate 36A tert-Butyl [(3S)-1-({4-[(5-{[tert-butyl(dimethyl) silyl]oxy}-2-fluoro-4-methylphenyl)amino]-5-oxo-6, 11-dihydro-5H-pyrido[2,3-b][1,5]benzodiazepin-8-yl}methyl)pyrrolidin-3-yl]carbamate trifluoroacetic acid salt

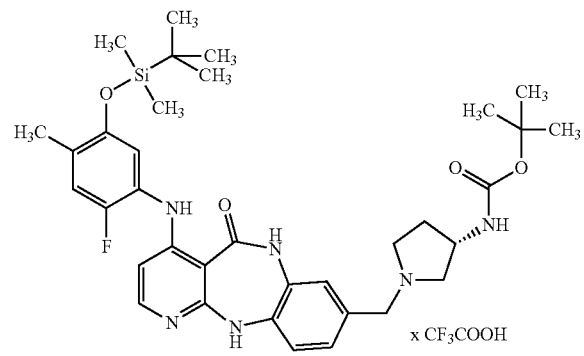 [SMILES: Cc1cc(F)c(Nc2ccnc3c2C(=O)Nc2cc(CN4CC[C@H](NC(=O)OC(C)(C)C)C4)ccc2N3)cc1O[Si](C)(C)C(C)(C)C]

In analogy to Intermediate 29A, 4-[(5-{[tert-butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was reacted with tert-butyl (3S)-pyrrolidin-3-ylcarbamate (75.6 mg, 0.406 mmol). 61 mg of the title compound were obtained.

LC/MS (Method 7): R$_t$=1.28 min; MS (ESIneg): m/z=661 [M–H]$^-$.

Intermediate 37A tert-Butyl [(3R)-1-({4-[(5-{[tert-butyl(dimethyl) silyl]oxy}-2-fluoro-4-methylphenyl)amino]-5-oxo-6, 11-dihydro-5H-pyrido[2,3-b][1,5]benzodiazepin-8-yl}methyl)pyrrolidin-3-yl]carbamate trifluoroacetic acid salt

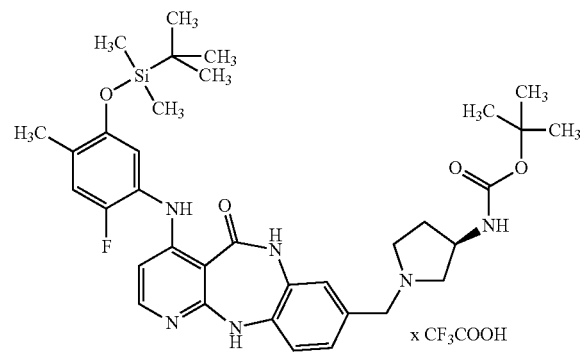 [SMILES: Cc1cc(F)c(Nc2ccnc3c2C(=O)Nc2cc(CN4CC[C@@H](NC(=O)OC(C)(C)C)C4)ccc2N3)cc1O[Si](C)(C)C(C)(C)C]

In analogy to Intermediate 29A, 4-[(5-{[tert-butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was reacted with tert-butyl (3R)-pyrrolidin-3-ylcarbamate (75.6 mg, 0.406 mmol). 30.2 mg of the title compound were obtained.

LC/MS (Method 7): R$_t$=1.32 min; MS (ESIneg): m/z=661 [M–H]$^-$.

Intermediate 38A

4-[(5-{[tert-Butyl(dimethyl)silyl]oxy}-2-fluoro-4-methylphenyl)amino]-8-{[(3R)-3-(dimethylamino) pyrrolidin-1-yl]methyl}-6,11-dihydro-5H-pyrido[2, 3-b][1,5]benzodiazepin-5-one trifluoroacetic acid salt

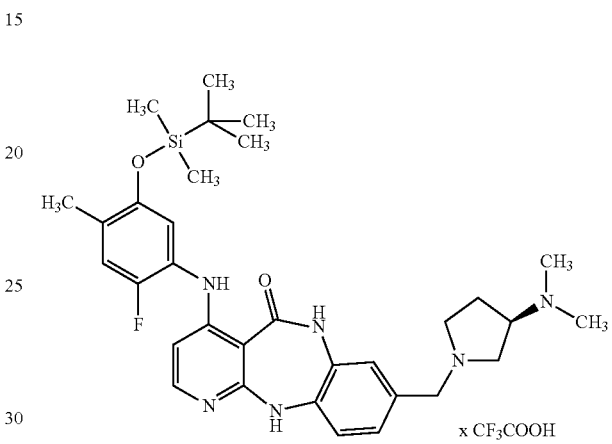

In analogy to Intermediate 29A, 4-[(5-{[tert-butyl(dimethyl)silyl]oxy}-2-fluoro-4-methylphenyl)amino]-5-oxo-6, 11-dihydro-5H-pyrido[2,3-b][1,5]benzodiazepine-8-carbaldehyde (50 mg, 0.101 mmol; Intermediate 19A) was reacted with (R)-3-(dimethylamino)pyrrolidine (46.4 mg, 0.406 mmol). 53.2 mg of the title compound were obtained.

LC/MS (Method 7): R$_t$=1.12 min; MS (ESIneg): m/z=589 [M–H]$^-$.

Intermediate 39A tert-Butyl [1-({4-[(5-{[tert-butyl(dimethyl) silyl] oxy}-2-fluoro-4-methylphenyl)amino]-5-oxo-6,11-dihydro-5H-pyrido[2,3-b][1,5]benzodiazepin-8-yl}methyl)piperidin-4-yl]carbamate

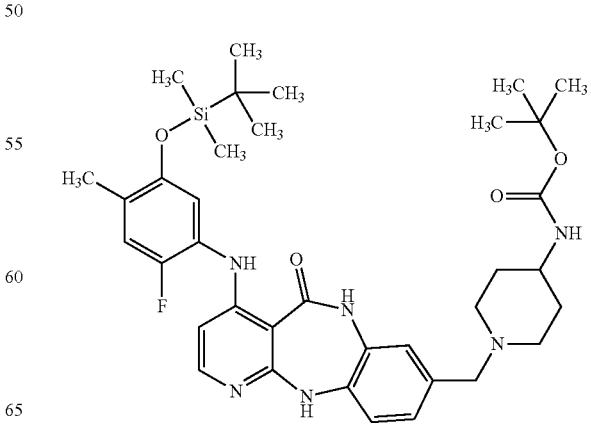

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (45 mg, 0.091 mmol; Intermediate 19A) was dissolved in THF (4.5 ml), and tert-butyl piperidin-4-ylcarbamate (73.18 mg, 0.365 mmol) and acetic acid (0.042 ml, 0.731 mmol) were added. The mixture was stirred at room temperature for 45 min. Subsequently, sodium cyanoborohydride (8.61 mg, 0.137 mmol) was added in portions and stirring of the mixture continued at room temperature overnight. The reaction mixture was then concentrated, and the residue was dissolved in a mixture of acetonitrile and water with addition of one drop of TFA and purified by preparative HPLC (Method 27). The product-containing fractions were combined and concentrated. The residue obtained was admixed with saturated aqueous sodium hydrogencarbonate solution and extracted three times with ethyl acetate. The organic phases were combined, dried over sodium sulphate, filtered and concentrated. The residue (46.7 mg) was used as such in subsequent reactions.

LC/MS (Method 7): $R_t$=1.27 min; MS (ESIneg): m/z=675 [M−H]$^-$.

Intermediate 40A tert-Butyl [(3S)-1-({4-[(5-{[tert-butyl(dimethyl)silyl]oxy}-2-fluoro-4-methylphenyl)amino]-5-oxo-6,11-dihydro-5H-pyrido[2,3-b][1,5]benzodiazepin-8-yl}methyl)piperidin-3-yl]carbamate trifluoroacetic acid salt

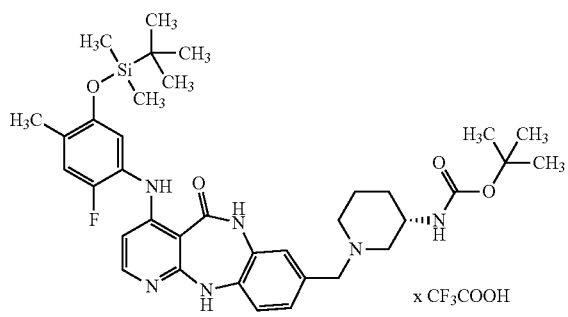 [SMILES: Cc1cc(F)c(Nc2ccnc3c2C(=O)Nc2cc(CN4CCC[C@H](NC(=O)OC(C)(C)C)C4)ccc2N3)cc1O[Si](C)(C)C(C)(C)C]

In analogy to Intermediate 29A, 4-[(5-{[tert-butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (45 mg, 0.091 mmol; Intermediate 19A) was reacted with tert-butyl (3S)-piperidin-3-ylcarbamate (73.18 mg, 0.365 mmol). 81.3 mg of the title compound were obtained.

LC/MS (Method 7): $R_t$=1.29 min; MS (ESIneg): m/z=675 [M−H]$^-$.

Intermediate 41A

4-[(5-{[tert-Butyl(dimethyl)silyl]oxy}-2-fluoro-4-methylphenyl)amino]-8-{[(3R)-3-(dimethylamino)pyrrolidin-1-yl]methyl}-6,11-dihydro-5H-pyrido[2,3-b][1,5]benzodiazepin-5-one

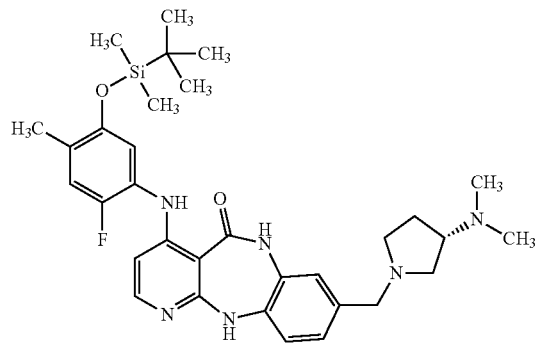

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and (S)-3-(dimethylamino)pyrrolidine (47.79 mg, 0.406 mmol) and acetic acid (0.046 ml, 0.812 mmol) were added. The mixture was stirred at room temperature for 45 min. Subsequently, sodium cyanoborohydride (9.57 mg, 0.152 mmol) was added in portions and stirring of the mixture continued at room temperature overnight. The reaction mixture was then concentrated, and the residue obtained was admixed with saturated aqueous sodium hydrogencarbonate solution and extracted three times with ethyl acetate. The organic phases were combined, dried over sodium sulphate, filtered and concentrated. The residue (82 mg) was used without further purification in subsequent reactions.

LC/MS (Method 25): $R_t$=1.55 min; MS (ESIneg): m/z=589 [M−H]$^-$.

Intermediate 42A

4-[(5-{[tert-Butyl(dimethyl)silyl]oxy}-2-fluoro-4-methylphenyl)amino]-8-{[(3-hydroxypropyl)(methyl)amino]methyl}-6,11-dihydro-5H-pyrido[2,3-b][1,5]benzodiazepin-5-one

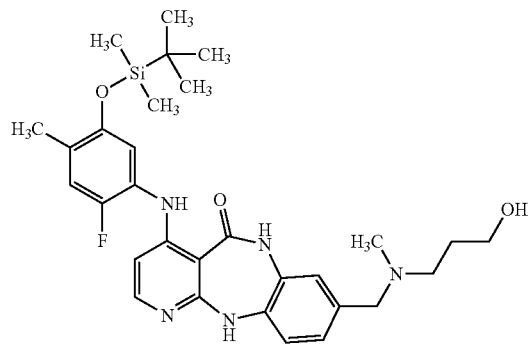 [SMILES: Cc1cc(F)c(Nc2ccnc3c2C(=O)Nc2cc(CN(C)CCCO)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and 3-(N-methylamino)-1-propanol (37.3 mg, 0.406 mmol) and acetic acid (0.046 ml, 0.812 mmol) were added. The mixture was stirred at room temperature for 45 min. Subsequently, sodium cyanoborohydride (9.57 mg, 0.152 mmol) was added in portions and stirring of the mixture continued at room temperature overnight. The reaction mixture was then concentrated, and the residue obtained was admixed with saturated aqueous sodium hydrogencarbonate solution and extracted three times with ethyl acetate. The organic phases were combined, dried over sodium sulphate, filtered and concentrated. The residue (96 mg, 70% purity) was used without further purification in subsequent reactions.

LC/MS (Method 5): $R_t$=0.93 min; MS (ESIpos): m/z=566 [M+H]$^+$.

Intermediate 43A

4-[(5-{[tert-Butyl(dimethyl)silyl]oxy}-2-fluoro-4-methylphenyl)amino]-8-{[ethyl(3-hydroxypropyl)amino]methyl}-6,11-dihydro-5H-pyrido[2,3-b][1,5]benzodiazepin-5-one

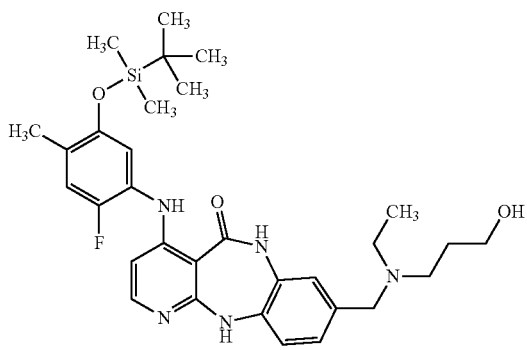 [SMILES: CCN(CCCO)Cc1ccc2c(c1)NC(=O)c1c(Nc3cc(O[Si](C)(C)C(C)(C)C)c(C)cc3F)ccnc1N2]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (50 mg, 0.101 mmol; Intermediate 19A) was dissolved in THF (5 ml), and 3-(N-ethylamino)propan-1-ol (44 mg, 0.406 mmol) and acetic acid (0.046 ml, 0.812 mmol) were added. The mixture was stirred at room temperature for 45 min. Subsequently, sodium cyanoborohydride (9.57 mg, 0.152 mmol) was added in portions and stirring of the mixture continued at room temperature overnight. The reaction mixture was then concentrated, and the residue obtained was admixed with saturated aqueous sodium hydrogencarbonate solution and extracted three times with ethyl acetate. The organic phases were combined, dried over sodium sulphate, filtered and concentrated. The residue (70 mg, 75% purity) was used without further purification in subsequent reactions.

Intermediate 44A

4-[(5-{[tert-Butyl(dimethyl)silyl]oxy}-2-fluoro-4-methylphenyl)amino]-8-{[(3S)-3-hydroxypiperidin-1-yl]methyl}-6,11-dihydro-5H-pyrido[2, 3-b][1,5]benzodiazepin-5-one

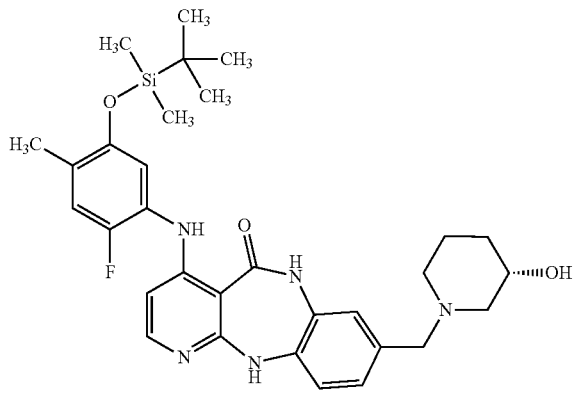 [SMILES: Cc1cc(F)c(Nc2ccnc3c2C(=O)Nc2cc(CN4CCC[C@H](O)C4)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (494 mg, 1.003 mmol; Intermediate 19A) was dissolved in THF (50 ml), and (S)-3-hydroxypiperidine hydrochloride (552 mg, 4.011 mmol), acetic acid (0.459 ml, 8.023 mmol) and N,N-diisopropylethylamine (0.70 ml, 4.011 mmol) were added. The mixture was stirred at 50° C. overnight. Then sodium cyanoborohydride (94.5 mg, 1.50 mmol) was added in portions and stirring of the mixture continued at room temperature overnight. Saturated aqueous sodium bicarbonate solution was then added, and the reaction mixture was extracted three times with ethyl acetate. The organic phases were combined, dried over sodium sulphate, filtered and concentrated. The residue (796 mg) was used without further purification in subsequent reactions.

LC/MS (Method 7): $R_t$=1.21 min; MS (ESIneg): m/z=576 [M−H]$^-$.

Intermediate 45A

4-[(5-{[tert-Butyl(dimethyl)silyl]oxy}-2-fluoro-4-methylphenyl)amino]-8-{[(3R)-3-hydroxypiperidin-1-yl]methyl}-6,11-dihydro-5H-pyrido[2, 3-b][1,5]benzodiazepin-5-one

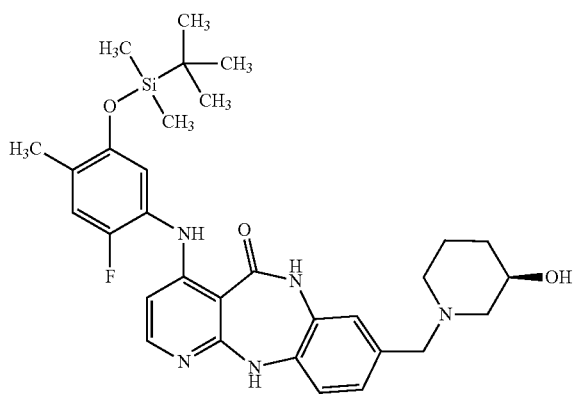 [SMILES: Cc1cc(F)c(Nc2ccnc3c2C(=O)Nc2cc(CN4CCC[C@@H](O)C4)ccc2N3)cc1O[Si](C)(C)C(C)(C)C]

4-[(5-{[tert-Butyl(dimethyl)silyl]oxy}-2-fluoro-4-methylphenyl)amino]-5-oxo-6,11-dihydro-5H-pyrido[2,3-b][1,5]benzodiazepine-8-carbaldehyde (30 mg, 0.061 mmol; Intermediate 19A) was dissolved in THF (3 ml), and (R)-3-hydroxypiperidine hydrochloride (33.52 mg, 0.244 mmol) and acetic acid (0.028 ml, 0.487 mmol) were added. The mixture was stirred at room temperature for 30 min. Subsequently, sodium cyanoborohydride (19.14 mg, 0.304 mmol) was added in portions and stirring of the mixture continued at room temperature overnight. Saturated aqueous sodium bicarbonate solution was then added, and the reaction mixture was extracted three times with ethyl acetate. The organic phases were combined, dried over sodium sulphate, filtered and concentrated. The residue (16.9 mg) was used without further purification in subsequent reactions.

LC/MS (Method 7): $R_t$=1.19 min; MS (ESIneg): m/z=576 [M−H]$^-$.

Intermediate 46A 3,4-Diamino-N-(3-chlorobenzyl)benzamide

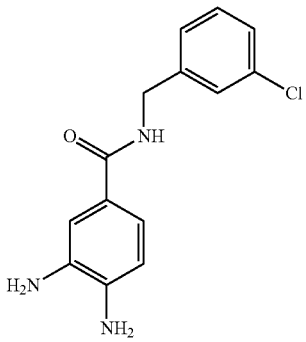 [SMILES: Nc1ccc(C(=O)NCc2cccc(Cl)c2)cc1N]

To a suspension of 3,4-diaminobenzoic acid (5.00 g, 32.9 mmol) in dichloromethane (300 ml) were added, at RT, 3-chlorobenzylamine (4.65 g, 32.9 mmol), DMAP (4.42 g, 36.1 mmol) and DCC (7.46 g, 36.1 mmol). The mixture was stirred at RT overnight, then silica gel was added and the mixture was concentrated to dryness on a rotary evaporator. The residue was purified by means of column chromatography on silica gel (dichloromethane/methanol gradient 30:1→20:1). 10.8 g (>100% of theory) of the title compound, still contaminated with dicyclohexylurea, were obtained. This product was used in the subsequent reaction without further purification.

LC/MS (Method 3, ESIpos): $R_t$=1.66 min, m/z=276 [M+H]$^+$.

Intermediate 47A

N-{2-Amino-5-[(3-chlorobenzyl)carbamoyl]phenyl}-4-{[5-(benzyloxy)-2-methylphenyl]amino}-2-chloronicotinamide

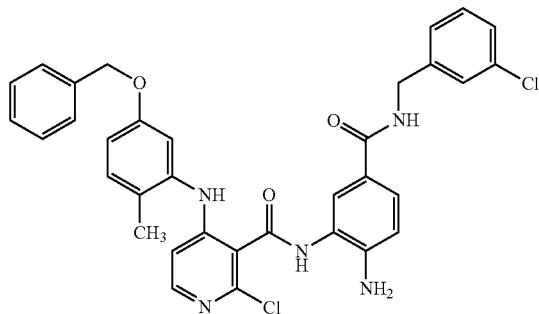 [SMILES: Cc1ccc(OCc2ccccc2)cc1Nc1ccnc(Cl)c1C(=O)Nc1cc(C(=O)NCc2cccc(Cl)c2)ccc1N]

To a solution of 4-{[5-(benzyloxy)-2-methylphenyl]amino}-2-chloropyridine-3-carboxylic acid (Intermediate 3A; 200 mg, 0.542 mmol) in DMF (2.0 ml) were added TBTU (192 mg, 0.596 mmol) and N,N-diisopropylethylamine (142 µl, 0.813 mmol). The mixture was stirred at RT for 30 min. Subsequently, 3,4-diamino-N-(3-chlorobenzyl)benzamide (Intermediate 46A; 224 mg, 0.813 mmol) was added and stirring of the mixture continued at RT overnight. The reaction mixture was then admixed with saturated aqueous ammonium chloride solution and extracted with ethyl acetate. The combined organic phases were washed with saturated aqueous sodium chloride solution, dried over sodium sulphate and concentrated. The residue obtained was purified by means of column chromatography on silica gel (eluent A: dichloromethane, eluent B: 7 M ammonia in methanol; gradient: 0-3% B). 160 mg (47% of theory) of the title compound were obtained.

LC/MS (Method 3, ESIpos): $R_t$=1.21 min, m/z=626 [M+H]$^+$.

Intermediate 48A

4-{[5-(Benzyloxy)-2-methylphenyl]amino}-N-(3-chlorobenzyl)-5-oxo-6,11-dihydro-5H-pyrido[2,3-b][1,5]benzodiazepine-8-carboxamide

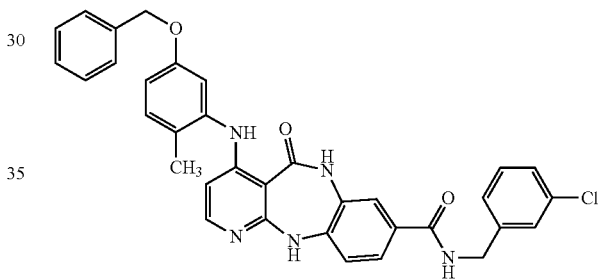

A solution of N-{2-amino-5-[(3-chlorobenzyl)carbamoyl]phenyl}-4-{[5-(benzyloxy)-2-methylphenyl]amino}-2-chloronicotinamide (Intermediate 47A; 160 mg, 0.255 mmol) in isopropanol (4.0 ml) was heated in a microwave reactor to 180° C. for 20 min. Removal of the solvent gave 151 mg (84% purity, 84% of theory) of the title compound which were used in subsequent reactions without further purification.

LC/MS (Method 3, ESIpos): $R_t$=1.16 min, m/z=590 [M+H]$^+$.

Intermediate 49A

N-Ethyl-N-(3-fluoro-4-nitrobenzyl)ethanamine

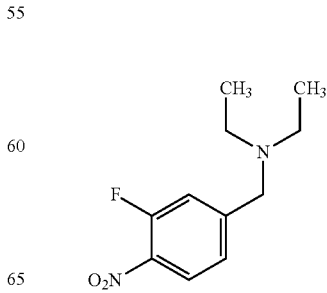

To a solution of 4-(bromomethyl)-2-fluoro-1-nitrobenzene (5.04 g, 21.5 mmol) in dichloromethane (100 ml) were added diethylamine (2.5 ml, 24 mmol) and N,N-diisopropylethylamine (5.6 ml, 32 mmol), and the mixture was stirred at RT overnight. The reaction mixture was then diluted with dichloromethane and water, the phases were separated and the organic phase was dried over magnesium sulphate, filtered and concentrated. Drying the residue gave 4.99 g (95% of theory) of the title compound which was used in subsequent reactions without further purification.

LC/MS (Method 26, ESIpos): $R_t$=1.64 min; m/z=227 $[M+H]^+$ $^1$H-NMR (400 MHz, DMSO-$d_6$): δ [ppm]=8.17-8.00 (m, 1H), 7.49 (d, 1H), 7.41 (d, 1H), 3.64 (s, 2H), 2.48 (q, 4H), 1.02-0.94 (m, 6H).

Intermediate 50A

5-[(Diethylamino)methyl]-2-nitroaniline

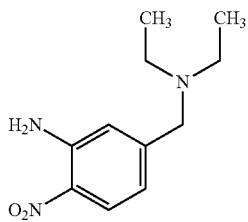 [SMILES: CCN(CC)Cc1ccc([N+](=O)[O-])c(N)c1]

N-Ethyl-N-(3-fluoro-4-nitrobenzyl)ethanamine (Intermediate 49A; 4.00 g, 17.7 mmol) was divided between 8 microwave reaction vessels (500 mg each) and dissolved in ethanol (5 ml in each case), and 25-30% aqueous ammonium hydroxide solution (10 ml in each case) was added. The mixtures were heated in a microwave reactor to 90° C. for 3 h. After cooling, the reaction mixtures were combined and concentrated. The residue was purified by means of column chromatography on silica gel (100 g of silica gel, eluent: 2.5-10% in dichloromethane). In this way, 3.29 g (83% of theory) of the title compound were obtained.

LC/MS (Method 26, ESIpos): $R_t$=1.16 min, m/z=224 $[M+H]^+$ $^1$H-NMR (400 MHz, DMSO-$d_6$): δ [ppm]=7.90 (d, 1H), 7.40 (br. s, 2H), 7.00 (s, 1H), 6.58 (d, 1H), 3.44 (s, 2H), 2.45 (q, 4H), 0.98 (t, 6H).

Intermediate 51A

2-Chloro-N-{5-[(diethylamino)methyl]-2-nitrophenyl}-4-methoxynicotinamide

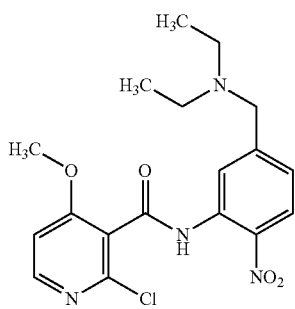 [SMILES: CCN(CC)Cc1ccc([N+](=O)[O-])c(NC(=O)c2c(OC)ccnc2Cl)c1]

To a solution of 2-chloro-4-methoxynicotinic acid (2.62 g, 13.9 mmol) in dichloromethane (30 ml) and DMF (2 drops) were slowly added dropwise, at 0° C., oxalyl chloride (2.4 ml, 28 mmol). After the addition had ended, the mixture was stirred at RT for another 2 h, then the solvent was removed at a bath temperature of 30° C. on a rotary evaporator and the residue was dried.

In a separate reaction vessel, sodium hydride (1.23 g, 60% in mineral oil, 31 mmol) was added in portions at 0° C. to a solution of 5-[(diethylamino)methyl]-2-nitroaniline (Intermediate 50A; 3.27 g, 14.6 mmol) in DMF (15 ml). After the addition had ended, stirring was continued at 0° C. for another 15 min before a solution of the previously prepared acid chloride in DMF (15 ml) was slowly added dropwise. After the addition had ended, the mixture was stirred at 0° C. for another 15 min, then the reaction mixture was poured onto ice-water. The mixture was extracted with ethyl acetate (4×100 ml), and the combined organic phases were washed with saturated aqueous sodium chloride solution, dried over magnesium sulphate and concentrated. The residue was purified by means of column chromatography on silica gel (100 g of silica gel, eluent: 0.5-5% ethanol in dichloromethane). 6.08 g (89% pure, 99% of theory) of the title compound were obtained, which, according to $^1$H NMR, still contained DMF (about 1:1). This product was used in subsequent reactions without further purification.

LC/MS (Method 3, ESIpos): $R_t$=0.48 min, m/z=393 $[M+H]^+$ $^1$H-NMR (400 MHz, DMSO-$d_6$): δ [ppm]=10.79 (s, 1H), 8.39 (d, 1H), 7.95 (s, 1H), 7.75 (s, 1H), 7.36 (d, 1H), 7.28 (d, 1H), 3.93 (s, 3H), 3.64 (s, 2H), 0.99 (t, 6H).

Intermediate 52A

N-{2-Amino-5-[(diethylamino)methyl]phenyl}-2-chloro-4-methoxynicotinamide

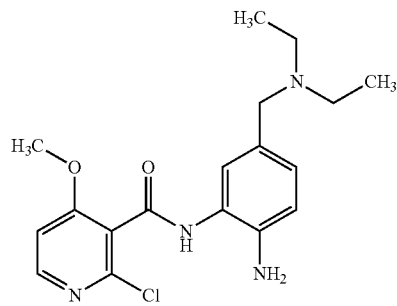 [SMILES: CCN(CC)Cc1ccc(N)c(NC(=O)c2c(OC)ccnc2Cl)c1]

To a solution of 2-chloro-N-{5-[(diethylamino)methyl]-2-nitrophenyl}-4-methoxynicotinamide (Intermediate 51A; 6.08 g, 89% purity, 13.8 mmol) in ethanol (27 ml) and ethyl acetate (27 ml) was added tin(II) chloride (7.84 g, 41.3 mmol). The mixture was treated in an ultrasound bath for 5 min and then stirred at RT overnight. Addition of 2.5 M sodium hydroxide solution (to pH>12) was followed by extraction with ethyl acetate (4×100 ml). The combined organic phases were washed with saturated aqueous sodium chloride solution, dried over magnesium sulphate and concentrated. Drying the residue gave 5.01 g (93% of theory) of the title compound which was used in subsequent reactions without further purification.

LC/MS (Method 3, ESIpos): $R_t$=0.26 min, m/z=363 $[M+H]^+$

¹H-NMR (400 MHz, DMSO-d₆): δ [ppm]=9.80 (s, 1H), 8.36 (d, 1H), 7.27 (d, 1H), 7.22 (d, 1H), 6.90 (dd, 1H), 6.69 (d, 1H), 4.77 (s, 2H), 3.93 (s, 3H), 3.38 (s, 2H), 2.43 (q, 4H), 0.96 (t, 6H).

Intermediate 53A

8-[(Diethylamino)methyl]-4-hydroxy-6,11-dihydro-5H-pyrido[2,3-b][1,5]benzodiazepin-5-one

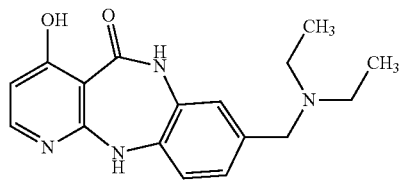 [SMILES: CCN(CC)Cc1ccc2c(c1)NC(=O)c1c(O)ccnc1N2]

N-{2-Amino-5-[(diethylamino)methyl]phenyl}-2-chloro-4-methoxynicotinamide (Intermediate 52A; 4.90 g, 13.5 mmol) was divided between 9 microwave reaction vessels (in each case 544 mg, 1.50 mmol) and dissolved in acetonitrile (15 ml in each case), and hydrogen chloride solution (4 M in dioxane, 525 µl in each case, 2.10 mmol) was added. The mixtures were heated in a microwave reactor to 120° C. for 2.5 h. After cooling, the reaction mixtures were combined and concentrated. Drying the residue gave 5.35 g (65% purity, 82% of theory) of the title compound which was used in subsequent reactions without further purification.

LC/MS (Method 3, ESIpos): R$_t$=0.37 min, m/z=313 [M+H]⁺.

Intermediate 54A

4-Chloro-8-[(diethylamino)methyl]-6,11-dihydro-5H-pyrido[2,3-b][1,5]benzodiazepin-5-one

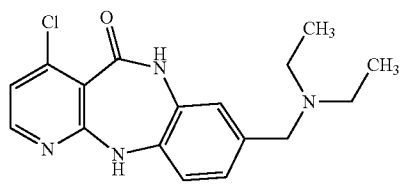 [SMILES: CCN(CC)Cc1ccc2c(c1)NC(=O)c1c(Cl)ccnc1N2]

While stirring vigorously, 8-[(diethylamino)methyl]-4-hydroxy-6,11-dihydro-5H-pyrido[2,3-b][1,5]benzodiazepin-5-one (intermediate 53A; 4.80 g, 15.4 mmol) was added at RT to phosphoryl chloride (29 ml, 310 mmol). Sulpholane (3.8 ml) was added to the mixture, which was heated to 80° C. overnight. After cooling, the reaction mixture was poured onto ice-water while stirring vigorously. The mixture was basified with 20% sodium hydroxide solution and extracted with ethyl acetate. The combined organic phases were washed with saturated aqueous sodium chloride solution, dried over magnesium sulphate and concentrated. The residue was stirred with toluene, and the solids were filtered off with suction and dried. In this way, a first fraction of the title compound was obtained (1.24 g, 88% purity, 22% of theory). The mother liquor was concentrated. Purification of the residue by means of column chromatography on silica gel (50 g of silica gel, eluent: 2.5-17.5% ethanol in dichloromethane) gave a second fraction of the title compound (309 mg, 62% purity, 4% of theory).

LC/MS (Method 3, ESIpos): R$_t$=0.44 min, m/z=331 [M+H]⁺.

Working Examples

Example 1

4-[(5-Hydroxy-2-methylphenyl)amino]-5-oxo-6,11-dihydro-5H-pyrido[2,3-b][1,5]benzodiazepine-8-carbonitrile

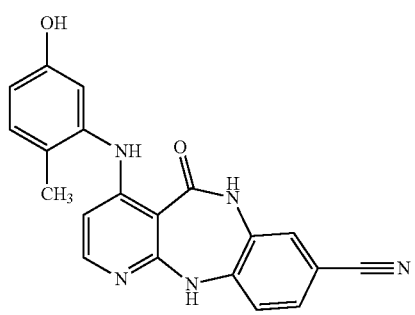

Method A:

94 mg (0.209 mmol) of 4-{[5-(benzyloxy)-2-methylphenyl]amino}-5-oxo-6,11-dihydro-5H-pyrido[2,3-b][1,5]benzodiazepine-8-carbonitrile (Intermediate 5A) were dissolved in 2 ml of trifluoroacetic acid. Then 49 µl (0.418 mmol) of (methylsulphanyl)benzene were added. The mixture was stirred at RT overnight. The reaction mixture was then concentrated on a rotary evaporator and the residue was purified by means of preparative HPLC. 23 mg (31% of theory) of the title compound were obtained.

LC/MS (Method 1, ESIpos): R$_t$=1.52 min, m/z=358 [M+H]⁺.

¹H-NMR (400 MHz, DMSO-d₆): δ [ppm]=2.06 (s, 3H), 6.29 (d, 1H), 6.51-6.64 (m, 2H), 7.09 (d, 1H), 7.26 (d, 1H), 7.33 (d, 1H), 7.46 (dd, 1H), 7.77 (d, 1H), 8.80 (s, 1H), 9.36 (s, 1H), 9.91 (s, 1H), 10.22 (s, 1H).

Method B:

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (2.80 g, 10.3 mmol) (Intermediate 10A) and 3-amino-4-methylphenol (1.40 g, 11.4 mmol) was initially charged in 36.4 ml of isopropanol. 2.8 ml of a 4 M solution of hydrogen chloride in dioxane were added and the mixture, divided between three reaction vessels, was heated in a microwave apparatus to 160° C. for 20 min. Thereafter, the reaction mixture was diluted with water and stirred for 10 min. The precipitate was filtered off with suction and washed with acetonitrile. The filtrate was concentrated somewhat under reduced pressure and the aqueous solution was extracted three times with ethyl acetate. The combined organic phases were dried over sodium sulphate and concentrated under reduced pressure. This gave 2.33 g (55% of theory) of the title compound in 87% purity.

Method C:

4-{[5-(Benzyloxy)-2-methylphenyl]amino}-5-oxo-6,11-dihydro-5H-pyrido[2,3-b][1,5]benzodiazepine-8-carbonitrile (2.00 g, 4.47 mmol) (Intermediate 5A) were dissolved in 20 ml of trifluoroacetic acid. Thioanisole (1.05 ml, 8.34 mmol) was added thereto and the reaction mixture was stirred at RT for 2 days. Then the same amount of thioanisole again was added and the mixture was stirred at RT for a further day. The reaction mixture was then concentrated under reduced pressure, toluene was added and the mixture was concentrated again. The residue was stirred with a mixture of dichloromethane/methanol/N,N-diisopropylethylamine (100:10:1) and the solid formed was filtered off with suction. The filtrate was concentrated and the residue was stirred again with the above solvent mixture. By filtration with suction, a further solid fraction was obtained. The solid was finally purified by means of silica gel chromatography. 1.19 g (71% of theory) of the title compound were obtained.

LC/MS (Method 1, ESIpos): $R_t$=1.52 min, m/z=358 [M+H]$^+$.

$^1$H-NMR (400 MHz, DMSO-d$_6$): δ [ppm]=2.06 (s, 3H), 6.29 (d, 1H), 6.57 (dd, 1H), 6.61 (d, 1H), 7.09 (d, 1H), 7.26 (d, 1H), 7.33 (d, 1H), 7.46 (dd, 1H), 7.77 (d, 1H), 8.80 (s, 1H), 9.36 (s, 1H), 9.91 (s, 1H), 10.22 (s, 1H).

Example 2

4-[(3-Hydroxy-4-propylphenyl)amino]-5-oxo-6,11-dihydro-5H-pyrido[2,3-b][1,5]benzodiazepine-8-carbonitrile

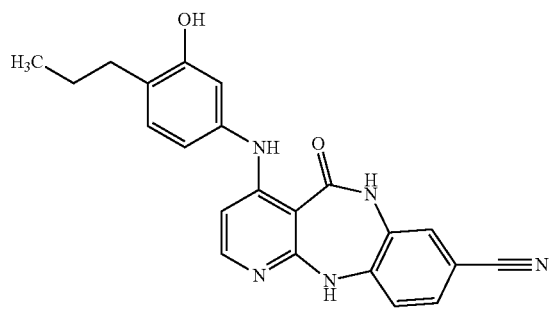 [SMILES: CCCc1ccc(Nc2ccnc3c2C(=O)Nc2cc(C#N)ccc2N3)cc1O]

5-Amino-2-propylphenol (Intermediate 14A) (50 mg, 0.33 mmol) and a mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (81 mg, 0.301 mmol) were dissolved in isopropanol (1.47 ml) and a 4 M solution of hydrogen chloride in dioxane (83 µl, 0.33 mmol). The mixture was stirred in a microwave apparatus at 160° C. for 1.5 h. The precipitate formed was filtered off with suction, washed with isopropanol and dried under reduced pressure. 52 mg (41% of theory) of the title compound were obtained.

LC/MS (Method 5, ESIpos): $R_t$=0.91 min, m/z=386 [M+H]$^+$.

$^1$H-NMR (400 MHz, DMSO-d$_6$): δ [ppm]=0.90 (t, 3H), 1.49-1.62 (m, 2H), 2.45-2.55 (m, 2H), 6.55 (d, 1H), 6.60 (d, 1H), 6.66 (s, 1H), 7.10 (d, 1H), 7.25 (d, 1H), 7.39 (s, 1H), 7.54 (d, 1H), 7.83 (d, 1H), 9.61 (br. s, 1H).

Example 3

4-[(3-Hydroxy-4-methylphenyl)amino]-5-oxo-6,11-dihydro-5H-pyrido[2,3-b][1,5]benzodiazepine-8-carbonitrile

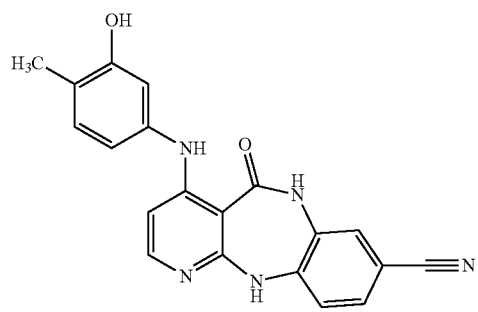 [SMILES: Cc1ccc(Nc2ccnc3c2C(=O)Nc2cc(C#N)ccc2N3)cc1O]

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (135 mg, 0.5 mmol) and 5-amino-2-methylphenol (68 mg, 0.55 mmol) were dissolved in isopropanol (3 ml) and a 4 M solution of hydrogen chloride in dioxane (138 µl, 0.55 mmol). The mixture was stirred in a microwave apparatus at 160° C. for 1 h. The reaction mixture was then admixed with saturated aqueous sodium carbonate solution and the precipitate formed was filtered off with suction. Chromatography on silica gel (eluent: dichloromethane→dichloromethane/methanol 10:1) and further purification by means of preparative HPLC (Method 12) gave 105 mg (59% of theory) of the title compound.

LC/MS (Method 5, ESIpos): $R_t$=0.75 min, m/z=358 [M+H]$^+$.

$^1$H-NMR (400 MHz, DMSO-d$_6$): δ [ppm]=2.10 (s, 3H), 6.51-6.56 (m, 2H), 6.61 (d, 1H), 7.06 (d, 1H), 7.26 (d, 1H), 7.32 (d, 1H), 7.46 (dd, 1H), 7.77 (d, 1H), 8.77 (s, 1H), 9.49 (s, 1H), 9.92 (s, 1H), 10.21 (s, 1H).

Example 4

Ethyl {4-[(8-cyano-5-oxo-6,11-dihydro-5H-pyrido[2,3-b][1,5]benzodiazepin-4-yl)amino]-2-hydroxyphenyl}carbamate

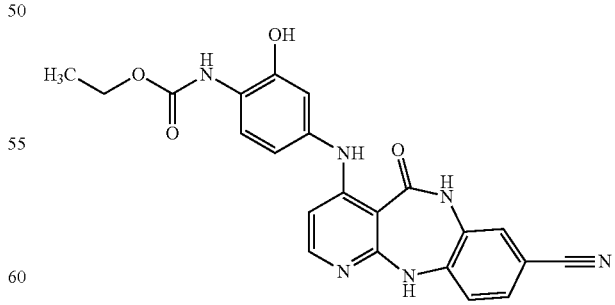

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (50 mg, 0.19 mmol) and ethyl (4-amino-2-hydroxyphenyl)carbamate (40 mg, 0.20 mmol) were dissolved in isopropanol (3 ml) and a 4 M solution of hydrogen chloride in dioxane (51 µl, 0.20 mmol). The mixture was stirred in a microwave apparatus at 160° C. for 2 h. The reaction mixture was then admixed with saturated aqueous sodium carbonate solution and concentrated. The residue was admixed with DMF and filtered, and the filtrate was concentrated again. Purification by means of preparative HPLC (column: Kinetex 5µ C18, 100 mm×21.2 mm; flow rate: 25 ml/min; eluent A: water 60%, eluent B: acetonitrile 35%, eluent C: 1% formic acid in water 5%; isocratic) gave 44 mg (52% of theory) of the title compound.

LC/MS (Method 5, ESIpos): $R_t$=0.77 min, m/z=431 [M+H]$^+$.

$^1$H-NMR (400 MHz, DMSO-d$_6$): δ [ppm]=1.23 (t, 3H), 4.10 (q, 2H), 6.53 (d, 1H), 6.62 (dd, 1H), 6.67 (d, 1H), 7.26 (d, 1H), 7.32 (d, 1H), 7.45 (dd, 1H), 7.51 (d, 1H), 7.78 (d, 1H), 8.22 (s, 1H), 8.77 (s, 1H), 9.89 (s, 1H), 9.91 (s, 1H), 10.2 (s, 1H).

Example 5

4-[(4-Bromo-3-hydroxyphenyl)amino]-5-oxo-6,11-dihydro-5H-pyrido[2,3-b][1,5]benzodiazepine-8-carbonitrile

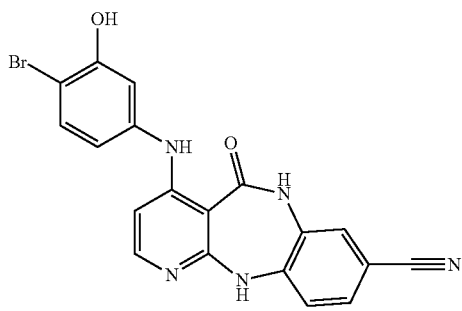

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (135 mg, 0.50 mmol) and 5-amino-2-bromophenol (Intermediate 15A) (103 mg, 0.55 mmol) were dissolved in isopropanol (3 ml) and a 4 M solution of hydrogen chloride in dioxane (138 µl, 0.55 mmol). The mixture was stirred in a microwave apparatus at 160° C. for 1 h. The reaction mixture was then admixed with saturated aqueous sodium carbonate solution and concentrated. The residue was chromatographed directly by means of silica gel (eluent: dichloromethane→dichloromethane/methanol 10:1) and then purified further by means of preparative HPLC (Method 13) and preparative HPLC once again (column: Kinetex C18 5 µm, 100 mm×30 mm; flow rate: 60 ml/min; eluent A: water, eluent B: acetonitrile, eluent C: 1% formic acid in water; gradient: 0-1 min 90% A, 5% B, 5% C→10 min 0% A, 95% B, 5% C). In this way, 16 mg (8% of theory) of the title compound were obtained.

LC/MS (Method 5, ESIpos): $R_t$=0.83 min, m/z=423 [M+H]$^+$.

$^1$H-NMR (400 MHz, DMSO-d$_6$): δ [ppm]=6.59 (dd, 1H), 6.62 (d, 1H), 6.79 (d, 1H), 7.26 (d, 1H), 7.32 (d, 1H), 7.44 (d, 1H), 7.46 (dd, 1H), 7.83 (d, 1H), 8.80 (s, 1H), 9.93 (s, 1H), 10.2 (s, 1H).

Example 6

N-{4-[(8-Cyano-5-oxo-6,11-dihydro-5H-pyrido[2,3-b][1,5]benzodiazepin-4-yl)amino]-2-hydroxyphenyl}benzenesulphonamide

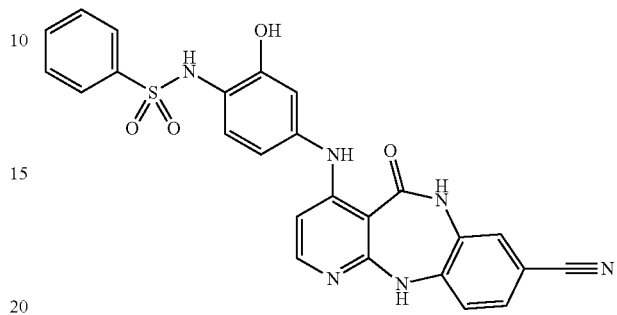

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (50 mg, 0.19 mmol) and N-(4-amino-2-hydroxyphenyl)benzenesulphonamide (54 mg, 0.20 mmol) were dissolved in isopropanol (3 ml) and a 4 M solution of hydrogen chloride in dioxane (51 µl, 0.20 mmol). The mixture was stirred in a microwave apparatus at 160° C. for 2.5 h. The reaction mixture was then admixed with saturated aqueous sodium carbonate solution and concentrated. The residue was taken up in DMF and filtered, and the filtrate was concentrated again. Purification by preparative HPLC (column: Kinetex 5µ C18, 100 mm×21.2 mm; flow rate: 25 ml/min; eluent A: water 52%, eluent B: acetonitrile 35%, eluent C: 1% formic acid in water 13%; isocratic) gave 19 mg (21% of theory) of the title compound.

LC/MS (Method 6, ESIpos): $R_t$=2.17 min; m/z=499 (Cl isotope pattern, M+H)$^+$ $^1$H-NMR (400 MHz, DMSO-d$_6$): δ [ppm]=6.44-6.52 (m, 3H), 7.03 (d, 1H), 7.25 (d, 1H), 7.30 (d, 1H), 7.40-7.55 (m, 4H), 7.70-7.73 (m, 2H), 7.75 (d, 1H), 8.74 (s, 1H), 9.84 (s, 1H), 10.17 (br. s, 1H).

Example 7

4-[(4-Bromo-2-fluoro-5-hydroxyphenyl)amino]-5-oxo-6,11-dihydro-5H-pyrido[2,3-b][1,5]benzodiazepine-8-carbonitrile

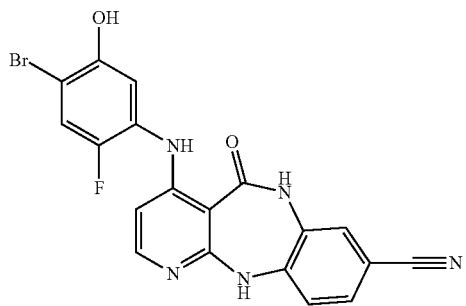 [SMILES: N#Cc1ccc2c(c1)NC(=O)c1c(Nc3cc(O)c(Br)cc3F)ccnc1N2]

A mixture of 4-chloro-5-oxo-6,11-dihydro-5H-pyrido[2,3-b][1,5]benzodiazepine-8-carbonitrile and 4,5-dichloro- 11H-pyrido[2,3-b][1,5]benzodiazepine-8-carbonitrile (Intermediate 10A) (135 mg, 0.50 mmol) and 5-amino-2-bromo-4-fluorophenol (113 mg, 0.55 mmol) were dissolved in isopropanol (3 ml) and a 4 M solution of hydrogen chloride in dioxane (137 µl, 0.55 mmol). The mixture was stirred in a microwave apparatus at 160° C. for 1 h. The reaction mixture was then admixed with saturated aqueous sodium carbonate solution and concentrated. The residue was taken up in DMF and filtered, and the filtrate was concentrated again. Purification by preparative HPLC (Method 14) and subsequent preparative HPLC once again (column: Kinetex C18 5 µm, 100 mm×30 mm; flow rate: 60 ml/min; eluent A: water, eluent B: acetonitrile, eluent C: 1% formic acid in water; gradient: 0-1 min 90% A, 5% B, 5% C, 10 min 0% A, 95% B, 5% C) gave 6 mg (3% of theory) of the title compound.

LC/MS (Method 5, ESIpos): $R_t$=0.87 min, m/z=442 [M+H]$^+$.

$^1$H-NMR (400 MHz, DMSO-d$_6$): δ [ppm]=6.50 (d, 1H), 6.92 (d, 1H), 7.27 (d, 1H), 7.33 (d, 1H), 7.47 (dd, 1H), 7.53 (d, 1H), 7.87 (d, 1H), 8.85 (s, 1H), 9.97 (s, 1H), 10.29 (br. s, 1H).

Example 8

4-[(3,4-Difluoro-5-hydroxyphenyl)amino]-5-oxo-6,11-dihydro-5H-pyrido[2,3-b][1,5]benzodiazepine-8-carbonitrile

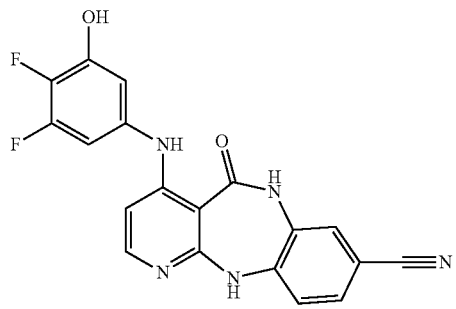 [SMILES: N#Cc1ccc2c(c1)NC(=O)c1c(Nc3cc(O)c(F)c(F)c3)ccnc1N2]

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (135 mg, 0.50 mmol) and 5-amino-2,3-difluorophenol (Intermediate 16A) (80 mg, 0.55 mmol) were dissolved in isopropanol (3 ml) and a 4 M solution of hydrogen chloride in dioxane (137 µl, 0.55 mmol). The mixture was stirred in a microwave apparatus at 160° C. for 1 h. The reaction mixture was then admixed with saturated aqueous sodium carbonate solution and filtered with suction. The residue was washed with water and subjected to preliminary purification by means of chromatography on silica gel (eluent: dichloromethane→dichloromethane/methanol 10:1).

Further purification by means of preparative HPLC twice (first Method 12, then Method 17) gave 76 mg (38% of theory) of the title compound.

LC/MS (Method 8, ESIpos): $R_t$=2.09 min, m/z=380 [M+H]$^+$.

$^1$H-NMR (400 MHz, DMSO-d$_6$): δ [ppm]=6.57-6.62 (m, 2H), 6.69-6.76 (m, 1H), 7.27 (d, 1H), 7.32 (d, 1H), 7.47 (dd, 1H), 7.83 (d, 1H), 8.82 (s, 1H), 9.83 (s, 1H), 10.25 (s, 1H), 10.57 (s, 1H).

Example 9

4-[(3-Hydroxy-5-methoxyphenyl)amino]-5-oxo-6,11-dihydro-5H-pyrido[2,3-b][1,5]benzodiazepine-8-carbonitrile

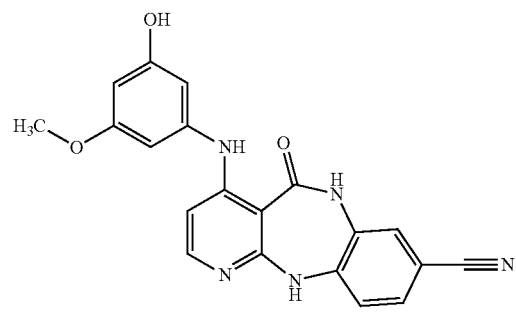 [SMILES: COc1cc(O)cc(Nc2ccnc3c2C(=O)Nc2cc(C#N)ccc2N3)c1]

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (135 mg, 0.50 mmol) and 3-amino-5-methoxyphenol (77 mg, 0.55 mmol) were dissolved in isopropanol (3 ml) and a 4 M solution of hydrogen chloride in dioxane (137 µl, 0.55 mmol). The mixture was stirred in a microwave apparatus at 160° C. for 1 h. The reaction mixture was then admixed with saturated aqueous sodium carbonate solution and the precipitate formed was filtered off with suction. Purification by means of preparative HPLC (Method 12) and subsequent stirring with diethyl ether gave 14 mg (7% of theory) of the title compound.

LC/MS (Method 5, ESIpos): $R_t$=0.69 min, m/z=374 [M+H]$^+$.

$^1$H-NMR (400 MHz, DMSO-d$_6$): δ [ppm]=3.69 (s, 3H), 6.13-6.15 (m, 1H), 6.18-6.22 (m, 2H), 6.67 (d, 1H), 7.26 (d, 1H), 7.32 (d, 1H), 7.46 (dd, 1H), 7.82 (d, 1H), 8.80 (s, 1H), 9.61 (s, 1H), 9.91 (s, 1H), 10.24 (s, 1H).

Example 10

4-[(2,4-Dichloro-5-hydroxyphenyl)amino]-5-oxo-6,11-dihydro-5H-pyrido[2,3-b][1,5]benzodiazepine-8-carbonitrile

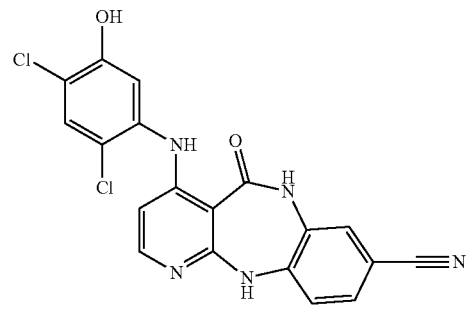 [SMILES: N#Cc1ccc2c(c1)NC(=O)c1c(Nc3cc(O)c(Cl)cc3Cl)ccnc1N2]

A mixture of 4-chloro-5-oxo-6,11-dihydro-5H-pyrido[2,3-b][1,5]benzodiazepine-8-carbonitrile and 4,5-dichloro-1H-pyrido[2,3-b][1,5]benzodiazepine-8-carbonitrile (Intermediate 10A) (80 mg, 0.296 mmol) and 5-amino-2,4-dichlorophenol (58 mg, 0.325 mmol) were dissolved in isopropanol (3 ml) and a 4 M solution of hydrogen chloride in dioxane (37 μl, 0.148 mmol). The mixture was stirred in a microwave apparatus at 160° C. for 1 h. Subsequently, 5-amino-2,4-dichlorophenol (58 mg, 0.325 mmol) and a 4 M solution of hydrogen chloride in dioxane (137 μl, 0.55 mmol) were added again and the mixture was stirred in a microwave at 160° C. for another 1.5 h. The solid formed was then filtered off with suction and washed with acetonitrile. Purification by means of preparative HPLC (column: Kinetex C18 5μ, 100×30 mm; flow rate: 75 ml/min; eluent A: water, eluent B: acetonitrile, eluent C: 1% formic acid in water; gradient: 0-1 min 90% A, 5% B, 5% C, 7.3 min 23.3% A, 71.7% B, 5% C) gave 25 mg (20% of theory) of the title compound.

LC/MS (Method 5, ESIpos): $R_t$=0.91 min, m/z=412 $[M+H]^+$.

$^1$H-NMR (400 MHz, DMSO-$d_6$): δ [ppm]=6.62 (d, 1H), 7.01 (s, 1H), 7.28 (d, 1H), 7.33 (d, 1H), 7.47 (dd, 1H), 7.57 (s, 1H), 7.89 (d, 1H), 8.89 (s, 1H), 10.23 (s, 1H), 10.33 (s, 1H), 10.61 (br. s, 1H).

Example 11

4-[(4-Chloro-3-hydroxyphenyl)amino]-5-oxo-6,11-dihydro-5H-pyrido[2,3-b][1,5]benzodiazepine-8-carbonitrile

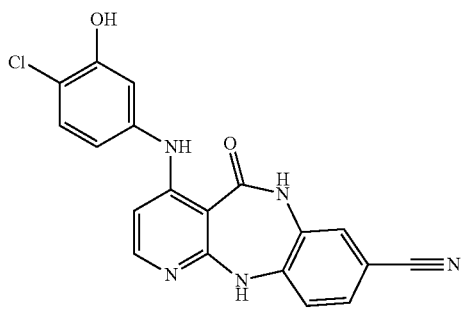 [SMILES: N#Cc1ccc2c(c1)NC(=O)c1c(Nc3ccc(Cl)c(O)c3)ccnc1N2]

A mixture of 4-chloro-5-oxo-6,11-dihydro-5H-pyrido[2,3-b][1,5]benzodiazepine-8-carbonitrile and 4,5-dichloro-1H-pyrido[2,3-b][1,5]benzodiazepine-8-carbonitrile (Intermediate 10A) (80 mg, 0.296 mmol) and 2-chloro-5-aminophenol (47 mg, 0.325 mmol) were dissolved in isopropanol (1.45 ml). A 4 M solution of hydrogen chloride in dioxane (81 μl, 0.325 mmol) was added, and the reaction mixture was stirred in a microwave apparatus at 160° C. for 1 h. After cooling to room temperature, the solids were filtered off with suction and crystallized from isopropanol. 46 mg (41% of theory) of the title compound were obtained.

LC/MS (Method 5, ESIpos): $R_t$=0.78 min, m/z=378 $[M+H]^+$.

$^1$H-NMR (400 MHz, DMSO-$d_6$): δ [ppm]=6.61 (d, 1H), 6.65-6.70 (m, 1H), 6.81 (d, 1H), 7.25 (d, 1H), 7.32-7.38 (m, 2H), 7.51 (d, 1H), 7.85 (d, 1H), 9.23 (s, 1H), 10.23 (s, 1H), 10.37 (s, 1H), 10.44 (s, 1H).

Example 12

4-[(3,4-Dihydroxyphenyl)amino]-5-oxo-6,11-dihydro-5H-pyrido[2,3-b][1,5]benzodiazepine-8-carbonitrile

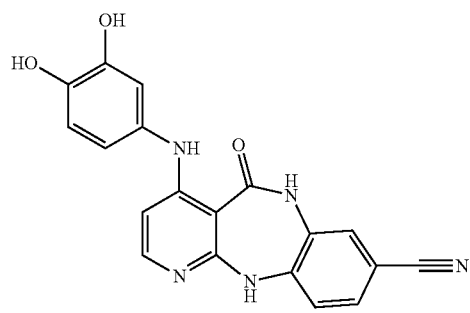 [SMILES: N#Cc1ccc2c(c1)NC(=O)c1c(Nc3ccc(O)c(O)c3)ccnc1N2]

In analogy to Example 11, a mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (80 mg, 0.296 mmol) was reacted with 4-aminocatechol hydrobromide (67 mg, 0.325 mmol). This gave 80 mg (74% of theory) of the title compound.

LC/MS (Method 5, ESIpos): $R_t$=0.55 min, m/z=360 $[M+H]^+$.

$^1$H-NMR (400 MHz, DMSO-$d_6$): δ [ppm]=6.43 (d, 1H), 6.51 (dd, 1H), 6.61 (d, 1H), 66.79 (d, 1H), 7.23 (d, 1H), 7.36-7.41 (m, 2H), 7.55 (dd, 1H), 7.80 (d, 1H), 9.27 (s, 1H), 9.61 (s, 1H), 10.37-10.50 (m, 2H).

Example 13

4-[(2-Fluoro-5-hydroxyphenyl)amino]-5-oxo-6,11-dihydro-5H-pyrido[2,3-b][1,5]benzodiazepine-8-carbonitrile

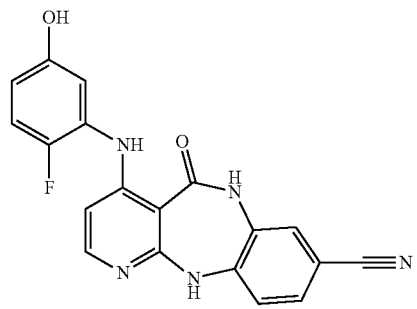

In analogy to Example 11, a mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A) (80 mg, 0.296 mmol) was reacted with 3-amino-4-fluorophenol (Intermediate 17A) (41 mg, 0.325 mmol). This gave 63 mg (59% of theory) of the title compound.

LC/MS (Method 5, ESIpos): $R_t$=0.72 min, m/z=362 $[M+H]^+$.

$^1$H-NMR (400 MHz, DMSO-$d_6$): δ [ppm]=6.48 (d, 1H), 6.60-6.68 (m, 1H), 6.70-6.76 (m, 1H), 7.10-7.20 (m, 1H), 7.26 (d, 1H), 7.35-7.38 (m, 1H), 7.52 (dd, 1H), 7.88 (d, 1H), 9.28 (s, 1H), 9.65 (s, 1H), 10.27 (s, 1H), 10.42 (s, 1H).

Example 14

4-[(5-Hydroxy-2-methylphenyl)amino]-8-{[(2,2,2-trifluoroethyl)amino]methyl}-6,11-dihydro-5H-pyrido[2,3-b][1,5]benzodiazepin-5-one

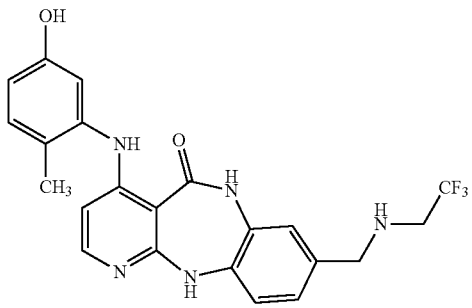 [SMILES: Cc1ccc(O)cc1Nc1ccnc2c1C(=O)Nc1cc(CNCC(F)(F)F)ccc1N2]

4-[(5-Hydroxy-2-methylphenyl)amino]-5-oxo-6,11-dihydro-5H-pyrido[2,3-b][1,5]benzodiazepine-8-carbaldehyde (49.8 mg, 0.138 mmol) from Intermediate 6A and 2,2,2-trifluoroethylamine (20.5 mg, 0.207 mmol) were initially charged in 2.0 ml of ethanol, and acetic acid (12 µl, 0.207 mmol) was added. Sodium cyanoborohydride (17.4 mg, 0.276 mmol) was added and the mixture was left to stir at RT for 2 h. The reaction mixture was then added to saturated aqueous sodium hydrogencarbonate solution and extracted with ethyl acetate. The organic phase was washed with saturated aqueous sodium chloride solution, dried over sodium sulphate and concentrated under reduced pressure. The residue was purified by preparative HPLC. 57.9 mg (85% of theory) of the title compound were obtained.

LC/MS (Method 5, ESIpos): $R_t$=0.73 min, m/z=444 [M+H]$^+$.

$^1$H-NMR (400 MHz, DMSO-d$_6$): δ [ppm]=2.06 (s, 3H), 2.75-2.85 (m, 1H), 3.16 (qd, 2H), 3.67 (d, 2H), 6.30 (d, 1H), 6.54 (dd, 1H), 6.61 (d, 1H), 6.92-6.98 (m, 2H), 7.04-7.09 (m, 2H), 7.75 (d, 1H), 8.10 (s, 1H), 9.35 (s, 1H), 9.85 (s, 1H), 10.08 (s, 1H).

Example 15

8-{[(3-Chlorobenzyl)amino]methyl}-4-[(5-hydroxy-2-methylphenyl)amino]-6,11-dihydro-5H-pyrido[2,3-b][1,5]benzodiazepin-5-one

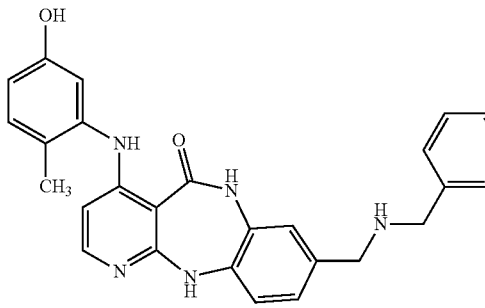

In analogy to Example 14, 4-[(5-hydroxy-2-methylphenyl)amino]-5-oxo-6,11-dihydro-5H-pyrido[2,3-b][1,5]benzodiazepine-8-carbaldehyde (78% purity, 77.0 mg, 0.166 mmol) from Intermediate 6A was reacted with 3-chlorobenzylamine (35 mg, 0.249 mmol). 72.1 mg (88% of theory) of the title compound were obtained.

LC/MS (Method 3, ESIpos): $R_t$=0.69 min, m/z=486 [M+H]$^+$.

$^1$H-NMR (400 MHz, DMSO-d$_6$): δ [ppm]=2.06 (s, 3H), 4.08-4.14 (m, 2H), 4.15-4.21 (m, 2H), 6.27 (d, 1H), 6.59 (d, 1H), 6.64 (dd, 1H), 7.09-7.15 (m, 3H), 7.19 (dd, 1H), 7.42-7.50 (m, 3H), 7.58-7.60 (m, 1H), 7.79 (d, 1H), 8.93 (br. s, 1H), 9.20 (br. s, 1H), 10.25 (br. s, 1H), 10.43 (s, 1H).

Example 16

N$^2$-({4-[(5-Hydroxy-2-methylphenyl)amino]-5-oxo-6,11-dihydro-5H-pyrido[2,3-b][1,5]benzodiazepin-8-yl}methyl)glycinamide

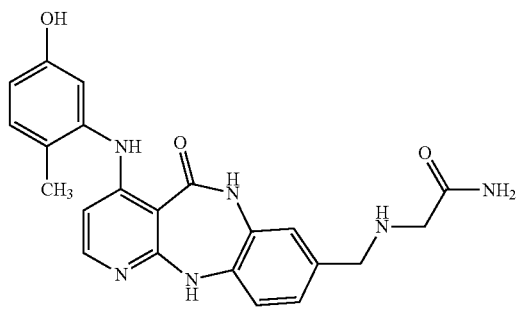 [SMILES: Cc1ccc(O)cc1Nc1ccnc2c1C(=O)Nc1cc(CNCC(N)=O)ccc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (35.0 mg, 0.097 mmol) from Intermediate 6A was reacted with glycinamide hydrochloride (16 mg, 0.146 mmol). 21.6 mg (53% of theory) of the title compound were obtained.

LC/MS (Method 3, ESIpos): $R_t$=0.46 min, m/z=419 [M+H]$^+$.

$^1$H-NMR (400 MHz, DMSO-d$_6$): δ [ppm]=2.06 (s, 3H), 3.13 (s, 2H), 3.67 (s, 2H), 6.30 (d, 1H), 6.54 (dd, 1H), 6.60 (d, 1H), 6.97-7.02 (m, 2H), 7.05-7.10 (m, 2H), 7.16 (br. s, 1H), 7.36 (br. s, 1H), 7.75 (d, 1H), 9.37 (br. s, 1H), 9.85 (s, 1H), 10.11 (s, 1H).

Example 17

8-{[(4-Hydroxybutyl)amino]methyl}-4-[(5-hydroxy-2-methylphenyl)amino]-6,11-dihydro-5H-pyrido[2,3-b][1,5]benzodiazepin-5-one

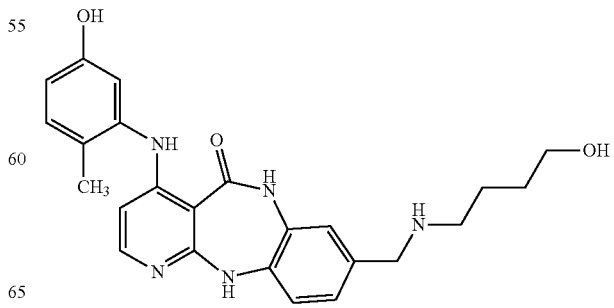

In analogy to Example 14, 4-[(5-hydroxy-2-methylphenyl)amino]-5-oxo-6,11-dihydro-5H-pyrido[2,3-b][1,5]benzodiazepine-8-carbaldehyde (49.8 mg, 0.138 mmol) from Intermediate 6A was reacted with 4-amino-1-butanol (18 mg, 0.207 mmol). 14.0 mg (23% of theory) of the title compound were obtained.

LC/MS (Method 3, ESIpos): $R_t$=0.51 min, m/z=434 [M+H]$^+$.

$^1$H-NMR (400 MHz, DMSO-d$_6$): δ [ppm]=1.39-1.49 (m, 2H), 1.53-1.64 (m, 2H), 2.06 (s, 3H), 2.74-2.83 (m, 2H), 3.39 (t, 1H), 3.91 (s, 2H), 6.30 (d, 1H), 6.55 (dd, 1H), 6.60 (d, 1H), 7.02-7.15 (m, 4H), 7.76 (d, 1H), 8.25 (s, 1H), 9.35 (br. s, 1H), 9.84 (s, 1H), 10.22 (s, 1H).

Example 18

4-[(5-Hydroxy-2-methylphenyl)amino]-8-({[2-(morpholin-4-yl)ethyl]amino}methyl)-6,11-dihydro-5H-pyrido[2,3-b][1,5]benzodiazepin-5-one

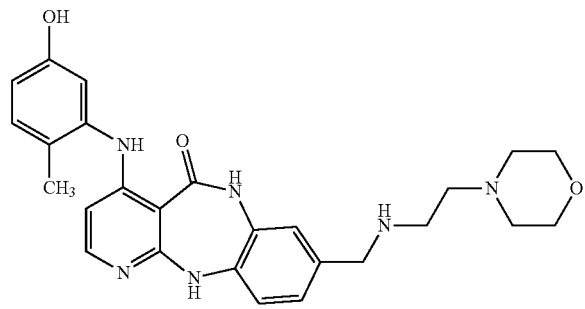 [SMILES: Cc1ccc(O)cc1Nc1ccnc2c1C(=O)Nc1cc(CNCCN3CCOCC3)ccc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (49.8 mg, 0.138 mmol) from Intermediate 6A was reacted with 2-morpholinoethylamine (27 mg, 0.207 mmol). 7.0 mg (11% of theory) of the title compound were obtained.

LC/MS (Method 2, ESIpos): $R_t$=1.07 min, m/z=475 [M+H]$^+$.

$^1$H-NMR (500 MHz, DMSO-d$_6$): δ [ppm]=2.06 (s, 3H), 3.20 (br. s, 4H), 3.32 (s, 4H), 4.15 (s, 2H), 6.26 (d, 1H), 6.60 (d, 1H), 6.69 (dd, 1H), 7.11-7.19 (m, 3H), 7.23 (d, 1H), 7.81 (d, 1H), 9.43 (s, 1H), 10.46 (s, 1H), 10.51 (s, 1H).

Example 19

4-[(5-Hydroxy-2-methylphenyl)amino]-8-[(isopropylamino)methyl]-6,11-dihydro-5H-pyrido[2,3-b][1,5]benzodiazepin-5-one

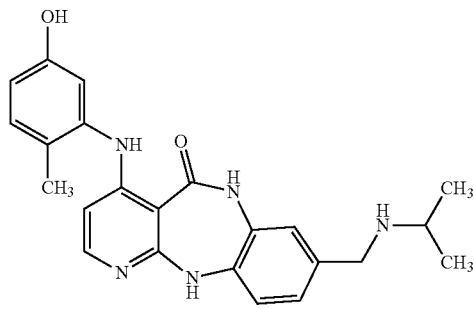 [SMILES: Cc1ccc(O)cc1Nc1ccnc2c1C(=O)Nc1cc(CNC(C)C)ccc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (49.8 mg, 0.138 mmol) from Intermediate 6A was reacted with isopropylamine (12 mg, 0.207 mmol). 28.0 mg (50% of theory) of the title compound were obtained.

LC/MS (Method 2, ESIpos): $R_t$=1.12 min, m/z=404 [M+H]$^+$.

$^1$H-NMR (400 MHz, DMSO-d$_6$): δ [ppm]=1.12 (d, 6H), 2.06 (s, 3H), 2.91-3.02 (m, 1H), 3.80 (s, 2H), 6.30 (d, 1H), 6.54 (dd, 1H), 6.60 (d, 1H), 7.00-7.14 (m, 4H), 7.75 (d, 1H), 8.18 (s, 1H), 8.25 (s, 2H), 9.84 (s, 1H), 10.16 (s, 1H).

Example 20

8-[(Cyclobutylamino)methyl]-4-[(5-hydroxy-2-methylphenyl)amino]-6,11-dihydro-5H-pyrido[2,3-b][1,5]benzodiazepin-5-one

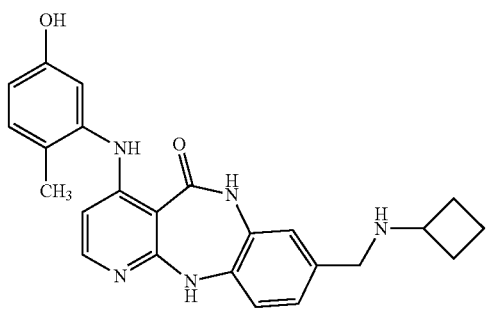 [SMILES: Cc1ccc(O)cc1Nc1ccnc2c1C(=O)Nc1cc(CNC3CCC3)ccc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (49.8 mg, 0.138 mmol) from Intermediate 6A was reacted with cyclobutylamine (15 mg, 0.207 mmol). 22.4 mg (37% of theory) of the title compound were obtained.

LC/MS (Method 3, ESIpos): $R_t$=0.58 min, m/z=416 [M+H]$^+$.

$^1$H-NMR (400 MHz, DMSO-d$_6$): δ [ppm]=1.51-1.69 (m, 2H), 1.69-1.82 (m, 2H), 2.02-2.11 (m, 2H), 2.06 (s, 3H), 3.57 (s, 2H), 6.30 (d, 1H), 6.54 (dd, 1H), 6.60 (d, 1H), 6.94-6.99 (m, 2H), 7.03-7.09 (m, 2H), 7.73-7.77 (m, 1H), 8.11 (s, 1H), 8.18 (s, 1H), 9.85 (s, 1H), 10.10 (s, 1H).

Example 21

4-[(5-Hydroxy-2-methylphenyl)amino]-8-{[(3-hydroxypropyl)amino]methyl}-6,11-dihydro-5H-pyrido[2,3-b][1,5]benzodiazepin-5-one

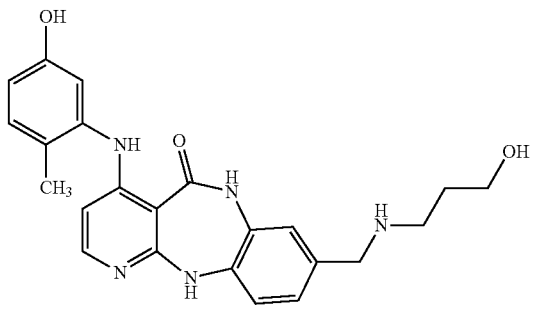 [SMILES: Cc1ccc(O)cc1Nc1ccnc2c1C(=O)Nc1cc(CNCCCO)ccc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (50.0 mg, 0.139 mmol) from Intermediate 6A was reacted with 3-amino-1-propanol (15 mg, 0.208 mmol). 31.4 mg (53% of theory) of the title compound were obtained.

LC/MS (Method 2, ESIpos): $R_t$=1.07 min, m/z=418 [M+H]$^+$.

$^1$H-NMR (400 MHz, DMSO-d$_6$): δ [ppm]=1.58-1.66 (m, 2H), 2.06 (s, 3H), 2.65 (t, 2H), 3.45 (t, 2H), 3.72 (s, 2H), 6.30 (d, 1H), 6.54 (dd, 1H), 6.60 (d, 1H), 6.98-7.03 (m, 2H), 7.05-7.10 (m, 2H), 7.75 (d, 1H), 8.15 (s, 1H), 8.24 (s, 2H), 9.85 (s, 1H), 10.13 (s, 1H).

Example 22

4-[(5-Hydroxy-2-methylphenyl)amino]-8-[(methylamino)methyl]-6,11-dihydro-5H-pyrido[2,3-b][1,5]benzodiazepin-5-one

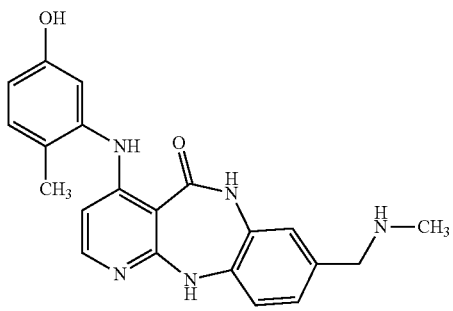 [SMILES: CNCc1ccc2c(c1)NC(=O)c1c(Nc3cc(O)ccc3C)ccnc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (50.0 mg, 0.139 mmol) from Intermediate 6A was reacted with methylamine hydrochloride (14 mg, 0.208 mmol). 21.0 mg (36% of theory) of the title compound were obtained.

LC/MS (Method 3, ESIpos): $R_t$=0.50 min, m/z=376 [M+H]$^+$.

$^1$H-NMR (400 MHz, DMSO-d$_6$): δ [ppm]=2.06 (s, 3H), 2.28 (s, 3H), 3.60 (s, 2H), 6.30 (d, 1H), 6.54 (dd, 1H), 6.60 (d, 1H), 6.92-6.99 (m, 2H), 7.04-7.10 (m, 2H), 7.75 (d, 1H), 8.11 (s, 1H), 9.33 (s, 1H), 9.85 (s, 1H), 10.10 (s, 1H).

Example 23

8-[(Butylamino)methyl]-4-[(5-hydroxy-2-methylphenyl)amino]-6,11-dihydro-5H-pyrido[2,3-b][1,5]benzodiazepin-5-one

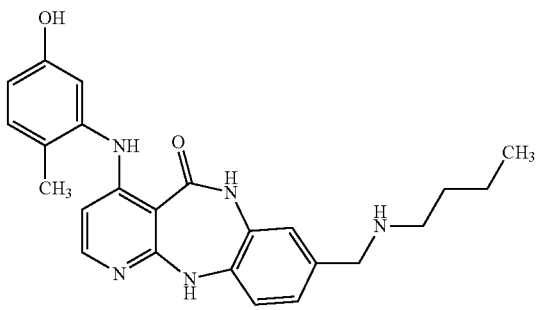 [SMILES: CCCCNCc1ccc2c(c1)NC(=O)c1c(Nc3cc(O)ccc3C)ccnc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (50.0 mg, 0.139 mmol) from Intermediate 6A was reacted with n-butylamine (15 mg, 0.208 mmol). 18.5 mg (30% of theory) of the title compound were obtained.

LC/MS (Method 3, ESIpos): $R_t$=0.61 min, m/z=418 [M+H]$^+$.

$^1$H-NMR (400 MHz, DMSO-d$_6$): δ [ppm]=0.86 (t, 3H), 1.24-1.35 (m, 2H), 1.44 (d, 2H), 2.06 (s, 3H), 2.58 (t, 2H), 3.72 (s, 2H), 6.30 (d, 1H), 6.54 (dd, 1H), 6.60 (d, 1H), 6.98-7.03 (m, 2H), 7.05-7.10 (m, 2H), 7.75 (d, 1H), 8.14 (s, 1H), 8.27 (s, 1H), 9.85 (s, 1H), 10.13 (s, 1H).

Example 24

8-{[(2-Hydroxyethyl)amino]methyl}-4-[(5-hydroxy-2-methylphenyl)amino]-6,11-dihydro-5H-pyrido[2,3-b][1,5]benzodiazepin-5-one

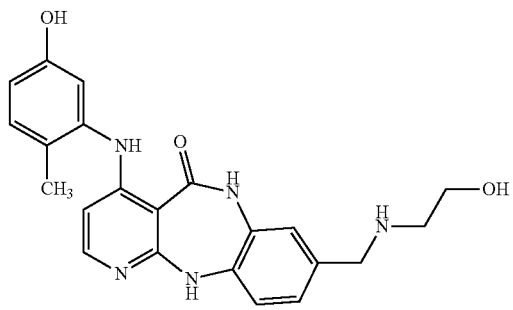 [SMILES: Cc1ccc(O)cc1Nc1ccnc2c1C(=O)Nc1cc(CNCCO)ccc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (50.0 mg, 0.139 mmol) from Intermediate 6A was reacted with ethanolamine (13 mg, 0.208 mmol) overnight. 7.8 mg (13% of theory) of the title compound were obtained.

LC/MS (Method 3, ESIpos): $R_t$=0.50 min, m/z=406 [M+H]$^+$.

$^1$H-NMR (400 MHz, DMSO-d$_6$): δ [ppm]=2.06 (s, 3H), 2.57 (t, 2H), 3.44-3.49 (m, 2H), 3.63 (s, 2H), 4.51 (br. s, 1H), 6.30 (d, 1H), 6.54 (dd, 1H), 6.60 (d, 1H), 6.95-6.99 (m, 2H), 7.03-7.09 (m, 2H), 7.74 (d, 1H), 8.09 (s, 1H), 9.33 (br. s, 1H), 9.85 (s, 1H), 10.08 (s, 1H).

Example 25

8-[(Ethylamino)methyl]-4-[(5-hydroxy-2-methylphenyl)amino]-6,11-dihydro-5H-pyrido[2,3-b][1,5]benzodiazepin-5-one

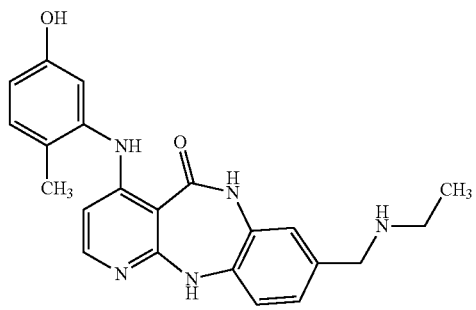 [SMILES: CCNCc1ccc2c(c1)NC(=O)c1c(Nc3cc(O)ccc3C)ccnc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (50.0 mg, 0.139 mmol) from Intermediate 6A was reacted with ethylamine (9 mg, 0.208 mmol) overnight. 15.5 mg (27% of theory) of the title compound were obtained.

LC/MS (Method 3, ESIpos): $R_t$=0.51 min, m/z=390 [M+H]$^+$.

$^1$H-NMR (400 MHz, DMSO-d$_6$): δ [ppm]=1.08 (t, 3H), 2.06 (s, 3H), 2.67 (q, 2H), 3.76 (s, 2H), 6.30 (d, 1H), 6.54 (dd, 1H), 6.60 (d, 1H), 6.99-7.05 (m, 2H), 7.06-7.11 (m, 2H), 7.75 (d, 1H), 8.16 (s, 1H), 8.23-8.25 (m, 1H), 9.84 (s, 1H), 10.15 (s, 1H).

Example 26

8-Anilinomethyl-4-[(5-hydroxy-2-methylphenyl)amino]-6,11-dihydro-5H-pyrido[2,3-b][1,5]benzodiazepin-5-one

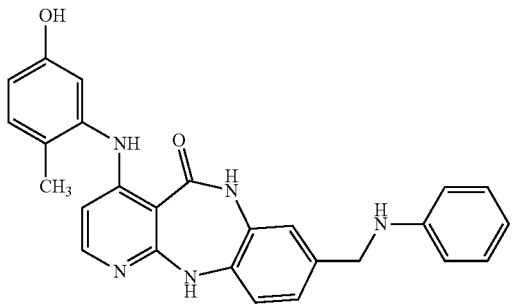 [SMILES: Cc1ccc(O)cc1Nc1ccnc2c1C(=O)Nc1cc(CNc3ccccc3)ccc1N2]

In analogy to Example 14, 4-[(5-hydroxy-2-methylphenyl)amino]-5-oxo-6,11-dihydro-5H-pyrido[2,3-b][1,5]benzodiazepine-8-carbaldehyde (73.9 mg, 0.205 mmol) from Intermediate 6A was reacted with aniline (28.6 mg, 0.308 mmol) overnight. 22.4 mg (24% of theory) of the title compound were obtained.

LC/MS (Method 9, ESIpos): $R_t$=0.94 min, m/z=438 [M+H]$^+$.

$^1$H-NMR (400 MHz, DMSO-d$_6$): δ [ppm]=2.06 (s, 3H), 4.13 (d, 2H), 6.11 (t, 1H), 6.29 (d, 1H), 6.47-6.56 (m, 4H), 6.60 (d, 1H), 6.97-7.09 (m, 6H), 7.74 (d, 1H), 8.07 (s, 1H), 9.31 (br. s, 1H), 9.84 (s, 1H), 10.08 (s, 1H).

Example 27

4-[(2-Fluoro-5-hydroxy-4-methylphenyl)amino]-5-oxo-6,11-dihydro-5H-pyrido[2,3-b][1,5]benzodiazepine-8-carbonitrile

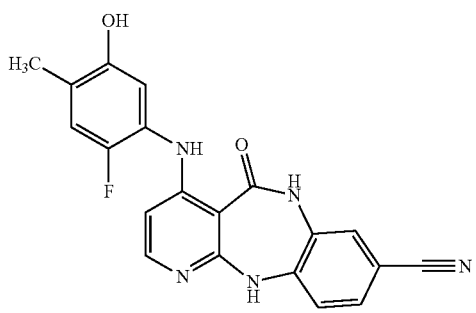 [SMILES: Cc1cc(F)c(Nc2ccnc3c2C(=O)Nc2cc(C#N)ccc2N3)cc1O]

Method A:

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (3.14 g, 11.6 mmol) from Intermediate 10A and 5-amino-4-fluoro-2-methylphenol (1.80 g, 12.8 mmol) was initially charged in 36 ml of isopropanol. 3.2 ml of a 4 M solution of hydrogen chloride in dioxane were added and the mixture was heated in a microwave apparatus to 160° C. for 20 min. Thereafter, the reaction mixture was diluted with water and stirred for 10 min. The precipitate formed was filtered off with suction and dried under reduced pressure. This gave 3.57 g (71% of theory) of the title compound in 87% purity.

Method B:

A mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (Intermediate 10A; 9.0 g, 33.3 mmol) and also pyridinium hydrochloride (3.84 g, 33.3 mmol) and 5-amino-4-fluoro-2-methylphenol (5.16 g, 36.6 mmol) were taken up in 2-ethoxyethanol (210 ml) and then stirred at bath temperature 150° C. for 1 h. After cooling, the mixture was poured onto 600 ml of water and stirred at room temperature for 1 h, and then the precipitate was filtered off with suction. The moist product was stirred with methanol for 10 h, filtered off with suction again, washed and dried under reduced pressure. Yield: 7.7 g (62% of theory).

LC/MS (Method 5, ESIpos): $R_t$=0.82 min, m/z=376 [M+H]$^+$.

$^1$H-NMR (400 MHz, DMSO-d$_6$): δ [ppm]=2.11 (s, 3H), 6.38 (dd, 1H), 6.72 (d, 1H), 7.05 (d, 1H), 7.26 (d, 1H), 7.33 (d, 1H), 7.47 (dd, 1H), 7.82 (d, 1H), 8.83 (s, 1H), 9.46 (s, 1H), 9.89 (s, 1H), 10.27 (s, 1H).

Example 28

8-[(Diethylamino)methyl]-4-[(2-fluoro-5-hydroxy-4-methylphenyl)amino]-6,11-dihydro-5H-pyrido[2,3-b][1,5]benzodiazepin-5-one

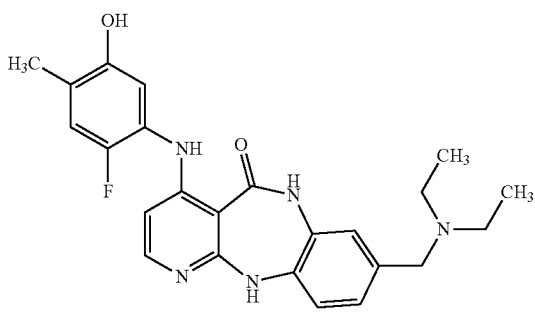 [SMILES: CCN(CC)Cc1ccc2c(c1)NC(=O)c1c(Nc3cc(O)c(C)cc3F)ccnc1N2]

Method A:

4-[(2-Fluoro-5-hydroxy-4-methylphenyl)amino]-5-oxo-6,11-dihydro-5H-pyrido[2,3-b][1,5]benzodiazepine-8-carbaldehyde (3.61 g, 9.54 mmol) from Intermediate 11A was dissolved in 94 ml of DMF. Diethylamine (2.79 g, 38.2 mmol) and trimethyl orthoformate (20.3 g, 191 mmol) were added, and the reaction mixture was stirred at RT for 1 h. Thereafter, sodium triacetoxyborohydride (8.09 g, 38.2 mmol) was added and stirring of the mixture continued at RT overnight. The reaction mixture was then poured onto 1 litre of aqueous sodium hydrogencarbonate solution and left to stir for 30 min. The precipitate formed was filtered off with suction, then stirred twice in succession with methanol and filtered off with suction again each time. The residue was purified by flash chromatography on 340 g of silica gel (eluent: dichloromethane/methanol; gradient: 2 CV 5% methanol, 8 CV gradient 5%→20% methanol, 2 CV 20% methanol, 3.1 CV 50% methanol; flow rate: 100 ml/min). This gave 1.84 g (44% of theory) of the title compound as colourless crystals. In order to remove trapped methanol, the product was boiled in water/isopropanol (5:1) and filtered off. Drying left 1.60 g (38% of theory) of the title compound.
Method B:

4-Chloro-8-[(diethylamino)methyl]-6,11-dihydro-5H-pyrido[2,3-b][1,5]benzodiazepin-5-one (Intermediate 54; 1.31 g, 3.95 mmol) was divided between two microwave reaction vessels (650 mg in each case) and dissolved in DMF (15 ml in each case), and pyridinium chloride (in each case 320 mg, 2.77 mmol) and 5-amino-4-fluoro-2-methylphenol (in each case 283 mg, 2.08 mmol) were added. The mixtures were heated in a microwave reactor to 140° C. for 1 h. After cooling, the reaction mixtures were combined and added to saturated aqueous sodium hydrogencarbonate solution. The solids were filtered off, dried and then purified in three portions by means of column chromatography on silica gel (50 g of silica gel, eluent: 5-15% methanol in dichloromethane). In this way, a first fraction of the title compound (994 mg, 58% of theory) was obtained. The mother liquor obtained beforehand was extracted with ethyl acetate, and the combined organic phases were washed with saturated aqueous sodium chloride solution, dried over magnesium sulphate and concentrated. Purification of the residue by means of column chromatography on silica gel (50 g of silica gel, eluent: 5-15% methanol in dichloromethane) gave a second fraction of the title compound (232 mg, 13% of theory).

LC/MS (Method 5, ESIpos): $R_t$=0.60 min, m/z=436 [M+H]$^+$.

$^1$H-NMR (400 MHz, DMSO-d$_6$): δ [ppm]=0.96 (t, 6H), 2.10 (s, 3H), 2.42 (q, 4H), 3.40 (s, 2H), 6.38 (dd, 1H), 6.73 (d, 1H), 6.93 (dd, 1H), 6.96 (d, 1H), 7.03 (d, 1H), 7.05 (d, 1H), 7.79 (d, 1H), 8.13 (s, 1H), 9.44 (s, 1H), 9.88 (s, 1H), 10.10 (s, 1H).

Example 29

4-[(2-Fluoro-5-hydroxy-4-methylphenyl)amino]-8-(morpholin-4-ylmethyl)-6,11-dihydro-5H-pyrido[2,3-b][1,5]benzodiazepin-5-one

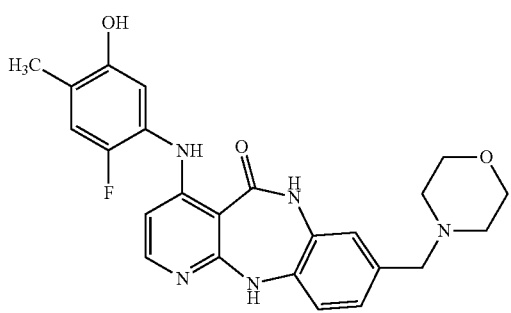 [SMILES: Cc1cc(F)c(Nc2ccnc3c2C(=O)Nc2cc(CN4CCOCC4)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (110 mg, 0.291 mmol) from Intermediate 11A was dissolved in 2.75 ml of DMF. Morpholine (101 mg, 1.16 mmol) and trimethyl orthoformate (617 mg, 5.81 mmol) were added, and the reaction mixture was stirred at RT for 1 h. Thereafter, sodium triacetoxyborohydride (246 mg, 1.16 mmol) was added and stirring of the mixture continued at RT overnight. The reaction solution was then taken up in water/ethyl acetate and the phases were separated. The organic phase was washed with saturated aqueous sodium chloride solution and dried over sodium sulphate. After the solvent had been removed under reduced pressure, the residue was purified by flash chromatography on 25 g of silica gel (eluent: dichloromethane/methanol; gradient: 2.5 CV 5% methanol, 6 CV 10% methanol, 7 CV 20% methanol, 4.5 CV 35% methanol; flow rate: 15 ml/min). This gave 30.3 mg (22% of theory) of the title compound as a yellowish solid.

LC/MS (Method 5, ESIneg): $R_t$=0.60 min, m/z=448 [M−H]$^−$.

$^1$H-NMR (400 MHz, DMSO-d$_6$): δ [ppm]=2.10 (s, 3H), 2.28-2.36 (m, 4H), 3.51-3.59 (m, 4H), 6.37 (dd, 1H), 6.72 (d, 1H), 6.90-6.97 (m, 2H), 7.01-7.08 (m, 2H), 7.79 (d, 1H), 8.16 (s, 1H), 9.44 (s, 1H), 9.85 (s, 1H), 10.11 (s, 1H).

Example 30

8-[(Cyclopropylamino)methyl]-4-[(2-fluoro-5-hydroxy-4-methylphenyl)amino]-6,11-dihydro-5H-pyrido[2,3-b][1,5]benzodiazepin-5-one

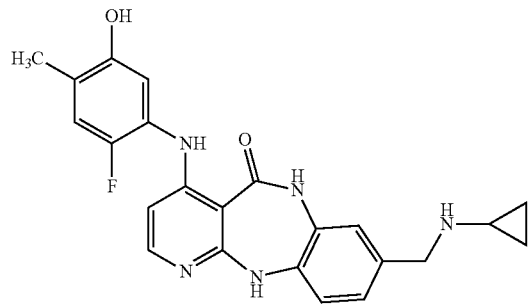 [SMILES: Cc1cc(F)c(Nc2ccnc3c2C(=O)Nc2cc(CNC4CC4)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (50 mg, 0.13 mmol) from Intermediate 11A was initially charged in 1.25 ml of THF and 125 μl of acetic acid. Cyclopropylamine (30 mg, 0.53 mmol) was added and the mixture was left to stir at RT for 1 h. Thereafter, sodium triacetoxyborohydride (112 mg, 0.53 mmol) was added and stirring of the mixture continued at RT overnight. The reaction solution was then admixed with aqueous sodium hydrogencarbonate solution and then extracted three times with ethyl acetate/THF (2:1). The combined organic phases were washed with water and saturated sodium chloride solution, dried over sodium sulphate and concentrated under reduced pressure. The residue was chromatographed on 10 g of silica gel (eluent A: dichloromethane, eluent B: dichloromethane/methanol 1:1; gradient: 3.0 CV 10% B, 13.5 CV gradient 10%→55% B, 7.5 CV 55% B; flow rate: 15 ml/min). This gave 16.6 mg (30% of theory) of the title compound as a colourless solid.

LC/MS (Method 5, ESIpos): $R_t$=0.56 min, m/z=420 [M+H]$^+$.

$^1$H-NMR (400 MHz, DMSO-d$_6$): δ [ppm]=0.20-0.26 (m, 2H), 0.31-0.37 (m, 2H), 1.99-2.07 (m, 1H), 2.10 (s, 3H), 3.61 (s, 2H), 6.37 (dd, 1H), 6.72 (d, 1H), 6.93-6.98 (m, 2H), 7.01-7.06 (m, 2H), 7.78 (d, 1H), 8.11 (s, 1H), 9.43 (s, 1H), 9.84 (s, 1H), 10.10 (s, 1H).

Example 31

8-[(Ethylamino)methyl]-4-[(2-fluoro-5-hydroxy-4-methylphenyl)amino]-6,11-dihydro-5H-pyrido[2,3-b][1,5]benzodiazepin-5-one

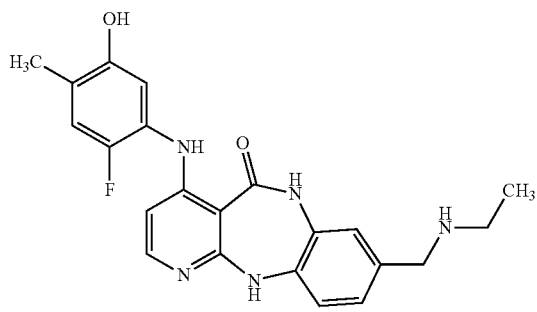 [SMILES: CCNCc1ccc2c(c1)NC(=O)c1c(Nc3cc(O)c(C)cc3F)ccnc1N2]

4-[(2-Fluoro-5-hydroxy-4-methylphenyl)amino]-5-oxo-6,11-dihydro-5H-pyrido[2,3-b][1,5]benzodiazepine-8-carbaldehyde (60 mg, 0.16 mmol) from Intermediate 11A was initially charged in 1.5 ml of DMF. Acetic acid (150 μl, 2.62 mmol) and a 2 M solution of ethylamine in THF (95 μl, 0.19 mmol) were added and the mixture was stirred at RT for 2 h. Then sodium triacetoxyborohydride (134 mg, 0.63 mmol) was added and the mixture was stirred at RT for a further 2 h. Thereafter, aqueous sodium hydrogencarbonate solution was added and the mixture was extracted three times with THF/ethyl acetate. The combined organic phases were washed with water and saturated sodium chloride solution and dried over sodium sulphate. After concentrating under reduced pressure, the residue was stirred with tert-butyl methyl ether/dichloromethane and the solids were filtered off with suction. In this way, 26.4 mg (41% of theory) of the title compound were obtained.

LC/MS (Method 5, ESIpos): $R_t$=0.59 min, m/z=408 [M+H]$^+$.

$^1$H-NMR (400 MHz, DMSO-$d_6$): δ [ppm]=1.17 (t, 3H), 2.10 (s, 3H), 2.90 (q, 2H), 3.99 (s, 2H), 6.37 (dd, 1H), 6.72 (d, 1H), 7.02-7.08 (m, 2H), 7.12-7.18 (m, 2H), 7.80 (d, 1H), 8.33 (s, 1H), 9.46 (s, 1H), 9.81 (s, 1H), 10.30 (s, 1H).

Example 32

4-[(2-Fluoro-5-hydroxy-4-methylphenyl)amino]-8-(pyrrolidin-1-ylmethyl)-6,11-dihydro-5H-pyrido[2,3-b][1,5]benzodiazepin-5-one

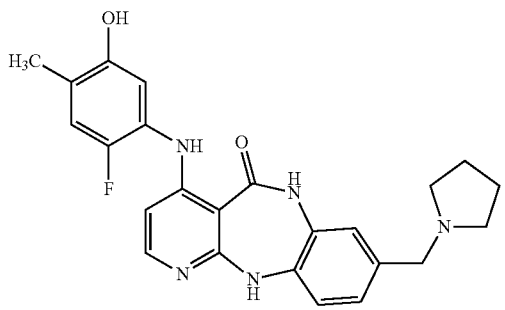 [SMILES: Cc1cc(F)c(Nc2ccnc3c2C(=O)Nc2cc(CN4CCCC4)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (100 mg, 0.264 mmol) from Intermediate 11A was dissolved in 2.5 ml of DMF. Pyrrolidine (75.2 mg, 1.06 mmol) and trimethyl orthoformate (561 mg, 5.29 mmol) were added, and the reaction mixture was stirred at RT for 1 h. Thereafter, sodium triacetoxyborohydride (224 mg, 1.06 mmol) was added and stirring of the mixture continued at RT overnight. The mixture was then poured onto aqueous sodium hydrogencarbonate solution and extracted three times with ethyl acetate/THF (2:1). The combined organic phases were washed with water and saturated sodium chloride solution, dried over sodium sulphate and concentrated under reduced pressure. The residue was crystallized from tert-butyl methyl ether/dichloromethane. The product thus obtained was purified further by chromatography on 10 g of silica gel (eluent A: dichloromethane, eluent B: dichloromethane/methanol 5:1; gradient: 3.5 CV 20% B, 6.5 CV 40% B, 6.5 CV 55% B, 7.5 CV 70% B, 5.0 CV 100% B; flow rate: 20 ml/min). This gave 19.5 mg (16% of theory) of the title compound as colourless crystals.

LC/MS (Method 5, ESIpos): $R_t$=0.60 min, m/z=434 [M+H]$^+$.

$^1$H-NMR (400 MHz, DMSO-$d_6$): δ [ppm]=1.65-1.69 (m, 4H), 2.10 (s, 3H), 2.36-2.41 (m, 4H), 3.44 (s, 2H), 6.38 (dd, 1H), 6.72 (d, 1H), 6.90-6.96 (m, 2H), 7.01-7.06 (m, 2H), 7.79 (d, 1H), 8.14 (s, 1H), 9.43 (s, 1H), 9.86 (s, 1H), 10.09 (s, 1H).

Example 33

8-[(Dimethylamino)methyl]-4-[(2-fluoro-5-hydroxy-4-methylphenyl)amino]-6,11-dihydro-5H-pyrido[2,3-b][1,5]benzodiazepin-5-one

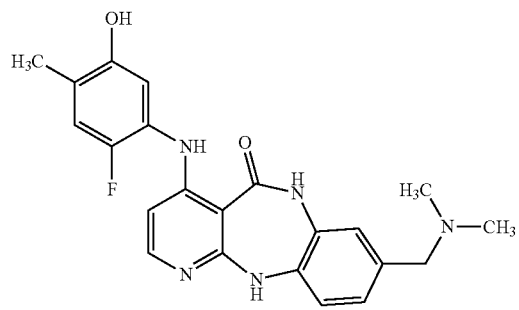

4-[(2-Fluoro-5-hydroxy-4-methylphenyl)amino]-5-oxo-6,11-dihydro-5H-pyrido[2,3-b][1,5]benzodiazepine-8-carbaldehyde (100 mg, 0.264 mmol) from Intermediate 11A was dissolved in 2.5 ml of DMF. A 2 M solution of dimethylamine in THF (529 μl, 1.06 mmol) and trimethyl orthoformate (561 mg, 5.29 mmol) were added, and the reaction mixture was stirred at RT for 1 h. Thereafter, sodium triacetoxyborohydride (224 mg, 1.06 mmol) was added and stirring of the mixture continued at RT overnight. The mixture was then poured onto aqueous sodium hydrogencarbonate solution and extracted three times with ethyl acetate/THF (2:1). The combined organic phases were washed with water and saturated sodium chloride solution, dried over sodium sulphate and concentrated under reduced pressure. The residue was crystallized from tert-butyl methyl ether/dichloromethane. This material was partly dissolved in a little acetonitrile, water was added and then the mixture was lyophilized. This gave 60.5 mg (53% of theory) of the title compound as yellow lyophilizate.

LC/MS (Method 5, ESIpos): $R_t$=0.56 min, m/z=408 [M+H]$^+$.

$^1$H-NMR (400 MHz, DMSO-d$_6$): δ [ppm]=2.10 (s, 3H), 2.12 (s, 6H), 3.28 (s, 2H), 6.38 (dd, 1H), 6.72 (d, 1H), 6.89-6.95 (m, 2H), 7.01-7.07 (m, 2H), 7.79 (d, 1H), 8.16 (s, 1H), 9.44 (s, 1H), 9.87 (s, 1H), 10.11 (s, 1H).

Example 34

8-[(Cyclopentylamino)methyl]-4-[(2-fluoro-5-hydroxy-4-methylphenyl)amino]-6,11-dihydro-5H-pyrido[2,3-b][1,5]benzodiazepin-5-one acetic acid salt

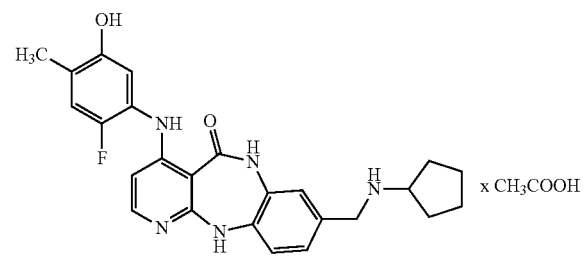 [SMILES: Cc1cc(F)c(Nc2ccnc3c2C(=O)Nc2cc(CNC4CCCC4)ccc2N3)cc1O]

In analogy to Example 31, 4-[(2-fluoro-5-hydroxy-4-methylphenyl)amino]-5-oxo-6,11-dihydro-5H-pyrido[2,3-b][1,5]benzodiazepine-8-carbaldehyde (60 mg, 0.16 mmol) from Intermediate 11A was reacted with cyclobutylamine (16 mg, 0.19 mmol). 34.1 mg (40% of theory) of the title compound were obtained.

LC/MS (Method 5, ESIpos): $R_t$=0.61 min, m/z=448 [M+H]$^+$.

$^1$H-NMR (400 MHz, DMSO-d$_6$): δ [ppm]=1.43-1.60 (m, 4H), 1.61-1.71 (m, 2H), 1.85-1.95 (m, 2H), 2.10 (s, 3H), 3.91 (br. s, 2H), 6.37 (dd, 2H), 6.54 (s, 1H), 6.72 (d, 1H), 7.02-7.07 (m, 2H), 7.10-7.15 (m, 2H), 7.80 (d, 1H), 8.29 (br. s, 1H), 9.46 (s, 1H), 9.82 (s, 1H), 10.25 (s, 1H).

Example 35

4-[(3-Hydroxyphenyl)amino]-5-oxo-6,11-dihydro-5H-pyrido[2,3-b][1,5]benzodiazepine-8-carbonitrile

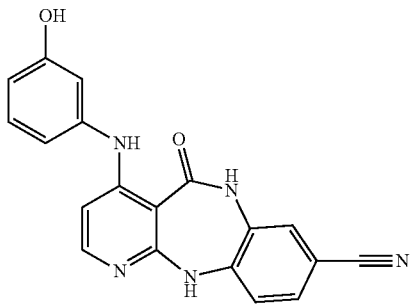 [SMILES: N#Cc1ccc2c(c1)NC(=O)c1c(Nc3cccc(O)c3)ccnc1N2]

A 1:1 mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (100 mg, 0.37 mmol) from Intermediate 10A and 3-aminophenol (44 mg, 0.41 mmol) was initially charged in 2.0 ml of isopropanol. 102 µl of a 4 M solution of hydrogen chloride in dioxane were added and the mixture was heated in a microwave apparatus to 160° C. for 20 min. Thereafter, the reaction mixture was diluted with 10 ml of water, and 2 drops of saturated aqueous sodium carbonate solution were added. The mixture was left to stir for 10 min, then the precipitate formed was filtered off with suction and washed with acetonitrile. The solids were stirred with acetonitrile and a few drops of methanol, filtered off with suction again and then dried under reduced pressure. 55.6 mg (42% of theory) of the title compound were obtained.

LC/MS (Method 5, ESIpos): $R_t$=0.69 min, m/z=344 [M+H]$^+$.

$^1$H-NMR (400 MHz, DMSO-d$_6$): δ [ppm]=6.60 (d, 1H), 6.62-6.73 (m, 3H), 7.23 (d, 1H), 7.27 (d, 1H), 7.40 (d, 1H), 7.56 (dd, 1H), 7.87 (d, 1H), 9.79 (br. s, 2H), 10.45-10.52 (m, 1H), 10.59 (br. s, 1H).

Example 36

4-[(2-Chloro-5-hydroxyphenyl)amino]-5-oxo-6,11-dihydro-5H-pyrido[2,3-b][1,5]benzodiazepine-8-carbonitrile

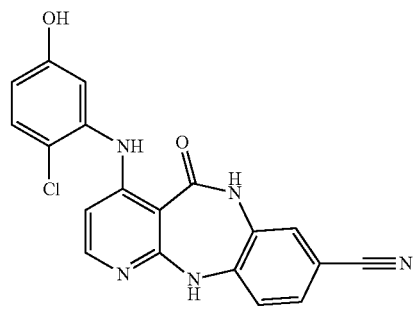

A 1:1 mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (100 mg, 0.37 mmol) from Intermediate 10A and 3-amino-4-chlorophenol (58 mg, 0.41 mmol) was initially charged in 2.0 ml of isopropanol. 102 µl of a 4 M solution of hydrogen chloride in dioxane were added and the mixture was heated in a microwave apparatus to 160° C. for 20 min. Thereafter, the reaction mixture was diluted with 10 ml of water, and 2 drops of saturated aqueous sodium carbonate solution were added. The mixture was left to stir for 10 min, then the precipitate formed was filtered off with suction and washed with acetonitrile. The solids were stirred with acetonitrile and a few drops of methanol, filtered off with suction again and then dried under reduced pressure. 55.4 mg (36% of theory) of the title compound were obtained.

LC/MS (Method 5, ESIpos): $R_t$=0.80 min, m/z=378 [M+H]$^+$.

$^1$H-NMR (400 MHz, DMSO-d$_6$): δ [ppm]=6.59 (dd, 1H), 6.62 (d, 1H), 6.81 (d, 1H), 7.28 (d, 1H), 7.31-7.35 (m, 2H), 7.48 (dd, 1H), 7.89 (d, 1H), 8.89 (s, 1H), 9.86 (br. s, 1H), 10.24 (s, 1H), 10.34 (br. s, 1H).

Example 37

4-[(4-Chloro-2-fluoro-5-hydroxyphenyl)amino]-5-oxo-6,11-dihydro-5H-pyrido[2,3-b][1,5]benzodiazepine-8-carbonitrile

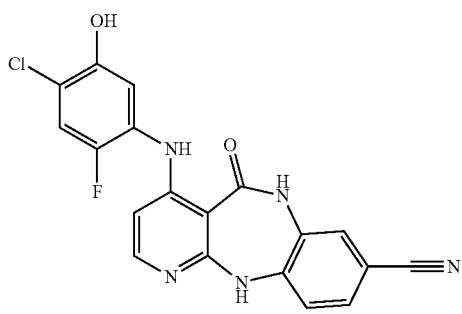 [SMILES: N#Cc1ccc2c(c1)NC(=O)c1c(Nc3cc(O)c(Cl)cc3F)ccnc1N2]

A 1:1 mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (100 mg, 0.37 mmol) from Intermediate 10A and 5-amino-2-chloro-4-fluorophenol (66 mg, 0.41 mmol) was initially charged in 2.0 ml of isopropanol. 102 µl of a 4 M solution of hydrogen chloride in dioxane were added and the mixture was heated in a microwave apparatus to 160° C. for 20 min. Thereafter, the reaction mixture was diluted with 10 ml of water, and 2 drops of saturated aqueous sodium carbonate solution were added. The mixture was left to stir for 10 min, then the precipitate formed was filtered off with suction and washed with acetonitrile. The solids were stirred with acetonitrile and a few drops of methanol, filtered off with suction again and then dried under reduced pressure. 91.8 mg (57% of theory) of the title compound were obtained.

LC/MS (Method 5, ESIpos): $R_t$=0.87 min, m/z=396 [M+H]$^+$.

$^1$H-NMR (400 MHz, DMSO-d$_6$): δ [ppm]=6.49 (d, 1H), 6.95 (d, 1H), 7.27 (d, 1H), 7.37 (s, 1H), 7.49 (d, 1H), 7.52 (d, 1H), 7.90 (d, 1H), 9.38 (br. s, 1H), 10.26 (br. s, 1H), 10.44 (br. s, 2H).

Example 38

4-[(2,4-Difluoro-5-hydroxyphenyl)amino]-5-oxo-6,11-dihydro-5H-pyrido[2,3-b][1,5]benzodiazepine-8-carbonitrile

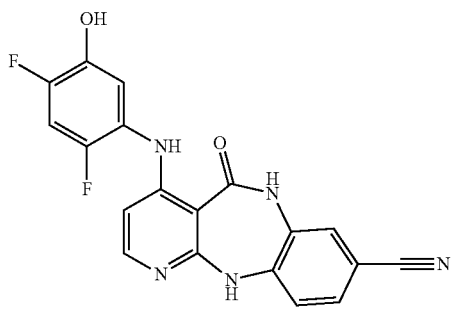 [SMILES: N#Cc1ccc2c(c1)NC(=O)c1c(Nc3cc(O)c(F)cc3F)ccnc1N2]

A 1:1 mixture of 4-chloro-5-oxo-6,11-dihydro-5H-pyrido[2,3-b][1,5]benzodiazepine-8-carbonitrile and 4,5-dichloro-11H-pyrido[2,3-b][1,5]benzodiazepine-8-carbonitrile (100 mg, 0.37 mmol) from Intermediate 10A and 5-amino-2,4-difluorophenol (59 mg, 0.41 mmol) was initially charged in 2.0 ml of isopropanol. 102 µl of a 4 M solution of hydrogen chloride in dioxane were added and the mixture was heated in a microwave apparatus to 160° C. for 20 min. Thereafter, the reaction mixture was diluted with 10 ml of water, and 2 drops of saturated aqueous sodium carbonate solution were added. The mixture was left to stir for 10 min, then the precipitate formed was filtered off with suction and washed with acetonitrile. The solids were stirred with acetonitrile and a few drops of methanol, filtered off with suction again and then dried under reduced pressure. 68.8 mg (44% of theory) of the title compound were obtained in 88% purity.

LC/MS (Method 5, ESIpos): $R_t$=0.77 min, m/z=380 [M+H]$^+$.

$^1$H-NMR (400 MHz, DMSO-d$_6$): δ [ppm]=6.33 (d, 1H), 6.91 (t, 1H), 7.26 (d, 1H), 7.34-7.36 (m, 1H), 7.39 (d, 1H), 7.48-7.51 (m, 1H), 7.84 (d, 1H), 9.09 (br. s, 1H), 9.99 (br. s, 1H), 10.08 (br. s, 1H), 10.35 (br. s, 1H).

Example 39

8-[(Diethylamino)methyl]-4-[(5-hydroxy-2-methylphenyl)amino]-6,11-dihydro-5H-pyrido[2,3-b][1,5]benzodiazepin-5-one

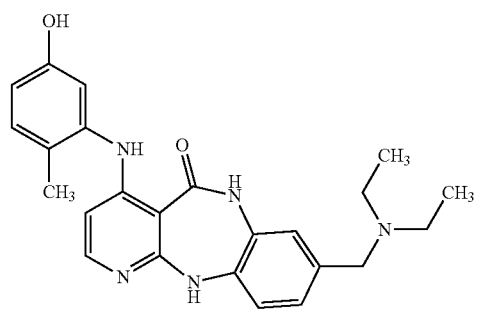 [SMILES: CCN(CC)Cc1ccc2c(c1)NC(=O)c1c(Nc3cc(O)ccc3C)ccnc1N2]

4-[(5-Hydroxy-2-methylphenyl)amino]-5-oxo-6,11-dihydro-5H-pyrido[2,3-b][1,5]benzodiazepine-8-carbaldehyde (50.0 mg, 0.14 mmol) from Intermediate 6A was initially charged in 1.5 ml of THF, and 0.13 µl of acetic acid was added. Diethylamine (40.6 mg, 0.56 mmol) was added and the mixture was left to stir at RT for 1 h. Then sodium triacetoxyborohydride (118 mg, 0.56 mmol) was added and stirring of the mixture continued at RT overnight. For workup, dilute aqueous sodium hydrogencarbonate solution was added and direct purification was effected by preparative HPLC (Method 15). This gave 13.4 mg (23% of theory) of the title compound.

LC/MS (Method 5, ESIpos): $R_t$=0.51 min, m/z=418 [M+H]$^+$.

$^1$H-NMR (400 MHz, DMSO-d$_6$): δ [ppm]=0.97 (t, 6H), 2.07 (s, 3H), 2.46 (q, 4H), 3.45 (s, 2H), 6.31 (d, 1H), 6.53 (dd, 1H), 6.61 (d, 1H), 6.92-6.98 (m, 2H), 7.04 (d, 1H), 7.08 (d, 1H), 7.75 (d, 1H), 8.11 (s, 1H), 8.17 (br. s, 1H), 9.87 (s, 1H), 10.07 (s, 1H).

Example 40

4-[(5-Hydroxy-2-methylphenyl)amino]-8-(pyrrolidin-1-ylmethyl)-6,11-dihydro-5H-pyrido[2,3-b][1,5]benzodiazepin-5-one

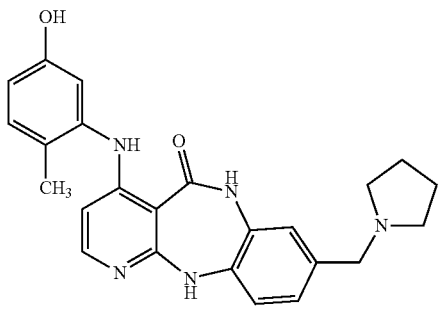 [SMILES: Cc1ccc(O)cc1Nc1ccnc2c1C(=O)Nc1cc(CN3CCCC3)ccc1N2]

4-[(5-Hydroxy-2-methylphenyl)amino]-5-oxo-6,11-dihydro-5H-pyrido[2,3-b][1,5]benzodiazepine-8-carbaldehyde (100 mg, 0.277 mmol) from Intermediate 6A was initially charged in 3.0 ml of THF and 0.26 ml of acetic acid. Pyrrolidine (79 mg, 1.11 mmol) was added and the mixture was left to stir at RT for 5 h. Then sodium triacetoxyborohydride (235 mg, 1.11 mmol) was added and stirring of the mixture continued at RT overnight. For workup, aqueous sodium hydrogencarbonate solution was added and direct purification was effected by preparative HPLC (Method 15). This gave 44.2 mg (38% of theory) of the title compound.

LC/MS (Method 5, ESIpos): $R_t$=0.46 min, m/z=416 [M+H]$^+$.

$^1$H-NMR (400 MHz, DMSO-$d_6$): δ [ppm]=1.67-1.75 (m, 4H), 2.07 (s, 3H), 2.51-2.55 (m, 4H), 3.58 (s, 2H), 6.31 (d, 1H), 6.54 (dd, 1H), 6.61 (d, 1H), 6.93-7.00 (m, 2H), 7.04-7.10 (m, 2H), 7.75 (d, 1H), 8.12-8.24 (m, 2H), 9.86 (s, 1H), 10.09 (s, 1H).

Example 41

4-[(5-Hydroxy-2-methylphenyl)amino]-8-(morpholin-4-ylmethyl)-6,11-dihydro-5H-pyrido[2,3-b][1,5]benzodiazepin-5-one formic acid salt

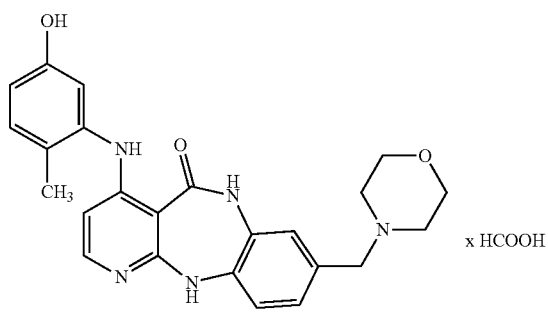 [SMILES: Cc1ccc(O)cc1Nc1ccnc2c1C(=O)Nc1cc(CN3CCOCC3)ccc1N2]

4-[(5-Hydroxy-2-methylphenyl)amino]-5-oxo-6,11-dihydro-5H-pyrido[2,3-b][1,5]benzodiazepine-8-carbaldehyde (100 mg, 0.277 mmol) from Intermediate 6A was initially charged in 3.0 ml of THF and 0.26 ml of acetic acid. Morpholine (97 mg, 1.11 mmol) was added and the mixture was left to stir at RT for 5 h. Then sodium triacetoxyborohydride (235 mg, 1.11 mmol) was added and stirring of the mixture continued at RT overnight. For workup, aqueous sodium hydrogencarbonate solution was added and direct purification was effected by preparative HPLC (Method 15). 76.6 mg (64% of theory) of the title compound were obtained.

LC/MS (Method 5, ESIpos): $R_t$=0.45 min, m/z=432 [M+H]$^+$.

$^1$H-NMR (400 MHz, DMSO-$d_6$): δ [ppm]=2.07 (s, 3H), 2.30-2.38 (m, 4H), 3.36 (s, 2H), 3.56 (t, 4H), 6.31 (d, 1H), 6.54 (dd, 1H), 6.61 (d, 1H), 6.91-6.97 (m, 2H), 7.07 (t, 2H), 7.75 (d, 1H), 8.12-8.17 (s, 4H), 9.86 (s, 1H), 10.08 (s, 1H).

Example 42

4-[(5-Hydroxy-2-methylphenyl)amino]-8-[(4-hydroxypiperidin-1-yl)methyl]-6,11-dihydro-5H-pyrido[2,3-b][1,5]benzodiazepin-5-one

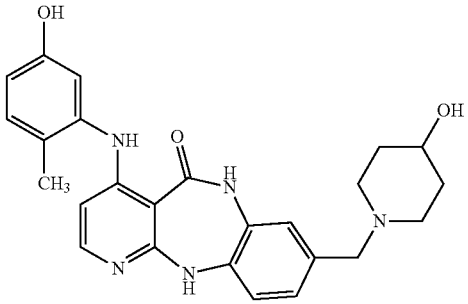 [SMILES: Cc1ccc(O)cc1Nc1ccnc2c1C(=O)Nc1cc(CN3CCC(O)CC3)ccc1N2]

In analogy to Example 39, 4-[(5-hydroxy-2-methylphenyl)amino]-5-oxo-6,11-dihydro-5H-pyrido[2,3-b][1,5]benzodiazepine-8-carbaldehyde (100 mg, 0.28 mmol) from Intermediate 6A was reacted with 4-hydroxypiperidine (112 mg, 1.11 mmol). 70.3 mg (53% of theory) of the title compound were obtained.

LC/MS (Method 5, ESIpos): $R_t$=0.44 min, m/z=446 [M+H]$^+$.

$^1$H-NMR (400 MHz, DMSO-$d_6$): δ [ppm]=1.29-1.42 (m, 2H), 1.62-1.73 (m, 2H), 1.92-2.03 (m, 2H), 2.07 (s, 3H), 2.58-2.69 (m, 2H), 3.31 (s, 2H), 4.53 (d, 1H), 6.31 (d, 1H), 6.53 (dd, 1H), 6.61 (d, 1H), 6.87-6.94 (m, 2H), 7.04 (d, 1H), 7.08 (d, 1H), 7.75 (d, 1H), 8.11 (s, 1H), 9.34 (s, 1H), 9.87 (s, 1H), 10.06 (s, 1H).

Example 43

4-[(5-Hydroxy-2-methylphenyl)amino]-8-[(4-methylpiperazin-1-yl)methyl]-6,11-dihydro-5H-pyrido[2,3-b][1,5]benzodiazepin-5-one

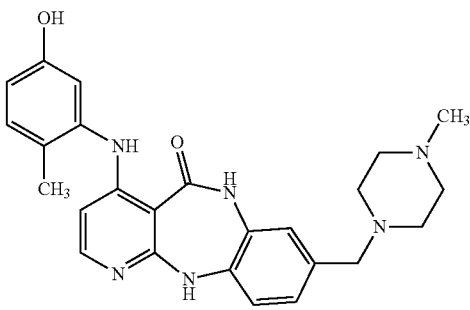 [SMILES: Cc1ccc(O)cc1Nc1ccnc2c1C(=O)Nc1cc(CN3CCN(C)CC3)ccc1N2]

4-[(5-Hydroxy-2-methylphenyl)amino]-5-oxo-6, 11-dihydro-5H-pyrido[2,3-b][1,5]benzodiazepine-8-carbaldehyde (100 mg, 0.277 mmol) from Intermediate 6A was initially charged in 3.0 ml of THF and 0.26 ml of acetic acid. 1-Methylpiperazine (111 mg, 1.11 mmol) was added and the mixture was left to stir at RT for 3 h. Then sodium triacetoxyborohydride (235 mg, 1.11 mmol) was added and stirring of the mixture continued at RT overnight. For workup, aqueous sodium hydrogencarbonate solution was added and direct purification was effected by preparative HPLC (Method 15). The product thus obtained (formate salt) was dissolved in water, 1 N sodium hydroxide solution was added and extraction was effected three times with ethyl acetate. The combined organic phases were dried over sodium sulphate and concentrated under reduced pressure. 83.2 mg (67% of theory) of the title compound were obtained.

LC/MS (Method 5, ESIpos): $R_t$=0.46 min, m/z=445 [M+H]$^+$.

$^1$H-NMR (400 MHz, DMSO-d$_6$): δ [ppm]=2.07 (s, 3H), 2.14 (s, 3H), 2.32 (br. s, 8H), 3.32 (br. s, 2H), 6.31 (d, 1H), 6.51-6.56 (m, 1H), 6.61 (d, 1H), 6.88-6.95 (m, 2H), 7.05 (d, 1H), 7.08 (d, 1H), 7.75 (d, 1H), 8.12 (s, 1H), 9.34 (s, 1H), 9.87 (s, 1H), 10.06 (s, 1H).

Example 44

8-{[4-(2-Hydroxyethyl)piperazin-1-yl]methyl}-4-[(5-hydroxy-2-methylphenyl)amino]-6,11-dihydro-5H-pyrido[2,3-b][1,5]benzodiazepin-5-one

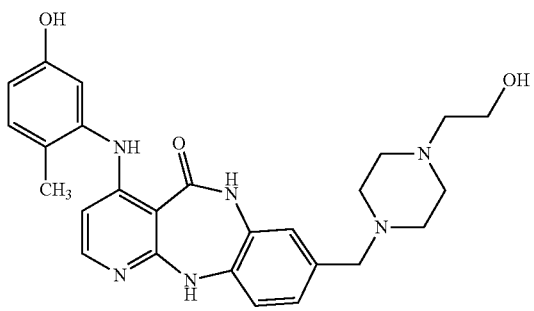 [SMILES: Cc1ccc(O)cc1Nc1ccnc2c1C(=O)Nc1cc(CN3CCN(CCO)CC3)ccc1N2]

4-[(5-Hydroxy-2-methylphenyl)amino]-5-oxo-6,11-dihydro-5H-pyrido[2,3-b][1,5]benzodiazepine-8-carbaldehyde (100 mg, 0.277 mmol) from Intermediate 6A was initially charged in 3.0 ml of THF and 0.26 ml of acetic acid. N-(2-Hydroxyethyl)piperazine (145 mg, 1.11 mmol) was added and the mixture was left to stir at RT for 3 h. Then sodium triacetoxyborohydride (235 mg, 1.11 mmol) was added and stirring of the mixture continued at RT overnight. For workup, aqueous sodium hydrogencarbonate solution was added and direct purification was effected by preparative HPLC (Method 15). The product thus obtained (formate salt) was dissolved in water, 1 N sodium hydroxide solution was added and extraction was effected three times with ethyl acetate. The combined organic phases were dried over sodium sulphate and concentrated under reduced pressure. 59.9 mg (45% of theory) of the title compound were obtained.

LC/MS (Method 5, ESIpos): $R_t$=0.44 min, m/z=475 [M+H]$^+$.

$^1$H-NMR (400 MHz, DMSO-d$_6$): δ [ppm]=2.07 (s, 3H), 2.26-2.45 (m, 6H), 3.32 (br. s, 2H), 3.39-3.52 (m, 6H), 4.35 (t, 1H), 6.31 (d, 1H), 6.53 (dd, 1H), 6.61 (d, 1H), 6.89-6.94 (m, 2H), 7.04 (d, 1H), 7.08 (d, 1H), 7.75 (d, 1H), 8.12 (s, 1H), 9.34 (s, 1H), 9.87 (s, 1H), 10.06 (s, 1H).

Example 45

4-[(2-Fluoro-5-hydroxy-4-methylphenyl)amino]-8-[(4-hydroxypiperidin-1-yl)methyl]-6,11-dihydro-5H-pyrido[2,3-b][1,5]benzodiazepin-5-one

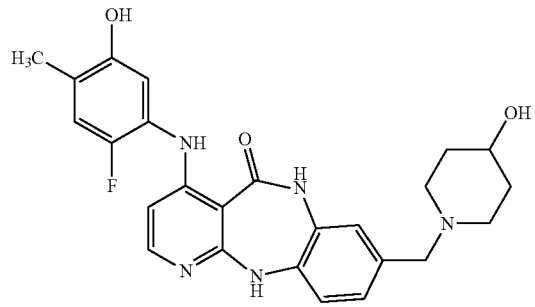 [SMILES: Cc1cc(F)c(Nc2ccnc3c2C(=O)Nc2cc(CN4CCC(O)CC4)ccc2N3)cc1O]

In analogy to Example 39, 4-[(2-fluoro-5-hydroxy-4-methylphenyl)amino]-5-oxo-6,11-dihydro-5H-pyrido[2,3-b][1,5]benzodiazepine-8-carbaldehyde (90 mg, 0.24 mmol) from Intermediate 11A was reacted with 4-hydroxypiperidine (96 mg, 0.95 mmol). 32.4 mg (26% of theory) of the title compound were obtained.

LC/MS (Method 5, ESIpos): $R_t$=0.54 min, m/z=464 [M+H]$^+$.

$^1$H-NMR (400 MHz, DMSO-d$_6$): δ [ppm]=1.29-1.42 (m, 2H), 1.63-1.72 (m, 2H), 1.92-2.02 (m, 2H), 2.10 (s, 3H), 2.58-2.67 (m, 2H), 3.30 (s, 2H), 4.54 (d, 1H), 6.38 (d, 1H), 6.72 (d, 1H), 6.88-6.94 (m, 2H), 7.04 (d, 2H), 7.79 (d, 1H), 8.15 (s, 1H), 9.46 (s, 1H), 9.87 (s, 1H), 10.10 (s, 1H).

Example 46

4-[(2-Fluoro-5-hydroxy-4-methylphenyl)amino]-8-[(4-methylpiperazin-1-yl)methyl]-6,11-dihydro-5H-pyrido[2,3-b][1,5]benzodiazepin-5-one

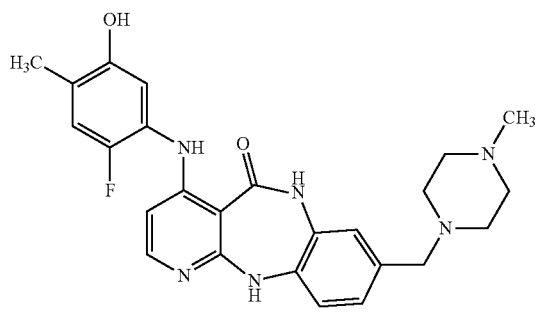

In analogy to Example 39, 4-[(2-fluoro-5-hydroxy-4-methylphenyl)amino]-5-oxo-6,11-dihydro-5H-pyrido[2,3-b][1,5]benzodiazepine-8-carbaldehyde (90 mg, 0.24 mmol) from Intermediate 11A was reacted with 1-methylpiperazine (95 mg, 0.95 mmol). 84.7 mg (77% of theory) of the title compound were obtained.

LC/MS (Method 5, ESIpos): $R_t$=0.55 min, m/z=463 [M+H]$^+$.

$^1$H-NMR (400 MHz, DMSO-d$_6$): δ [ppm]=2.10 (s, 3H), 2.13 (s, 3H), 2.19-2.43 (m, 8H), 3.32 (s, 2H), 6.38 (dd, 1H), 6.72 (d, 1H), 6.89-6.94 (m, 2H), 7.03 (d, 1H), 7.05 (s, 1H), 7.79 (d, 1H), 8.16 (s, 1H), 9.47 (s, 1H), 9.86 (s, 1H), 10.11 (s, 1H).

Example 47

4-[(2-Fluoro-5-hydroxy-4-methylphenyl)amino]-8-{[4-(2-hydroxyethyl)piperazin-1-yl]methyl}-6,11-dihydro-5H-pyrido[2,3-b][1,5]benzodiazepin-5-one

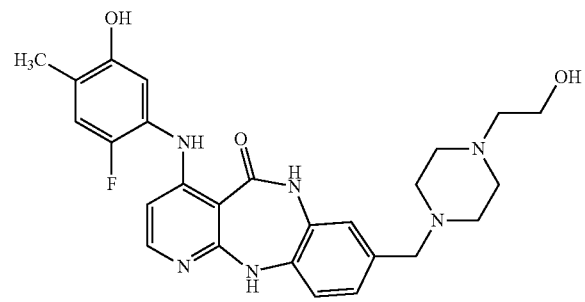

In analogy to Example 39, 4-[(2-fluoro-5-hydroxy-4-methylphenyl)amino]-5-oxo-6,11-dihydro-5H-pyrido[2,3-b][1,5]benzodiazepine-8-carbaldehyde (90 mg, 0.24 mmol) from Intermediate 11A was reacted with N-(2-hydroxyethyl)piperazine (124 mg, 0.95 mmol). 124.1 mg (98% of theory) of the title compound were obtained.

LC/MS (Method 5, ESIpos): $R_t$=0.53 min, m/z=493 [M+H]$^+$.

$^1$H-NMR (400 MHz, DMSO-d$_6$): δ [ppm]=inter al. 6.38 (dd, 1H), 6.72 (d, 1H), 6.89-6.95 (m, 2H), 7.01-7.07 (m, 2H), 7.79 (d, 1H), 8.15 (s, 1H), 9.46 (br. s, 1H), 9.86 (s, 1H), 10.10 (s, 1H).

Example 48

4-[(2-Fluoro-5-hydroxy-4-methylphenyl)amino]-8-[(isopropylamino)methyl]-6,11-dihydro-5H-pyrido[2,3-b][1,5]benzodiazepin-5-one

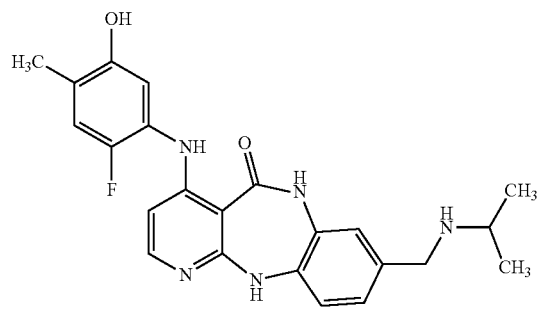 [SMILES: Cc1cc(F)c(Nc2ccnc3c2C(=O)Nc2cc(CNC(C)C)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A) (110 mg, 71% purity, 0.206 mmol) was initially charged in 2.0 ml of DMF and 0.2 ml of acetic acid. At RT, isopropylamine (49 mg, 0.83 mmol) was added and the mixture was stirred at RT for 9 h. Then sodium triacetoxyborohydride (175 mg, 0.83 mmol) was added and stirring of the mixture continued at RT overnight. The mixture was then admixed with aqueous sodium hydrogencarbonate solution and concentrated. The residue was taken up in 15 ml of DMF, filtered and concentrated again. Further purification was effected by preparative HPLC (column: Sunfire C18 5μ, 150×19 mm; flow rate: 25 ml/min; eluent A: water, eluent B: acetonitrile, eluent C: 1% formic acid in water; isocratic 56% A, 30% B, 14% C). The product thus obtained was dissolved in acetonitrile (5 ml) and admixed with a little aqueous sodium hydrogencarbonate solution. The organic solvent was removed on a rotary evaporator and the residue was diluted with water. The remaining solid was filtered off with suction and washed with a little water. 29 mg (27% of theory; purity 82% by LC/MS) of the title compound were obtained.

LC/MS (Method 5, ESIpos): $R_t$=0.57 min, m/z=422 [M+H]$^+$.

$^1$H-NMR (400 MHz, DMSO-d$_6$): δ [ppm]=0.97 (d, 6H), 2.08 (s, 3H), 2.63-2.76 (m, 1H), 3.52-3.61 (m, 2H), 6.37 (d, 1H), 6.68 (d, 1H), 6.89-7.05 (m, 4H), 7.75 (d, 1H), 8.06 (s, 1H), 9.83 (s, 1H), 10.06 (s, 1H).

Example 49

8-{[Ethyl(methyl)amino]methyl}-4-[(2-fluoro-5-hydroxy-4-methylphenyl)amino]-6,11-dihydro-5H-pyrido[2,3-b][1,5]benzodiazepin-5-one

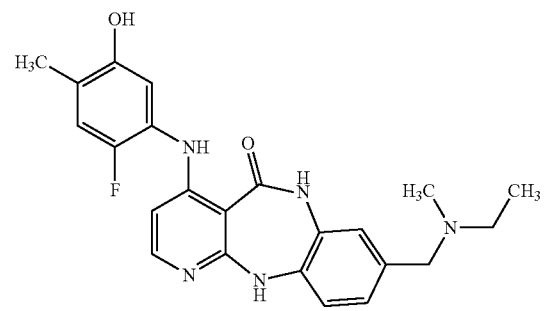 [SMILES: CCN(C)Cc1ccc2c(c1)NC(=O)c1c(Nc3cc(O)c(C)cc3F)ccnc1N2]

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was initially charged in 2.5 ml of DMF. At RT, N-ethylmethylamine (59 mg, 1.0 mmol) and trimethyl orthoformate (531 mg, 5 mmol) were added and the mixture was stirred at RT for 5 h.

Then sodium triacetoxyborohydride (212 mg, 1.0 mmol) was added and stirring of the mixture continued at RT overnight. The mixture was then admixed with aqueous sodium hydrogencarbonate solution and concentrated. The residue was taken up in 15 ml of DMF, filtered and concentrated again. Purification by preparative HPLC (Method 16) gave 14 mg (13% of theory) of the title compound.

LC/MS (Method 5, ESIpos): $R_t$=0.56 min, m/z=422 [M+H]$^+$.

$^1$H-NMR (400 MHz, DMSO-d$_6$): δ [ppm]=1.02 (t, 3H), 2.10 (s, 3H), 2.12 (s, 3H), 2.35-2.45 (m, 2H), 3.35-3.50 (m, 2H), 6.35-6.40 (m, 1H), 6.72 (d, 1H), 6.90-7.00 (m, 2H), 7.00-7.10 (m, 2H), 7.79 (d, 1H), 8.15 (s, 1H), 9.42 (s, 1H), 9.87 (s, 1H), 10.09 (s, 1H).

Example 50

8-{[(2-Ethoxyethyl)(ethyl)amino]methyl}-4-[(2-fluoro-5-hydroxy-4-methylphenyl)amino]-6,11-dihydro-5H-pyrido[2,3-b][1,5]benzodiazepin-5-one

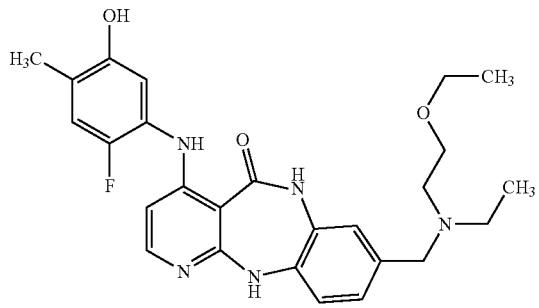 [SMILES: CCOCCN(CC)Cc1ccc2c(c1)NC(=O)c1c(Nc3cc(O)c(C)cc3F)ccnc1N2]

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with N-(2-ethoxyethyl)ethylamine (117 mg, 1 mmol). 86 mg (71% of theory) of the title compound were obtained.

LC/MS (Method 7, ESIneg): $R_t$=0.85 min, m/z=478 [M−H]⁻.

$^1$H-NMR (400 MHz, DMSO-$d_6$): δ [ppm]=1.14 (t, 3H), 1.24 (t, 3H), 2.11 (s, 3H), 3.05-3.25 (m, 4H), 3.58-3.75 (m, 2H), 4.18-4.34 (m, 2H), 6.32-6.44 (m, 1H), 6.71 (d, 1H), 7.05 (d, 1H), 7.12 (s, 1H), 7.18 (s, 1H), 7.81 (d, 1H), 8.50 (br. s, 1H), 9.21 (br. s, 1H), 9.47 (s, 1H), 9.87 (br. s, 1H), 10.31 (s, 1H).

Example 51

8-{[Ethyl(isopropyl)amino]methyl}-4-[(2-fluoro-5-hydroxy-4-methylphenyl)amino]-6,11-dihydro-5H-pyrido[2,3-b][1,5]benzodiazepin-5-one

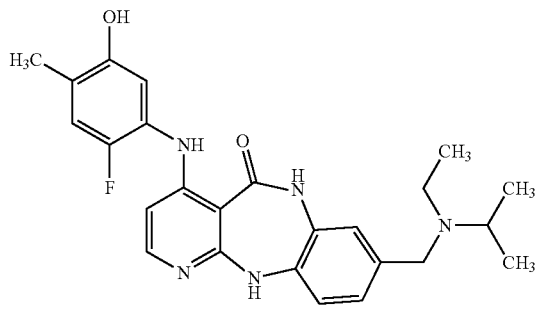 [SMILES: CCN(Cc1ccc2c(c1)NC(=O)c1c(Nc3cc(O)c(C)cc3F)ccnc1N2)C(C)C]

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with N-ethylisopropylamine (87 mg, 1 mmol). 57 mg (48% of theory, 95% purity) of the title compound were obtained.

LC/MS (Method 5, ESIpos): $R_t$=0.67 min, m/z=450 [M+H]⁺.

$^1$H-NMR (400 MHz, DMSO-$d_6$): δ [ppm]=0.93 (t, 3H), 0.96 (d, 6H), 2.10 (s, 3H), 2.39 (q, 2H), 2.85-2.95 (m, 1H), 3.39 (s, 2H), 6.35-6.40 (m, 1H), 6.72 (d, 1H), 6.92-6.97 (m, 1H), 6.99 (s, 1H), 7.02 (s, 1H), 7.04 (d, 1H), 7.78 (d, 1H), 8.08 (s, 1H), 9.41 (s, 1H), 9.88 (s, 1H), 10.08 (s, 1H).

Example 52

8-{[Ethyl(2-hydroxyethyl)amino]methyl}-4-[(2-fluoro-5-hydroxy-4-methylphenyl)amino]-6,11-dihydro-5H-pyrido[2,3-b][1,5]benzodiazepin-5-one

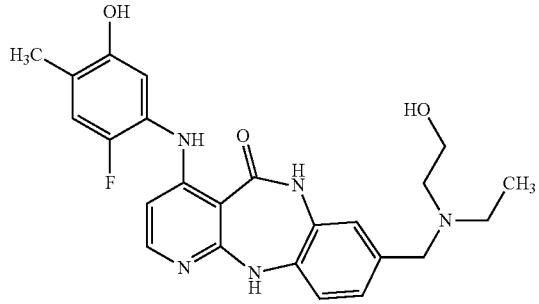 [SMILES: CCN(CCO)Cc1ccc2c(c1)NC(=O)c1c(Nc3cc(O)c(C)cc3F)ccnc1N2]

Method A:

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with 2-(ethylamino)ethanol (89 mg, 1 mmol). 60 mg (53% of theory) of the title compound were obtained.

Method B:

8-{[(2-{[tert-Butyl(dimethyl)silyl]oxy}ethyl)(ethyl)amino]methyl}-4-[(5-{[tert-butyl(dimethyl)silyl]oxy}-2-fluoro-4-methylphenyl)amino]-6,11-dihydro-5H-pyrido[2,3-b][1,5]benzodiazepin-5-one (10.2 g, 12.89 mmol) from Intermediate 20A was taken up in a mixture of 4 N hydrochloric acid and 4 N hydrogen chloride in 1,4-dioxane (1:1 mixture, 50 ml) and the mixture was stirred at room temperature for 20 min. Thereafter, the solvent was drawn off under reduced pressure, and the residue was admixed with 100 ml of toluene and concentrated again. The residue thus obtained was admixed with 350 ml of saturated sodium hydrogencarbonate solution. The precipitated solid was filtered off with suction, washed with a little water and dried. Yield: 5.82 g (86% of theory).

LC/MS (Method 5, ESIpos): $R_t$=0.59 min, m/z=452 [M+H]⁺.

$^1$H-NMR (400 MHz, DMSO-$d_6$): δ [ppm]=0.96 (t, 3H), 2.10 (s, 3H), 2.43-2.48 (m, 4H), 3.41-3.47 (m, 4H), 4.26 (t, 1H), 6.37 (dd, 1H), 6.72 (d, 1H), 6.92-6.97 (m, 2H), 7.01-7.06 (m, 2H), 7.79 (d, 1H), 8.11 (s, 1H), 9.43 (s, 1H), 9.87 (s, 1H), 10.07 (s, 1H).

Example 53

8-{[Butyl(ethyl)amino]methyl}-4-[(2-fluoro-5-hydroxy-4-methylphenyl)amino]-6,11-dihydro-5H-pyrido[2,3-b][1,5]benzodiazepin-5-one

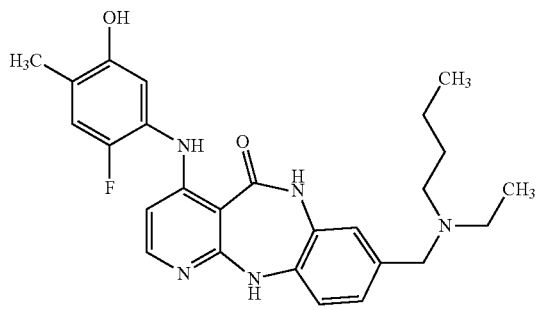

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with N-ethyl-n-butylamine (101 mg, 1 mmol). 87 mg (73% of theory) of the title compound were obtained.

LC/MS (Method 5, ESIpos): $R_t$=0.66 min, m/z=464 [M+H]$^+$.

$^1$H-NMR (400 MHz, DMSO-d$_6$): δ [ppm]=0.85 (t, 3H), 0.95 (t, 3H), 1.20-1.33 (m, 2H), 1.33-1.45 (m, 2H), 2.10 (s, 3H), 2.30-2.45 (m, 4H), 3.39 (s, 2H), 6.36-6.40 (m, 1H), 6.72 (d, 1H), 6.90-6.94 (m, 1H), 6.95 (s, 1H), 7.02 (s, 1H), 7.04 (d, 1H), 7.79 (d, 1H), 8.12 (s, 1H), 9.44 (s, 1H), 9.88 (s, 1H), 10.11 (s, 1H).

Example 54

4-[(2-Fluoro-5-hydroxy-4-methylphenyl)amino]-8-[(4-propylpiperidin-1-yl)methyl]-6,11-dihydro-5H-pyrido[2,3-b][1,5]benzodiazepin-5-one

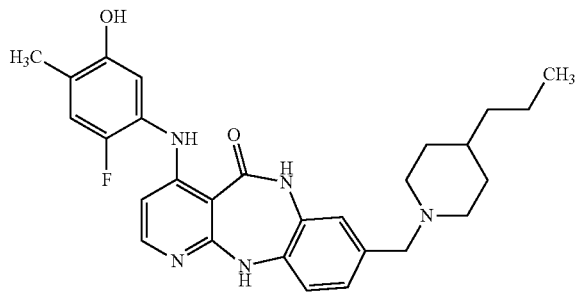 [SMILES: CCCC1CCN(Cc2ccc3c(c2)NC(=O)c2c(Nc4cc(O)c(C)cc4F)ccnc2N3)CC1]

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with 4-n-propylpiperidine (127 mg, 1 mmol). 31 mg (25% of theory) of the title compound were obtained.

LC/MS (Method 5, ESIpos): $R_t$=0.74 min, m/z=490 [M+H]$^+$.

$^1$H-NMR (400 MHz, DMSO-d$_6$): δ [ppm]=0.84 (t, 3H), 1.01-1.32 (m, 8H), 1.52-1.63 (m, 2H), 1.77-1.91 (m, 2H), 2.10 (s, 3H), 2.70-2.82 (m, 2H), 3.45-3.60 (m, 1H), 6.35-6.40 (m, 1H), 6.72 (d, 1H), 6.88-6.92 (m, 1H), 6.93 (s, 1H), 7.01-7.04 (m, 1H), 7.05 (s, 1H), 7.79 (d, 1H), 8.12 (s, 1H), 9.42 (s, 1H), 9.87 (s, 1H), 9.87 (s, 1H), 10.07 (s, 1H).

Example 55

8-{[Ethyl(2-methoxyethyl)amino]methyl}-4-[(2-fluoro-5-hydroxy-4-methylphenyl)amino]-6,11-dihydro-5H-pyrido[2,3-b][1,5]benzodiazepin-5-one

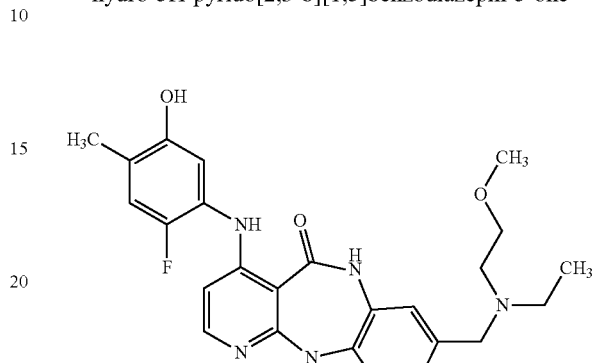

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with N-(2-methoxyethyl)ethylamine (103 mg, 1 mmol). 96 mg (78% of theory) of the title compound were obtained.

LC/MS (Method 5, ESIpos): $R_t$=0.60 min, m/z=466 [M+H]$^+$.

$^1$H-NMR (400 MHz, DMSO-d$_6$): δ [ppm]=0.96 (t, 3H), 2.10 (s, 3H), 2.42-2.48 (m, 2H), 2.52-2.57 (m, 4H), 3.21 (s, 3H), 3.37-3.42 (m, 2H), 3.45-3.50 (m, 2H), 6.35-6.40 (m, 1H), 6.72 (d, 1H), 6.89-6.98 (m, 2H), 7.03 (s, 1H), 7.04-7.07 (m, 1H), 7.79 (d, 1H), 8.13 (s, 1H), 9.44 (s, 1H), 9.87 (s, 1H), 10.11 (s, 1H).

Example 56

8-[(4,4-Dimethylpiperidin-1-yl)methyl]-4-[(2-fluoro-5-hydroxy-4-methylphenyl)amino]-6,11-dihydro-5H-pyrido[2,3-b][1,5]benzodiazepin-5-one

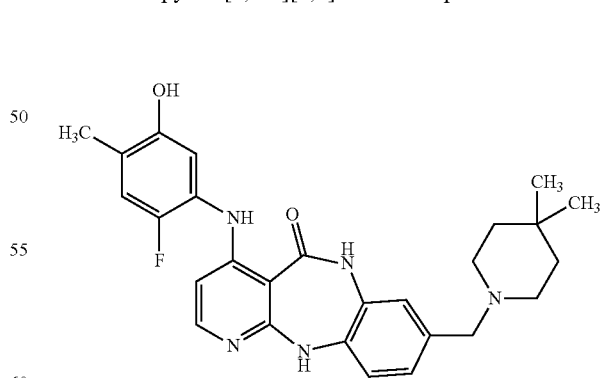

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with 4,4-dimethylpiperidine (113 mg, 1 mmol). 57 mg (48% of theory) of the title compound were obtained.

LC/MS (Method 5, ESIpos): R$_t$=0.67 min, m/z=476 [M+H]$^+$.

$^1$H-NMR (400 MHz, DMSO-d$_6$): δ [ppm]=0.88 (s, 6H), 1.26-1.34 (m, 4H), 2.10 (s, 3H), 2.25-2.35 (m, 4H), 2.54 (s, 2H), 6.38 (d, 1H), 6.72 (d, 1H), 6.87-6.95 (m, 2H), 7.00-7.08 (m, 2H), 7.79 (d, 1H), 8.14 (s, 1H), 9.43 (s, 1H), 9.87 (s, 1H), 10.09 (s, 1H).

Example 57 rac-1-({4-[(2-Fluoro-5-hydroxy-4-methylphenyl)amino]-5-oxo-6,11-dihydro-5H-pyrido[2,3-b][1,5]benzodiazepin-8-yl}methyl)piperidine-3-carboxamide

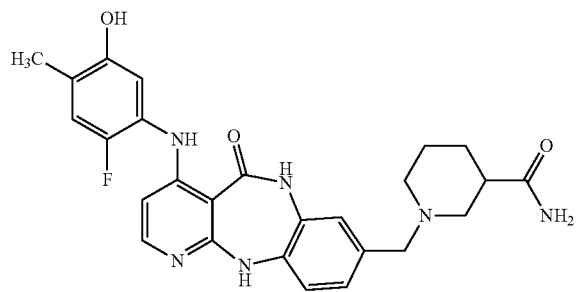 [SMILES: Cc1cc(F)c(Nc2ccnc3c2C(=O)Nc2cc(CN4CCCC(C(N)=O)C4)ccc2N3)cc1O]

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with piperidine-3-carboxamide (128 mg, 1 mmol). 58 mg (45% of theory) of the title compound were obtained.

LC/MS (Method 5, ESIpos): R$_t$=0.54 min, m/z=491 [M+H]$^+$.

$^1$H-NMR (400 MHz, DMSO-d$_6$): δ [ppm]=1.23-1.35 (m, 1H), 1.35-1.48 (m, 1H), 1.54-1.65 (m, 1H), 1.65-1.76 (m, 1H), 1.80-1.89 (m, 1H), 1.90-1.98 (m, 1H), 2.10 (s, 3H), 2.24-2.35 (m, 1H), 2.54 (s, 2H), 2.64-2.80 (m, 2H), 6.35-6.40 (m, 1H), 6.68-6.75 (m, 2H), 6.88-6.94 (m, 2H), 7.00-7.08 (m, 2H), 7.78 (d, 1H), 8.15 (s, 1H), 9.86 (s, 1H), 10.11 (s, 1H).

Example 58 rac-4-[(2-Fluoro-5-hydroxy-4-methylphenyl)amino]-8-{[3-(2-hydroxyethyl)piperidin-1-yl]methyl}-6,11-dihydro-5H-pyrido[2,3-b][1,5]benzodiazepin-5-one

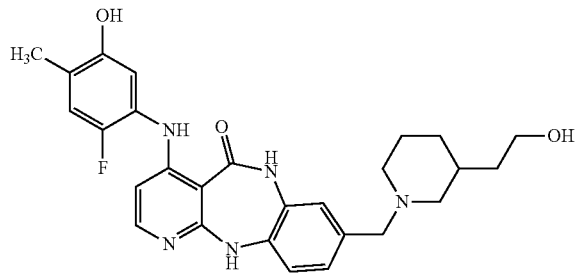 [SMILES: Cc1cc(F)c(Nc2ccnc3c2C(=O)Nc2cc(CN4CCCC(CCO)C4)ccc2N3)cc1O]

In analogy to Example 49, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (158 mg, 60% purity, 0.250 mmol) was reacted with 2-(piperidin-3-yl)ethanol (129 mg, 1 mmol). 29 mg (22% of theory) of the title compound were obtained.

LC/MS (Method 7, ESIneg): R$_t$=0.81 min, m/z=490 [M−H]$^−$.

$^1$H-NMR (400 MHz, DMSO-d$_6$): δ [ppm]=0.76-0.91 (m, 1H), 1.20-1.48 (m, 3H), 1.50-1.70 (m, 4H), 1.75-1.88 (m, 1H), 2.10 (s, 3H), 2.60-2.76 (m, 2H), 3.22-3.30 (m, 2H), 3.36-3.42 (m, 2H), 4.31 (t, 1H), 6.35-6.40 (m, 1H), 6.72 (d, 1H), 6.87-6.94 (m, 2H), 7.02 (d, 1H), 7.05 (s, 1H), 7.79 (d, 1H), 8.15 (s, 1H), 9.44 (s, 1H), 9.87 (s, 1H), 10.10 (s, 1H).

Example 59

4-[(2-Fluoro-5-hydroxy-4-methylphenyl)amino]-8-[(3-hydroxy-4-methylpiperidin-1-yl)methyl]-6,11-dihydro-5H-pyrido[2,3-b][1,5]benzodiazepin-5-one

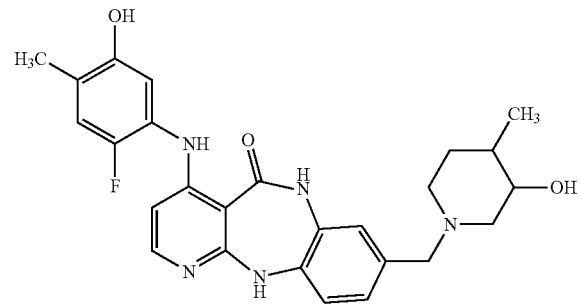 [SMILES: Cc1cc(F)c(Nc2ccnc3c2C(=O)Nc2cc(CN4CCC(C)C(O)C4)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A) (69 mg, 69% purity, 0.125 mmol) was initially charged in 1.5 ml of 1,4-dioxane. At RT, 4-methylpiperidin-3-ol hydrochloride (76 mg, 0.5 mmol), triethylamine (51 mg, 0.5 mmol) and trimethyl orthoformate (265 mg, 2.5 mmol) were added and the mixture was stirred at 45° C. overnight. Then sodium triacetoxyborohydride (106 mg, 2.5 mmol) was added and stirring of the mixture continued at RT overnight. The mixture was then admixed with aqueous sodium hydrogencarbonate solution and concentrated. The residue was taken up in 15 ml of DMF, filtered and concentrated again. Purification by chromatography on silica gel (eluent: dichloromethane→16.5% methanol in dichloromethane) and subsequent preparative HPLC (Method 16) gave 28 mg (47% of theory) of the title compound as a stereoisomer mixture.

LC/MS (Method 5, ESIpos): R$_t$=0.57 min, m/z=478 [M+H]$^+$.

$^1$H-NMR (400 MHz, DMSO-d$_6$): δ [ppm]=0.85 (d, 3H), 1.3-1.6 (m, 3H), 1.98-2.18 (m, 2H), 2.09 (s, 3H), 3.45-3.55 (m, 1H), 3.85-4.05 (m, 1H), 6.34-6.40 (m, 1H), 6.70 (d, 1H), 6.90-6.97 (m, 2H), 6.98-7.07 (m, 2H), 7.77 (d, 1H), 8.11 (s, 1H), 9.86 (s, 1H), 10.05 (s, 1H).

Example 60 rac-8-{[3-(Cyclobutylmethoxy)piperidin-1-yl]methyl}-4-[(2-fluoro-5-hydroxy-4-methylphenyl)amino]-6,11-dihydro-5H-pyrido[2,3-b][1,5]benzodiazepin-5-one

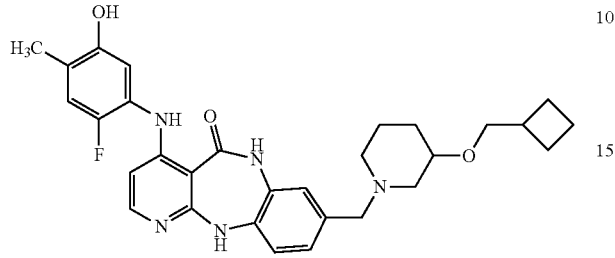

In analogy to Example 59, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (69 mg, 69% purity, 0.125 mmol) was reacted with rac-3-(cyclobutylmethoxy)piperidine hydrochloride (103 mg, 0.500 mmol). 20 mg (30% of theory) of the title compound were obtained.

LC/MS (Method 5, ESIpos): $R_t$=0.73 min, m/z=532 [M+H]$^+$.

$^1$H-NMR (400 MHz, DMSO-d$_6$): δ [ppm]=1.00-1.13 (m, 1H), 1.30-1.45 (m, 1H), 1.55-1.69 (m, 3H), 1.71-1.99 (m, 7H), 2.10 (s, 3H), 2.35-2.45 (m, 1H), 2.55-2.60 (m, 1H), 2.80-2.89 (m, 1H), 3.20-3.30 (m, 1H), 3.33-3.36 (m, 3H), 6.35-6.42 (m, 1H), 6.72 (d, 1H), 6.89-6.94 (m, 2H), 7.01-7.07 (m, 2H), 7.79 (d, 1H), 8.14 (s, 1H), 9.14 (s, 1H), 9.88 (s, 1H), 10.09 (s, 1H).

Example 61 rac-N,N-Diethyl-2-{[1-({4-[(2-fluoro-5-hydroxy-4-methylphenyl)amino]-5-oxo-6,11-dihydro-5H-pyrido[2,3-b][1,5]benzodiazepin-8-yl}methyl)piperidin-3-yl]oxy}acetamide

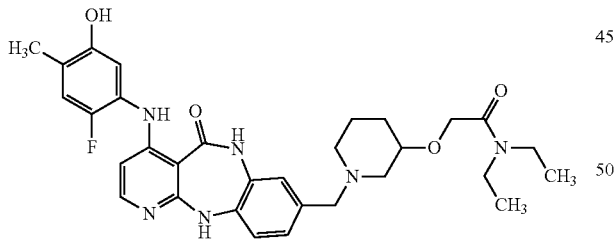

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A) (69 mg, 69% purity, 0.125 mmol) was initially charged in 1.5 ml of 1,4-dioxane. At RT, rac-N,N-diethyl-2-(piperidin-3-yloxy)acetamide (107 mg, 0.5 mmol) and trimethyl orthoformate (265 mg, 2.5 mmol) were added and the mixture was stirred at 45° C. overnight. Then sodium triacetoxyborohydride (106 mg, 2.5 mmol) was added and stirring of the mixture continued at RT overnight. The mixture was then admixed with aqueous sodium hydrogencarbonate solution and concentrated. The residue was taken up in 15 ml of DMF, filtered and concentrated again. Purification by chromatography on silica gel (eluent: dichloromethane→16.5% methanol in dichloromethane) and subsequent preparative HPLC (Method 16) gave 34 mg (46% of theory) of the title compound.

LC/MS (Method 5, ESIpos): $R_t$=0.68 min, m/z=577 [M+H]$^+$.

$^1$H-NMR (400 MHz, DMSO-d$_6$): δ [ppm]=0.95 (t, 3H), 1.02 (t, 3H), 1.10-1.20 (m, 1H), 1.30-1.45 (m, 1H), 1.58-1.67 (m, 1H), 1.82-1.97 (m, 3H), 2.10 (s, 3H), 2.79-2.85 (m, 1H), 3.14-3.25 (m, 4H), 3.32-3.43 (m, 3H), 4.05 (s, 2H), 6.37-6.42 (m, 1H), 6.72 (d, 1H), 6.88-6.93 (m, 2H), 7.00-7.07 (m, 2H), 7.79 (d, 1H), 8.13 (s, 1H), 9.42 (s, 1H), 9.87 (s, 1H), 10.09 (s, 1H).

Example 62 rac-4-[(2-Fluoro-5-hydroxy-4-methylphenyl)amino]-8-[(4-hydroxyazepan-1-yl)methyl]-6,11-dihydro-5H-pyrido[2,3-b][1,5]benzodiazepin-5-one

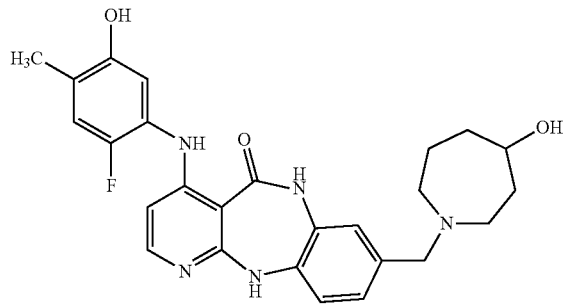 [SMILES: Cc1cc(F)c(Nc2ccnc3c2C(=O)Nc2cc(CN4CCCC(O)CC4)ccc2N3)cc1O]

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (70 mg, 0.185 mmol) was reacted with rac-azepan-4-ol (85 mg, 0.740 mmol). 13 mg (15% of theory) of the title compound were obtained.

LC/MS (Method 5, ESIpos): $R_t$=0.56 min, m/z=478 [M+H]$^+$.

$^1$H-NMR (400 MHz, DMSO-d$_6$): δ [ppm]=1.35-1.70 (m, 4H), 1.72-1.85 (m, 2H), 2.10 (s, 3H), 3.40-3.50 (m, 1H), 3.65-3.77 (m, 1H), 4.31-4.40 (m, 1H), 6.36-6.39 (m, 1H), 6.72 (d, 1H), 6.90-6.98 (m, 2H), 7.01-7.07 (m, 2H), 7.78 (d, 1H), 8.11 (s, 1H), 9.41 (s, 1H), 9.87 (s, 1H), 10.09 (s, 1H).

Example 63

8-(Azepan-1-ylmethyl)-4-[(2-fluoro-5-hydroxy-4-methylphenyl)amino]-6,11-dihydro-5H-pyrido[2,3-b][1,5]benzodiazepin-5-one

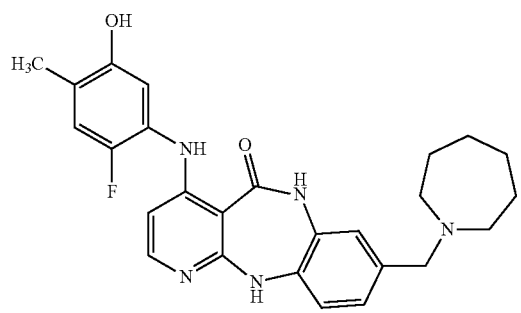 [SMILES: Cc1cc(F)c(Nc2ccnc3c2C(=O)Nc2cc(CN4CCCCCC4)ccc2N3)cc1O]

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (70 mg, 0.185 mmol) was reacted with azepane (74 mg, 0.740 mmol). 21 mg (24% of theory) of the title compound were obtained.

LC/MS (Method 5, ESIpos): $R_t$=0.66 min, m/z=461 [M+H]$^+$.

$^1$H-NMR (400 MHz, DMSO-$d_6$): δ [ppm]=1.56 (s, 8H), 2.10 (s, 3H), 2.51-2.55 (m, 4H), 3.47 (s, 2H), 6.36-6.39 (m, 1H), 6.73 (d, 1H), 6.92-6.98 (m, 2H), 7.01-7.05 (m, 2H), 7.78 (d, 1H), 8.11 (s, 1H), 9.41 (s, 1H), 9.88 (s, 1H), 10.09 (s, 1H).

Example 64

4-[(2-Fluoro-5-hydroxy-4-methylphenyl)amino]-8-{[(2S,4R)-4-hydroxy-2-(hydroxymethyl)pyrrolidin-1-yl]methyl}-6,11-dihydro-5H-pyrido[2,3-b][1,5]benzodiazepin-5-one

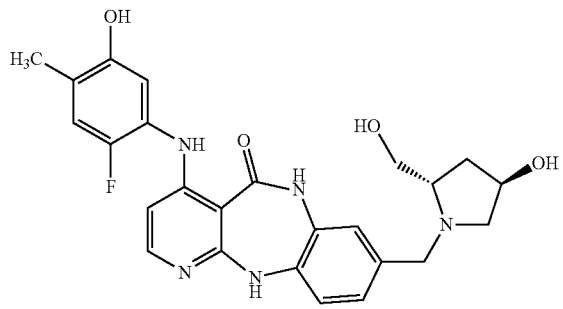 [SMILES: Cc1cc(F)c(Nc2ccnc3c2C(=O)Nc2cc(CN4C[C@H](O)C[C@H]4CO)ccc2N3)cc1O]

In analogy to Example 59, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (69 mg, 69% purity, 0.125 mmol) was reacted with (3R,5S)-5-(hydroxymethyl)pyrrolidin-3-ol hydrochloride (77 mg, 0.500 mmol). 24 mg (40% of theory) of the title compound were obtained.

LC/MS (Method 5, ESIpos): $R_t$=0.52 min, m/z=480 [M+H]$^+$.

$^1$H-NMR (400 MHz, DMSO-$d_6$): δ [ppm]=1.64-1.76 (m, 2H), 2.00-2.10 (m, 2H), 2.10 (s, 3H), 2.70-2.82 (m, 1H), 2.90-3.30 (m, 1H), 3.38-3.45 (m, 1H), 3.85-3.95 (m, 1H), 4.00-4.11 (m, 1H), 4.25-4.40 (m, 1H), 4.59-4.70 (m, 1H), 6.36-6.39 (m, 1H), 6.72 (d, 1H), 6.86-6.96 (m, 2H), 7.01-7.06 (m, 2H), 7.78 (d, 1H), 8.11 (s, 1H), 9.42 (s, 1H), 9.87 (s, 1H), 10.05 (s, 1H).

Example 65 rac-4-[(2-Fluoro-5-hydroxy-4-methylphenyl)amino]-8-[(3-hydroxypyrrolidin-1-yl)methyl]-6,11-dihydro-5H-pyrido[2,3-b][1,5]benzodiazepin-5-one

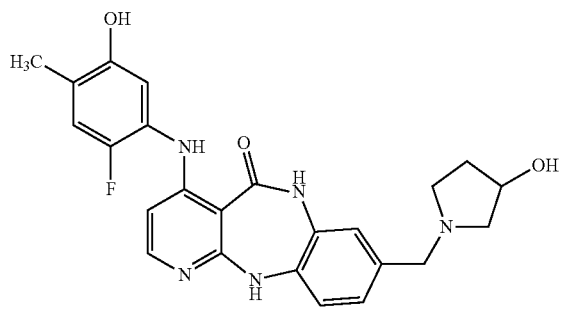 [SMILES: Cc1cc(F)c(Nc2ccnc3c2C(=O)Nc2cc(CN4CCC(O)C4)ccc2N3)cc1O]

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (69 mg, 69% purity, 0.125 mmol) was reacted with rac-pyrrolidin-3-ol (44 mg, 0.500 mmol). Purification by means of preparative HPLC twice (first Method 16, then Method 17) gave 32 mg (58% of theory) of the title compound.

LC/MS (Method 5, ESIpos): $R_t$=0.55 min, m/z=450 [M+H]$^+$.

$^1$H-NMR (400 MHz, DMSO-$d_6$): δ [ppm]=1.46-1.59 (m, 1H), 1.90-2.03 (m, 1H), 2.10 (s, 3H), 2.30 (dd, 1H), 2.36-2.46 (m, 1H), 2.55-2.60 (m, 1H), 2.65-2.72 (m, 1H), 3.47 (dd, 2H), 4.14-4.25 (m, 1H), 4.70 (br. s, 1H), 6.35-6.39 (m, 1H), 6.72 (d, 1H), 6.90-6.96 (m, 2H), 7.00-7.07 (m, 2H), 7.79 (d, 1H), 8.13 (s, 1H), 8.17 (s, 1H), 9.86 (s, 1H), 10.09 (s, 1H).

Example 66 rac-4-[(2-Fluoro-5-hydroxy-4-methylphenyl)amino]-8-[(3-methoxypiperidin-1-yl)methyl]-6,11-dihydro-5H-pyrido[2,3-b][1,5]benzodiazepin-5-one

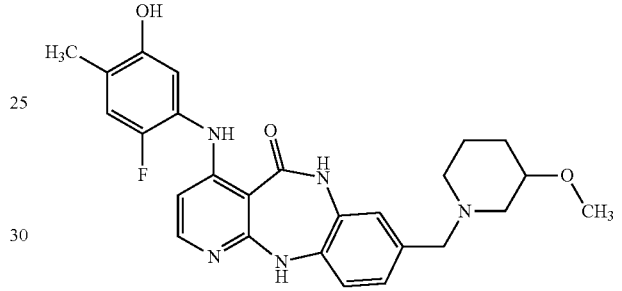

In analogy to Example 59, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (69 mg, 69% purity, 0.125 mmol) was reacted with rac-3-methoxypiperidine hydrochloride (76 mg, 0.500 mmol). 44 mg (74% of theory) of the title compound were obtained.

LC/MS (Method 5, ESIpos): $R_t$=0.59 min, m/z=478 [M+H]$^+$.

$^1$H-NMR (400 MHz, DMSO-$d_6$): δ [ppm]=1.00-1.12 (m, 1H), 1.30-1.45 (m, 1H), 1.55-1.66 (m, 1H), 1.75-1.83 (m, 1H), 1.84-1.96 (m, 2H), 2.10 (s, 3H), 2.53-2.60 (m, 1H), 2.82-2.89 (m, 1H), 3.15-3.23 (m, 1H), 3.20 (s, 3H), 3.32-3.37 (m, 2H), 6.35-6.40 (m, 1H), 6.71 (d, 1H), 6.87-6.94 (m, 2H), 7.00-7.08 (m, 2H), 7.79 (d, 1H), 8.14 (s, 1H), 9.42 (s, 1H), 9.88 (s, 1H), 10.09 (s, 1H).

Example 67 rac-8-[(3-Ethoxypiperidin-1-yl)methyl]-4-[(2-fluoro-5-hydroxy-4-methylphenyl)amino]-6,11-dihydro-5H-pyrido[2,3-b][1,5]benzodiazepin-5-one

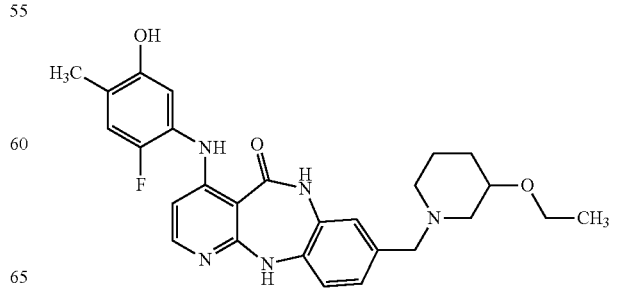

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (137 mg, 69% purity, 0.250 mmol) was reacted with rac-3-ethoxypiperidine (129 mg, 1.00 mmol). 66 mg (54% of theory) of the title compound were obtained.

LC/MS (Method 5, ESIpos): $R_t$=0.64 min, m/z=492 [M+H]$^+$.

$^1$H-NMR (400 MHz, DMSO-d$_6$): δ [ppm]=1.00-1.12 (m, 1H), 1.05 (t, 3H), 1.30-1.45 (m, 1H), 1.55-1.66 (m, 1H), 1.70-1.80 (m, 1H), 1.80-1.96 (m, 2H), 2.10 (s, 3H), 2.55-2.63 (m, 1H), 2.83-2.89 (m, 1H), 3.22-3.30 (m, 1H), 3.32-3.37 (m, 2H), 3.37-3.48 (m, 2H), 6.35-6.40 (m, 1H), 6.71 (d, 1H), 6.87-6.94 (m, 2H), 7.00-7.08 (m, 2H), 7.79 (d, 1H), 8.14 (s, 1H), 9.42 (s, 1H), 9.88 (s, 1H), 10.08 (s, 1H).

Example 68 rac-4-[(2-Fluoro-5-hydroxy-4-methylphenyl)amino]-8-[(3-propoxypiperidin-1-yl)methyl]-6,11-dihydro-5H-pyrido[2,3-b][1,5]benzodiazepin-5-one

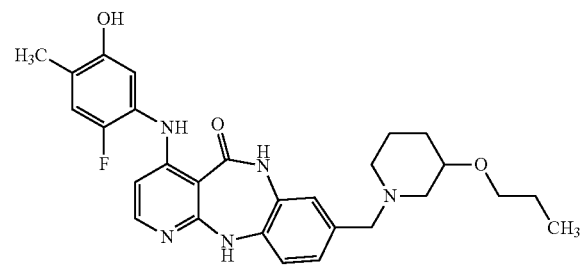 [SMILES: CCCOC1CCCN(Cc2ccc3c(c2)NC(=O)c2c(Nc4cc(O)c(C)cc4F)ccnc2N3)C1]

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (137 mg, 69% purity, 0.250 mmol) was reacted with rac-3-propoxypiperidine (143 mg, 1.00 mmol). 85 mg (67% of theory) of the title compound were obtained.

LC/MS (Method 5, ESIpos): $R_t$=0.69 min, m/z=506 [M+H]$^+$.

$^1$H-NMR (400 MHz, DMSO-d$_6$): δ [ppm]=0.82 (t, 3H), 1.00-1.13 (m, 1H), 1.30-1.50 (m, 3H), 1.57-1.66 (m, 1H), 1.72-1.80 (m, 1H), 1.81-1.95 (m, 2H), 2.10 (s, 3H), 2.55-2.62 (m, 1H), 2.82-2.91 (m, 1H), 3.22-3.33 (m, 3H), 3.34-3.37 (m, 2H), 6.35-6.40 (m, 1H), 6.72 (d, 1H), 6.87-6.94 (m, 2H), 7.00-7.08 (m, 2H), 7.79 (d, 1H), 8.14 (s, 1H), 9.42 (s, 1H), 9.88 (s, 1H), 10.09 (s, 1H).

Example 69 rac-4-[(2-Fluoro-5-hydroxy-4-methylphenyl)amino]-8-[(3-hydroxypiperidin-1-yl)methyl]-6,11-dihydro-5H-pyrido[2,3-b][1,5]benzodiazepin-5-one

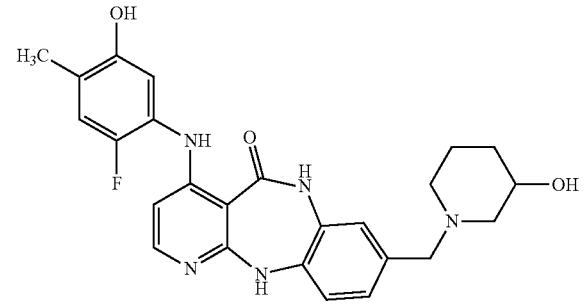 [SMILES: Cc1cc(F)c(Nc2ccnc3c2C(=O)Nc2cc(CN4CCCC(O)C4)ccc2N3)cc1O]

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (120 mg, 0.317 mmol) was reacted with rac-3-hydroxypiperidine (128 mg, 1.27 mmol). 61 mg (42% of theory) of the title compound were obtained.

LC/MS (Method 5, ESIpos): $R_t$=0.57 min, m/z=464 [M+H]$^+$.

$^1$H-NMR (400 MHz, DMSO-d$_6$): δ [ppm]=0.98-1.10 (m, 1H), 1.30-1.47 (m, 1H), 1.52-1.70 (m, 2H), 1.71-1.86 (m, 2H), 2.10 (s, 3H), 2.58-2.63 (m, 1H), 2.70-2.78 (m, 1H), 3.21-3.41 (m, 2H), 3.39-3.47 (m, 1H), 4.51 (d, 1H), 6.36-6.40 (m, 1H), 6.72 (d, 1H), 6.87-6.95 (m, 2H), 7.00-7.08 (m, 2H), 7.79 (d, 1H), 8.13 (s, 1H), 9.41 (s, 1H), 9.86 (s, 1H), 10.09 (s, 1H).

Example 70 ent-4-[(2-Fluoro-5-hydroxy-4-methylphenyl)amino]-8-[(3-hydroxypiperidin-1-yl)methyl]-6,11-dihydro-5H-pyrido[2,3-b][1,5]benzodiazepin-5-one
(Enantiomer 1)

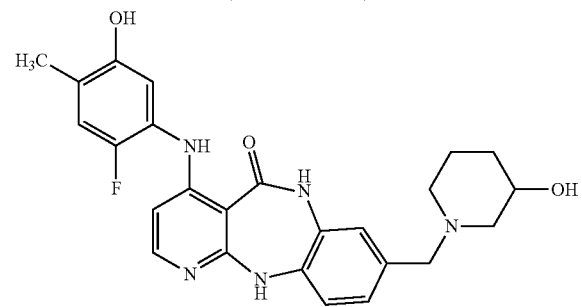 [SMILES: Cc1cc(F)c(Nc2ccnc3c2C(=O)Nc2cc(CN4CCCC(O)C4)ccc2N3)cc1O]

The title compound was obtained by separating 40 mg of the racemic compound from Example 69 into the enantiomers by means of preparative chiral HPLC (Method 18).

Yield: 15 mg.

HPLC (Method 19): $R_t$=7.42 min, ee=98%.

LC/MS (Method 5, ESIpos): $R_t$=0.57 min, m/z=464 [M+H]$^+$.

$^1$H-NMR (400 MHz, DMSO-d$_6$): δ [ppm]=0.98-1.10 (m, 1H), 1.30-1.47 (m, 1H), 1.52-1.70 (m, 2H), 1.71-1.86 (m, 2H), 2.10 (s, 3H), 2.58-2.63 (m, 1H), 2.70-2.78 (m, 1H), 3.21-3.41 (m, 2H), 3.39-3.47 (m, 1H), 4.51 (d, 1H), 6.36-6.40 (m, 1H), 6.72 (d, 1H), 6.87-6.95 (m, 2H), 7.00-7.08 (m, 2H), 7.79 (d, 1H), 8.13 (s, 1H), 9.42 (s, 1H), 9.86 (s, 1H), 10.09 (s, 1H).

Example 71 ent-4-[(2-Fluoro-5-hydroxy-4-methylphenyl)amino]-8-[(3-hydroxypiperidin-1-yl)methyl]-6,11-dihydro-5H-pyrido[2,3-b][1,5]benzodiazepin-5-one
(Enantiomer 2)

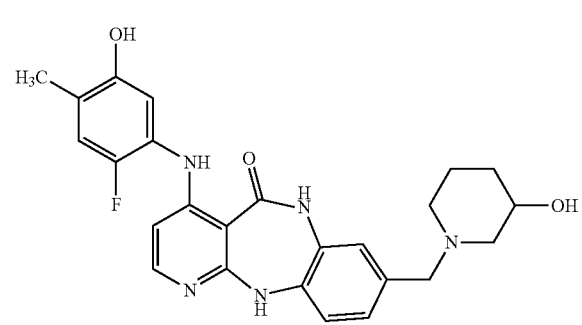 [SMILES: Cc1cc(F)c(Nc2ccnc3c2C(=O)Nc2cc(CN4CCCC(O)C4)ccc2N3)cc1O]

The title compound was obtained by separating 40 mg of the racemic compound from Example 69 into the enantiomers by means of preparative chiral HPLC (Method 18).

Yield: 15 mg.

HPLC (Method 19): $R_t$=9.04 min, ee=96%.

LC/MS (Method 5, ESIpos): $R_t$=0.56 min, m/z=464 [M+H]$^+$.

$^1$H-NMR (400 MHz, DMSO-d$_6$): δ [ppm]=0.98-1.10 (m, 1H), 1.30-1.47 (m, 1H), 1.52-1.70 (m, 2H), 1.71-1.86 (m, 2H), 2.10 (s, 3H), 2.58-2.63 (m, 1H), 2.70-2.78 (m, 1H), 3.21-3.41 (m, 2H), 3.39-3.47 (m, 1H), 4.51 (d, 1H), 6.36-6.40 (m, 1H), 6.72 (d, 1H), 6.87-6.95 (m, 2H), 7.00-7.08 (m, 2H), 7.79 (d, 1H), 8.13 (s, 1H), 9.41 (s, 1H), 9.86 (s, 1H), 10.09 (s, 1H).

Example 72 rac-4-[(2-Fluoro-5-hydroxy-4-methylphenyl)amino]-8-[(3-phenoxypiperidin-1-yl)methyl]-6,11-dihydro-5H-pyrido[2,3-b][1,5]benzodiazepin-5-one

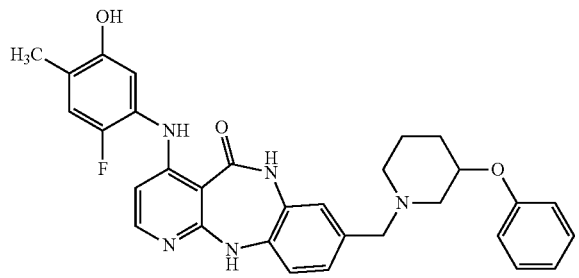 [SMILES: Cc1cc(F)c(Nc2ccnc3c2C(=O)Nc2cc(CN4CCCC(Oc5ccccc5)C4)ccc2N3)cc1O]

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (137 mg, 69% purity, 0.250 mmol) was reacted with rac-3-phenoxypiperidine (177 mg, 1.00 mmol). 94 mg (70% of theory) of the title compound were obtained.

LC/MS (Method 5, ESIpos): $R_t$=0.72 min, m/z=540 [M+H]$^+$.

$^1$H-NMR (400 MHz, DMSO-d$_6$): δ [ppm]=1.29-1.40 (m, 1H), 1.45-1.60 (m, 1H), 1.67-1.79 (m, 1H), 1.92-2.07 (m, 3H), 2.10 (s, 3H), 2.58-2.67 (m, 1H), 2.85-2.95 (m, 1H), 3.35-3.47 (m, 2H), 4.29-4.40 (m, 1H), 6.36-6.42 (m, 1H), 6.72 (d, 1H), 6.80-6.87 (m, 1H), 6.87-6.95 (m, 3H), 6.95-6.98 (m, 1H), 7.00-7.07 (m, 2H), 7.17-7.25 (m, 2H), 7.79 (d, 1H), 8.13 (s, 1H), 9.42 (s, 1H), 9.90 (s, 1H), 10.09 (s, 1H).

Example 73 rac-4-[(2-Fluoro-5-hydroxy-4-methylphenyl)amino]-8-[(3-hydroxy-3-phenylpiperidin-1-yl)methyl]-6,11-dihydro-5H-pyrido[2,3-b][1,5]benzodiazepin-5-one

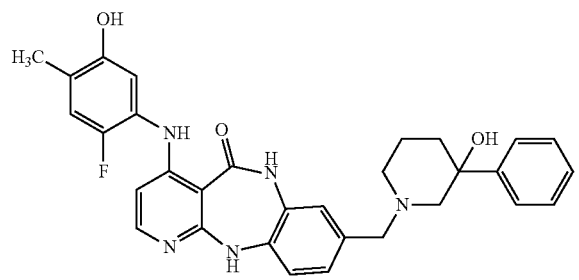 [SMILES: Cc1cc(F)c(Nc2ccnc3c2C(=O)Nc2cc(CN4CCCC(O)(c5ccccc5)C4)ccc2N3)cc1O]

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (137 mg, 69% purity, 0.250 mmol) was reacted with rac-3-phenylpiperidin-3-ol (177 mg, 1.00 mmol). 56 mg (41% of theory) of the title compound were obtained.

LC/MS (Method 5, ESIpos): $R_t$=0.67 min, m/z=540 [M+H]$^+$.

$^1$H-NMR (400 MHz, DMSO-d$_6$): δ [ppm]=1.40-1.49 (m, 1H), 1.51-1.60 (m, 1H), 1.73-1.89 (m, 2H), 2.10 (s, 3H), 2.12-2.20 (m, 1H), 2.38-2.44 (m, 2H), 2.57-2.65 (m, 1H), 3.39-3.43 (m, 2H), 4.55 (s, 1H), 6.34-6.40 (m, 1H), 6.72 (d, 1H), 6.95-7.00 (m, 2H), 7.00-7.08 (m, 2H), 7.15-7.23 (m, 1H), 7.25-7.33 (m, 2H), 7.48-7.55 (m, 2H), 7.78 (d, 1H), 8.14 (s, 1H), 9.41 (s, 1H), 9.88 (s, 1H), 10.06 (s, 1H).

Example 74

4-[(2-Fluoro-5-hydroxy-4-methylphenyl)amino]-8-({[2-(pyridin-4-yl)ethyl]amino}methyl)-6,11-dihydro-5H-pyrido[2,3-b][1,5]benzodiazepin-5-one

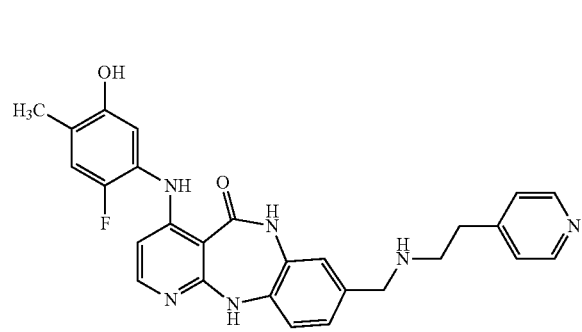 [SMILES: Cc1cc(F)c(Nc2ccnc3c2C(=O)Nc2cc(CNCCc4ccncc4)ccc2N3)cc1O]

To an initial charge of 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (51.6 mg, 80% purity, 0.110 mmol) in methanol (5.0 ml) were added 2-(pyridin-4-yl)ethanamine (108 mg, 0.884 mmol), acetic acid (50.6 µl, 0.884 mmol) and sodium cyanoborohydride (34.7 mg, 0.552 mmol). The mixture was stirred at RT for 1 h, then admixed with water and extracted with ethyl acetate. The combined organic phases were washed with saturated aqueous sodium chloride solution, dried over sodium sulphate, filtered and concentrated to dryness. The residue was purified by means of preparative HPLC (column: Kinetex C18 5µ, 100×30 mm; eluent A: water, eluent B: methanol, eluent C: 1% formic acid in water; gradient: 0-1 min 90% A, 5% B, 5% C→1-5.50 min 66.2% A, 28.8% B, 5% C→5.51-5.92 min 0% A, 95% B, 5% C). 19.8 mg (37% of theory) of the title compound were obtained.

LC/MS (Method 6, ESIpos): $R_t$=2.10 min, m/z=485 [M+H]$^+$.

$^1$H-NMR (400 MHz, DMSO-d$_6$): δ [ppm]=2.10 (s, 3H), 2.70-2.81 (m, 4H), 3.63 (s, 2H), 6.37 (dd, 1H), 6.72 (d, 1H), 6.90-6.99 (m, 2H), 6.99-7.07 (m, 2H), 7.23 (d, 2H), 7.79 (d, 1H), 8.11 (s, 1H), 8.19 (br. s, 1H), 8.43 (d, 2H), 9.85 (s, 1H), 10.11 (s, 1H).

Example 75 rac-4-[(2-Fluoro-5-hydroxy-4-methylphenyl)amino]-8-{[(1-hydroxy-3-methylbutan-2-yl)amino]methyl}-6,11-dihydro-5H-pyrido[2,3-b][1,5]benzodiazepin-5-one

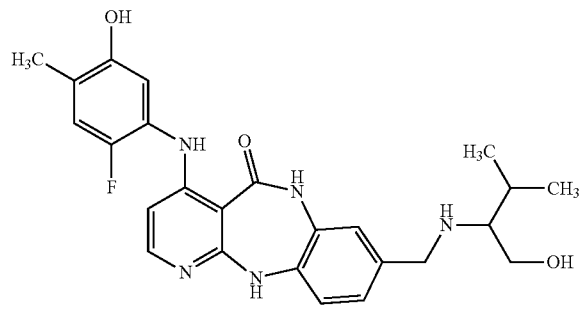 [SMILES: Cc1cc(F)c(Nc2ccnc3c2C(=O)Nc2cc(CNC(CO)C(C)C)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A) (60.0 mg, 80% purity, 0.127 mmol), analogously to Example 74, was reacted with 2-amino-3-methyl-1-butanol (105 mg, 1.02 mmol). The crude product was purified by means of preparative HPLC (column: Kinetex C18, 100×30 mm, 5 µm; eluent A: water, eluent B: acetonitrile, eluent C: 1% formic acid in water; gradient: 0-1 min 90% A, 5% B, 5% C→6.66 min 60% A, 35% B, 5% C). 38.0 mg (64% of theory) of the title compound were obtained.

LC/MS (Method 6, ESIpos): $R_t$=2.18 min, m/z=466 [M+H]$^+$.

$^1$H-NMR (400 MHz, DMSO-d$_6$): δ [ppm]=0.86 (dd, 6H), 1.73-1.87 (m, 1H), 2.10 (s, 3H), 2.32 (m, 1H), 3.33 (dd, 1H), 3.47 (dd, 1H), 3.64 (d, 1H), 3.70 (d, 1H), 6.37 (d, 1H), 6.72 (d, 1H), 6.96-7.09 (m, 4H), 7.79 (d, 1H), 8.12 (s, 1H), 8.18 (br. s, 1H), 9.86 (s, 1H), 10.11 (s, 1H).

Example 76

4-[(2-Fluoro-5-hydroxy-4-methylphenyl)amino]-8-{[(trans-4-hydroxycyclohexyl)amino]methyl}-6,11-dihydro-5H-pyrido[2,3-b][1,5]benzodiazepin-5-one

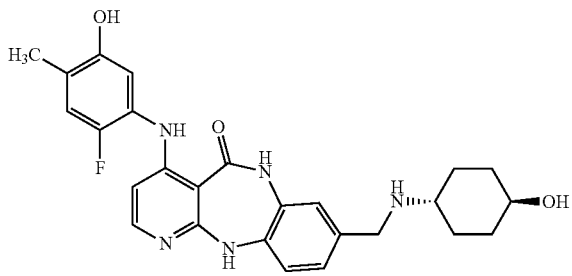 [SMILES: Cc1cc(F)c(Nc2ccnc3c2C(=O)Nc2cc(CN[C@H]4CC[C@H](O)CC4)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A) (60.0 mg, 80% purity, 0.127 mmol), analogously to Example 74, was reacted with trans-4-aminocyclohexanol (119 mg, 1.02 mmol). The crude product was purified by means of preparative HPLC (column: Kinetex C18, 100×30 mm, 5 µm; flow rate: 60 ml/min; eluent A: water, eluent B: acetonitrile, eluent C: 1% formic acid in water; gradient: 0-1 min 90% A, 5% B, 5% C→1.01-4.96 min 69% A, 26% B, 5% C→5.11 min 0% A, 95% B, 5% C). 17.3 mg (27% of theory) of the title compound were obtained.

LC/MS (Method 6, ESIpos): $R_t$=1.95 min, m/z=478 [M+H]$^+$.

$^1$H-NMR (400 MHz, DMSO-d$_6$): δ [ppm]=1.04-1.20 (m, 4H), 1.73-1.85 (m, 2H), 1.85-1.97 (m, 2H), 2.10 (s, 3H), 3.28-3.40 (m, 1H), 3.73 (s, 2H), 6.37 (dd, 1H), 6.72 (d, 1H), 6.96-7.12 (m, 4H), 7.79 (d, 1H), 8.15 (s, 1H), 8.22 (br. s, 1H), 9.84 (s, 1H), 10.14 (s, 1H).

Example 77 rac-8-{[(1-Cyclohexylethyl)amino]methyl}-4-[(2-fluoro-5-hydroxy-4-methylphenyl)amino]-6,11-dihydro-5H-pyrido[2,3-b][1,5]benzodiazepin-5-one

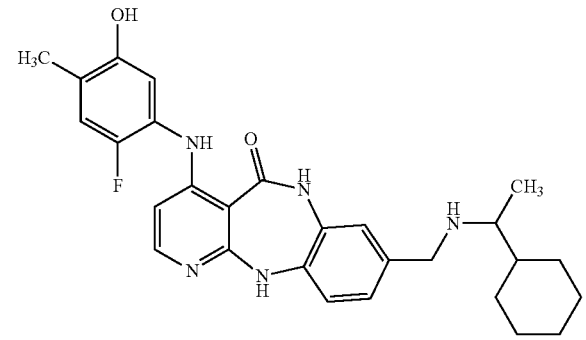 [SMILES: Cc1cc(F)c(Nc2ccnc3c2C(=O)Nc2cc(CNC(C)C4CCCCC4)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A) (60.0 mg, 80% purity, 0.127 mmol), analogously to Example 74, was reacted with rac-1-cyclohexylethylamine (129 mg, 1.02 mmol). The crude product was purified by means of preparative HPLC (Method 20). 42 mg (67% of theory) of the title compound were obtained.

LC/MS (Method 6, ESIpos): $R_t$=2.65 min, m/z=490 [M+H]$^+$.

$^1$H-NMR (400 MHz, DMSO-d$_6$): δ [ppm]=0.89-1.02 (m, 5H), 1.03-1.25 (m, 3H), 1.28-1.40 (m, 1H), 1.55-1.75 (m, 5H), 2.10 (s, 3H), 2.39-2.48 (m, 1H), 3.56-3.62 (m, 1H), 3.65-3.77 (m, 1H), 6.37 (dd, 1H), 6.72 (d, 1H), 6.96-7.08 (m, 4H), 7.79 (d, 1H), 8.11 (s, 1H), 8.21 (br. s, 1H), 9.85 (s, 1H), 10.11 (s, 1H).

Example 78

8-{[(1,3-Dihydroxypropan-2-yl)amino]methyl}-4-[(2-fluoro-5-hydroxy-4-methylphenyl)amino]-6,11-dihydro-5H-pyrido[2,3-b][1,5]benzodiazepin-5-one

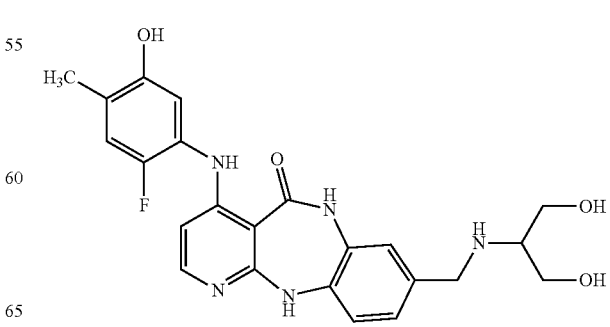

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A) (60.0 mg, 80% purity, 0.127 mmol), analogously to Example 74, was reacted with 2-aminopropane-1,3-diol (92.5 mg, 1.02 mmol). The crude product was purified by means of preparative HPLC (Method 20). 34 mg (57% of theory) of the title compound were obtained.

LC/MS (Method 6, ESIpos): $R_t$=1.88 min, m/z=454 [M+H]$^+$.

$^1$H-NMR (400 MHz, DMSO-d$_6$): δ [ppm]=2.10 (s, 3H), 2.55-2.62 (m, 1H), 3.34-3.39 (m, 2H), 3.40-3.46 (m, 2H), 3.71 (s, 2H), 6.37 (dd, 1H), 6.72 (d, 1H), 6.94-7.08 (m, 4H), 7.79 (d, 1H), 8.12 (s, 1H), 8.18 (br. s, 1H), 9.85 (s, 1H), 10.10 (s, 1H).

Example 79

4-[(2-Fluoro-5-hydroxy-4-methylphenyl)amino]-5-oxo-6,11-dihydro-5H-pyrido[2,3-b][1,5]benzodiazepine-8-carboxylic acid

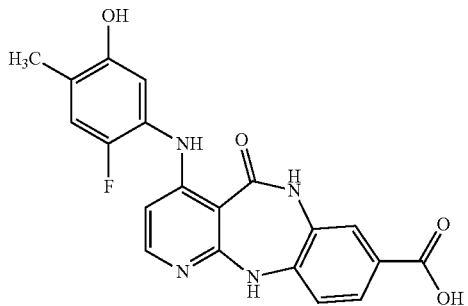 [SMILES: Cc1cc(F)c(Nc2ccnc3c2C(=O)Nc2cc(C(=O)O)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbonitrile (Example 27) (100 mg, 0.27 mmol) was heated under reflux with concentrated hydrochloric acid (37% in water, 1.5 ml) overnight. The mixture was then cooled to room temperature and admixed with saturated aqueous sodium carbonate solution. Purification by preparative HPLC (Method 16) gave 38 mg (36% of theory) of the title compound.

LC/MS (Method 5, ESIpos): $R_t$=0.70 min, m/z=395 [M+H]$^+$.

$^1$H-NMR (400 MHz, DMSO-d$_6$): δ [ppm]=2.09 (s, 3H), 6.37-6.42 (m, 1H), 6.75 (d, 1H), 6.95 (d, 1H), 7.02 (d, 1H), 7.44-7.49 (m, 1H), 7.51 (d, 1H), 7.78 (d, 1H), 8.09 (s, 1H), 9.88 (s, 1H), 10.07 (s, 1H).

Example 80

4-[(2-Fluoro-5-hydroxy-4-methylphenyl)amino]-5-oxo-6,11-dihydro-5H-pyrido[2,3-b][1,5]benzodiazepine-8-carboxamide

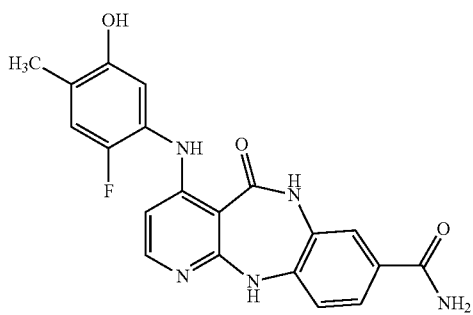 [SMILES: Cc1cc(F)c(Nc2ccnc3c2C(=O)Nc2cc(C(N)=O)ccc2N3)cc1O]

Under an argon atmosphere, the compound from Example 79 (12 mg, 0.032 mmol) was dissolved in DMF (0.45 ml) and cooled to 0° C. HATU (24 mg, 0.064 mmol) was added, and the mixture was stirred for 20 min. Subsequently, ammonium chloride (9 mg, 0.16 mmol) and N,N-diisopropylethylamine (29 mg, 0.44 mmol) were added and the reaction mixture was stirred at RT for 90 min. Direct purification by preparative HPLC (Method 16) gave 8 mg (63% of theory) of the title compound.

LC/MS (Method 5, ESIpos): $R_t$=0.64 min, m/z=394 [M+H]$^+$.

$^1$H-NMR (400 MHz, DMSO-d$_6$): δ [ppm]=2.10 (s, 3H), 6.37-6.40 (m, 1H), 6.72 (d, 1H), 7.04 (d, 1H), 7.14 (d, 1H), 7.22 (s, 1H), 7.49-7.54 (m, 2H), 7.75-7.82 (m, 2H), 8.45 (s, 1H), 9.42 (s, 1H), 9.86 (s, 1H), 10.19 (s, 1H).

Example 81

4-[(2-Fluoro-5-hydroxy-4-methylphenyl)amino]-N-(3-hydroxycyclohexyl)-5-oxo-6,11-dihydro-5H-pyrido[2,3-b][1,5]benzodiazepine-8-carboxamide

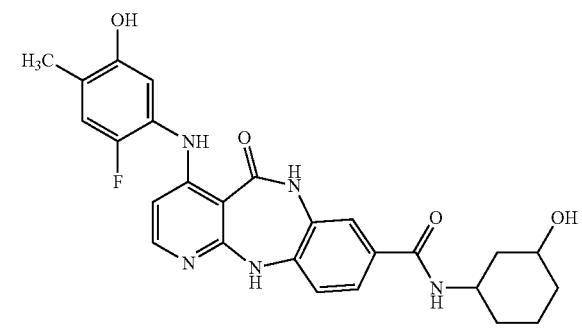 [SMILES: Cc1cc(F)c(Nc2ccnc3c2C(=O)Nc2cc(C(=O)NC4CCCC(O)C4)ccc2N3)cc1O]

In analogy to Example 80, 4-[(2-fluoro-5-hydroxy-4-methylphenyl)amino]-5-oxo-6,11-dihydro-5H-pyrido[2,3-b][1,5]benzodiazepine-8-carboxylic acid (Example 79) (100 mg, 0.253 mmol) was reacted with 3-aminocyclohexanol (146 mg, 1.267 mmol). 13 mg (10% of theory) of the title compound were obtained as a stereoisomer mixture.

LC/MS (Method 7, ESIpos): $R_t$=0.88 min; m/z=492 (Cl isotope pattern, M+H)$^+$ $^1$H-NMR (400 MHz, DMSO-d$_6$): δ [ppm]=0.95-1.60 (m, 5H), 1.60-1.85 (m, 3.2H), 1.91-2.01 (m, 0.8H), 2.10 (s, 3H), 3.40-3.55 (m, 2H), 3.70-3.85 (m, 0.8H), 3.93-4.00 (m, 0.3H), 4.10-4.20 (m, 0.2H), 4.35-4.50 (m, 0.3H), 4.60-4.75 (m, 0.6H), 6.35-6.40 (m, 1H), 6.71 (d, 1H), 7.03 (d, 1H), 7.14 (d, 1H), 7.42-7.60 (m, 2H), 7.79 (d, 1H), 7.93 (d, 0.3H), 8.11 (d, 0.7H), 8.40-8.50 (m, 1H), 9.85 (s, 1H), 9.98 (s, 0.2H), 10.17 (s, 0.8H).

Example 82 rac-4-[(2-Fluoro-5-hydroxy-4-methylphenyl)amino]-8-[(3-hydroxypiperidin-1-yl)carbonyl]-6,11-dihydro-5H-pyrido[2,3-b][1,5]benzodiazepin-5-one

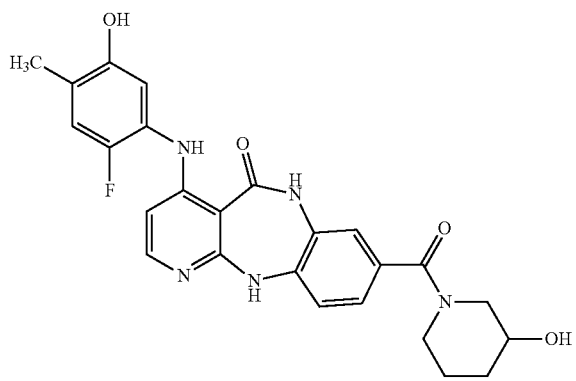 [SMILES: Cc1cc(F)c(Nc2ccnc3c2C(=O)Nc2cc(C(=O)N4CCCC(O)C4)ccc2N3)cc1O]

In analogy to Example 80, 4-[(2-fluoro-5-hydroxy-4-methylphenyl)amino]-5-oxo-6,11-dihydro-5H-pyrido[2,3-b][1,5]benzodiazepine-8-carboxylic acid (Example 79) (100 mg, 0.253 mmol) was reacted with 3-hydroxypiperidine (128 mg, 1.267 mmol). After purification by means of silica gel chromatography (eluent: dichloromethane/methanol 10:1), 118 mg (97% of theory) of the title compound were obtained.

LC/MS (Method 5, ESIpos): $R_t$=0.62 min, m/z=478 [M+H]$^+$.

$^1$H-NMR (400 MHz, DMSO-d$_6$): δ [ppm]=1.25-1.40 (m, 2H), 1.64-1.80 (m, 2H), 2.10 (s, 3H), 3.07-3.20 (m, 2H), 3.40-4.10 (m, 3H), 4.76 (d, 1H), 6.36-6.40 (m, 1H), 6.71 (d, 1H), 7.00-7.08 (m, 3H), 7.12-7.18 (m, 1H), 7.81 (d, 1H), 8.41 (s, 1H), 9.43 (s, 1H), 9.88 (s, 1H), 10.18 (s, 1H).

Example 83

N-Ethyl-4-[(2-fluoro-5-hydroxy-4-methylphenyl)amino]-5-oxo-6,11-dihydro-5H-pyrido[2,3-b][1,5]benzodiazepine-8-carboxamide

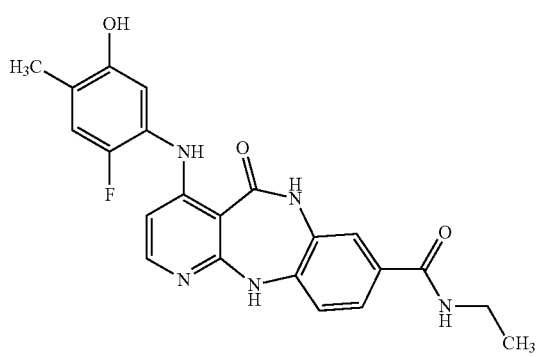 [SMILES: CCNC(=O)c1ccc2c(c1)NC(=O)c1c(Nc3cc(O)c(C)cc3F)ccnc1N2]

In analogy to Example 80, 4-[(2-fluoro-5-hydroxy-4-methylphenyl)amino]-5-oxo-6,11-dihydro-5H-pyrido[2,3-b][1,5]benzodiazepine-8-carboxylic acid (Example 79) (100 mg, 0.253 mmol) was reacted with ethylamine (57 mg, 1.267 mmol). After purification by means of preparative HPLC (Method 11) and another postpurification by means of preparative HPLC (column: Kinetex C18 5μ, 100×21.2 mm; flow rate: 25 ml/min; eluent A: water, eluent B: acetonitrile, eluent C: 1% formic acid in water; isocratic 52% A, 35% B, 13% C), 35 mg (33% of theory) of the title compound were obtained.

LC/MS (Method 5, ESIpos): $R_t$=0.68 min, m/z=421 [M+H]$^+$.

$^1$H-NMR (400 MHz, DMSO-d$_6$): δ [ppm]=1.10 (t, 3H), 2.10 (s, 3H), 3.25 (q, 2H), 6.38 (d, 1H), 6.72 (d, 1H), 7.04 (d, 1H), 7.14 (d, 1H), 7.45-7.51 (m, 2H), 7.80 (d, 1H), 8.29 (t, 1H), 8.44 (s, 1H), 9.43 (s, 1H), 9.86 (s, 1H), 10.19 (s, 1H).

Example 84

N,N-Diethyl-4-[(2-fluoro-5-hydroxy-4-methylphenyl)amino]-5-oxo-6,11-dihydro-5H-pyrido[2,3-b][1,5]benzodiazepine-8-carboxamide

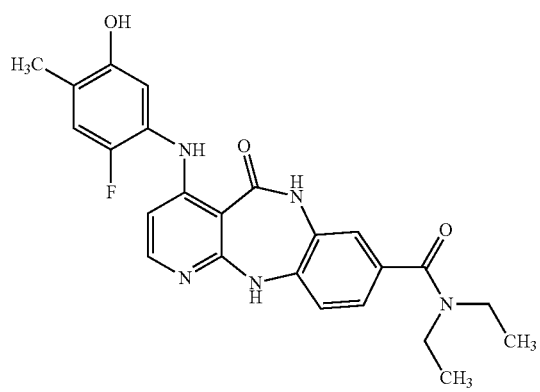 [SMILES: CCN(CC)C(=O)c1ccc2c(c1)NC(=O)c1c(Nc3cc(O)c(C)cc3F)ccnc1N2]

Under an argon atmosphere, 4-[(2-fluoro-5-hydroxy-4-methylphenyl)amino]-5-oxo-6,11-dihydro-5H-pyrido[2,3-b][1,5]benzodiazepine-8-carboxylic acid (Example 79) (100 mg, 0.253 mmol) was initially charged in DMF (1 ml) and cooled to 0° C. HATU (193 mg, 0.507 mmol) was added, and the mixture was stirred for 20 min. Subsequently, diethylamine (93 mg, 1.267 mmol) and N,N-diisopropylethylamine (229 mg, 1.775 mmol) were added and stirring of the mixture at RT continued overnight. The reaction mixture was then admixed with water and extracted with ethyl acetate. The combined organic phases were dried over sodium sulphate, filtered and concentrated. Purification by means of silica gel chromatography (eluent: dichloromethane/methanol 10:1) and subsequent purification by means of preparative HPLC (Method 16) gave 19 mg (17% of theory) of the title compound.

LC/MS (Method 5, ESIpos): $R_t$=0.77 min, m/z=450 [M+H]$^+$.

$^1$H-NMR (400 MHz, DMSO-d$_6$): δ [ppm]=1.09 (t, 6H), 2.10 (s, 3H), 3.15-3.40 (m, 4H), 6.36-6.41 (m, 1H), 6.73 (d, 1H), 6.96-6.98 (m, 1H), 7.00 (dd, 1H), 7.04 (d, 1H), 7.14 (d, 1H), 7.81 (d, 1H), 8.40 (s, 1H), 9.43 (s, 1H), 9.89 (s, 1H), 10.17 (s, 1H).

Example 85

4-[(2-Fluoro-5-hydroxy-4-methylphenyl)amino]-8-(morpholin-4-ylcarbonyl)-6,11-dihydro-5H-pyrido[2,3-b][1,5]benzodiazepin-5-one

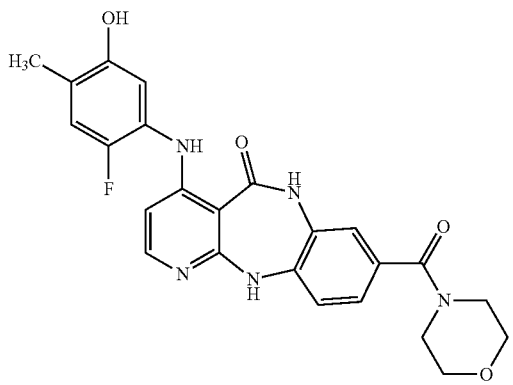 [SMILES: Cc1cc(F)c(Nc2ccnc3c2C(=O)Nc2cc(C(=O)N4CCOCC4)ccc2N3)cc1O]

Under an argon atmosphere, 4-[(2-fluoro-5-hydroxy-4-methylphenyl)amino]-5-oxo-6,11-dihydro-5H-pyrido[2,3-b][1,5]benzodiazepine-8-carboxylic acid (Example 79) (100 mg, 0.253 mmol) was initially charged in DMF (1 ml) and cooled to 0° C. HATU (193 mg, 0.507 mmol) was added, and the mixture was stirred for 20 min. Subsequently, morpholine (110 mg, 1.267 mmol) and N,N-diisopropylethylamine (229 mg, 1.775 mmol) were added and stirring of the mixture at RT continued overnight. The reaction mixture was then concentrated. Purification of the residue by means of silica gel chromatography (eluent: dichloromethane/methanol 10:1) and subsequent purification by means of preparative HPLC (Method 16) gave 20 mg (17% of theory) of the title compound.

LC/MS (Method 5, ESIpos): $R_t$=0.69 min, m/z=464 [M+H]$^+$.

$^1$H-NMR (400 MHz, DMSO-d$_6$): δ [ppm]=2.10 (s, 3H), 3.40-3.70 (m, 8H), 6.35-6.41 (m, 1H), 6.72 (d, 1H), 7.02-7.09 (m, 3H), 7.16 (d, 1H), 7.80 (d, 1H), 8.44 (s, 1H), 9.43 (s, 1H), 9.87 (s, 1H), 10.19 (s, 1H).

Example 86 rac-4-[(2-Fluoro-5-hydroxy-4-methylphenyl)amino]-8-[(3-hydroxypyrrolidin-1-yl)carbonyl]-6,11-dihydro-5H-pyrido[2,3-b][1,5]benzodiazepin-5-one

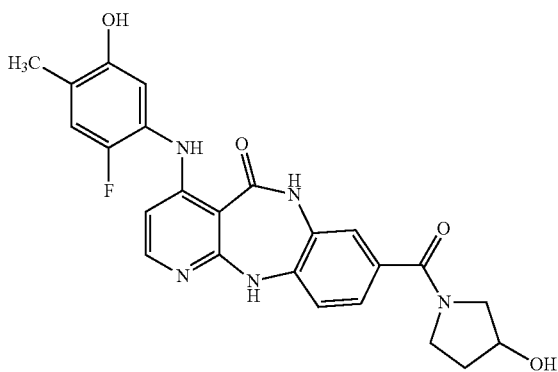 [SMILES: Cc1cc(F)c(Nc2ccnc3c2C(=O)Nc2cc(C(=O)N4CCC(O)C4)ccc2N3)cc1O]

In analogy to Example 85, 4-[(2-fluoro-5-hydroxy-4-methylphenyl)amino]-5-oxo-6,11-dihydro-5H-pyrido[2,3-b][1,5]benzodiazepine-8-carboxylic acid (Example 79) (100 mg, 0.253 mmol) was reacted with 3-hydroxypyrrolidine (111 mg, 1.267 mmol). 49 mg (40% of theory) of the title compound were obtained.

LC/MS (Method 5, ESIpos): $R_t$=0.63 min, m/z=464 [M+H]$^+$.

$^1$H-NMR (400 MHz, DMSO-d$_6$): δ [ppm]=1.70-2.00 (m, 2H), 2.10 (s, 3H), 3.17 (d, 1H), 3.40-3.60 (m, 3H), 4.19-4.33 (m, 1H), 4.89-5.01 (m, 1H), 6.38 (d, 1H), 6.73 (d, 1H), 7.04 (d, 1H), 7.10-7.27 (m, 3H), 7.81 (d, 1H), 8.44 (s, 1H), 9.43 (s, 1H), 8.80 (s, 1H), 9.89 (s, 1H), 10.18 (br. s, 1H).

Example 87

8-(Aminomethyl)-4-[(2-fluoro-5-hydroxy-4-methylphenyl)amino]-6,11-dihydro-5H-pyrido[2,3-b][1,5]benzodiazepin-5-one

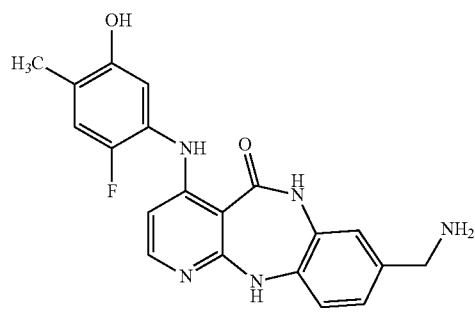 [SMILES: Cc1cc(F)c(Nc2ccnc3c2C(=O)Nc2cc(CN)ccc2N3)cc1O]

Under an argon atmosphere, 4-[(2-fluoro-5-hydroxy-4-methylphenyl)amino]-5-oxo-6,11-dihydro-5H-pyrido[2,3-b][1,5]benzodiazepine-8-carbonitrile (Example 27) (188 mg, 0.500 mmol) was initially charged in THF (5 ml), lithium aluminium hydride (2 N solution in THF, 1.25 ml, 2.50 mmol) was added at RT and the mixture was heated under reflux for 90 min. The reaction mixture was then admixed with water and filtered with suction through kieselguhr. The residue was washed with methanol and the filtrate was concentrated. Purification by means of preparative HPLC (Method 16) and subsequent postpurification by means of preparative HPLC (column: Kinetex C18 5µ, 100×21.2 mm; flow rate: 25 ml/min; eluent A: water, eluent B: acetonitrile, eluent C: 1% formic acid in water; gradient: 0-1 min 90% A, 5% B, 5% C, 7 min 30% A, 65% B, 5% C) gave 5 mg (3% of theory) of the title compound.

LC/MS (Method 5, ESIpos): $R_t$=0.51 min, m/z=380 [M+H]$^+$.

$^1$H-NMR (400 MHz, DMSO-d$_6$): δ [ppm]=2.10 (s, 3H), 3.72 (s, 2H), 6.35-6.40 (m, 1H), 6.72 (d, 1H), 6.96-7.10 (m, 4H), 7.78 (d, 1H), 8.14 (s, 1H), 8.28 (s, 1H), 9.45 (br. s, 1H), 9.83 (s, 1H), 10.16 (s, 1H).

Example 88 rac-4-[(2-Fluoro-5-hydroxy-4-methylphenyl)amino]-8-[(3-hydroxy-3-methylpiperidin-1-yl)methyl]-6,11-dihydro-5H-pyrido[2,3-b][1,5]benzodiazepin-5-one

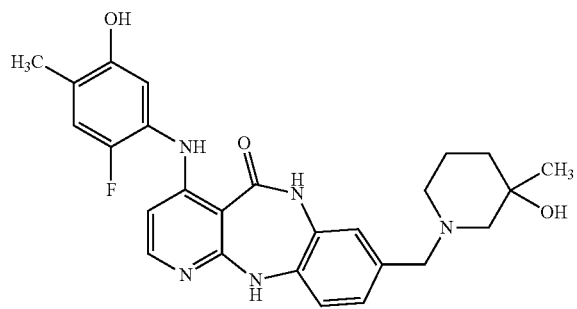 [SMILES: Cc1cc(F)c(Nc2ccnc3c2C(=O)Nc2cc(CN4CCCC(C)(O)C4)ccc2N3)cc1O]

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (120 mg, 0.317 mmol) was reacted with rac-methylpiperidin-3-ol (146 mg, 1.27 mmol). 58 mg (38% of theory) of the title compound were obtained.

LC/MS (Method 7, ESIneg): $R_t$=0.77 min, m/z=476 [M−H]⁻.

¹H-NMR (400 MHz, DMSO-$d_6$): δ [ppm]=1.10 (s, 3H), 1.28-1.50 (m, 3H), 1.52-1.68 (m, 1H), 2.00-2.08 (m, 1H), 2.10 (s, 3H), 2.12-2.24 (m, 1H), 2.25-2.35 (m, 1H), 3.25-3.42 (m, 3H), 4.07 (s, 1H), 6.36-6.40 (m, 1H), 6.72 (d, 1H), 6.90-6.97 (m, 2H), 7.00-7.08 (m, 2H), 7.79 (d, 1H), 8.13 (s, 1H), 9.42 (s, 1H), 9.88 (s, 1H), 10.08 (s, 1H).

Example 89 rac-4-[(2-Fluoro-5-hydroxy-4-methylphenyl)amino]-8-{[3-(2,2,2-trifluoroethoxy)piperidin-1-yl]methyl}-6,11-dihydro-5H-pyrido[2,3-b][1,5]benzodiazepin-5-one

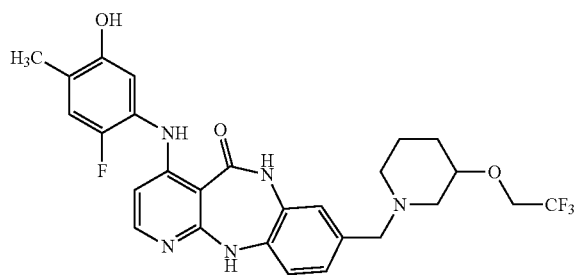

In analogy to Example 61, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (137 mg, 69% purity, 0.250 mmol) was reacted with rac-3-(2,2,2-trifluoroethoxy)piperidine (183 mg, 1.00 mmol). 82 mg (60% of theory) of the title compound were obtained.

LC/MS (Method 5, ESIpos): $R_t$=0.67 min, m/z=546 [M+H]⁺.

¹H-NMR (400 MHz, DMSO-$d_6$): δ [ppm]=1.08-1.20 (m, 1H), 1.30-1.45 (m, 1H), 1.57-1.70 (m, 1H), 1.81-1.98 (m, 2H), 2.09 (s, 3H), 2.83-2.90 (m, 1H), 3.36-3.38 (m, 2H), 3.45-3.55 (m, 1H), 3.96-4.11 (m, 2H), 6.35-6.40 (m, 1H), 6.70 (d, 1H), 6.88-6.95 (m, 2H), 6.99-7.08 (m, 2H), 7.77 (d, 1H), 8.13 (s, 1H), 9.86 (s, 1H), 10.08 (s, 1H).

Example 90

4-[(4-Chloro-2-fluoro-5-hydroxyphenyl)amino]-8-{[ethyl(2-hydroxyethyl)amino]methyl}-6,11-dihydro-5H-pyrido[2,3-b][1,5]benzodiazepin-5-one

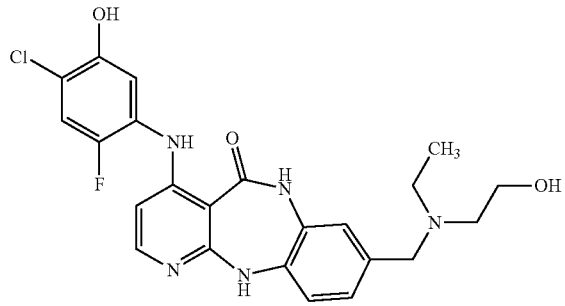 [SMILES: CCN(CCO)Cc1ccc2c(c1)NC(=O)c1c(Nc3cc(O)c(Cl)cc3F)ccnc1N2]

To a solution of 4-[(4-chloro-2-fluoro-5-hydroxyphenyl)amino]-5-oxo-6,11-dihydro-5H-pyrido[2,3-b][1,5]benzodiazepine-8-carbaldehyde (Intermediate 13A) (60.0 mg, 88% purity, 0.132 mmol) in DMF (1.30 ml) were added 2-(ethylamino)ethanol (47.2 mg, 0.530 mmol) and trimethyl orthoformate (281 mg, 2.65 mmol), and the mixture was stirred at RT for 5 h. Subsequently, sodium triacetoxyborohydride (112 mg, 0.530 mmol) was added and the mixture was stirred at RT overnight. Then saturated aqueous sodium hydrogencarbonate solution was added and the mixture was extracted three times with ethyl acetate. The combined organic phases were washed with saturated aqueous sodium chloride solution, dried over sodium sulphate and concentrated to dryness. The crude product obtained was purified by means of preparative HPLC (column: Sunfire C18, 75 mm×30 mm, 5 μm, flow rate: 75 ml/min; eluent A: water, eluent B: acetonitrile, eluent C: 1% formic acid in water; gradient: 0-1 min 90% A, 5% B, 5% C→1.01-9.50 min 0% A, 95% B, 5% C). 14.5 mg (23% of theory) of the title compound were obtained.

LC/MS (Method 5, ESIpos): $R_t$=0.59 min, m/z=472 [M+H]⁺.

¹H-NMR (400 MHz, DMSO-$d_6$): δ [ppm]=0.97 (t, 3H), 2.44-2.49 (m, 4H), 3.44 (t, 2H), 3.47 (s, 2H), 6.48 (d, 1H), 6.90-6.98 (m, 3H), 7.04 (d, 1H), 7.42 (d, 1H), 7.84 (d, 1H), 8.16 (br. s, 1H), 8.17 (s, 1H), 9.98 (s, 1H), 10.12 (s, 1H).

Example 91

4-[(2-Fluoro-5-hydroxy-4-methylphenyl)amino]-8-({3-hydroxy-4-[(2-hydroxyethyl)amino]pyrrolidin-1-yl}methyl)-6,11-dihydro-5H-pyrido[2, 3-b][1,5]benzodiazepin-5-one

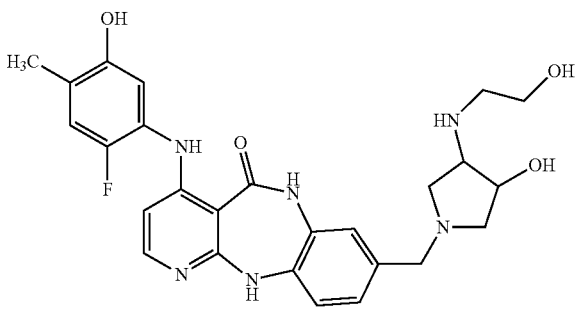 [SMILES: Cc1cc(F)c(Nc2ccnc3c2C(=O)Nc2cc(CN4CC(O)C(NCCO)C4)ccc2N3)cc1O]

In analogy to Example 59, 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A) (69 mg, 69% purity, 0.125 mmol) was reacted with 4-[(2-hydroxyethyl)amino]pyrrolidin-3-ol hydrochloride (91 mg, 0.500 mmol). After purification by preparative HPLC (column: Kinetex C18 5μ, 100×21.2 mm; flow rate: 25 ml/min; eluent A: water, eluent B: acetonitrile, eluent C: 1% formic acid in water; isocratic 48% A, 40% B, 12% C) and another postpurification by preparative HPLC (Method 16), 5 mg (7% of theory) of the title compound were obtained.

LC/MS (Method 5, ESIpos): $R_t$=0.51 min, m/z=509 [M+H]$^+$.

$^1$H-NMR (400 MHz, DMSO-$d_6$): δ [ppm]=2.10 (s, 3H), 2.09-2.17 (m, 1H), 2.30-2.39 (m, 1H), 2.50-2.70 (m, 3H), 2.72-2.81 (m, 1H), 2.82-2.94 (m, 1H), 3.33-3.49 (m, 4H), 3.75-3.85 (m, 1H), 4.40-4.49 (m, 1H), 4.74-4.80 (m, 1H), 6.35-6.40 (m, 1H), 6.72 (d, 1H), 6.86-6.95 (m, 2H), 7.00-7.08 (m, 2H), 7.50-7.70 (m, 1H), 7.78 (d, 1H), 8.12 (s, 1H), 9.41 (s, 1H), 9.86 (s, 1H), 10.08 (s, 1H).

Example 92

8-({[(1-Ethylpyrrolidin-2-yl)methyl]amino}methyl)-4-[(5-hydroxy-2-methylphenyl)amino]-6,11-dihydro-5H-pyrido[2,3-b][1,5]benzodiazepin-5-one

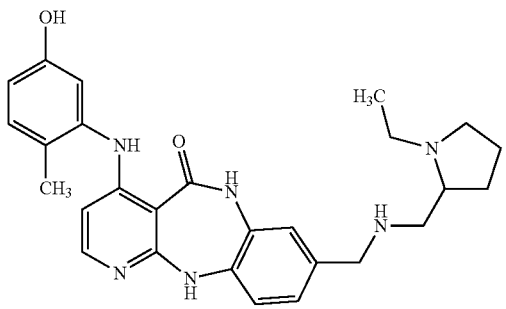 [SMILES: CCN1CCCC1CNCc1ccc2c(c1)NC(=O)c1c(Nc3cc(O)ccc3C)ccnc1N2]

To an initial charge of 19 mg (0.15 mmol) of 1-(1-ethylpyrrolidin-2-yl)methanamine in a well of a 96-well multititre plate was added a solution of 36 mg (0.10 mmol) of 4-[(5-hydroxy-2-methylphenyl)amino]-5-oxo-6,11-dihydro-5H-pyrido[2,3-b][1,5]benzodiazepine-8-carbaldehyde (Intermediate 6A) in 0.6 ml of ethanol. To this solution were added 9 mg (0.15 mmol) of acetic acid and 13 mg (0.2 mmol) of sodium cyanoborohydride. The multititre plate was covered and shaken at RT for 18 h. The mixture was then filtered off and the filtrate was concentrated fully. The residue obtained was taken up in 0.6 ml of DMSO and purified by preparative LC/MS by the following method:

MS instrument: Waters, HPLC instrument: Waters; column: Waters X-Bridge C18, 18 mm×50 mm, 5 μm; eluent A: water+0.05% triethylamine, eluent B: acetonitrile+0.05% triethylamine; gradient: 0.0 min 95% A→0.15 min 95% A→8.0 min 5% A→9.0 min 5% A; flow rate: 40 ml/min; UV detection: DAD, 210-400 nm.

or

MS instrument: Waters, HPLC instrument: Waters; column: Phenomenex Luna 5μ C18(2) 100A, AXIA Tech., 50 mm×21.2 mm; eluent A: water+0.05% formic acid, eluent B: acetonitrile+0.05% formic acid; gradient: 0.0 min 95% A→0.15 min 95% A→8.0 min 5% A→9.0 min 5% A; flow rate: 40 ml/min; UV detection: DAD, 210-400 nm.

The product-containing fractions were concentrated under reduced pressure using a centrifugal dryer. The residues of each individual fraction were dissolved in 0.6 ml of DMSO and combined. Subsequently, the solvent was evaporated off completely in a centifugal dryer. In this way, 16.5 g (35% of theory) of target product were obtained in a purity of 100%.

LC/MS (Method 10, ESIpos): $R_t$=0.94 min; m/z=473 (M+H)$^+$.

By way of parallel synthesis analogously to Example 92, the following compounds were prepared proceeding from 4-[(5-hydroxy-2-methylphenyl)amino]-5-oxo-6,11-dihydro-5H-pyrido[2,3-b][1,5]benzodiazepine-8-carbaldehyde (Intermediate 6A) and the appropriate amine component:

| Example No. | IUPAC name/structure | Yield | LC/MS (Method 10) |
|---|---|---|---|
| 93 | 8-{[2-Ethylbutyl)amino]methyl}-4-[(5-hydroxy-2-methylphenyl)amino]-6,11-dihydro-5H-pyrido[2,3-b][1,5]benzodiazepan-5-one 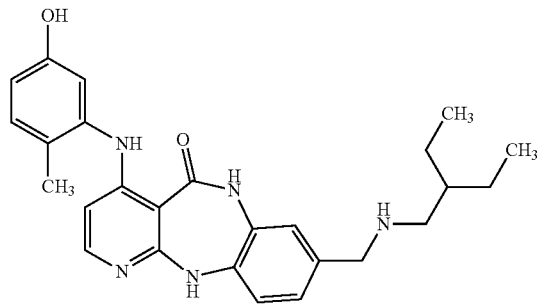 | 11.7 mg, 26% of theory | $R_t$ = 1.21 min; m/z = 446 (M + H)$^+$ Purity: 100% |

-continued

| Example No. | IUPAC name/structure | Yield | LC/MS (Method 10) |
|---|---|---|---|
| 94 | 8-{[(2,3-Difluorobenzyl)amino]methyl}-4-[(5-hydroxy-2-methylphenyl)amino]-6,11-dihydro-5H-pyrido[2,3-b][1,5]benzodiazepin-5-one | 4.4 mg, 9% of theory | $R_t$ = 1.19 min; m/z = 488 (M + H)$^+$ Purity: 100% |
| 95 | 8-({[(6-Chloropyridin-3-yl)methyl]amino}methyl)-4-[(5-hydroxy-2-methylphenyl)amino]-6,11-dihydro-5H-pyrido[2,3-b][1,5]benzodiazepin-5-one | 12.0 mg, 25% of theory | $R_t$ = 1.13 min; m/z = 487 (M + H)$^+$ Purity: 100% |
| 96 | 4-[(5-Hydroxy-2-methylphenyl)amino]-8-{[(3-methoxybenzyl)amino]methyl}-6,11-dihydro-5H-pyrido[2,3-b][1,5]benzodiazepin-5-one | 13.6 mg, 28% of theory | $R_t$ = 1.21 min; m/z = 482 (M + H)$^+$ Purity: 100% |
| 97 | 4-[(5-Hydroxy-2-methylphenyl)amino]-8-({[2-(1H-1,2,3-triazol-1-yl)ethyl]amino}methyl)-6,11-dihydro-5H-pyrido[2,3-b][1,5]benzodiazepin-5-one | 19.3 mg, 42% of theory | $R_t$ = 1.04 min; m/z = 457 (M + H)$^+$ Purity: 100% |

| Example No. | IUPAC name/structure | Yield | LC/MS (Method 10) |
|---|---|---|---|
| 98 | 4-[(5-Hydroxy-2-methylphenyl)amino]-8-{[3-methyl-1,1-dioxidotetrahydrothiophen-3-yl)amino]methyl}-6,11-dihydro-5H-pyrido[2,3-b][1,5]benzodiazepin-5-one | 11.0 mg, 22% of theory | $R_t$ = 1.07 min; m/z = 494 $(M + H)^+$ Purity: 100% |
| 99 | 4-[(5-Hydroxy-2-methylphenyl)amino]-8-[(tetrahydrofuran-3-ylamino)methyl]-6,11-dihydro-5H-pyrido[2,3-b][1,5]benzodiazepin-5-one | 6.8 mg, 16% of theory | $R_t$ = 1.04 min; m/z = 432 $(M + H)^+$ Purity: 100% |
| 100 | 8-({[1-(Cyclohex-3-en-1-yl)ethyl]amino}methyl)-4-[(5-hydroxy-2-methylphenyl)amino]-6,11-dihydro-5H-pyrido[2,3-b][1,5]benzodiazepin-5-one | 5.9 mg, 13% of theory | $R_t$ = 1.23 min; m/z = 470 $(M + H)^+$ Purity: 100% |
| 101 | 4-[(5-Hydroxy-2-methylphenyl)amino]-8-({[3-(3-methyl-1H-pyrazol-1-yl)propyl]amino}methyl)-6,11-dihydro-5H-pyrido[2,3-b][1,5]benzodiazepin-5-one | 17.2 mg, 36% of theory | $R_t$ = 1.14 min; m/z = 484 $(M + H)^+$ Purity: 100% |

| Example No. | IUPAC name/structure | Yield | LC/MS (Method 10) |
|---|---|---|---|
| 102 | 8-({[(1R)-1-Cyclohexylethyl]amino}methyl)-4-[(5-hydroxy-2-methylphenyl)amino]6,11-dihydro-5H-pyrido[2,3-b][1,5]benzodiazepin-5-one | 2.6 mg, 6% of theory | $R_t$ = 1.26 min; m/z = 472 (M + H)$^+$ Purity: 100% |
| 103 | 8-({[(1-Ethyl-1H-pyrazol-3-yl)methyl]amino}methyl)-4-[(5-hydroxy-2-methylphenyl)amino]-6,11-dihydro-5H-pyrido[2,3-b][1,5]benzodiazepin-5-one | 9.1 mg, 19% of theory | $R_t$ = 1.13 min; m/z = 470 (M + H)$^+$ Purity: 100% |
| 104 | 8-[(1H-Benzimidazol-5-ylamino)methyl]-4-[(5-hydroxy-2-methylphenyl)amino]-6,11-dihydro-5H-pyrido[2,3-b][1,5]benzodiazepin-5-one | 12.5 mg, 26% of theory | $R_t$ = 1.14 min; m/z = 478 (M + H)$^+$ Purity: 100% |
| 105 | 4-[(5-Hydroxy-2-methylphenyl)amino]-8-{[(1-methyl-1H-pyrazol-3-yl)amino]methyl}-6,11-dihydro-5H-pyrido[2,3-b][1,5]benzodiazepin-5-one | 8.6 mg, 19% of theory | $R_t$ = 1.25 min; m/z = 442 (M + H)$^+$ Purity: 100% |

| Example No. | IUPAC name/structure | Yield | LC/MS (Method 10) |
|---|---|---|---|
| 106 | 4-[(5-Hydroxy-2-methylphenyl)amino]-8-{[(2-hydroxy-1-phenylethyl)amino]methyl}-6,11-dihydro-5H-pyrido[2,3-b][1,5]benzodiazepin-5-one | 16.0 mg, 33% of theory | $R_t$ = 1.16 min; m/z = 482 (M + H)⁺ Purity: 100% |
| 107 | 8-{[(3-Fluoro-4-methoxyphenyl)amino]methyl}-4-[(5-hydroxy-2-methylphenyl)amino]-6,11-dihydro-5H-pyrido[2,3-b][1,5]benzodiazepin-5-one | 7.2 mg, 15% of theory | $R_t$ = 1.48 min; m/z = 486 (M + H)⁺ Purity: 100% |
| 108 | 4-[(5-Hydroxy-2-methylphenyl)amino]-8-{[(2-methoxybenzyl)amino]methyl}-6,11-dihydro-5H-pyrido[2,3-b][1,5]benzodiazepin-5-one | 12.3 mg, 26% of theory | $R_t$ = 1.21 min; m/z = 482 (M + H)⁺ Purity: 100% |
| 109 | 4-[(5-Hydroxy-2-methylphenyl)amino]-8-({[2-(4-methylpiperazin-1-yl)ethyl]amino}methyl)-6,11-dihydro-5H-pyrido[2,3-b][1,5]benzodiazepin-5-one | 14.3 mg, 29% of theory | $R_t$ = 0.94 min; m/z = 488 (M + H)⁺ Purity: 100% |

-continued

| Example No. | IUPAC name/structure | Yield | LC/MS (Method 10) |
|---|---|---|---|
| 110 | 4-[(5-Hydroxy-2-methylphenyl)amino]-8-({[2-(4-methylpiperidin-1-yl)ethyl]amino}methyl)-6,11-dihydro-5H-pyrido[2,3-b][1,5]benzodiazepin-5-one | 16.5 mg, 34% of theory | $R_t$ = 0.98 min; m/z = 487 (M + H)⁺ Purity: 100% |
| 111 | 8-({[2-(Azepan-1-yl)ethyl]amino}methyl)-4-[(5-hydroxy-2-methylphenyl)amino]-6,11-dihydro-5H-pyrido[2,3-b][1,5]benzodiazepin-5-one | 2.3 mg, 5% of theory | $R_t$ = 0.96 min; m/z = 487 (M + H)⁺ Purity: 100% |
| 112 | 8-({[1-(Diethylamino)propan-2-yl]amino}methyl)-4-[(5-hydroxy-2-methylphenyl)amino]-6,11-dihydro-5H-pyrido[2,3-b][1,5]benzodiazepin-5-one | 15.6 mg, 33% of theory | $R_t$ = 0.98 min; m/z = 475 (M + H)⁺ Purity: 100% |
| 113 | 8-{[(1,1-Dioxidotetrahydrothiophen-3-yl)amino]methyl}-4-[(5-hydroxy-2-methylphenyl)amino]-6,11-dihydro-5H-pyrido[2,3-b][1,5]benzodiazepin-5-one | 8.6 mg, 18% of theory | $R_t$ = 1.05 min; m/z = 480 (M + H)⁺ Purity: 100% |

-continued

| Example No. | IUPAC name/structure | Yield | LC/MS (Method 10) |
|---|---|---|---|
| 114 | 4-[(5-Hydroxy-2-methylphenyl)amino]-8-({[2-methyl-3-(1H-pyrazol-1-yl)propyl]amino}methyl)-6,11-dihydro-5H-pyrido[2,3-b][1,5]benzodiazepin-5-one | 12.5 mg, 26% of theory | $R_t$ = 1.14 min; m/z = 484 $(M + H)^+$ Purity: 100% |
| 115 | 4-[(5-Hydroxy-2-methylphenyl)amino]-8-{[(3,3,3-trifluoropropyl)amino]methyl}-6,11-dihydro-5H-pyrido[2,3-b][1,5]benzodiazepin-5-one | 15.7 mg, 34% of theory | $R_t$ = 1.11 min; m/z = 458 $(M + H)^+$ Purity: 100% |
| 116 | 4-[(5-Hydroxy-2-methylphenyl)amino]-8-({[3-(2-methoxyethoxy)propyl]amino}methyl)-6,11-dihydro-5H-pyrido[2,3-b][1,5]benzodiazepin-5-one | 12.6 mg, 26% of theory | $R_t$ = 1.11 min; m/z = 478 $(M + H)^+$ Purity: 100% |

| Example No. | IUPAC name/structure | Yield | LC/MS (Method 10) |
|---|---|---|---|
| 117 | 4-[(5-Hydroxy-2-methylphenyl)amino]-8-({[(2R)-2-phenylpropyl]amino}methyl)-6,11-dihydro-5H-pyrido[2,3-b][1,5]benzodiazepin-5-one | 10.8 mg, 23% of theory | $R_t$ = 1.26 min; m/z = 480 (M + H)$^+$ Purity: 100% |
| 118 | 8-{[(4-Ethoxybutan-2-yl)amino]methyl}-4-[(5-hydroxy-2-methylphenyl)amino]-6,11-dihydro-5H-pyrido[2,3-b][1,5]benzodiazepin-5-one | 11.2 mg, 24% of theory | $R_t$ = 1.15 min; m/z = 462 (M + H)$^+$ Purity: 100% |
| 119 | 8-{[(4-Fluorobenzyl)amino]methyl}-4-[(5-hydroxy-2-methylphenyl)amino]-6,11-dihydro-5H-pyrido[2,3-b][1,5]benzodiazepin-5-one | 9.7 mg, 21% of theory | $R_t$ = 1.20 min; m/z = 470 (M + H)$^+$ Purity: 100% |
| 120 | 8-{[(3-Fluorobenzyl)amino]methyl}-4-[(5-hydroxy-2-methylphenyl)amino]-6,11-dihydro-5H-pyrido[2,3-b][1,5]benzodiazepin-5-one | 11.6 mg, 25% of theory | $R_t$ = 1.20 min; m/z = 470 (M + H)$^+$ Purity: 100% |

-continued

| Example No. | IUPAC name/structure | Yield | LC/MS (Method 10) |
|---|---|---|---|
| 121 | 8-{[(2-Fluorobenzyl)amino]methyl}-4-[(5-hydroxy-2-methylphenyl)amino]-6,11-dihydro-5H-pyrido[2,3-b][1,5]benzodiazepin-5-one | 12.8 mg, 27% of theory | $R_t$ = 1.17 min; m/z = 470 (M + H)$^+$ Purity: 100% |
| 122 | 8-({[1-(Dimethylamino)propan-2-yl]amino}methyl)-4-[(5-hydroxy-2-methylphenyl)amino]-6,11-dihydro-5H-pyrido[2,3-b][1,5]benzodiazepin-5-one | 14.1 mg, 32% of theory | $R_t$ = 0.94 min; m/z = 447 (M + H)$^+$ Purity: 100% |
| 123 | 4-[(5-Hydroxy-2-methylphenyl)amino]-8-({[2-(pyridin-4-yl)ethyl]amino}methyl)-6,11-dihydro-5H-pyrido[2,3-b][1,5]benzodiazepin-5-one | 14.5 mg, 31% of theory | $R_t$ = 0.95 min; m/z = 467 (M + H)$^+$ Purity: 100% |
| 124 | 4-[(5-Hydroxy-2-methylphenyl)amino]-8-{[(2-methylcyclohexyl)amino]methyl}-6,11-dihydro-5H-pyrido[2,3-b][1,5]benzodiazepin-5-one | 15.8 mg, 35% of theory | $R_t$ = 1.21 min; m/z = 458 (M + H)$^+$ Purity: 100% |

| Example No. | IUPAC name/structure | Yield | LC/MS (Method 10) |
|---|---|---|---|
| 125 | 4-[(5-Hydroxy-2-methylphenyl)amino]-8-[(propylamino)methyl]-6,11-dihydro-5H-pyrido[2,3-b][1,5]benzodiazepin-5-one | 11.8 mg, 29% of theory | $R_t$ = 1.07 min; m/z = 404 (M + H)$^+$ Purity: 100% |
| 126 | 8-{[(2-Fluoroethyl)amino]methyl}-4-[(5-hydroxy-2-methylphenyl)amino]-6,11-dihydro-5H-pyrido[2,3-b][1,5]benzodiazepin-5-one | 7.5 mg, 18% of theory | $R_t$ = 1.03 min; m/z = 408 (M + H)$^+$ Purity: 100% |
| 127 | 8-{[(Cyclopropylmethyl)amino]methyl}-4-[(5-hydroxy-2-methylphenyl)amino]-6,11-dihydro-5H-pyrido[2,3-b][1,5]benzodiazepin-5-one | 4.4 mg, 11% of theory | $R_t$ = 1.11 min; m/z = 416 (M + H)$^+$ Purity: 100% |
| 128 | 4-[(5-Hydroxy-2-methylphenyl)amino]-8-({[(1S)-2-hydroxy-1-phenylethyl]amino}methyl)-6,11-dihydro-5H-pyrido[2,3-b][1,5]benzodiazepin-5-one | 21.7 mg, 45% of theory | $R_t$ = 1.18 min; m/z = 482 (M + H)$^+$ Purity: 100% |

| Example No. | IUPAC name/structure | Yield | LC/MS (Method 10) |
|---|---|---|---|
| 129 | 4-[(5-Hydroxy-2-methylphenyl)amino]-8-{[(3-methoxypropyl)amino]methyl}-6,11-dihydro-5H-pyrido[2,3-b][1,5]benzodiazepin-5-one 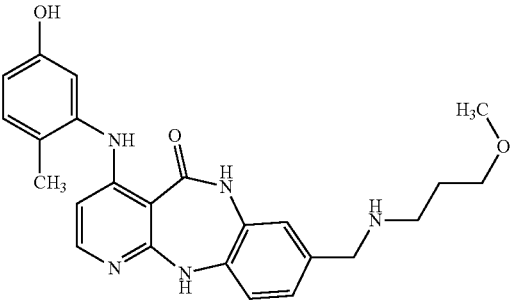 | 12.3 mg, 28% of theory | $R_t$ = 1.09 min; m/z = 434 (M + H)$^+$ Purity: 100% |
| 130 | 4-[(5-Hydroxy-2-methylphenyl)amino]-8-({[(5-oxopyrrolidin-3-yl)methyl]amino}methyl)-6,11-dihydro-5H-pyrido[2,3-b][1,5]benzodiazepin-5-one 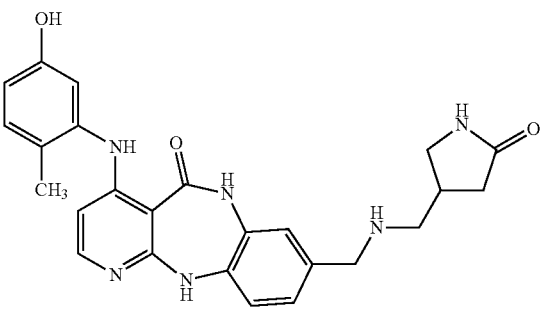 | 8.0 mg, 17% of theory | $R_t$ = 1.03 min; m/z = 459 (M + H)$^+$ Purity: 100% |
| 131 | 4-[(5-Hydroxy-2-methylphenyl)amino]-8-({[2-methyl-1-(pyrrolidin-1-yl)propan-2-yl]amino}methyl)-6,11-dihydro-5H-pyrido[2,3-b][1,5]benzodiazepin-5-one 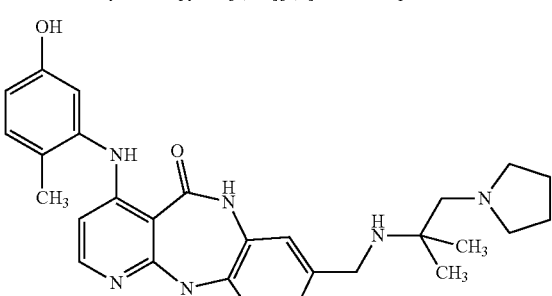 | 19.6 mg, 40% of theory | $R_t$ = 0.99 min; m/z = 487 (M + H)$^+$ Purity: 100% |
| 132 | 8-({[1-(2-Furyl)ethyl]amino}methyl)-4-[(5-hydroxy-2-methylphenyl)amino]-6,11-dihydro-5H-pyrido[2,3-b][1,5]benzodiazepin-5-one 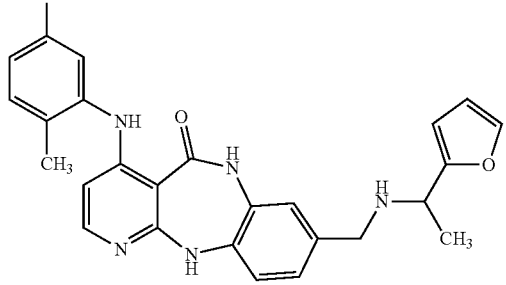 | 22.8 mg, 50% of theory | $R_t$ = 1.16 min; m/z = 456 (M + H)$^+$ Purity: 100% |

-continued

| Example No. | IUPAC name/structure | Yield | LC/MS (Method 10) |
|---|---|---|---|
| 133 | 4-[(5-Hydroxy-2-methylphenyl)amino]-8-({[2-(tetrahydrofuran-2-ylmethoxy)ethyl]amino}methyl)-6,11-dihydro-5H-pyrido[2,3-b][1,5]benzodiazepin-5-one | 16.3 mg, 33% of theory | $R_t$ = 1.14 min; m/z = 490 (M + H)+ Purity: 100% |
| 134 | 4-[(5-Hydroxy-2-methylphenyl)amino]-8-{[(1-methylcyclobutyl)amino]methyl}-6,11-dihydro-5H-pyrido[2,3-b][1,5]benzodiazepin-5-one | 15.7 mg, 37% of theory | $R_t$ = 1.13 min; m/z = 430 (M + H)+ Purity: 100% |
| 135 | 4-[(5-Hydroxy-2-methylphenyl)amino]-8-({[2-(morpholin-4-yl)propyl]amino}methyl)-6,11-dihydro-5H-pyrido[2,3-b][1,5]benzodiazepin-5-one | 18.0 mg, 37% of theory | $R_t$ = 1.05 min; m/z = 489 (M + H)+ Purity: 100% |
| 136 | 4-[(5-Hydroxy-2-methylphenyl)amino]-8-[(tetrahydro-2H-pyran-4-ylamino)methyl]-6,11-dihydro-5H-pyrido[2,3-b][1,5]benzodiazepin-5-one | 8.7 mg, 20% of theory | $R_t$ = 1.08 min; m/z = 446 (M + H)+ Purity: 100% |

-continued

| Example No. | IUPAC name/structure | Yield | LC/MS (Method 10) |
|---|---|---|---|
| 137 | 4-[(5-Hydroxy-2-methylphenyl)amino]-8-({[(1-methyl-5-oxopyrrolidin-2-yl)methyl]amino}methyl)-6,11-dihydro-5H-pyrido[2,3-b][1,5]benzodiazepin-5-one | 19.6 mg, 41% of theory | $R_t$ = 1.05 min; m/z = 473 (M + H)⁺ Purity: 100% |
| 138 | 4-[(5-Hydroxy-2-methylphenyl)amino]-8-{[(1-methylpiperidin-4-yl)amino]methyl}-6,11-dihydro-5H-pyrido[2,3-b][1,5]benzodiazepin-5-one | 14.8 mg, 32% of theory | $R_t$ = 0.93 min; m/z = 459 (M + H)⁺ Purity: 100% |
| 139 | 4-[(5-Hydroxy-2-methylphenyl)amino]-8-{[(2-oxopiperidin-3-yl)amino]methyl}-6,11-dihydro-5H-pyrido[2,3-b][1,5]benzodiazepin-5-one | 11.5 mg, 25% of theory | $R_t$ = 1.07 min; m/z = 459 (M + H)⁺ Purity: 100% |
| 140 | 4-[(5-Hydroxy-2-methylphenyl)amino]-8-({[(1-isopropylpyrrolidin-3-yl)methyl]amino}methyl)-6,11-dihydro-5H-pyrido[2,3-b][1,5]benzodiazepin-5-one | 22.9 mg, 47% of theory | $R_t$ = 0.95 min; m/z = 487 (M + H)⁺ Purity: 100% |

| Example No. | IUPAC name/structure | Yield | LC/MS (Method 10) |
|---|---|---|---|
| 141 | 4-[(5-Hydroxy-2-methylphenyl)amino]-8-({[2-(2-oxopyrrolidin-1-yl)ethyl]amino}methyl)-6,11-dihydro-5H-pyrido[2,3-b][1,5]benzodiazepin-5-one | 22.5 mg, 48% of theory | $R_t$ = 1.07 min; m/z = 473 $(M + H)^+$ Purity: 100% |
| 142 | 8-{[(2,2-Dimethylpropyl)amino]methyl}-4-[(5-hydroxy-2-methylphenyl)amino]-6,11-dihydro-5H-pyrido[2,3-b][1,5]benzodiazepin-5-one | 21.2 mg, 49% of theory | $R_t$ = 1.14 min; m/z = 432 $(M + H)^+$ Purity: 100% |
| 143 | $N^3$-({4-[(5-Hydroxy-2-methylphenyl)amino]-5-oxo-6,11-dihydro-5H-pyrido[2,3-b][1,5]benzodiazepin-8-yl}methyl)-N,N-dimethyl-β-alaninamide | 21.7 mg, 47% of theory | $R_t$ = 1.07 min; m/z = 461 $(M + H)^+$ Purity: 100% |

| Example No. | IUPAC name/structure | Yield | LC/MS (Method 10) |
|---|---|---|---|
| 144 | 8-({[2-(Dimethylamino)-2-methylpropyl]amino}methyl)-4-[(5-hydroxy-2-methylphenyl)amino]-6,11-dihydro-5H-pyrido[2,3-b][1,5]benzodiazepin-5-one | 25.7 mg, 56% of theory | $R_t$ = 1.01 min; m/z = 461 (M + H)$^+$ Purity: 100% |
| 145 | 8-[(Benzylamino)methyl]-4-[(5-hydroxy-2-methylphenyl)amino]-6,11-dihydro-5H-pyrido[2,3-b][1,5]benzodiazepin-5-one | 12.9 mg, 29% of theory | $R_t$ = 1.17 min; m/z = 452 (M + H)$^+$ Purity: 100% |
| 146 | 4-[(5-Hydroxy-2-methylphenyl)amino]-8-{[(pyridin-3-ylmethyl)amino]methyl}-6,11-dihydro-5H-pyrido[2,3-b][1,5]benzodiazepin-5-one | 20.5 mg, 45% of theory | $R_t$ = 1.02 min; m/z = 453 (M + H)$^+$ Purity: 100% |
| 147 | 8-{[(2-Fluorophenyl)amino]methyl}-4-[(5-hydroxy-2-methylphenyl)amino]-6,11-dihydro-5H-pyrido[2,3-b][1,5]benzodiazepin-5-one | 8.9 mg, 20% of theory | $R_t$ = 1.56 min; m/z = 456 (M + H)$^+$ Purity: 100% |

-continued

| Example No. | IUPAC name/structure | Yield | LC/MS (Method 10) |
|---|---|---|---|
| 148 | 8-{[(2,3-Dihydroxypropyl)amino]methyl}-4-[(5-hydroxy-2-methylphenyl)amino]-6,11-dihydro-5H-pyrido[2,3-b][1,5]benzodiazepin-5-one | 13.0 mg, 30% of theory | $R_t$ = 1.01 min; m/z = 436 (M + H)$^+$ Purity: 100% |
| 149 | 4-[(5-Hydroxy-2-methylphenyl)amino]-8-{[(3-isopropoxypropyl)amino]methyl}-6,11-dihydro-5H-pyrido[2,3-b][1,5]benzodiazepin-5-one | 11.3 mg, 24% of theory | $R_t$ = 1.16 min; m/z = 462 (M + H)$^+$ Purity: 100% |
| 150 | 8-({[(2R)-1-Hydroxy-3-methylbutan-2-yl]amino}methyl)-4-[(5-hydroxy-2-methylphenyl)amino]-6,11-dihydro-5H-pyrido[2,3-b][1,5]benzodiazepin-5-one | 19.4 mg, 43% of theory | $R_t$ = 1.10 min; m/z = 448 (M + H)$^+$ Purity: 100% |

-continued

| Example No. | IUPAC name/structure | Yield | LC/MS (Method 10) |
|---|---|---|---|
| 151 | 8-[(Cyclopropylamino)methyl]-4-[(5-hydroxy-2-methylphenyl)amino]-6,11-dihydro-5H-pyrido[2,3-b][1,5]benzodiazepin-5-one 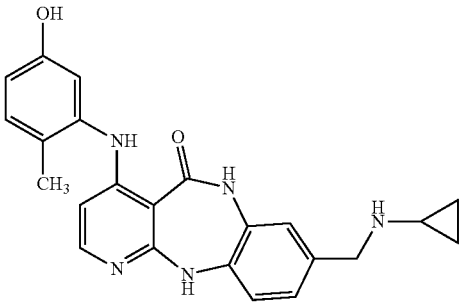 | 14.9 mg, 37% of theory | $R_t$ = 1.05 min; m/z = 402 (M + H)$^+$ Purity: 100% |
| 152 | 4-[(5-Hydroxy-2-methylphenyl)amino]-8-[(isobutylamino)methyl]-6,11-dihydro-5H-pyrido[2,3-b][1,5]benzodiazepin-5-one 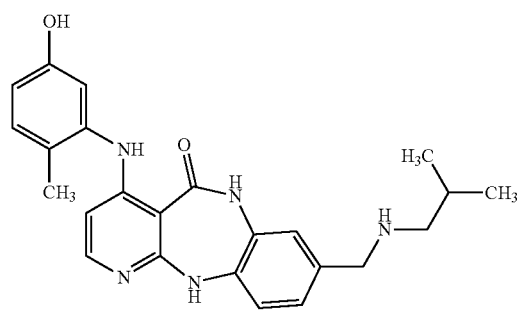 | 15.4 mg, 37% of theory | $R_t$ = 1.11 min; m/z = 418 (M + H)$^+$ Purity: 100% |
| 153 | 4-[(5-Hydroxy-2-methylphenyl)amino]-8-{[(2-methylbutyl)amino]methyl}-6,11-dihydro-5H-pyrido[2,3-b][1,5]benzodiazepin-5-one 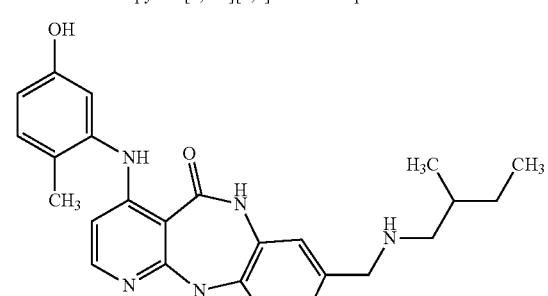 | 18.2 mg, 42% of theory | $R_t$ = 1.16 min; m/z = 432 (M + H)$^+$ Purity: 100% |
| 154 | 8-[(Cyclopentylamino)methyl]-4-[(5-hydroxy-2-methylphenyl)amino]-6,11-dihydro-5H-pyrido[2,3-b][1,5]benzodiazepin-5-one 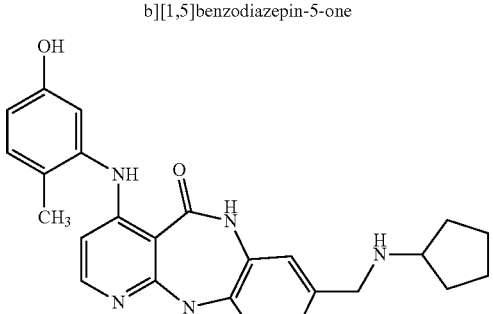 | 12.9 mg, 30% of theory | $R_t$ = 1.12 min; m/z = 430 (M + H)$^+$ Purity: 100% |

| Example No. | IUPAC name/structure | Yield | LC/MS (Method 10) |
|---|---|---|---|
| 155 | 4-[(5-Hydroxy-2-methylphenyl)amino]-8-[(pentan-3-ylamino)methyl]-6,11-dihydro-5H-pyrido[2,3-b][1,5]benzodiazepin-5-one 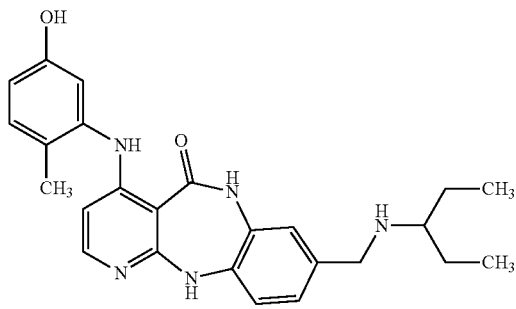 | 16.1 mg, 37% of theory | $R_t$ = 1.15 min; m/z = 432 (M + H)$^+$ Purity: 100% |
| 156 | 8-({[2-(Dimethylamino)ethyl]amino}methyl)-4-[(5-hydroxy-2-methylphenyl)amino]-6,11-dihydro-5H-pyrido[2,3-b][1,5]benzodiazepin-5-one 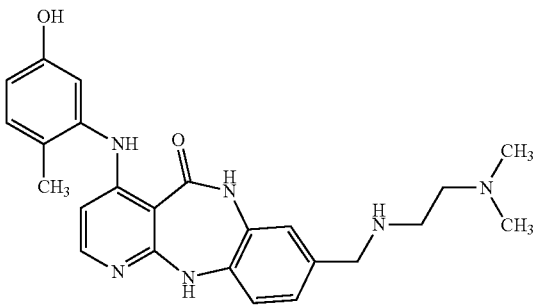 | 16.1 mg, 37% of theory | $R_t$ = 0.93 min; m/z = 433 (M + H)$^+$ Purity: 100% |
| 157 | 4-[(5-Hydroxy-2-methylphenyl)amino]-8-{[(3-methylbutan-2-yl)amino]methyl}-6,11-dihydro-5H-pyrido[2,3-b][1,5]benzodiazepin-5-one 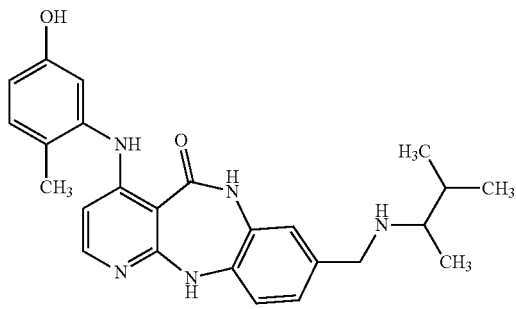 | 12.7 mg, 29% of theory | $R_t$ = 1.14 min; m/z = 432 (M + H)$^+$ Purity: 100% |

Example 158 ent-4-[(2-Fluoro-5-hydroxy-4-methylphenyl)amino]-8-{[3-(2-hydroxyethyl)piperidin-1-yl]methyl}-6,11-dihydro-5H-pyrido[2,3-b][1,5]benzodiazepin-5-one (Enantiomer 1)

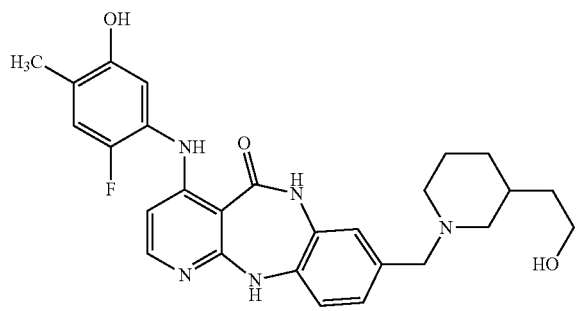 [SMILES: Cc1cc(F)c(Nc2ccnc3c2C(=O)Nc2cc(CN4CCCC(CCO)C4)ccc2N3)cc1O]

The title compound was obtained by separating the racemic compound from Example 58 (14 mg) into the enantiomers by means of preparative chiral HPLC (Method 21). Yield: 2 mg.

HPLC (Method 22): $R_t$=9.91 min, ee=97%.

LC/MS (Method 5, ESIpos): $R_t$=0.53 min, m/z=492 [M+H]$^+$.

$^1$H-NMR (400 MHz, DMSO-d$_6$): δ [ppm]=0.76-0.91 (m, 1H), 1.20-1.48 (m, 3H), 1.50-1.70 (m, 4H), 1.75-1.88 (m, 1H), 2.10 (s, 3H), 2.60-2.76 (m, 2H), 3.36-3.42 (m, 2H), 4.30 (t, 1H), 6.35-6.41 (m, 1H), 6.74 (d, 1H), 6.87-6.94 (m, 2H), 7.03 (d, 1H), 7.06 (s, 1H), 7.80 (d, 1H), 8.14 (s, 1H), 9.42 (s, 1H), 9.89 (s, 1H), 10.09 (s, 1H).

Example 159 ent-4-[(2-Fluoro-5-hydroxy-4-methylphenyl)amino]-8-{[3-(2-hydroxyethyl)piperidin-1-yl]methyl}-6,11-dihydro-5H-pyrido[2,3-b][1,5]benzodiazepin-5-one (Enantiomer 2)

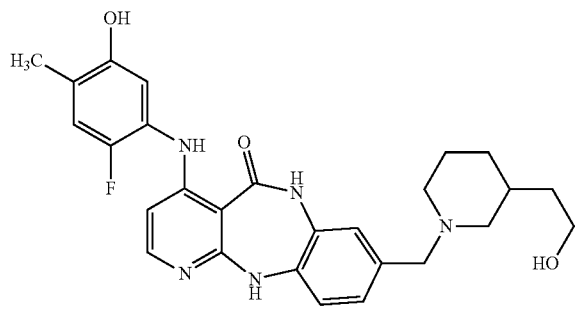 [SMILES: Cc1cc(F)c(Nc2ccnc3c2C(=O)Nc2cc(CN4CCCC(CCO)C4)ccc2N3)cc1O]

The title compound was obtained by separating the racemic compound from Example 58 (14 mg) into the enantiomers by means of preparative chiral HPLC (Method 21). Yield: 2 mg.

HPLC (Method 22): $R_t$=13.19 min, ee=87%.

LC/MS (Method 5, ESIpos): $R_t$=0.57 min, m/z=492 [M+H]$^+$.

$^1$H-NMR (400 MHz, DMSO-d$_6$): δ [ppm]=0.76-0.91 (m, 1H), 1.20-1.48 (m, 3H), 1.50-1.70 (m, 4H), 1.75-1.88 (m, 1H), 2.11 (s, 3H), 2.63-2.77 (m, 2H), 3.36-3.42 (m, 2H), 4.30 (t, 1H), 6.35-6.41 (m, 1H), 6.74 (d, 1H), 6.87-6.96 (m, 2H), 7.03 (d, 1H), 7.06 (s, 1H), 7.80 (d, 1H), 8.14 (s, 1H), 9.42 (s, 1H), 9.89 (s, 1H), 10.09 (s, 1H).

Example 160

4-[(2-Fluoro-5-hydroxy-4-methylphenyl)amino]-8-{[(2S,4R)-4-hydroxy-2-(hydroxymethyl)pyrrolidin-1-yl]carbonyl}-6,11-dihydro-5H-pyrido[2, 3-b][1,5]benzodiazepin-5-one

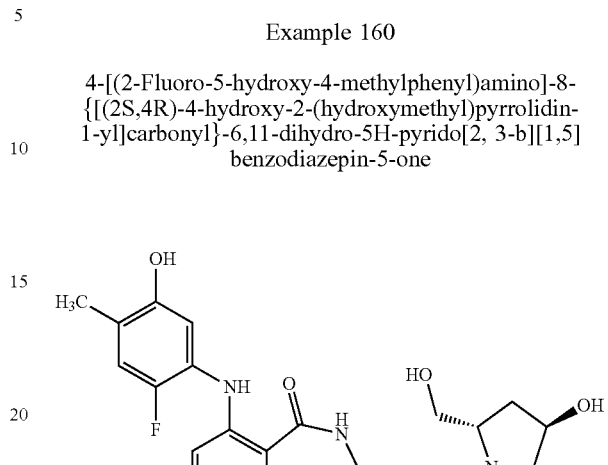

Under an argon atmosphere, the compound from Example 79 (99 mg, 0.250 mmol) was dissolved in DMF (1 ml) and cooled to 0° C. HATU (190 mg, 0.5 mmol) was added, and the mixture was stirred for a further 20 min. Subsequently, (3R,5S)-5-hydroxymethyl-3-pyrrolidinol hydrochloride (77 mg, 0.5 mmol) and N,N-diisopropylethylamine (129 mg, 1 mmol) were added and the reaction mixture was stirred at RT for a further 30 min. Purification by silica gel chromatography (eluent: dichloromethane/methanol 9:1→8:2) and subsequent purification by preparative HPLC (Method 16) gave 15 mg (12% of theory) of the title compound.

LC/MS (Method 5, ESIpos): $R_t$=0.59 min, m/z=494 [M+H]$^+$.

$^1$H-NMR (400 MHz, DMSO-d$_6$): δ [ppm]=1.85-1.93 (m, 1H), 1.94-2.03 (m, 1H), 2.11 (s, 3H), 3.50-3.57 (m, 2H), 3.59-3.65 (m, 1H), 4.13-4.20 (m, 1H), 4.20-4.30 (m, 1H), 4.73 (br. s, 1H), 6.36-6.40 (m, 1H), 6.72 (d, 1H), 7.04 (d, 1H), 7.10-7.20 (m, 3H), 7.81 (d, 1H), 8.45 (s, 1H), 9.43 (s, 1H), 9.91 (s, 1H), 10.19 (s, 1H).

Example 161

4-[(2-Fluoro-5-hydroxy-4-methylphenyl)amino]-8-{[4-(2-hydroxyethyl)piperidin-1-yl]carbonyl}-6,11-dihydro-5H-pyrido[2,3-b][1,5]benzodiazepin-5-one

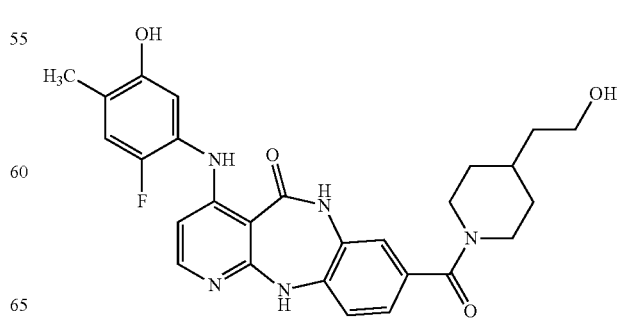

Under an argon atmosphere, the compound from Example 79 (100 mg, 0.253 mmol) was dissolved in DMF (1 ml) and cooled to 0° C. HATU (193 mg, 0.507 mmol) was added, and the mixture was stirred for a further 20 min. Subsequently, 4-piperidineethanol (66 mg, 0.507 mmol) and N,N-diisopropylethylamine (66 mg, 0.507 mmol) were added and the reaction mixture was stirred at RT for a further 30 min. Purification by silica gel chromatography (eluent: dichloromethane/methanol 95:5→85:15) and subsequent purification by preparative HPLC (Method 16) gave 30 mg (23% of theory) of the title compound.

LC/MS (Method 7, ESIpos): $R_t$=0.89 min, m/z=506 [M+H]$^+$.

$^1$H-NMR (400 MHz, DMSO-d$_6$): δ [ppm]=1.00-1.15 (m, 2H), 1.37 (q, 2H), 1.58-1.74 (m, 3H), 2.10 (s, 3H), 2.60-3.10 (m, 2H), 3.40-3.50 (m, 2H), 3.51-3.80 (m, 1H), 4.10-4.50 (m, 1H), 4.36 (t, 1H), 6.36-6.40 (m, 1H), 6.72 (d, 1H), 6.99-7.07 (m, 3H), 7.15 (d, 1H), 7.81 (d, 1H), 8.40 (s, 1H), 9.43 (s, 1H), 9.88 (s, 1H), 10.17 (s, 1H).

Example 162

N-Ethyl-4-[(2-fluoro-5-hydroxy-4-methylphenyl)amino]-N-(2-hydroxyethyl)-5-oxo-6,11-dihydro-5H-pyrido[2,3-b][1,5]benzodiazepine-8-carboxamide

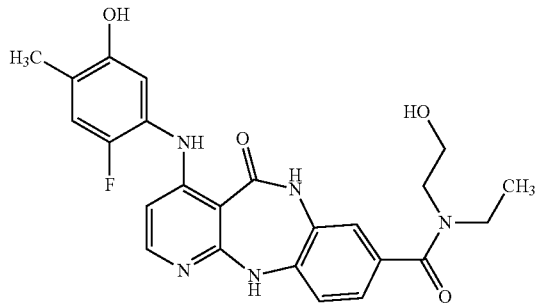 [SMILES: CCN(CCO)C(=O)c1ccc2c(c1)NC(=O)c1c(Nc3cc(O)c(C)cc3F)ccnc1N2]

In analogy to Example 161, the compound from Example 79 (100 mg, 0.254 mmol) was reacted with 2-(ethylamino)ethanol (45 mg, 0.507 mmol). 29 mg (25% of theory) of the title compound were obtained.

LC/MS (Method 7, ESIpos): $R_t$=0.86 min, m/z=466 [M+H]$^+$.

$^1$H-NMR (400 MHz, DMSO-d$_6$): δ [ppm]=1.02-1.15 (m, 3H), 2.01 (s, 3H), 3.35-3.60 (m, 4H), 4.73 (t, 1H), 6.36-6.40 (m, 1H), 6.72 (d, 1H), 6.99-7.07 (m, 3H), 7.14 (d, 1H), 7.81 (d, 1H), 8.38 (s, 1H), 9.43 (s, 1H), 9.88 (s, 1H), 10.16 (s, 1H).

Example 163

4-[(2-Fluoro-5-hydroxy-4-methylphenyl)amino]-8-{[4-(2-hydroxyethyl)piperidin-1-yl]methyl}-6,11-dihydro-5H-pyrido[2,3-b][1,5]benzodiazepin-5-one

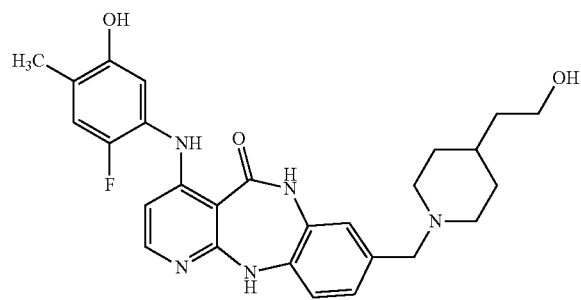 [SMILES: Cc1cc(F)c(Nc2ccnc3c2C(=O)Nc2cc(CN4CCC(CCO)CC4)ccc2N3)cc1O]

Intermediate 11A (95 mg, 80% purity, 0.200 mmol) was dissolved in 1.2 ml of DMF. At RT, 4-piperidineethanol (103 mg, 0.8 mmol) and trimethyl orthoformate (531 mg, 4 mmol) were added. The resulting mixture was stirred at RT overnight. Then sodium triacetoxyborohydride (170 mg, 0.8 mmol) was added and the mixture was again stirred at RT overnight. Then aqueous sodium hydrogencarbonate solution was added and the mixture was concentrated. The residue was taken up in 15 ml of DMF and filtered, and the filtrate was concentrated again. Purification by preparative HPLC (Method 16) gave 25 mg (24% of theory) of the title compound.

LC/MS (Method 7, ESIneg): $R_t$=0.74 min, m/z=490 [M–H]$^-$.

$^1$H-NMR (400 MHz, DMSO-d$_6$): δ [ppm]=1.05-1.16 (m, 2H), 1.26-1.40 (m, 3H), 1.53-1.65 (m, 2H), 1.84 (t, 2H), 2.10 (s, 3H), 2.70-2.78 (m, 2H), 3.36-3.45 (m, 2H), 4.29 (t, 1H), 6.36-6.40 (m, 1H), 6.72 (d, 1H), 6.88-6.95 (m, 2H), 7.00-7.07 (m, 2H), 7.78 (d, 1H), 8.12 (s, 1H), 9.41 (s, 1H), 9.87 (s, 1H), 10.07 (s, 1H).

Example 164

4-[(2-Fluoro-5-hydroxy-4-methylphenyl)amino]-8-{[cis-2-(hydroxymethyl)-3-azabicyclo[3.1.0]hex-3-yl]methyl}-6,11-dihydro-5H-pyrido[2,3-b][1,5]benzodiazepin-5-one

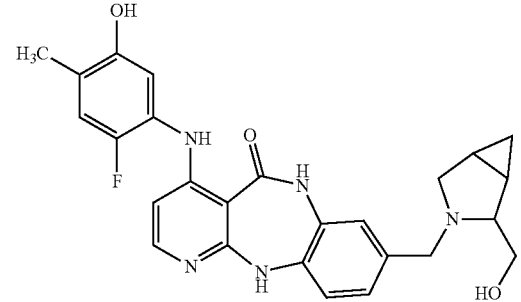 [SMILES: Cc1cc(F)c(Nc2ccnc3c2C(=O)Nc2cc(CN4CC5CC5C4CO)ccc2N3)cc1O]

Intermediate 11A (200 mg, 60% purity, 0.317 mmol) was dissolved in 1.9 ml of DMF. cis-3-Azabicyclo[3.1.0]hex-2-ylmethanol (143 mg, 1.269 mmol) [for preparation see, for example, WO 2008/150364-A1, p. 34] and trimethyl orthoformate (673 mg, 6.34 mmol) were added. The resulting mixture was stirred at 40° C. overnight. Then sodium triacetoxyborohydride (269 mg, 1.27 mmol) was added at RT and the mixture was once again stirred at RT overnight. Then aqueous sodium hydrogencarbonate solution was added and the mixture was concentrated. The residue was taken up in 5 ml of DMF and filtered, and the filtrate was concentrated again. Purification by preparative HPLC (Method 16) gave 49 mg (32% of theory) of the title compound as an isomer mixture.

LC/MS (Method 5, ESIpos): $R_t$=0.58 min, m/z=476 [M+H]$^+$.

$^1$H-NMR (400 MHz, DMSO-d$_6$): δ [ppm]=0.14-0.25 (m, 1H), 0.57-0.62 (m, 1H), 1.20-1.33 (m, 2H), 1.48-1.55 (m, 1H), 2.10 (s, 3H), 2.26-2.35 (m, 1H), 2.66-2.70 (m, 1H), 2.77-2.82 (m, 1H), 3.13-3.18 (m, 1H), 3.52-3.59 (m, 1H), 3.82-3.88 (m, 1H), 4.53 (t, 1H), 6.36-6.40 (m, 1H), 6.74 (d, 1H), 6.83-6.95 (m, 2H), 7.00-7.07 (m, 2H), 7.78 (d, 1H), 8.09 (s, 1H), 9.48 (s, 1H), 9.87 (s, 1H), 10.05 (s, 1H).

Example 165

4-[(2-Fluoro-5-hydroxy-4-methylphenyl)amino]-8-[(4-hydroxy-3,4-dimethylpiperidin-1-yl)methyl]-6,11-dihydro-5H-pyrido[2,3-b][1,5]benzodiazepin-5-one

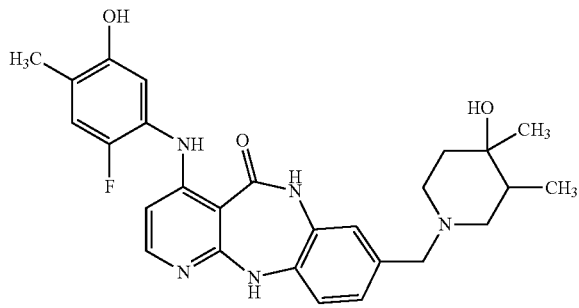

In analogy to Example 164, Intermediate 11A (200 mg, 60% purity, 0.317 mmol) was reacted with 3,4-dimethylpiperidin-4-ol (164 mg, 1.27 mmol). 90 mg (58% of theory) of the title compound were obtained.

LC/MS (Method 5, ESIpos): $R_t$=0.59 min, m/z=492 [M+H]$^+$.

$^1$H-NMR (400 MHz, DMSO-d$_6$): δ [ppm]=0.78 (d, 3H), 0.95 (s, 3H), 1.47-1.55 (m, 2H), 1.55-1.65 (m, 1H), 1.70-1.85 (m, 1H), 1.97-2.09 (m, 1H), 2.10 (s, 3H), 4.13 (s, 1H), 6.36-6.40 (m, 1H), 6.73 (d, 1H), 6.88-6.95 (m, 2H), 7.00-7.07 (m, 2H), 7.78 (d, 1H), 8.12 (s, 1H), 9.44 (s, 1H), 9.88 (s, 1H), 10.08 (s, 1H).

Example 166 rac-4-[(2-Fluoro-5-hydroxy-4-methylphenyl)amino]-8-[(4-hydroxy-3,3-dimethylpiperidin-1-yl)methyl]-6,11-dihydro-5H-pyrido[2,3-b][1,5]benzodiazepin-5-one

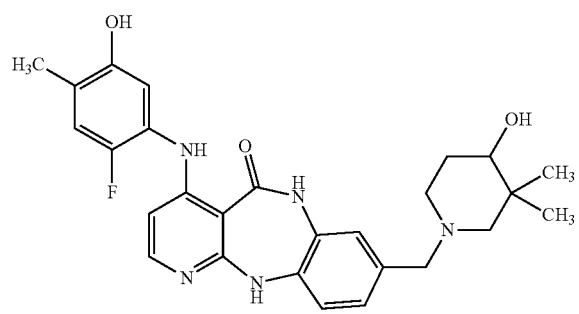

In analogy to Example 164, Intermediate 11A (200 mg, 60% purity, 0.317 mmol) was reacted with rac-3,3-dimethylpiperidin-4-ol (164 mg, 1.27 mmol). 123 mg (71% of theory) of the title compound were obtained.

LC/MS (Method 5, ESIpos): $R_t$=0.57 min, m/z=492 [M+H]$^+$.

$^1$H-NMR (400 MHz, DMSO-d$_6$): δ [ppm]=0.82 (s, 3H), 0.88 (s, 3H), 1.47-1.55 (m, 2H), 1.60-1.70 (m, 1H), 1.91-2.00 (m, 1H), 2.10 (s, 3H), 2.27-2.33 (m, 1H), 2.61-2.70 (m, 1H), 3.02-3.09 (m, 1H), 3.20-3.30 (m, 2H), 4.41 (d, 1H), 6.36-6.40 (m, 1H), 6.76 (d, 1H), 6.88-6.95 (m, 2H), 7.01-7.05 (m, 2H), 7.78 (d, 1H), 8.12 (s, 1H), 9.49 (s, 1H), 9.88 (s, 1H), 10.10 (s, 1H).

Example 167

4-[(2-Fluoro-5-hydroxy-4-methylphenyl)amino]-8-{[(2-hydroxyethyl)amino]methyl}-6,11-dihydro-5H-pyrido[2,3-b][1,5]benzodiazepin-5-one

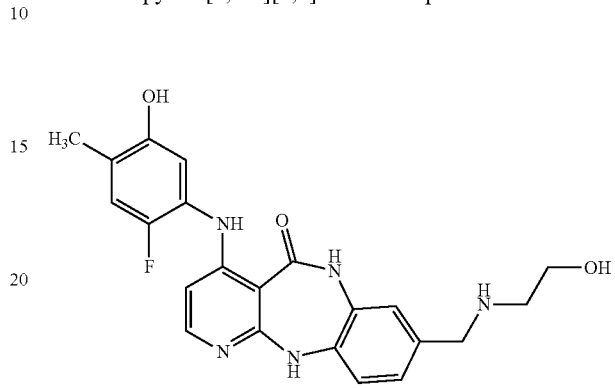

Intermediate 11A (110 mg, 71% purity, 0.206 mmol) was dissolved in DMF (2 ml) and acetic acid (0.2 ml). Ethanolamine (50 mg, 0.826 mmol) was added and the mixture was stirred at RT overnight. Then sodium triacetoxyborohydride (175 mg, 0.826 mmol) was added and the mixture was again stirred at RT overnight. Then aqueous sodium hydrogencarbonate solution was added and the mixture was concentrated. The residue was taken up in 10 ml of DMF and filtered, and the filtrate was concentrated again. Purification by preparative HPLC (Method 16) gave 19 mg (22% of theory) of the title compound.

LC/MS (Method 7, ESIneg): $R_t$=0.68 min, m/z=422 [M−H]$^−$.

$^1$H-NMR (400 MHz, DMSO-d$_6$): δ [ppm]=2.11 (s, 3H), 2.88-2.98 (m, 2H), 3.60-3.65 (m, 2H), 4.03-4.07 (m, 2H), 5.18 (br. s, 1H), 6.35-6.40 (m, 1H), 6.71 (d, 1H), 7.01-7.09 (m, 2H), 7.12-7.18 (m, 2H), 7.80 (d, 1H), 8.37 (s, 1H), 8.70 (br. s, 1H), 9.44 (s, 1H), 9.84 (s, 1H), 10.28 (s, 1H).

Example 168 rac-4-[(2-Fluoro-5-hydroxy-4-methylphenyl)amino]-8-{[(1-hydroxypropan-2-yl)amino]methyl}-6,11-dihydro-5H-pyrido[2,3-b][1,5]benzodiazepin-5-one

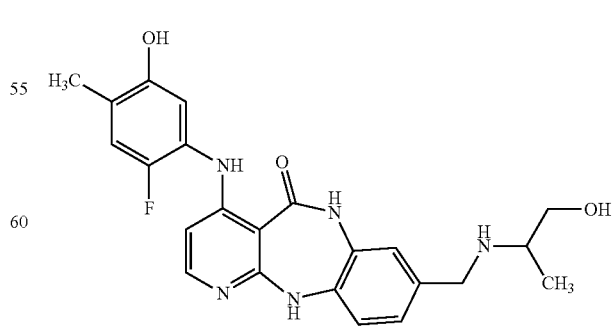

In analogy to Example 167, Intermediate 11A (110 mg, 71% purity, 0.206 mmol) was reacted with rac-2-aminopropan-1-ol (62 mg, 0.826 mmol). Purification was effected by preparative HPLC (Method 23). The product-containing fractions were combined, admixed with aqueous sodium hydrogencarbonate solution and concentrated. The residue was triturated with dichloromethane/methanol (2:1, 30 ml) and the solids were filtered off with suction. The filtrate was concentrated and the residue was taken up in ethyl acetate and extracted with water. The organic phase was dried over sodium sulphate, filtered and concentrated. In this way, 29 mg (29% of theory) of the title compound were obtained.

LC/MS (Method 5, ESIpos): $R_t$=0.52 min, m/z=438 [M+H]$^+$.

$^1$H-NMR (400 MHz, DMSO-d$_6$): δ [ppm]=1.11 (d, 3H), 2.10 (s, 3H), 2.86-3.05 (m, 1H), 3.35-3.45 (m, 1H), 3.46-3.60 (m, 1H), 3.80-4.05 (m, 2H), 5.09 (br. s, 1H), 6.35-6.40 (m, 1H), 6.72 (d, 1H), 7.01-7.07 (m, 2H), 7.10-7.16 (m, 2H), 7.79 (d, 1H), 8.25 (s, 1H), 9.43 (s, 1H), 9.83 (s, 1H), 10.22 (s, 1H).

Example 169

4-[(2-Fluoro-5-hydroxy-4-methylphenyl)amino]-8-({[1-hydroxy-3-(methylsulphanyl)propan-2-yl]amino}methyl)-6,11-dihydro-5H-pyrido[2,3-b][1,5]benzodiazepin-5-one

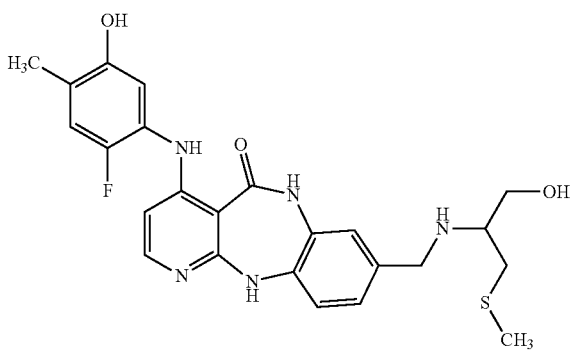 [SMILES: CSCC(CO)NCc1ccc2c(c1)NC(=O)c1c(Nc3cc(O)c(C)cc3F)ccnc1N2]

In analogy to Example 167, Intermediate 11A (110 mg, 70% purity, 0.204 mmol) was reacted with rac-2-amino-3-(methylsulphanyl)propan-1-ol (123 mg, 0.814 mmol). Purification was effected by preparative HPLC (Method 23). The product-containing fractions were combined, admixed with aqueous sodium hydrogencarbonate solution and concentrated. The residue was triturated with dichloromethane/methanol (2:1, 30 ml) and the solids were filtered off with suction. The filtrate was concentrated and the residue was taken up in ethyl acetate and extracted with water. The organic phase was dried over sodium sulphate, filtered and concentrated. 71 mg (66% of theory) of the title compound were obtained.

LC/MS (Method 5, ESIpos): $R_t$=0.56 min, m/z=464 [M+H]$^+$.

$^1$H-NMR (400 MHz, DMSO-d$_6$): δ [ppm]=2.03 (s, 3H), 2.10 (s, 3H), 2.55-3.00 (m, 3H), 3.40-3.53 (m, 2H), 3.70-3.80 (m, 2H), 4.74 (br. s, 1H), 6.36-6.40 (m, 1H), 6.72 (d, 1H), 7.01-7.09 (m, 4H), 7.79 (d, 1H), 8.15 (s, 1H), 9.43 (s, 1H), 9.85 (s, 1H), 10.14 (s, 1H).

Example 170 rac-8-[(3,4-cis-Dihydroxypiperidin-1-yl)methyl]-4-[(2-fluoro-5-hydroxy-4-methylphenyl)amino]-6,11-dihydro-5H-pyrido[2,3-b][1,5]benzodiazepin-5-one

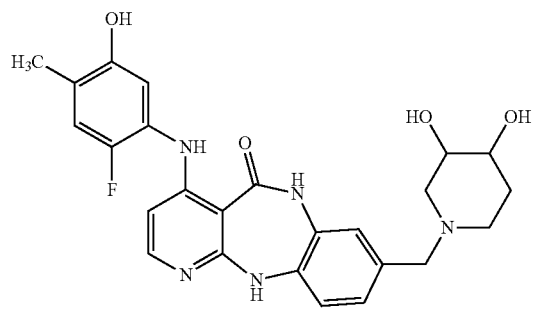 [SMILES: Cc1cc(F)c(Nc2ccnc3c2C(=O)Nc2cc(CN4CCC(O)C(O)C4)ccc2N3)cc1O]

In analogy to Example 164, Intermediate 11A (200 mg, 60% purity, 0.317 mmol) was reacted with rac-cis-3,4-piperidinediol (149 mg, 1.27 mmol). 34 mg (21% of theory) of the title compound were obtained.

LC/MS (Method 5, ESIpos): $R_t$=0.54 min, m/z=480 [M+H]$^+$.

$^1$H-NMR (400 MHz, DMSO-d$_6$): δ [ppm]=1.45-1.56 (m, 1H), 1.57-1.67 (m, 1H), 2.10 (s, 3H), 2.17-2.37 (m, 4H), 3.40-3.57 (m, 2H), 3.60-3.65 (m, 1H), 4.17 (d, 1H), 4.26 (d, 1H), 6.36-6.40 (m, 1H), 6.72 (d, 1H), 6.90-6.95 (m, 2H), 7.01-7.05 (m, 2H), 7.78 (d, 1H), 8.12 (s, 1H), 9.42 (s, 1H), 9.86 (s, 1H), 10.08 (s, 1H).

Example 171 rac-8-[(3,4-trans-Dihydroxypiperidin-1-yl)methyl]-4-[(2-fluoro-5-hydroxy-4-methylphenyl)amino]-6,11-dihydro-5H-pyrido[2,3-b][1,5]benzodiazepin-5-one

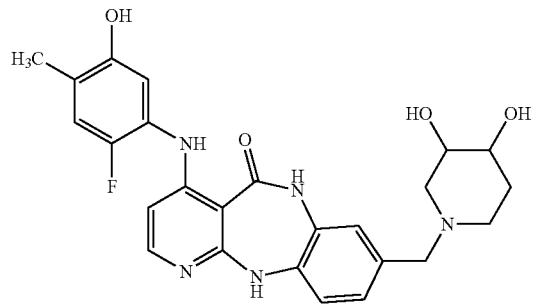 [SMILES: Cc1cc(F)c(Nc2ccnc3c2C(=O)Nc2cc(CN4CCC(O)C(O)C4)ccc2N3)cc1O]

In analogy to Example 164, Intermediate 11A (200 mg, 60% purity, 0.317 mmol) was reacted with rac-trans-3,4-piperidinediol (149 mg, 1.27 mmol). 25 mg (15% of theory) of the title compound were obtained.

LC/MS (Method 5, ESIpos): $R_t$=0.55 min, m/z=480 [M+H]$^+$.

$^1$H-NMR (400 MHz, DMSO-d$_6$): δ [ppm]=1.29-1.39 (m, 1H), 1.64-1.75 (m, 2H), 1.85-1.93 (m, 1H), 2.09 (s, 3H), 2.61-2.69 (m, 1H), 2.70-2.76 (m, 1H), 3.06-3.15 (m, 1H), 3.15-3.23 (m, 1H), 4.63 (br. s, 2H), 6.35-6.40 (m, 1H), 6.70

(d, 1H), 6.87-6.93 (m, 2H), 7.01-7.06 (m, 2H), 7.77 (d, 1H), 8.12 (s, 1H), 9.86 (s, 1H), 10.08 (br. s, 1H).

Example 172

4-[(2-Fluoro-5-hydroxy-4-methylphenyl)amino]-8-({[(2S,3R)-1-hydroxy-3-methylpentan-2-yl]amino}methyl)-6,11-dihydro-5H-pyrido[2,3-b][1,5]benzodiazepin-5-one

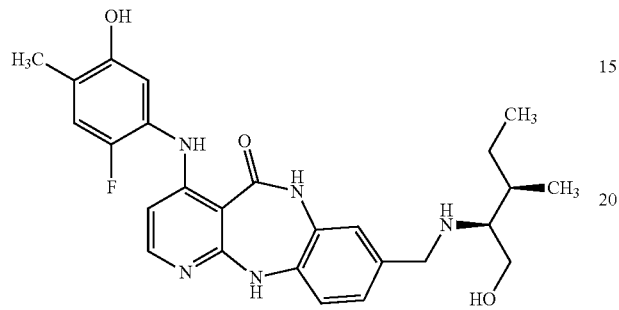

In analogy to Example 167, Intermediate 11A (110 mg, 70% purity, 0.204 mmol) was reacted with (S)-(+)-isoleucinol (95 mg, 0.814 mmol). Purification was effected by preparative HPLC (Method 23). The product-containing fractions were combined, admixed with aqueous sodium hydrogencarbonate solution and substantially concentrated. The remaining aqueous phase was extracted repeatedly with ethyl acetate. The combined organic phases were dried over sodium sulphate, filtered and concentrated. 64 mg (60% of theory) of the title compound were obtained.

LC/MS (Method 7, ESIneg): $R_t$=0.79 min, m/z=478 [M−H]⁻.

¹H-NMR (400 MHz, DMSO-$d_6$): δ [ppm]=0.80-0.90 (m, 6H), 1.08-1.17 (m, 1H), 1.41-1.49 (m, 1H), 1.49-1.60 (m, 1H), 2.10 (s, 3H), 2.30-2.40 (m, 1H), 3.40-3.52 (m, 1H), 3.57-3.65 (m, 2H), 4.35 (br. s, 1H), 6.35-6.40 (m, 1H), 6.72 (d, 1H), 6.92-7.00 (m, 2H), 7.01-7.06 (m, 2H), 7.78 (d, 1H), 8.10 (s, 1H), 9.41 (s, 1H), 9.86 (s, 1H), 10.10 (br. s, 1H).

Example 173

N²-({4-[(2-Fluoro-5-hydroxy-4-methylphenyl)amino]-5-oxo-6,11-dihydro-5H-pyrido[2,3-b][1,5]benzodiazepin-8-yl}methyl)-L-serinamide

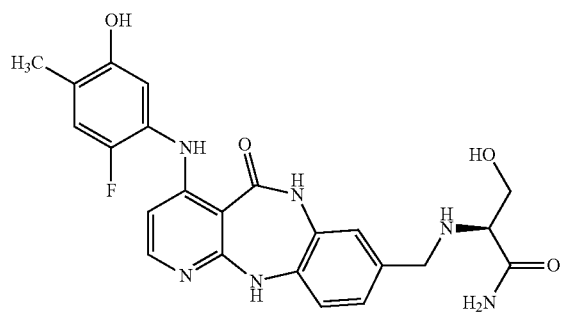 [SMILES: Cc1cc(F)c(Nc2ccnc3c2C(=O)Nc2cc(CN[C@@H](CO)C(N)=O)ccc2N3)cc1O]

In analogy to Example 167, Intermediate 11A (110 mg, 70% purity, 0.204 mmol) was reacted with L-serinamide hydrochloride (114 mg, 0.814 mmol). Purification was effected by preparative HPLC (Method 23). The product-containing fractions were combined, admixed with aqueous sodium hydrogencarbonate solution and substantially concentrated. The remaining aqueous phase was extracted repeatedly with ethyl acetate. The combined organic phases were dried over sodium sulphate, filtered and concentrated. 61 mg (64% of theory) of the title compound were obtained.

LC/MS (Method 7, ESIpos): $R_t$=0.66 min, m/z=467 [M+H]⁺.

¹H-NMR (400 MHz, DMSO-$d_6$): δ [ppm]=2.10 (s, 3H), 2.95-3.00 (m, 1H), 3.40-3.54 (m, 3H), 3.60-3.67 (m, 1H), 4.68 (t, 1H), 6.35-6.40 (m, 1H), 6.72 (d, 1H), 6.95-7.00 (m, 2H), 7.01-7.11 (m, 3H), 7.26 (m, 1H), 7.78 (d, 1H), 8.11 (s, 1H), 9.42 (s, 1H), 9.85 (s, 1H), 10.08 (br. s, 1H).

Example 174

4-[(4-Chloro-2-fluoro-5-hydroxyphenyl)amino]-8-[(diethylamino)methyl]-6,11-dihydro-5H-pyrido[2,3-b][1,5]benzodiazepin-5-one

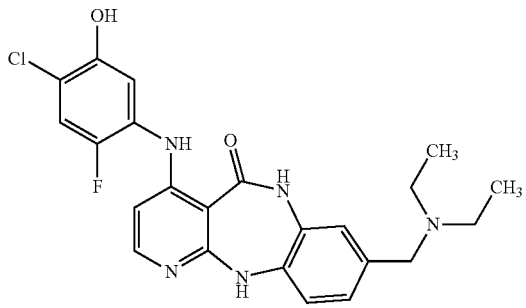 [SMILES: CCN(CC)Cc1ccc2c(c1)NC(=O)c1c(Nc3cc(O)c(Cl)cc3F)ccnc1N2]

Intermediate 13A (65 mg, 88% purity, 0.143 mmol) was reacted analogously to Example 90 with diethylamine (42 mg, 0.574 mmol). The crude product was purified by means of preparative HPLC (Method 16). 6 mg (9% of theory) of the title compound were obtained.

LC/MS (Method 5, ESIpos): $R_t$=0.63 min, m/z=456 [M+H]⁺.

¹H-NMR (400 MHz, DMSO-$d_6$): δ [ppm]=0.95 (t, 6H), 2.42 (q, 4H), 3.40 (s, 2H), 6.49 (d, 1H), 6.91-6.98 (m, 3H), 7.04 (d, 1H), 7.42 (d, 1H), 7.84 (d, 1H), 8.17 (s, 1H), 9.99 (s, 1H), 10.13 (s, 1H), 10.24 (br. s, 1H).

Example 175

4-[(4-Chloro-2-fluoro-5-hydroxyphenyl)amino]-8-[(4-hydroxypiperidin-1-yl)methyl]-6,11-dihydro-5H-pyrido[2,3-b][1,5]benzodiazepin-5-one

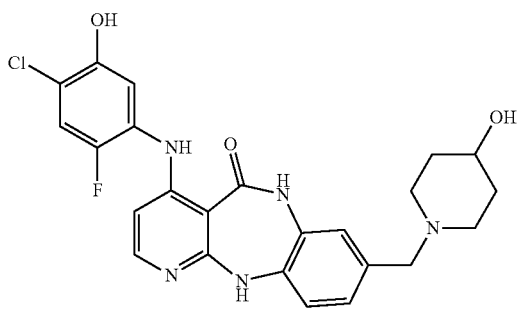 [SMILES: O=C1Nc2cc(CN3CCC(O)CC3)ccc2Nc2nccc(Nc3cc(O)c(Cl)cc3F)c21]

Intermediate 13A (65 mg, 88% purity, 0.143 mmol) was reacted analogously to Example 90 with 4-hydroxypiperidine (58 mg, 0.574 mmol). The crude product was purified by means of preparative HPLC (Method 16). 7 mg (10% of theory) of the title compound were obtained.

LC/MS (Method 5): $R_t$=0.59 min, m/z=484 [M+H]$^+$.

$^1$H-NMR (400 MHz, DMSO-d$_6$): δ [ppm]=1.30-1.42 (m, 2H), 1.62-1.74 (m, 2H), 1.92-2.05 (m, 2H), 2.57-2.71 (m, 2H), 3.38-3.51 (m, 1H), 4.51 (d, 1H), 6.49 (d, 1H), 6.87-6.97 (m, 3H), 7.05 (d, 1H), 7.42 (d, 1H), 7.84 (d, 1H), 8.19 (s, 1H), 9.98 (s, 1H), 10.13 (s, 1H), 10.24 (s, 1H).

Example 176 tert-Butyl (3S,4S)-4-{[({4-[(2-fluoro-5-hydroxy-4-methylphenyl)amino]-5-oxo-6,11-dihydro-5H-pyrido[2,3-b][1,5]benzodiazepin-8-yl}methyl)amino]methyl}-3-hydroxypiperidine-1-carboxylate

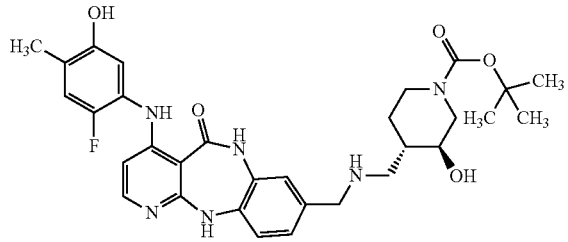 [SMILES: Cc1cc(F)c(Nc2ccnc3c2C(=O)Nc2cc(CNC[C@@H]4CCN(C(=O)OC(C)(C)C)C[C@H]4O)ccc2N3)cc1O]

Intermediate 11A (250 mg, 60% purity, 0.396 mmol) was dissolved in 0.95 ml of DMF. tert Butyl (3S,4S)-4-(aminomethyl)-3-hydroxy-1-piperidinecarboxylate (365 mg, 1.586 mmol) and trimethyl orthoformate (841 mg, 7.93 mmol) were added and the mixture was stirred at 40° C. overnight. Then sodium triacetoxyborohydride (336 mg, 1.59 mmol) was added at RT and stirring of the reaction mixture at RT continued overnight. Then aqueous sodium hydrogencarbonate solution was added and the mixture was subsequently concentrated. The residue was taken up in 10 ml of DMF, filtered and concentrated again. Purification of the residue by preparative HPLC (Method 16) gave 40 mg (17% of theory) of the title compound.

LC/MS (Method 5, ESIpos): $R_t$=0.68 min, m/z=593 [M+H]$^+$.

$^1$H-NMR (400 MHz, DMSO-d$_6$): δ [ppm]=0.95-1.05 (m, 1H), 1.37 (s, 9H), 1.55-1.70 (m, 1H), 2.10 (s, 3H), 2.2-2.45 (m, 3H), 2.6-2.75 (m, 3H), 3.09-3.17 (m, 1H), 3.50-3.62 (m, 2H), 3.80-4.00 (m, 3H), 6.35-6.40 (m, 1H), 6.72 (d, 1H), 6.83-6.97 (m, 2H), 7.00-7.07 (m, 2H), 7.78 (d, 1H), 8.10 (s, 1H), 9.85 (s, 1H), 10.10 (s, 1H).

Example 177 rac-4-[(2-Fluoro-5-hydroxy-4-methylphenyl)amino]-8-{[3-(hydroxymethyl)pyrrolidin-1-yl]methyl}-6,11-dihydro-5H-pyrido[2,3-b][1,5]benzodiazepin-5-one

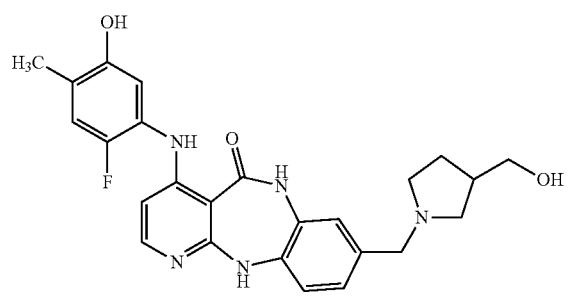 [SMILES: Cc1cc(F)c(Nc2ccnc3c2C(=O)Nc2cc(CN4CCC(CO)C4)ccc2N3)cc1O]

In analogy to Example 176, Intermediate 11A (250 mg, 60% purity, 0.396 mmol) was reacted with pyrrolidin-3-ylmethanol (160 mg, 1.59 mmol). 31 mg (17% of theory) of the title compound were obtained.

LC/MS (Method 5, ESIpos): $R_t$=0.52 min, m/z=464 [M+H]$^+$.

$^1$H-NMR (400 MHz, DMSO-d$_6$): δ [ppm]=1.31-1.36 (m, 1H), 1.74-1.85 (m, 1H), 2.10 (s, 3H), 2.15-2.25 (m, 2H), 2.37-2.43 (m, 2H), 3.22-3.29 (m, 2H), 3.38-3.60 (m, 3H), 4.50 (br. s, 1H), 6.35-6.40 (m, 1H), 6.72 (d, 1H), 6.87-6.94 (m, 2H), 7.00-7.07 (m, 2H), 7.78 (d, 1H), 8.12 (s, 1H), 9.47 (br. s, 1H), 9.86 (s, 1H), 10.08 (s, 1H).

Example 178

4-[(2-Fluoro-5-hydroxy-4-methylphenyl)amino]-8-[(4-hydroxypiperidin-1-yl)carbonyl]-6,11-dihydro-5H-pyrido[2,3-b][1,5]benzodiazepin-5-one

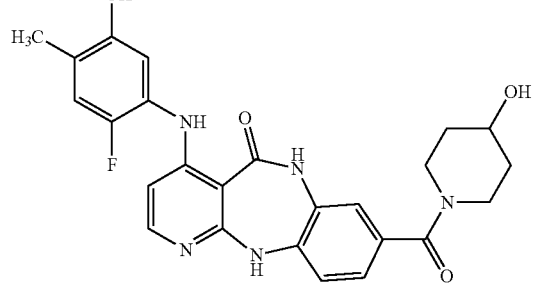

Under an argon atmosphere, the compound from Example 79 (100 mg, 0.254 mmol) was dissolved in DMF (1.0 ml) and cooled to 0° C. HATU (193 mg, 0.507 mmol) was added, and the mixture was stirred for 20 min. Subsequently, 4-hydroxypiperidine (51 mg, 0.507 mmol) and N,N-diisopropylethylamine (66 mg, 0.507 mmol) were added and the reaction mixture was stirred at RT for 30 min. Direct purification by preparative HPLC (Method 16) gave 40 mg (31% of theory) of the title compound.

LC/MS (Method 7, ESIpos): $R_t$=0.82 min, m/z=478 [M+H]$^+$.

$^1$H-NMR (400 MHz, DMSO-d$_6$): δ [ppm]=1.31-1.35 (m, 2H), 1.70-1.75 (m, 2H), 2.10 (s, 3H), 3.10-3.18 (m, 2H), 3.47-3.71 (m, 1H), 3.71-3.73 (m, 1H), 3.73-4.00 (m, 1H), 4.76 (d, 1H), 6.35-6.40 (m, 1H), 6.72 (d, 1H), 7.00-7.04 (m, 1H), 7.03-7.06 (m, 1H), 7.12-7.17 (m, 1H), 7.80 (d, 1H), 8.41 (s, 1H), 9.44 (br. s, 1H), 9.88 (s, 1H), 10.18 (s, 1H).

Example 179 rac-4-[(2-Fluoro-5-hydroxy-4-methylphenyl)amino]-8-{[3-(2-hydroxyethyl)piperidin-1-yl]carbonyl}-6,11-dihydro-5H-pyrido[2,3-b][1,5]benzodiazepin-5-one

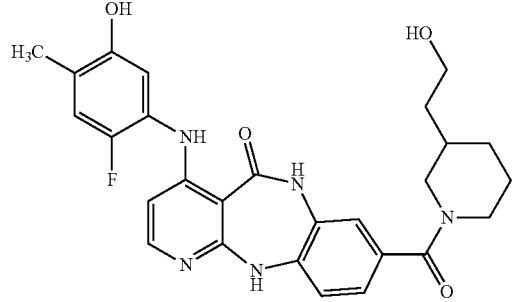 [SMILES: Cc1cc(F)c(Nc2ccnc3c2C(=O)Nc2cc(C(=O)N4CCCC(CCO)C4)ccc2N3)cc1O]

181

In analogy to Example 178, the compound from Example 79 (100 mg, 0.254 mmol) was reacted with 2-(piperidin-3-yl)ethanol (66 mg, 0.507 mmol). After purification by means of silica gel chromatography (eluent: dichloromethane→dichloromethane/methanol 9:1) and further purification by preparative HPLC (Method 16), 32 mg (25% of theory) of the title compound were obtained.

LC/MS (Method 7, ESIpos): $R_t$=0.92 min, m/z=506 [M+H]$^+$.

$^1$H-NMR (400 MHz, DMSO-d$_6$): δ [ppm]=1.13-1.40 (m, 4H), 1.50-1.71 (m, 2H), 1.79-1.85 (m, 1H), 3.10 (s, 3H), 2.60-3.00 (m, 2H), 3.36-3.72 (m, 3H), 4.00-4.40 (m, 2H), 6.35-6.40 (m, 1H), 6.72 (d, 1H), 7.00-7.07 (m, 3H), 7.12-7.17 (m, 1H), 7.80 (d, 1H), 8.41 (s, 1H), 9.43 (s, 1H), 9.89 (s, 1H), 10.17 (s, 1H).

Example 180

4-[(2-Fluoro-5-hydroxy-4-methylphenyl)amino]-N-(trans-4-hydroxycyclohexyl)-5-oxo-6,11-dihydro-5H-pyrido[2,3-b][1,5]benzodiazepine-8-carboxamide

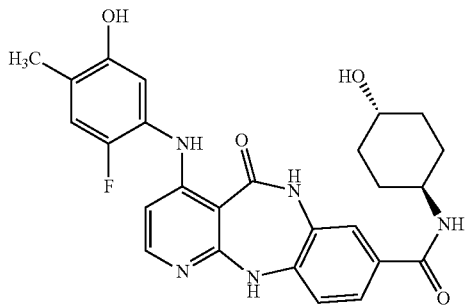 [SMILES: Cc1cc(F)c(Nc2ccnc3c2C(=O)Nc2cc(C(=O)N[C@H]4CC[C@H](O)CC4)ccc2N3)cc1O]

In analogy to Example 178, the compound from Example 79 (100 mg, 0.254 mmol) was reacted with trans-4-aminocyclohexanol (58 mg, 0.507 mmol). After purification by means of silica gel chromatography (eluent: dichloromethane/methanol 95:5→dichloromethane/methanol 90:10) and further purification by preparative HPLC (Method 16), 30 mg (22% of theory) of the title compound were obtained.

LC/MS (Method 7, ESIpos): $R_t$=0.86 min, m/z=492 [M+H]$^+$.

$^1$H-NMR (400 MHz, DMSO-d$_6$): δ [ppm]=1.17-1.40 (m, 4H), 1.75-1.86 (m, 4H), 2.10 (s, 3H), 3.33-3.39 (m, 1H), 3.63-3.71 (m, 1H), 4.53 (d, 1H), 6.35-6.40 (m, 1H), 6.71 (d, 1H), 7.04 (d, 1H), 7.13 (d, 1H), 7.46-7.50 (m, 1H), 7.80 (d, 1H), 7.99 (d, 1H), 8.52 (s, 1H), 9.44 (s, 1H), 9.85 (s, 1H), 10.16 (s, 1H).

Example 181 rac-4-[(2-Fluoro-5-hydroxy-4-methylphenyl)amino]-8-{[3-(2-hydroxyethyl)pyrrolidin-1-yl]carbonyl}-6,11-dihydro-5H-pyrido[2,3-b][1,5]benzodiazepin-5-one

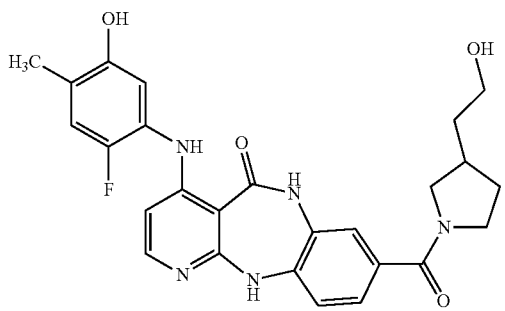 [SMILES: Cc1cc(F)c(Nc2ccnc3c2C(=O)Nc2cc(C(=O)N4CCC(CCO)C4)ccc2N3)cc1O]

182

In analogy to Example 178, the compound from Example 79 (100 mg, 0.254 mmol) was reacted with 2-(pyrrolidin-3-yl)ethanol (58 mg, 0.507 mmol). After purification by means of silica gel chromatography (eluent: dichloromethane→dichloromethane/methanol 90:10) and further purification by preparative HPLC (Method 16), 14 mg (11% of theory) of the title compound were obtained.

LC/MS (Method 5, ESIpos): $R_t$=0.67 min, m/z=492 [M+H]$^+$.

$^1$H-NMR (400 MHz, DMSO-d$_6$): δ [ppm]=1.39-1.57 (m, 3H), 1.93-2.09 (m, 1H), 2.11 (s, 3H), 2.13-2.24 (m, 1H), 3.00-3.15 (m, 1H), 3.38-3.66 (m, 5H), 6.35-6.40 (m, 1H), 6.71 (d, 1H), 7.04 (d, 1H), 7.11-7.21 (m, 3H), 7.81 (d, 1H), 8.46 (s, 1H), 9.43 (s, 1H), 9.91 (s, 1H), 10.18 (s, 1H).

Example 182 rac-4-[(2-Fluoro-5-hydroxy-4-methylphenyl)amino]-8-{[3-(2-hydroxyethyl)pyrrolidin-1-yl]methyl}-6,11-dihydro-5H-pyrido[2,3-b][1,5]benzodiazepin-5-one

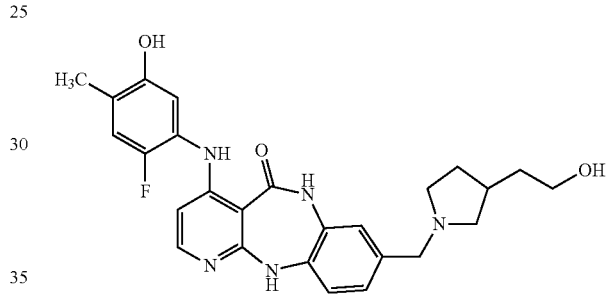

Intermediate 11A (135 mg, 70% purity, 0.250 mmol) was dissolved in 2.6 ml of dioxane. 2-(Pyrrolidin-3-yl)ethanol (115 mg, 1.00 mmol) and trimethyl orthoformate (530 mg, 5.00 mmol) were added and the mixture was stirred at 40° C. for 6 h. Then sodium triacetoxyborohydride (212 mg, 1.00 mmol) was added at RT and stirring of the reaction mixture at RT continued overnight. Then aqueous sodium hydrogencarbonate solution was added and the mixture was subsequently concentrated. The residue was taken up in 15 ml of DMF, filtered and concentrated again. Purification of the residue by preparative HPLC (Method 16) gave 70 mg (56% of theory) of the title compound.

LC/MS (Method 7, ESIneg): $R_t$=0.72 min, m/z=476 [M−H]$^-$.

$^1$H-NMR (400 MHz, DMSO-d$_6$): δ [ppm]=1.26-1.36 (m, 1H), 1.43-1.50 (m, 2H), 1.83-1.93 (m, 1H), 1.96-2.02 (m, 1H), 2.09-2.17 (m, 1H), 2.10 (s, 3H), 2.30-2.38 (m, 1H), 2.62-2.68 (m, 1H), 3.34-3.37 (m, 2H), 3.42 (s, 2H), 4.34 (br. s, 1H), 6.35-6.40 (m, 1H), 6.72 (d, 1H), 6.87-6.95 (m, 2H), 7.00-7.07 (m, 2H), 7.78 (d, 1H), 8.12 (s, 1H), 9.45 (br. s, 1H), 9.87 (s, 1H), 10.08 (s, 1H).

Example 183

4-[(2-Fluoro-5-hydroxy-4-methylphenyl)amino]-8-[(4a-hydroxyoctahydroisoquinolin-2(1H)-yl)methyl]-6,11-dihydro-5H-pyrido[2,3-b][1,5]benzodiazepin-5-one

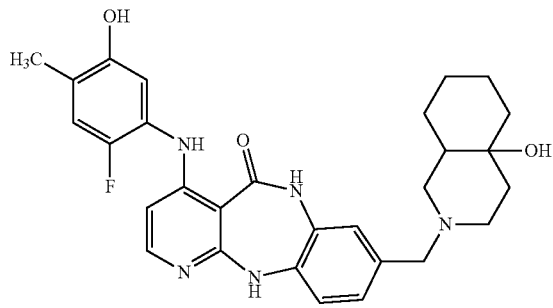 [SMILES: Cc1cc(F)c(Nc2ccnc3c2C(=O)Nc2cc(CN4CCC5(O)CCCCC5C4)ccc2N3)cc1O]

In analogy to Example 176, Intermediate 11A (250 mg, 60% purity, 0.396 mmol) was reacted with octahydroisoquinolin-4a(2H)-ol (246 mg, 1.59 mmol). 31 mg (14% of theory) of the title compound were obtained.

LC/MS (Method 5, ESIpos): $R_t$=0.64 min, m/z=518 [M+H]$^+$.

$^1$H-NMR (400 MHz, DMSO-d$_6$): δ [ppm]=1.00-1.65 (m, 12H), 2.10 (s, 3H), 2.17-2.25 (m, 1H), 2.45-2.49 (m, 1H), 3.25-3.29 (m, 2H), 4.00 (s, 1H), 6.35-6.40 (m, 1H), 6.72 (d, 1H), 6.87-6.94 (m, 2H), 7.00-7.07 (m, 2H), 7.78 (d, 1H), 8.11 (s, 1H), 9.41 (br. s, 1H), 9.88 (s, 1H), 10.09 (s, 1H).

Example 184

4-[(2-Fluoro-5-hydroxy-4-methylphenyl)amino]-8-({[(2R)-1-hydroxy-3-(1H-imidazol-5-yl)propan-2-yl]amino}methyl)-6,11-dihydro-5H-pyrido[2,3-b][1,5]benzodiazepin-5-one

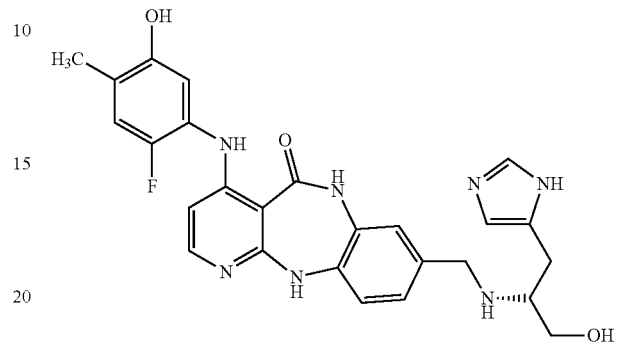

Intermediate 11A (110 mg, 70% purity, 0.204 mmol) was dissolved in 2 ml of DMF and 0.197 ml of acetic acid. L-(−)-Histidinol dihydrochloride (174 mg, 0.814 mmol) was added and the mixture was stirred at RT overnight. Then sodium triacetoxyborohydride (173 mg, 0.814 mmol) was added at RT and stirring of the reaction mixture at RT continued overnight. Then aqueous sodium hydrogencarbonate solution was added and the mixture was subsequently concentrated. The residue was taken up in 15 ml of DMF, filtered and concentrated again. Purification of the residue by preparative HPLC (Method 16) gave 28 mg (26% of theory) of the title compound.

LC/MS (Method 7, ESIneg): $R_t$=0.62 min, m/z=502 [M−H]$^-$.

$^1$H-NMR (400 MHz, DMSO-d$_6$): δ [ppm]=1.80-1.90 (m, 1H), 2.09 (s, 3H), 2.50-2.60 (m, 2H), 2.66-2.73 (m, 1H), 3.60-3.64 (m, 2H), 6.35-6.40 (m, 1H), 6.70 (d, 1H), 6.87-6.96 (m, 2H), 6.99-7.07 (m, 2H), 7.49 (s, 1H), 7.77 (d, 1H), 8.07 (s, 1H), 9.85 (s, 1H), 10.06 (br. s, 1H).

Example 185

4-[(2-Fluoro-5-hydroxy-4-methylphenyl)amino]-8-(2,5,8,11,14,17,20,23-octaoxa-26-azaheptacosan-27-yl)-6,11-dihydro-5H-pyrido[2,3-b][1,5]benzodiazepin-5-one

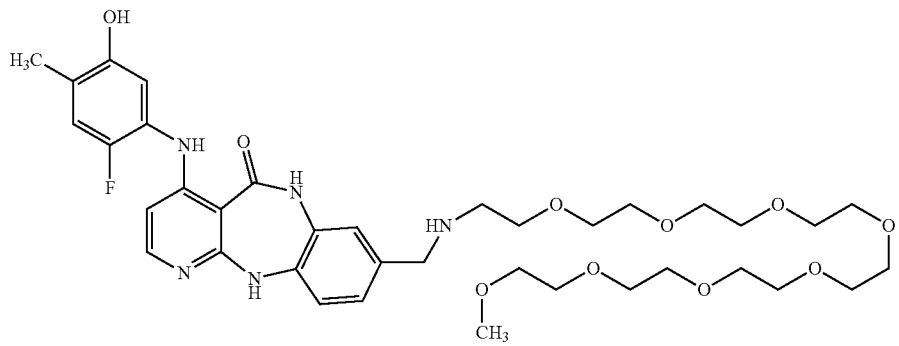 [SMILES: COCCOCCOCCOCCOCCOCCOCCOCCNCc1ccc2c(c1)NC(=O)c1c(Nc3cc(O)c(C)cc3F)ccnc1N2]

In analogy to Example 184, Intermediate 11A (81 mg, 70% purity, 0.150 mmol) was reacted with 2,5,8,11,14,17,20,23-octaoxapentacosan-25-amine (230 mg, 0.600 mmol). 58 mg (52% of theory) of the title compound were obtained.

LC/MS (Method 5, ESIpos): $R_t$=0.65 min, m/z=746 [M+H]$^+$.

$^1$H-NMR (400 MHz, DMSO-d$_6$): δ [ppm]=2.10 (s, 3H), 2.61 (t, 2H), 3.40-3.55 (m, 30H), 3.59 (s, 2H), 6.36-6.40 (m, 1H), 6.72 (d, 1H), 6.87-6.97 (m, 2H), 7.00-7.07 (m, 2H), 7.78 (d, 1H), 8.09 (s, 1H), 9.42 (br. s, 1H), 9.87 (s, 1H), 10.09 (s, 1H).

Example 186

4-[(2-Fluoro-5-hydroxy-4-methylphenyl)amino]-8-(13-hydroxy-5,8,11-trioxa-2-azatridec-1-yl)-6,11-dihydro-5H-pyrido[2,3-b][1,5]benzodiazepin-5-one

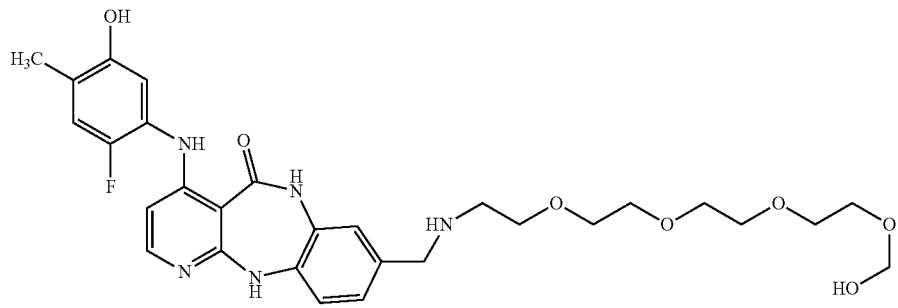 [SMILES: Cc1cc(F)c(Nc2ccnc3c2C(=O)Nc2cc(CNCCOCCOCCOCCOCO)ccc2N3)cc1O]

In analogy to Example 184, Intermediate 11A (108 mg, 70% purity, 0.200 mmol) was reacted with 2-{2-[2-(2-aminoethoxy)ethoxy]ethoxy}ethanol (155 mg, 0.800 mmol). 59 mg (49% of theory) of the title compound were obtained.

LC/MS (Method 5, ESIpos): $R_t$=0.55 min, m/z=556 [M+H]$^+$.

$^1$H-NMR (400 MHz, DMSO-d$_6$): δ [ppm]=1.83-1.95 (m, 1H), 2.09 (s, 3H), 2.58-2.63 (m, 2H), 3.35-3.54 (m, 16H), 3.56-3.61 (m, 2H), 6.36-6.40 (m, 1H), 6.70 (d, 1H), 6.93-6.97 (m, 2H), 6.98-7.07 (m, 2H), 7.76 (d, 1H), 8.08 (s, 1H), 9.85 (s, 1H), 10.08 (br. s, 1H).

Example 187

4-[(2-Fluoro-5-hydroxy-4-methylphenyl)amino]-8-{[(3-hydroxycyclobutyl)amino]methyl}-6,11-dihydro-5H-pyrido[2,3-b][1,5]benzodiazepin-5-one

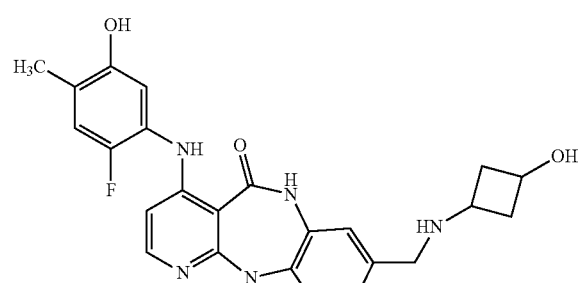

In analogy to Example 184, Intermediate 11A (108 mg, 70% purity, 0.200 mmol) was reacted with 3-aminocyclobutanol hydrochloride (99 mg, 0.800 mmol). 29 mg (31% of theory) of the title compound were obtained as a mixture of cis and trans isomer.

LC/MS (Method 5, ESIpos): $R_t$=0.52 min, m/z=450 [M+H]$^+$.

$^1$H-NMR (400 MHz, DMSO-d$_6$): δ [ppm]=1.47-1.53 (m, 1.4H), 1.88-1.97 (m, 1.2H), 2.10 (s, 3H), 2.33-2.43 (m, 1.5H), 3.19-3.23 (m, 0.2H), 3.45-3.49 (m, 2H), 3.67-3.75 (m, 0.7H), 4.21-4.25 (m, 0.2H), 4.78 (d, 0.2H), 4.84 (d, 0.7H), 6.35-6.40 (m, 1H), 6.70 (d, 1H), 6.88-6.97 (m, 2H), 6.98-7.07 (m, 2H), 7.78 (d, 1H), 8.08 (s, 1H), 9.41 (s, 1H), 9.85 (s, 1H), 10.08 (s, 1H).

Example 188

8-[(Cyclobutylamino)methyl]-4-[(2-fluoro-5-hydroxy-4-methylphenyl)amino]-6,11-dihydro-5H-pyrido[2,3-b][1,5]benzodiazepin-5-one

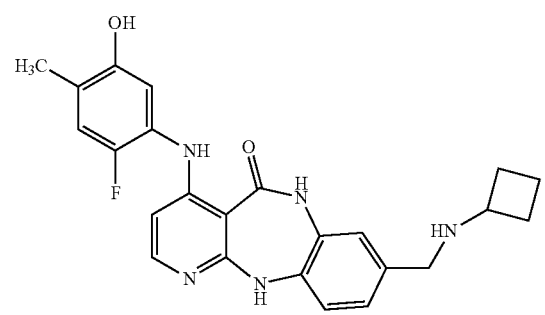 [SMILES: Cc1cc(F)c(Nc2ccnc3c2C(=O)Nc2cc(CNC4CCC4)ccc2N3)cc1O]

In analogy to Example 184, Intermediate 11A (108 mg, 70% purity, 0.200 mmol) was reacted with cyclobutylamine (57 mg, 0.800 mmol). 38 mg (42% of theory) of the title compound were obtained.

LC/MS (Method 5, ESIpos): $R_t$=0.57 min, m/z=434 [M+H]$^+$.

$^1$H-NMR (400 MHz, DMSO-d$_6$): δ [ppm]=1.46-1.72 (m, 6H), 2.00-2.08 (m, 2H), 2.10 (s, 3H), 3.06-3.15 (m, 1H), 3.48 (s, 2H), 6.35-6.40 (m, 1H), 6.72 (d, 1H), 6.88-6.99 (m, 2H), 6.99-7.07 (m, 2H), 7.78 (d, 1H), 8.08 (s, 1H), 9.41 (s, 1H), 9.85 (s, 1H), 10.08 (s, 1H).

Example 189

8-{[(3,3-Difluorocyclobutyl)amino]methyl}-4-[(2-fluoro-5-hydroxy-4-methylphenyl)amino]-6,11-dihydro-5H-pyrido[2,3-b][1,5]benzodiazepin-5-one

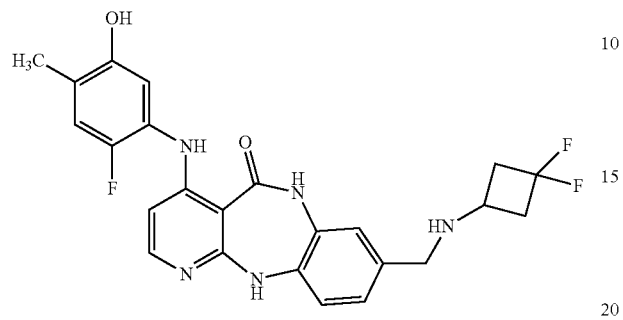

In analogy to Example 184, Intermediate 11A (108 mg, 70% purity, 0.200 mmol) was reacted with 3,3-difluorocyclobutylamine (115 mg, 0.800 mmol). 57 mg (58% of theory) of the title compound were obtained.

LC/MS (Method 5, ESIpos): $R_t$=0.58 min, m/z=470 [M+H]$^+$.

$^1$H-NMR (400 MHz, DMSO-d$_6$): δ [ppm]=2.10 (s, 3H), 2.22-2.38 (m, 2H), 2.62-2.75 (m, 2H), 3.03-3.15 (m, 1H), 3.51 (s, 2H), 6.35-6.40 (m, 1H), 6.72 (d, 1H), 6.88-6.99 (m, 2H), 7.01-7.07 (m, 2H), 7.78 (d, 1H), 8.10 (s, 1H), 9.41 (s, 1H), 9.85 (s, 1H), 10.09 (s, 1H).

Example 190

4-[(2-Fluoro-5-hydroxy-4-methylphenyl)amino]-8-{[(3-isopropoxycyclobutyl)amino]methyl}-6,11-dihydro-5H-pyrido[2,3-b][1,5]benzodiazepin-5-one

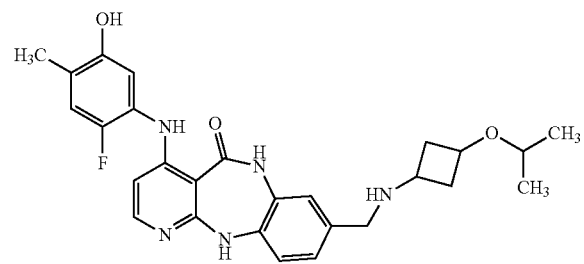 [SMILES: Cc1cc(F)c(Nc2ccnc3c2C(=O)Nc2cc(CNC4CC(OC(C)C)C4)ccc2N3)cc1O]

In analogy to Example 184, Intermediate 11A (108 mg, 70% purity, 0.200 mmol) was reacted with 3-isopropoxycyclobutylamine (103 mg, 0.800 mmol). 63 mg (61% of theory) of the title compound were obtained as a mixture of cis and trans isomer.

LC/MS (Method 5, ESIpos): $R_t$=0.67 min, m/z=492 [M+H]$^+$.

$^1$H-NMR (400 MHz, DMSO-d$_6$): δ [ppm]=1.02 (d, 3H), 1.03 (d, 3H), 1.48-1.57 (m, 1H), 1.91-2.00 (m, 1.6H), 2.10 (s, 3H), 2.38-2.46 (m, 1H), 2.61-2.68 (m, 0.7H), 3.15-3.21 (m, 0.4H), 3.46-3.54 (m, 3H), 3.57-3.66 (m, 0.6H), 4.12-4.17 (m, 0.4H), 6.35-6.40 (m, 1H), 6.72 (d, 1H), 6.88-6.99 (m, 2H), 7.01-7.07 (m, 2H), 7.78 (d, 1H), 8.08 (s, 1H), 9.41 (s, 1H), 9.85 (s, 1H), 10.08 (s, 1H).

Example 191 cis-Ethyl 3-[({4-[(2-fluoro-5-hydroxy-4-methylphenyl)amino]-5-oxo-6,11-dihydro-5H-pyrido[2,3-b][1,5]benzodiazepin-8-yl}methyl)amino]cyclobutanecarboxylate

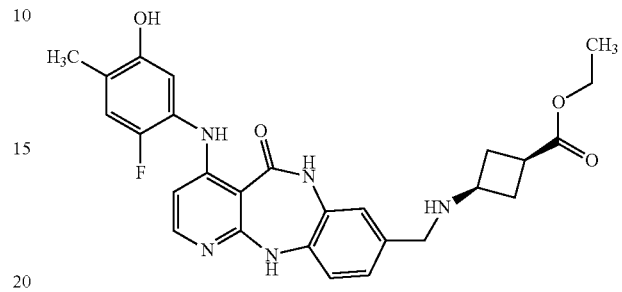

In analogy to Example 184, Intermediate 11A (108 mg, 70% purity, 0.200 mmol) was reacted with cis-ethyl 3-aminocyclobutanecarboxylate hydrochloride (97 mg, 0.800 mmol). Purification was effected by preparative HPLC (Method 23). The product-containing fractions were combined and admixed with aqueous sodium hydrogencarbonate solution. The mixture was concentrated almost completely and then extracted with ethyl acetate. The combined organic phases were dried over sodium sulphate, filtered and concentrated. 9 mg (9% of theory) of the title compound were obtained.

LC/MS (Method 7, ESIneg): $R_t$=0.82 min, m/z=504 [M−H]$^−$.

$^1$H-NMR (400 MHz, DMSO-d$_6$): δ [ppm]=1.16 (t, 3H), 1.95-2.05 (m, 2H), 2.10 (s, 3H), 2.20-2.31 (m, 2H), 2.90-3.05 (m, 1H), 3.45-3.60 (m, 2H), 4.05 (q, 2H), 6.35-6.40 (m, 1H), 6.72 (d, 1H), 6.88-6.99 (m, 2H), 7.01-7.07 (m, 2H), 7.78 (d, 1H), 8.10 (s, 1H), 9.41 (s, 1H), 9.85 (s, 1H), 10.10 (s, 1H).

Example 192 trans-Ethyl 3-[({4-[(2-fluoro-5-hydroxy-4-methylphenyl)amino]-5-oxo-6,11-dihydro-5H-pyrido[2,3-b][1,5]benzodiazepin-8-yl}methyl)amino]cyclobutanecarboxylate

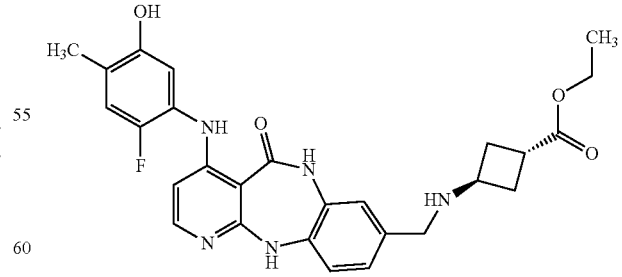

In analogy to Example 184, Intermediate 11A (108 mg, 70% purity, 0.200 mmol) was reacted with trans-ethyl 3-aminocyclobutanecarboxylate hydrochloride (97 mg, 0.800 mmol). 47 mg (45% of theory) of the title compound were obtained.

LC/MS (Method 5, ESIpos): $R_t$=0.61 min, m/z=506 [M+H]$^+$.

$^1$H-NMR (400 MHz, DMSO-d$_6$): δ [ppm]=1.16 (t, 3H), 1.77-1.87 (m, 2H), 2.10 (s, 3H), 2.24-2.34 (m, 2H), 2.60-2.73 (m, 1H), 2.99-3.06 (m, 1H), 3.49 (s, 2H), 4.02 (q, 2H), 6.35-6.40 (m, 1H), 6.72 (d, 1H), 6.88-6.99 (m, 2H), 7.00-7.07 (m, 2H), 7.78 (d, 1H), 8.10 (s, 1H), 9.41 (s, 1H), 9.85 (s, 1H), 10.08 (s, 1H).

Example 193

8-[(Diethylamino)methyl]-4-[(2-fluoro-5-hydroxy-4-methylphenyl)amino]-6,11-dihydro-5H-pyrido[2,3-b][1,5]benzodiazepin-5-one hydrochloride

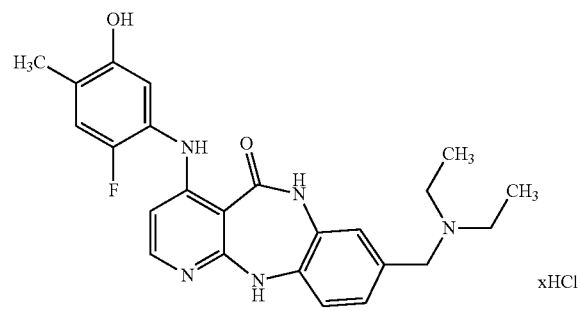 [SMILES: CCN(CC)Cc1ccc2c(c1)NC(=O)c1c(Nc3cc(O)c(C)cc3F)ccnc1N2]

The compound from Example 28 (138 mg, 0.317 mmol) was dissolved in acetone (16.5 ml), and 1 N hydrochloric acid (317 µl, 0.317 mmol) was added. The mixture was gradually concentrated to dryness at RT over 2 days. 133 mg (89% of theory) of the title compound were obtained.

LC/MS (Method 5, ESIpos): $R_t$=0.56 min, m/z=436 [M+H]$^+$.

Ion chromatography (Method 24): found: 8.5% chloride; calculated for monohydrochloride: 7.51% chloride.

$^1$H-NMR (400 MHz, DMSO-d$_6$): δ [ppm]=1.23 (t, 6H), 2.11 (s, 3H), 3.01 (q, 4H), 4.10-4.20 (m, 2H), 6.35-6.40 (m, 1H), 6.72 (d, 1H), 7.04 (d, 1H), 7.13 (s, 1H), 7.16-7.20 (m, 1H), 7.23-7.30 (m, 1H), 7.81 (d, 1H), 8.48 (s, 1H), 9.51 (s, 1H), 9.89 (s, 1H), 10.02 (br. s, 1H), 10.27 (s, 1H).

Example 194 rac-8-({4-[(2-Fluoro-5-hydroxy-4-methylphenyl)amino]-5-oxo-6,11-dihydro-5H-pyrido[2,3-b][1,5]benzodiazepin-8-yl}methyl)-3-methyltetrahydro-2H-pyrazino[1,2-a]pyrazine-1,4(3H,6H)-dione

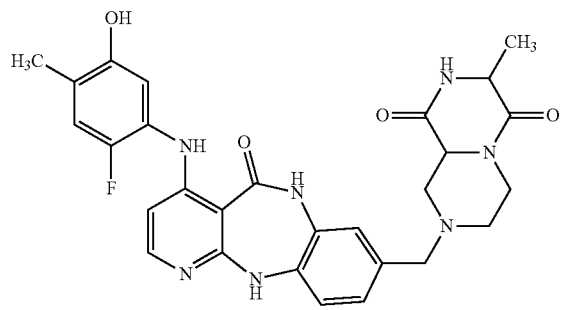 [SMILES: Cc1cc(F)c(Nc2ccnc3c2C(=O)Nc2cc(CN4CCN5C(=O)C(C)NC(=O)C5C4)ccc2N3)cc1O]

Intermediate 11A (250 mg, 60% purity, 0.396 mmol) was dissolved in 1.8 ml of DMF. 3-Methyltetrahydro-2H-pyrazino[1,2-a]pyrazine-1,4(3H,6H)-dione (291 mg, 1.586 mmol) and trimethyl orthoformate (841 mg, 7.93 mmol) were added and the mixture was stirred at RT overnight. Then sodium triacetoxyborohydride (336 mg, 1.59 mmol) was added at RT and stirring of the reaction mixture at RT continued overnight. Then aqueous sodium hydrogencarbonate solution was added and the mixture was subsequently concentrated. The residue was taken up in 15 ml of DMF, filtered and concentrated again. Purification of the residue by preparative HPLC (Method 16) gave 19 mg (8% of theory) of the title compound.

LC/MS (Method 7, ESIpos): $R_t$=0.77 min, m/z=546 [M+H]$^+$.

$^1$H-NMR (400 MHz, DMSO-d$_6$): δ [ppm]=1.29 (d, 3H), 1.84-1.94 (m, 2H), 2.09 (s, 3H), 2.60-2.70 (m, 1H), 2.77-2.85 (m, 1H), 3.10-3.20 (m, 1H), 3.43 (s, 2H), 3.87-4.04 (m, 2H), 4.20-4.30 (m, 1H), 6.35-6.40 (m, 1H), 6.72 (d, 1H), 6.90-6.98 (m, 2H), 7.00-7.09 (m, 2H), 7.78 (d, 1H), 8.16 (s, 1H), 9.30 (s, 1H), 9.85 (s, 1H), 10.11 (br. s, 1H).

Example 195 trans-3-[({4-[(2-Fluoro-5-hydroxy-4-methylphenyl)amino]-5-oxo-6,11-dihydro-5H-pyrido[2,3-b][1,5]benzodiazepin-8-yl}methyl)amino]cyclobutanecarboxylic acid

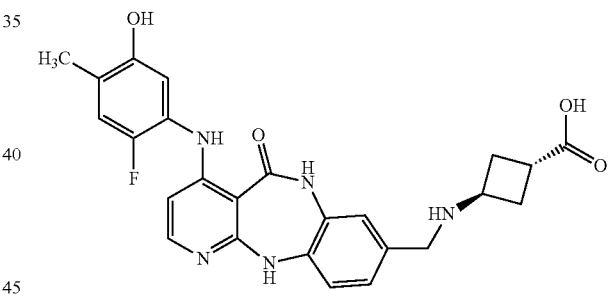

The compound from Example 192 (43 mg, 0.085 mmol) was initially charged in THF/water (4:1, 5 ml), lithium hydroxide (2 mg, 0.1 mmol) was added at RT and the mixture was stirred at RT for 90 min. The reaction solution was then concentrated, the residue was taken up in THF (5 ml), and 1 N sodium hydroxide solution (408 µl, 0.408 mmol) was added. After stirring at RT for 30 min, 1 M hydrochloric acid (0.306 ml) was added and the mixture was concentrated fully. Purification of the residue by means of preparative HPLC (Method 16) gave 28 mg (41% of theory) of the title compound.

LC/MS (Method 5, ESIpos): $R_t$=0.51 min, m/z=478 [M+H]$^+$.

$^1$H-NMR (400 MHz, DMSO-d$_6$): δ [ppm]=1.77-1.87 (m, 2H), 2.10 (s, 3H), 2.24-2.34 (m, 2H), 2.55-2.64 (m, 1H), 2.99-3.10 (m, 1H), 3.52 (s, 2H), 6.35-6.40 (m, 1H), 6.72 (d, 1H), 6.90-6.98 (m, 2H), 7.00-7.07 (m, 2H), 7.78 (d, 1H), 8.09 (s, 1H), 9.41 (s, 1H), 9.85 (s, 1H), 10.09 (s, 1H).

Example 196

4-[(2-Fluoro-5-hydroxy-4-methylphenyl)amino]-8-[(4-isopropyl-3,3-dimethyl-5-oxopiperazin-1-yl)methyl]-6,11-dihydro-5H-pyrido[2,3-b][1,5]benzodiazepin-5-one

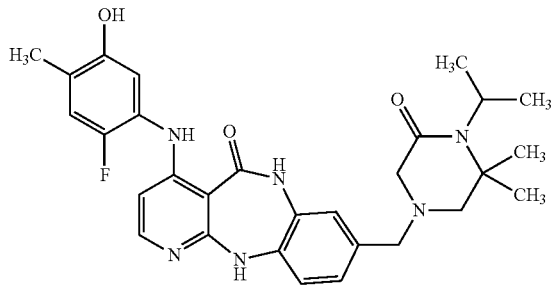 [SMILES: Cc1cc(F)c(Nc2ccnc3c2C(=O)Nc2cc(CN4CC(=O)N(C(C)C)C(C)(C)C4)ccc2N3)cc1O]

In analogy to Example 176, Intermediate 11A (250 mg, 60% purity, 0.396 mmol) was reacted with 1-isopropyl-6,6-dimethylpiperazin-2-one (270 mg, 1.59 mmol). 39 mg (19% of theory) of the title compound were obtained.

LC/MS (Method 5, ESIpos): $R_t$=0.82 min, m/z=533 [M+H]$^+$.

$^1$H-NMR (400 MHz, DMSO-d$_6$): δ [ppm]=1.21 (s, 6H), 1.31 (d, 6H), 2.10 (s, 3H), 2.32 (s, 2H), 2.87 (s, 2H), 3.34 (s, 2H), 3.44-3.54 (m, 1H), 6.35-6.40 (m, 1H), 6.72 (d, 1H), 6.90-6.97 (m, 2H), 7.00-7.09 (m, 2H), 7.78 (d, 1H), 8.17 (s, 1H), 9.41 (s, 1H), 9.88 (s, 1H), 10.12 (s, 1H).

Example 197

4-[(2-Fluoro-5-hydroxy-4-methylphenyl)amino]-8-(piperazin-1-ylmethyl)-6,11-dihydro-5H-pyrido[2,3-b][1,5]benzodiazepin-5-one

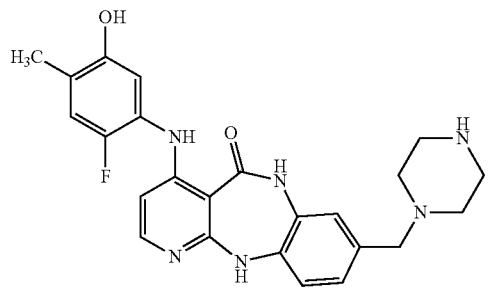 [SMILES: Cc1cc(F)c(Nc2ccnc3c2C(=O)Nc2cc(CN4CCNCC4)ccc2N3)cc1O]

tert-Butyl 4-({4-[(5-{[tert-butyl(dimethyl) silyl]oxy}-2-fluoro-4-methylphenyl)amino]-5-oxo-6,11-dihydro-5H-pyrido[2,3-b][1,5]benzodiazepin-8-yl}methyl)piperazine-1-carboxylate (Intermediate 21A; 46.4 mg, 0.070 mmol) was taken up in a 4 N solution of hydrogen chloride in 1,4-dioxane/water (1:1, 3.3 ml) and stirred at room temperature for 20 min. The reaction mixture was then concentrated, and the residue was dissolved in a mixture of acetonitrile and water, and purified by preparative HPLC (Method 29). The product-containing fractions were combined and concentrated. The residue obtained was admixed with saturated aqueous sodium hydrogencarbonate solution and extracted three times with ethyl acetate. The organic phases were combined, dried over sodium sulphate, filtered and concentrated. 12 mg (38% of theory) of the title compound were obtained.

LC/MS (Method 26): $R_t$=1.33 min; MS (ESIneg): m/z=447 [M–H]$^-$ $^1$H-NMR (500 MHz, DMSO-d$_6$): δ [ppm]=2.10 (s, 3H), 2.25 (br. s, 4H), 2.66 (t, 4H), 6.38 (dd, 1H), 6.73 (d, 1H), 6.88-6.95 (m, 2H), 7.00-7.07 (m, 2H), 7.79 (d, 1H), 8.12 (s, 1H), 9.43 (br. s, 1H), 9.86 (s, 1H), 10.08 (s, 1H).

Example 198

4-[(2-Fluoro-5-hydroxy-4-methylphenyl)amino]-8-{[(2-hydroxyethyl)(methyl)amino]methyl}-6,11-dihydro-5H-pyrido[2,3-b][1,5]benzodiazepin-5-one

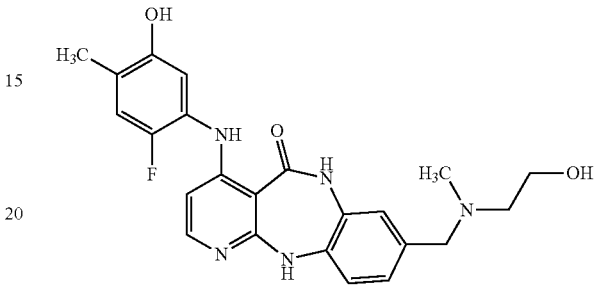

4-[(5-{[tert-Butyl(dimethyl)silyl]oxy}-2-fluoro-4-methylphenyl)amino]-8-{[(2-hydroxyethyl)(methyl)amino]methyl}-6,11-dihydro-5H-pyrido[2,3-b][1,5]benzodiazepin-5-one (Intermediate 22A; 50 mg, 0.091 mmol) was taken up in a mixture of 1,4-dioxane (3.7 ml) and 37% hydrochloric acid (1.8 ml) and the mixture was stirred at room temperature for 30 min. The reaction mixture was then concentrated, and the residue was dissolved in a mixture of acetonitrile and water, and purified by preparative HPLC (Method 30). The product-containing fractions were combined and concentrated. The residue obtained was admixed with saturated aqueous sodium hydrogencarbonate solution and extracted three times with ethyl acetate. The organic phases were combined, dried over sodium sulphate, filtered and concentrated. 15.4 mg (40% of theory) of the title compound were obtained.

LC/MS (Method 7): $R_t$=0.70 min; MS (ESIpos): m/z=438 [M+H]$^+$ $^1$H-NMR (500 MHz, DMSO-d$_6$): δ [ppm]=2.10 (s, 3H), 2.10-2.19 (m, 3H), 2.36-2.45 (m, 2H), 3.34-3.43 (m, 2H), 3.44-3.55 (m, 2H), 4.32 (br. s, 1H), 6.35-6.40 (m, 1H), 6.72 (d, 1H), 6.89-6.99 (m, 2H), 6.99-7.09 (m, 2H), 7.79 (d, 1H), 8.13 (br. s, 1H), 9.41 (s, 1H), 9.87 (s, 1H), 10.08 (br. s, 1H).

Example 199

8-({[2-(Dimethylamino)ethyl](ethyl)amino}methyl)-4-[(2-fluoro-5-hydroxy-4-methylphenyl)amino]-6,11-dihydro-5H-pyrido[2,3-b][1,5]benzodiazepin-5-one

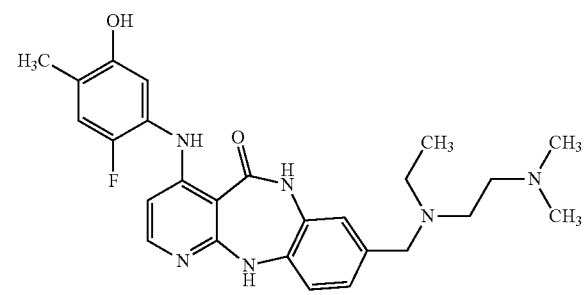

In analogy to Example 197, 4-[(5-{[tert-butyl(dimethyl)silyl]oxy}-2-fluoro-4-methylphenyl)amino]-8-({[2-(dimethylamino)ethyl](ethyl)amino}methyl)-6,11-dihydro-5H-pyrido[2,3-b][1,5]benzodiazepin-5-one (trifluoroacetic acid salt, Intermediate 23A; 57 mg, 0.081 mmol) was reacted with a 4 N solution of hydrogen chloride in 1,4-dioxane/water (1:1). 30.1 mg (39% of theory) of the title compound were obtained.

LC/MS (Method 26): R$_t$=1.49 min; MS (ESIneg): m/z=477 [M−H]$^−$ $^1$H-NMR (500 MHz, DMSO-d$_6$): δ [ppm]=0.95 (t, 3H), 2.10 (s, 9H), 2.27-2.34 (m, 2H), 2.40-2.48 (m, 4H), 3.43 (s, 2H), 6.38 (d, 1H), 6.72 (d, 1H), 6.90-6.97 (m, 2H), 7.03 (d, 2H), 7.79 (d, 1H), 8.11 (s, 1H), 9.42 (s, 1H), 9.88 (s, 1H), 10.09 (s, 1H).

Example 200

8-{[(2-Aminoethyl)(ethyl)amino]methyl}-4-[(2-fluoro-5-hydroxy-4-methylphenyl)amino]-6,11-dihydro-5H-pyrido[2,3-b][1,5]benzodiazepin-5-one

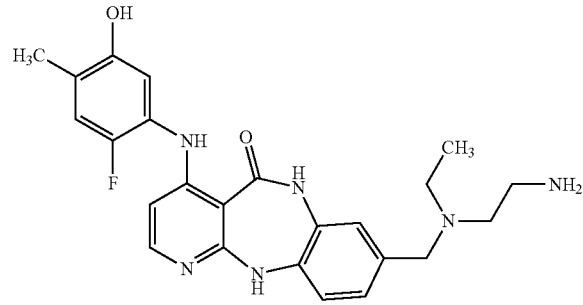 [SMILES: CCN(CCN)Cc1ccc2c(c1)NC(=O)c1c(Nc3cc(O)c(C)cc3F)ccnc1N2]

In analogy to Example 197, 8-{[(2-aminoethyl)(ethyl)amino]methyl}-4-[(5-{[tert-butyl(dimethyl)silyl]oxy}-2-fluoro-4-methylphenyl)amino]-6,11-dihydro-5H-pyrido[2,3-b][1,5]benzodiazepin-5-one (Intermediate 25A; 40.5 mg, 0.072 mmol) was reacted with a 4 N solution of hydrogen chloride in 1,4-dioxane/water (1:1). 31 mg (96% of theory) of the title compound were obtained.

LC/MS (Method 7): R$_t$=0.64 min; MS (ESIneg): m/z=449 [M−H]$^−$ $^1$H-NMR (500 MHz, DMSO-d$_6$): δ [ppm]=0.96 (t, 3H), 2.10 (s, 3H), 2.37 (t, 2H), 2.43 (q, 2H), 2.57 (t, 2H), 3.42 (s, 2H), 3.45-3.52 (m, 1H), 3.65-3.73 (m, 1H), 6.37 (dd, 1H), 6.72 (d, 1H), 6.93 (dd, 1H), 6.98 (s, 1H), 7.00-7.07 (m, 2H), 7.79 (d, 1H), 8.11 (s, 1H), 9.88 (s, 1H), 10.10 (br. s, 1H).

Example 201

4-[(2-Fluoro-5-hydroxy-4-methylphenyl)amino]-8-({[(2R)-2-hydroxypropyl](methyl)amino}methyl)-6,11-dihydro-5H-pyrido[2,3-b][1,5]benzodiazepin-5-one

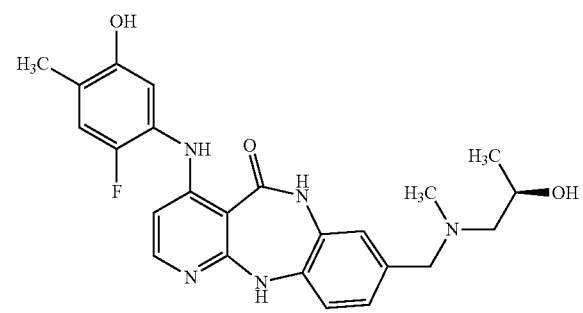 [SMILES: Cc1cc(F)c(Nc2ccnc3c2C(=O)Nc2cc(CN(C)C[C@@H](C)O)ccc2N3)cc1O]

In analogy to Example 197, 4-[(5-{[tert-butyl(dimethyl)silyl]oxy}-2-fluoro-4-methylphenyl)amino]-8-({[(2R)-2-hydroxypropyl](methyl)amino}methyl)-6,11-dihydro-5H-pyrido[2,3-b][1,5]benzodiazepin-5-one (Intermediate 26A; 73.1 mg, 0.129 mmol) was reacted with a 4 N solution of hydrogen chloride in 1,4-dioxane/water (1:1). 22 mg (38% of theory) of the title compound were obtained.

LC/MS (Method 7): R$_t$=0.74 min; MS (ESIneg): m/z=450 [M−H]$^−$ $^1$H-NMR (400 MHz, DMSO-d$_6$): δ [ppm]=1.04 (d, 3H), 2.10 (s, 3H), 2.11 (s, 3H), 2.14-2.31 (m, 2H), 3.37 (q, 2H), 3.69-3.80 (m, 1H), 4.21 (d, 1H), 6.37 (dd, 1H), 6.72 (d, 1H), 6.90-6.97 (m, 2H), 7.00-7.07 (m, 2H), 7.79 (d, 1H), 8.13 (s, 1H), 9.41 (s, 1H), 9.88 (s, 1H), 10.08 (s, 1H).

Example 202

4-[(2-Fluoro-5-hydroxy-4-methylphenyl)amino]-8-({[(2S)-2-hydroxypropyl](methyl)amino}methyl)-6,11-dihydro-5H-pyrido[2,3-b][1,5]benzodiazepin-5-one

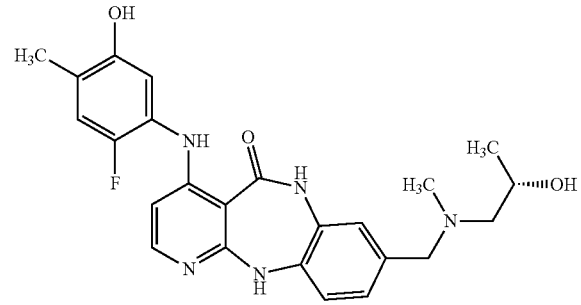 [SMILES: Cc1cc(F)c(Nc2ccnc3c2C(=O)Nc2cc(CN(C)C[C@H](C)O)ccc2N3)cc1O]

In analogy to Example 197, 4-[(5-{[tert-butyl(dimethyl)silyl]oxy}-2-fluoro-4-methylphenyl)amino]-8-({[(2S)-2-hydroxypropyl](methyl)amino}methyl)-6,11-dihydro-5H-pyrido[2,3-b][1,5]benzodiazepin-5-one (Intermediate 27A; 74.8 mg, 0.132 mmol) was reacted with a 4 N solution of hydrogen chloride in 1,4-dioxane/water (1:1). 24.2 mg (41% of theory) of the title compound were obtained.

LC/MS (Method 7): R$_t$=0.73 min; MS (ESIneg): m/z=450 [M−H]$^−$ $^1$H-NMR (400 MHz, DMSO-d$_6$): δ [ppm]=1.04 (d, 3H), 2.10 (s, 3H), 2.11 (s, 3H), 2.14-2.31 (m, 2H), 3.37 (q, 2H), 3.70-3.81 (m, 1H), 4.21 (d, 1H), 6.37 (dd, 1H), 6.72 (d, 1H), 6.90-6.97 (m, 2H), 7.00-7.07 (m, 2H), 7.79 (d, 1H), 8.13 (s, 1H), 9.42 (s, 1H), 9.88 (s, 1H), 10.08 (s, 1H).

Example 203

8-({[2-(Dimethylamino)ethyl](methyl)amino}methyl)-4-[(2-fluoro-5-hydroxy-4-methylphenyl)amino]-6,11-dihydro-5H-pyrido[2,3-b][1,5]benzodiazepin-5-one

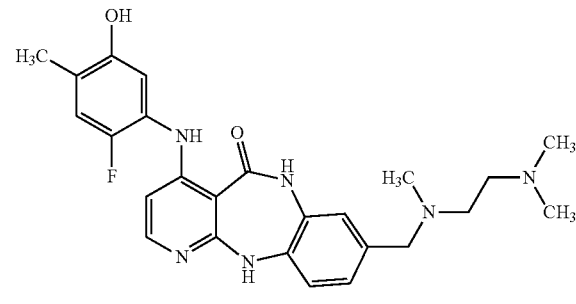

4-[(5-{[tert-Butyl(dimethyl)silyl]oxy}-2-fluoro-4-methylphenyl)amino]-8-({[2-(dimethylamino)ethyl](methyl)amino}methyl)-6,11-dihydro-5H-pyrido[2,3-b][1,5]benzodiazepin-5-one (trifluoroacetic acid salt; Intermediate 28A; 50 mg, 0.072 mmol) was taken up in a 4 N solution of hydrogen chloride in 1,4-dioxane/water (1:1; 3.3 ml) and the mixture was stirred at room temperature for 20 min. The reaction mixture was then concentrated. The residue obtained was admixed with saturated aqueous sodium hydrogencarbonate solution and extracted three times with ethyl acetate. The organic phases were combined, dried over sodium sulphate, filtered and concentrated. 30.5 mg (91% of theory) of the title compound were obtained.

LC/MS (Method 7): $R_t$=0.66 min; MS (ESIneg): m/z=463 [M–H]$^-$ $^1$H-NMR (500 MHz, DMSO-d$_6$): δ [ppm]=2.07-2.11 (m, 6H), 2.11 (s, 6H), 2.29-2.43 (m, 4H), 3.35 (s, 2H), 6.38 (dd, 1H), 6.72 (d, 1H), 6.89-6.95 (m, 2H), 7.00-7.06 (m, 2H), 7.79 (d, 1H), 8.12 (s, 1H), 9.42 (s, 1H), 9.88 (s, 1H), 10.09 (s, 1H).

Example 204 rac-8-{[Ethyl(2-hydroxypropyl)amino]methyl}-4-[(2-fluoro-5-hydroxy-4-methylphenyl)amino]-6,11-dihydro-5H-pyrido[2,3-b][1,5]benzodiazepin-5-one

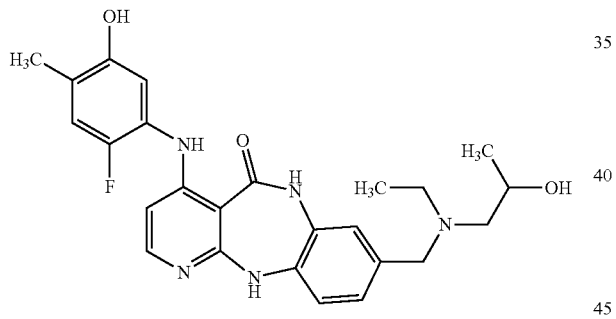

In analogy to Example 203, 4-[(5-{[tert-butyl(dimethyl)silyl]oxy}-2-fluoro-4-methylphenyl)amino]-8-{[ethyl(2-hydroxypropyl)amino]methyl}-6,11-dihydro-5H-pyrido[2,3-b][1,5]benzodiazepin-5-one (trifluoroacetic acid salt, Intermediate 29A; 40 mg, 0.058 mmol) was reacted with a 4 N solution of hydrogen chloride in 1,4-dioxane/water (1:1). 30.2 mg (quant.) of the title compound were obtained.

LC/MS (Method 7): $R_t$=0.73 min; MS (ESIneg): m/z=464 [M–H]$^-$ $^1$H-NMR (500 MHz, DMSO-d$_6$): δ [ppm]=0.95 (t, 3H), 1.03 (d, 3H), 2.10 (s, 3H), 2.22-2.36 (m, 2H), 2.38-2.47 (m, 2H), 3.46 (q, 2H), 3.65-3.73 (m, 1H), 4.15 (d, 1H), 6.37 (dd, 1H), 6.72 (d, 1H), 6.92-6.98 (m, 2H), 7.00-7.06 (m, 2H), 7.79 (d, 1H), 8.11 (s, 1H), 9.41 (s, 1H), 9.89 (s, 1H), 10.08 (s, 1H).

Example 205 ent-8-{[Ethyl(2-hydroxypropyl)amino]methyl}-4-[(2-fluoro-5-hydroxy-4-methylphenyl)amino]-6,11-dihydro-5H-pyrido[2,3-b][1,5]benzodiazepin-5-one (Enantiomer 1)

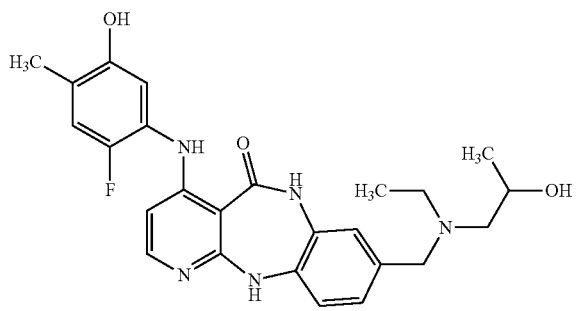 [SMILES: CCN(Cc1ccc2c(c1)NC(=O)c1c(Nc3cc(O)c(C)cc3F)ccnc1N2)CC(C)O]

The title compound was obtained by separating 30 mg of the racemic compound from Example 204 by means of preparative HPLC on a chiral stationary phase (Method 31).
Yield: 5 mg
HPLC (Method 32): $R_t$=7.32 min, ee-Wert=98%
LC/MS (Method 25): $R_t$=0.87 min; MS (ESIneg): m/z=464 [M–H]$^-$ $^1$H-NMR (500 MHz, DMSO-d$_6$): δ [ppm]=0.95 (t, 3H), 1.03 (d, 3H), 2.10 (s, 3H), 2.22-2.28 (m, 1H), 2.30-2.35 (m, 1H), 2.40-2.46 (m, 2H), 3.46 (q, 2H), 3.65-3.73 (m, 1H), 4.15 (d, 1H), 6.37 (dd, 1H), 6.73 (d, 1H), 6.92-6.99 (m, 2H), 7.00-7.06 (m, 2H), 7.79 (d, 1H), 8.11 (s, 1H), 9.44 (br. s, 1H), 9.89 (s, 1H), 10.08 (s, 1H).

Example 206 ent-8-{[Ethyl(2-hydroxypropyl)amino]methyl}-4-[(2-fluoro-5-hydroxy-4-methylphenyl)amino]-6,11-dihydro-5H-pyrido[2,3-b][1,5]benzodiazepin-5-one (Enantiomer 2)

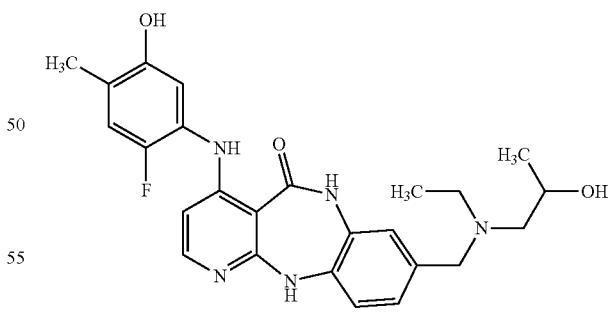

The title compound was obtained by separating 30 mg of the racemic compound from Example 204 by means of preparative HPLC on a chiral stationary phase (Method 31).
Yield: 3.5 mg
HPLC (Method 32): $R_t$=8.62 min, ee=98%
LC/MS (Method 25): $R_t$=0.87 min; MS (ESIneg): m/z=464 [M–H]$^-$ $^1$H-NMR (500 MHz, DMSO-d$_6$): δ [ppm]=0.95 (t, 3H), 1.03 (d, 3H), 2.10 (s, 3H), 2.22-2.28 (m, 1H), 2.29-2.34 (m, 1H), 2.40-2.46 (m, 2H), 3.46 (q, 2H), 3.65-3.74 (m, 1H), 4.15 (d, 1H), 6.37 (dd, 1H), 6.73 (d, 1H), 6.92-6.99 (m, 2H), 7.00-7.06 (m, 2H), 7.79 (d, 1H), 8.11 (s, 1H), 9.42 (s, 1H), 9.89 (s, 1H), 10.08 (s, 1H).

Example 207

4-[(2-Fluoro-5-hydroxy-4-methylphenyl)amino]-8-{[(3S)-3-hydroxypyrrolidin-1-yl]methyl}-6,11-dihydro-5H-pyrido[2,3-b][1,5]benzodiazepin-5-one

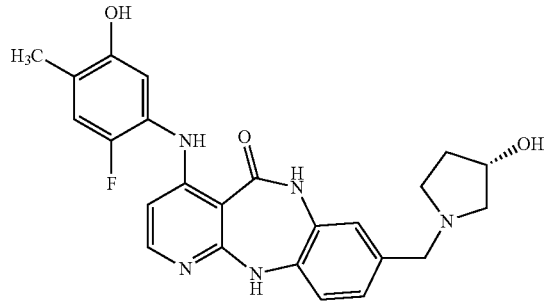 [SMILES: Cc1cc(F)c(Nc2ccnc3c2C(=O)Nc2cc(CN4CC[C@H](O)C4)ccc2N3)cc1O]

In analogy to Example 203, 4-[(5-{[tert-butyl(dimethyl)silyl]oxy}-2-fluoro-4-methylphenyl)amino]-8-{[(3S)-3-hydroxypyrrolidin-1-yl]methyl}-6,11-dihydro-5H-pyrido[2,3-b][1,5]benzodiazepin-5-one (trifluoroacetic acid salt, Intermediate 30A; 50 mg, 0.074 mmol) was reacted with a 4 N solution of hydrogen chloride in 1,4-dioxane/water (1:1). 30 mg (91% of theory) of the title compound were obtained.

LC/MS (Method 7): $R_t$=0.68 min; MS (ESIneg): m/z=448 [M−H]⁻

¹H-NMR (500 MHz, DMSO-$d_6$): δ [ppm]=1.47-1.57 (m, 1H), 1.92-2.01 (m, 1H), 2.10 (s, 3H), 2.26 (dd, 1H), 2.38 (td, 1H), 2.48-2.56 (m, 1H), 2.65 (dd, 1H), 3.43 (q, 2H), 4.13-4.21 (m, 1H), 4.63 (d, 1H), 6.38 (dd, 1H), 6.72 (d, 1H), 6.89-6.96 (m, 2H), 7.00-7.06 (m, 2H), 7.79 (d, 1H), 8.12 (s, 1H), 9.42 (s, 1H), 9.87 (s, 1H), 10.08 (s, 1H).

Example 208

4-[(2-Fluoro-5-hydroxy-4-methylphenyl)amino]-8-{[(3R)-3-hydroxypyrrolidin-1-yl]methyl}-6,11-dihydro-5H-pyrido[2,3-b][1,5]benzodiazepin-5-one

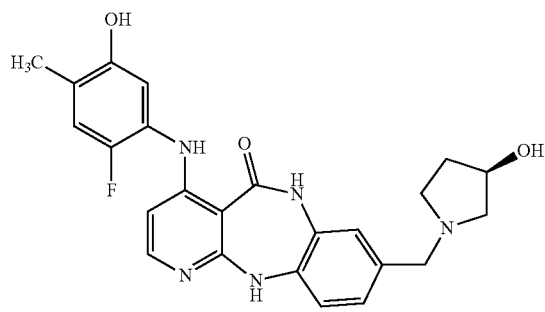 [SMILES: Cc1cc(F)c(Nc2ccnc3c2C(=O)Nc2cc(CN4CC[C@@H](O)C4)ccc2N3)cc1O]

In analogy to Example 203, 4-[(5-{[tert-butyl(dimethyl)silyl]oxy}-2-fluoro-4-methylphenyl)amino]-8-{[(3R)-3-hydroxypyrrolidin-1-yl]methyl}-6,11-dihydro-5H-pyrido[2,3-b][1,5]benzodiazepin-5-one (trifluoroacetic acid salt, Intermediate 31A; 47 mg, 0.069 mmol) was reacted with a 4 N solution of hydrogen chloride in 1,4-dioxane/water (1:1). 28 mg (90% of theory) of the title compound were obtained.

LC/MS (Method 7): $R_t$=0.69 min; MS (ESIneg): m/z=448 [M−H]⁻

¹H-NMR (400 MHz, DMSO-$d_6$): δ [ppm]=1.46-1.57 (m, 1H), 1.91-2.02 (m, 1H), 2.10 (s, 3H), 2.26 (dd, 1H), 2.38 (td, 1H), 2.49-2.56 (m, 1H), 2.65 (dd, 1H), 3.43 (q, 2H), 4.13-4.21 (m, 1H), 4.63 (d, 1H), 6.38 (d, 1H), 6.72 (d, 1H), 6.88-6.96 (m, 2H), 7.00-7.07 (m, 2H), 7.79 (d, 1H), 8.11 (s, 1H), 9.41 (s, 1H), 9.87 (s, 1H), 10.07 (s, 1H).

Example 209

8-{[(2-Aminoethyl)(methyl)amino]methyl}-4-[(2-fluoro-5-hydroxy-4-methylphenyl)amino]-6,11-dihydro-5H-pyrido[2,3-b][1,5]benzodiazepin-5-one

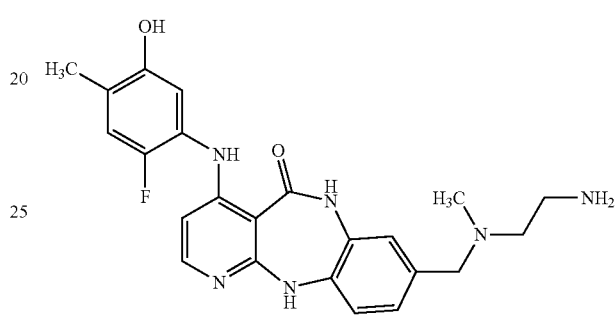

In analogy to Example 203, tert-butyl {2-[(({4-[(5-{[tert-butyl(dimethyl)silyl]oxy}-2-fluoro-4-methylphenyl)amino]-5-oxo-6,11-dihydro-5H-pyrido[2,3-b][1,5]benzodiazepin-8-yl}methyl)(methyl)amino]ethyl}carbamate (trifluoroacetic acid salt, Intermediate 32A; 26 mg, 0.035 mmol) was reacted with a 4 N solution of hydrogen chloride in 1,4-dioxane/water (1:1). 14.3 mg (93% of theory) of the title compound were obtained.

LC/MS (Method 25): $R_t$=0.67 min; MS (ESIneg): m/z=435 [M−H]⁻

¹H-NMR (500 MHz, DMSO-$d_6$): δ [ppm]=2.09 (s, 3H), 2.10 (s, 3H), 2.30 (t, 2H), 2.61 (t, 2H), 3.44-3.54 (m, 2H), 3.62-3.76 (m, 2H), 6.37 (dd, 1H), 6.72 (d, 1H), 6.88-7.00 (m, 2H), 7.00-7.09 (m, 2H), 7.79 (d, 1H), 8.12 (s, 1H), 9.87 (s, 1H), 10.07 (br. s, 1H).

Example 210

8-{[(3,4-cis-Dihydroxypyrrolidin-1-yl]methyl}-4-[(2-fluoro-5-hydroxy-4-methylphenyl)amino]-6,11-dihydro-5H-pyrido[2,3-b][1,5]benzodiazepin-5-one

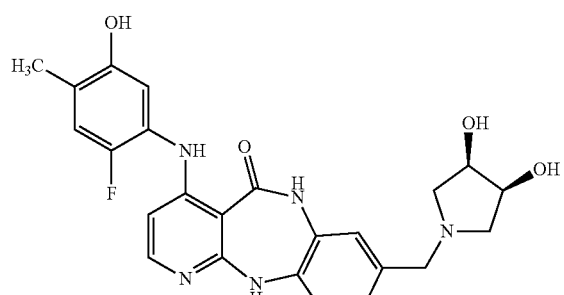

In analogy to Example 203, 4-[(5-{[tert-butyl(dimethyl)silyl]oxy}-2-fluoro-4-methylphenyl)amino]-8-{[3,4-cis-dihydroxypyrrolidin-1-yl]methyl}-6,11-dihydro-5H-pyrido[2,3-b][1,5]benzodiazepine-5-one (Intermediate 33A; 22.8 mg, 0.039 mmol) was reacted with a 4 N solution of hydrogen chloride in 1,4-dioxane/water (1:1). 11.5 mg (58% of theory) of the title compound were obtained.

LC/MS (Method 7): $R_t$=0.67 min; MS (ESIneg): m/z=464 [M–H]⁻

¹H-NMR (500 MHz, DMSO-$d_6$): δ [ppm]=2.10 (s, 3H), 2.26 (dd, 2H), 2.82 (dd, 2H), 3.45-3.53 (m, 1H), 3.64-3.74 (m, 1H), 3.88-3.95 (m, 2H), 4.50 (d, 2H), 6.38 (dd, 1H), 6.72 (d, 1H), 6.88-6.93 (m, 2H), 7.00-7.06 (m, 2H), 7.79 (d, 1H), 8.12 (s, 1H), 9.41 (s, 1H), 9.86 (s, 1H), 10.07 (s, 1H).

Example 211

8-{[4-(Dimethylamino)piperidin-1-yl]methyl}-4-[(2-fluoro-5-hydroxy-4-methylphenyl)amino]-6,11-dihydro-5H-pyrido[2,3-b][1,5]benzodiazepin-5-one

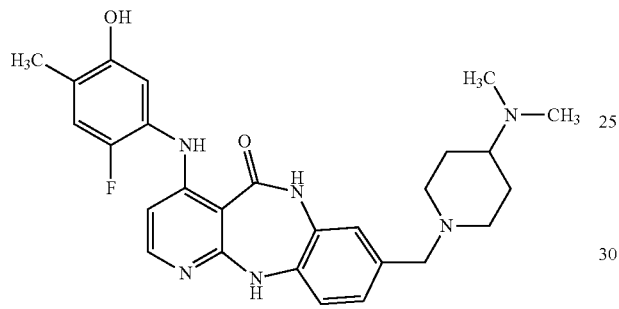

In analogy to Example 203, 4-[(5-{[tert-butyl(dimethyl)silyl]oxy}-2-fluoro-4-methylphenyl)amino]-8-{[4-(dimethylamino)piperidin-1-yl]methyl}-6,11-dihydro-5H-pyrido[2,3-b][1,5]benzodiazepin-5-one (trifluoroacetic acid salt, Intermediate 34A; 61 mg, 0.085 mmol) was reacted with a 4 N solution of hydrogen chloride in 1,4-dioxane/water (1:1). 35.8 mg (79% of theory) of the title compound were obtained.

LC/MS (Method 7): $R_t$=0.55 min; MS (ESIneg): m/z=489 [M–H]⁻

¹H-NMR (400 MHz, DMSO-$d_6$): δ [ppm]=1.36-1.45 (m, 2H), 1.67-1.75 (m, 2H), 1.88 (t, 2H), 2.10 (s, 3H), 2.24 (br. s, 6H), 2.81 (d, 2H), 3.43-3.53 (m, 1H), 3.65-3.73 (m, 1H), 6.38 (dd, 1H), 6.72 (d, 1H), 6.86-6.96 (m, 2H), 7.00-7.07 (m, 2H), 7.79 (d, 1H), 8.13 (s, 1H), 9.42 (s, 1H), 9.87 (s, 1H), 10.08 (s, 1H).

Example 212

8-{[(3R)-3-Aminopiperidin-1-yl]methyl}-4-[(2-fluoro-5-hydroxy-4-methylphenyl)amino]-6,11-dihydro-5H-pyrido[2,3-b][1,5]benzodiazepin-5-one

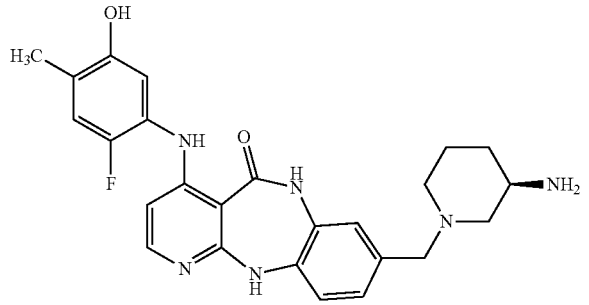 [SMILES: Cc1cc(F)c(Nc2ccnc3c2C(=O)Nc2cc(CN4CCC[C@@H](N)C4)ccc2N3)cc1O]

In analogy to Example 203, tert-butyl [(3R)-1-({4-[(5-{[tert-butyl(dimethyl)silyl]oxy}-2-fluoro-4-methylphenyl)amino]-5-oxo-6,11-dihydro-5H-pyrido[2,3-b][1,5]benzodiazepin-8-yl}methyl)piperidin-3-yl]carbamate (trifluoroacetic acid salt, Intermediate 35A; 71 mg, 0.09 mmol) was reacted with a 4 N solution of hydrogen chloride in 1,4-dioxane/water (1:1). 37.6 mg (91% of theory) of the title compound were obtained.

LC/MS (Method 7): $R_t$=0.61 min; MS (ESIneg): m/z=461 [M–H]⁻

¹H-NMR (400 MHz, DMSO-$d_6$): δ [ppm]=1.11-1.22 (m, 1H), 1.39-1.52 (m, 1H), 1.59-1.70 (m, 1H), 1.71-1.88 (m, 2H), 1.96-2.06 (m, 1H), 2.10 (s, 3H), 2.63-2.71 (m, 1H), 2.83-2.94 (m, 1H), 3.42-3.51 (m, 1H), 3.65-3.73 (m, 1H), 5.57 (br. s, 2H), 6.36 (dd, 1H), 6.72 (d, 1H), 6.89-6.97 (m, 2H), 7.00-7.09 (m, 2H), 7.79 (d, 1H), 8.15 (s, 1H), 9.44 (br. s, 1H), 9.85 (s, 1H), 10.10 (br. s, 1H).

Example 213 ent-8-[(3,4-cis-Dihydroxypiperidin-1-yl)methyl]-4-[(2-fluoro-5-hydroxy-4-methylphenyl)amino]-6,11-dihydro-5H-pyrido[2,3-b][1,5]benzodiazepin-5-one (Enantiomer 1)

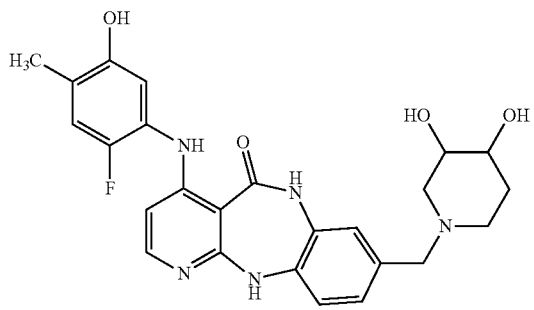 [SMILES: Cc1cc(F)c(Nc2ccnc3c2C(=O)Nc2cc(CN4CCC(O)C(O)C4)ccc2N3)cc1O]

The title compound was obtained by separating 21 mg of the racemic compound from Example 170 by means of preparative HPLC on a chiral stationary phase (Method 33).

Yield: 5 mg

HPLC (Method 34): $R_t$=10.25 min, ee=97.5%

¹H-NMR (500 MHz, DMSO-$d_6$): δ [ppm]=1.47-1.56 (m, 1H), 1.59-1.67 (m, 1H), 2.10 (s, 3H), 2.18-2.38 (m, 4H), 3.43-3.50 (m, 1H), 3.59-3.66 (m, 1H), 4.18 (d, 1H), 4.27 (d, 1H), 6.37 (dd, 1H), 6.72 (d, 1H), 6.89-6.95 (m, 2H), 7.00-7.07 (m, 2H), 7.79 (d, 1H), 8.12 (s, 1H), 9.42 (s, 1H), 9.86 (s, 1H), 10.08 (s, 1H).

Example 214 ent-8-[(3,4-cis-Dihydroxypiperidin-1-yl)methyl]-4-[(2-fluoro-5-hydroxy-4-methylphenyl)amino]-6,11-dihydro-5H-pyrido[2,3-b][1,5]benzodiazepin-5-one (Enantiomer 2)

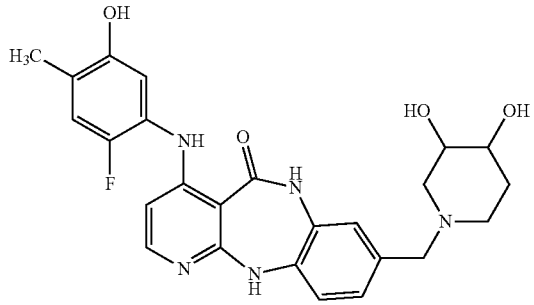 [SMILES: Cc1cc(F)c(Nc2ccnc3c2C(=O)Nc2cc(CN4CCC(O)C(O)C4)ccc2N3)cc1O]

The title compound was obtained by separating 21 mg of the racemic compound from Example 170 by means of preparative HPLC on a chiral stationary phase (Method 33).

Yield: 5 mg

HPLC (Method 34): $R_t$=11.21 min, ee=98.1%

¹H-NMR (500 MHz, DMSO-$d_6$): δ [ppm]=1.47-1.57 (m, 1H), 1.58-1.68 (m, 1H), 2.10 (s, 3H), 2.18-2.38 (m, 4H), 3.43-3.50 (m, 1H), 3.59-3.66 (m, 1H), 4.18 (d, 1H), 4.27 (d, 1H), 6.37 (dd, 1H), 6.72 (d, 1H), 6.89-6.96 (m, 2H), 7.00-7.07 (m, 2H), 7.79 (d, 1H), 8.12 (s, 1H), 9.43 (s, 1H), 9.86 (s, 1H), 10.07 (s, 1H).

Example 215

8-{[(3S)-3-Aminopyrrolidin-1-yl]methyl}-4-[(2-fluoro-5-hydroxy-4-methylphenyl)amino]-6,11-dihydro-5H-pyrido[2,3-b][1,5]benzodiazepin-5-one

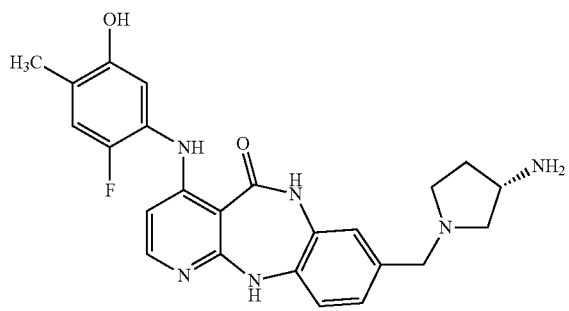 [SMILES: Cc1cc(F)c(Nc2ccnc3c2C(=O)Nc2cc(CN4CC[C@H](N)C4)ccc2N3)cc1O]

In analogy to Example 203, tert-butyl [(3S)-1-({4-[(5-{[tert-butyl(dimethyl)silyl]oxy}-2-fluoro-4-methylphenyl)amino]-5-oxo-6,11-dihydro-5H-pyrido[2,3-b][1,5]benzodiazepin-8-yl}methyl)pyrrolidin-3-yl]carbamate (trifluoroacetic acid salt, Intermediate 36A; 61 mg, 0.079 mmol) was reacted with a 4 N solution of hydrogen chloride in 1,4-dioxane/water (1:1). 27.6 mg (74% of theory) of the title compound were obtained.

LC/MS (Method 26): $R_t$=1.25 min; MS (ESIneg): m/z=447 [M−H]⁻

¹H-NMR (400 MHz, DMSO-$d_6$): δ [ppm]=1.37-1.45 (m, 1H), 1.98-2.05 (m, 1H), 2.10 (s, 3H), 2.15-2.20 (m, 1H), 2.35-2.43 (m, 1H), 2.57-2.63 (m, 1H), 3.43-3.53 (m, 1H), 3.64-3.74 (m, 1H), 6.37 (dd, 1H), 6.72 (d, 1H), 6.90-6.97 (m, 2H), 6.99-7.09 (m, 2H), 7.79 (d, 1H), 8.13 (s, 1H), 9.45 (br. s, 1H), 9.86 (s, 1H), 10.08 (br. s, 1H).

Example 216

8-{[(3R)-3-Aminopyrrolidin-1-yl]methyl}-4-[(2-fluoro-5-hydroxy-4-methylphenyl)amino]-6,11-dihydro-5H-pyrido[2,3-b][1,5]benzodiazepin-5-one

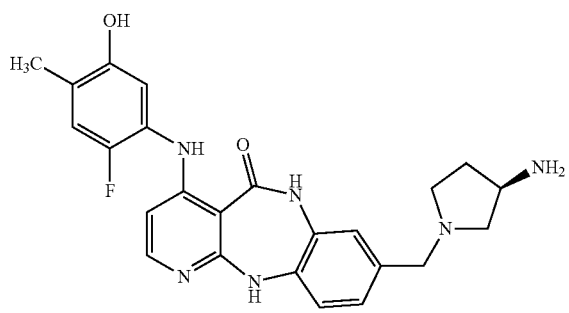 [SMILES: Cc1cc(F)c(Nc2ccnc3c2C(=O)Nc2cc(CN4CC[C@@H](N)C4)ccc2N3)cc1O]

In analogy to Example 203, tert-butyl [(3R)-1-({4-[(5-{[tert-butyl(dimethyl)silyl]oxy}-2-fluoro-4-methylphenyl)amino]-5-oxo-6,11-dihydro-5H-pyrido[2,3-b][1,5]benzodiazepin-8-yl}methyl)pyrrolidin-3-yl]carbamate (trifluoroacetic acid salt, Intermediate 37A; 30.2 mg, 0.039 mmol) was reacted with a 4 N solution of hydrogen chloride in 1,4-dioxane/water (1:1). 9.6 mg (55% of theory) of the title compound were obtained.

LC/MS (Method 26): $R_t$=1.24 min; MS (ESIneg): m/z=447 [M−H]⁻

¹H-NMR (500 MHz, DMSO-$d_6$): δ [ppm]=1.44-1.55 (m, 1H), 2.00-2.11 (m, 1H), 2.10 (s, 3H), 2.30 (dd, 1H), 2.35-2.42 (m, 1H), 2.54-2.65 (m, 1H), 3.43-3.54 (m, 1H), 3.64-3.74 (m, 1H), 6.37 (dd, 1H), 6.72 (d, 1H), 6.89-6.98 (m, 2H), 7.00-7.09 (m, 2H), 7.79 (d, 1H), 8.14 (s, 1H), 9.43 (br. s, 1H), 9.85 (s, 1H), 10.09 (br. s, 1H).

Example 217

8-{[(3R)-3-(Dimethylamino)pyrrolidin-1-yl]methyl}-4-[(2-fluoro-5-hydroxy-4-methylphenyl)amino]-6,11-dihydro-5H-pyrido[2,3-b][1,5]benzodiazepin-5-one

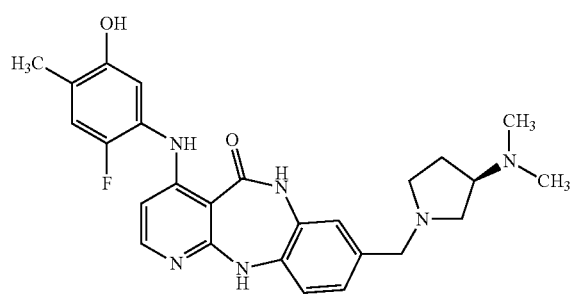

In analogy to Example 203, 4-[(5-{[tert-butyl(dimethyl)silyl]oxy}-2-fluoro-4-methylphenyl)amino]-8-{[(3R)-3-(dimethylamino)pyrrolidin-1-yl]methyl}-6,11-dihydro-5H-pyrido[2,3-b][1,5]benzodiazepin-5-one (trifluoroacetic acid salt, Intermediate 38A; 53.2 mg, 0.075 mmol) was reacted with a 4 N solution of hydrogen chloride in 1,4-dioxane/water (1:1). 25.3 mg (69% of theory) of the title compound were obtained.

LC/MS (Method 25): $R_t$=0.72 min; MS (ESIneg): m/z=475 [M−H]⁻

¹H-NMR (400 MHz, DMSO-$d_6$): δ [ppm]=1.54-1.65 (m, 1H), 1.77-1.89 (m, 1H), 2.10 (br. s, 9H), 2.24 (t, 1H), 2.35-2.44 (m, 1H), 2.59-2.76 (m, 2H), 3.43-3.54 (m, 1H), 3.64-3.74 (m, 1H), 6.38 (dd, 1H), 6.72 (d, 1H), 6.89-6.95 (m, 2H), 7.00-7.08 (m, 2H), 7.79 (d, 1H), 8.13 (s, 1H), 9.42 (s, 1H), 9.87 (s, 1H), 10.09 (s, 1H).

Example 218

8-[(4-Aminopiperidin-1-yl)methyl]-4-[(2-fluoro-5-hydroxy-4-methylphenyl)amino]-6,11-dihydro-5H-pyrido[2,3-b][1,5]benzodiazepin-5-one

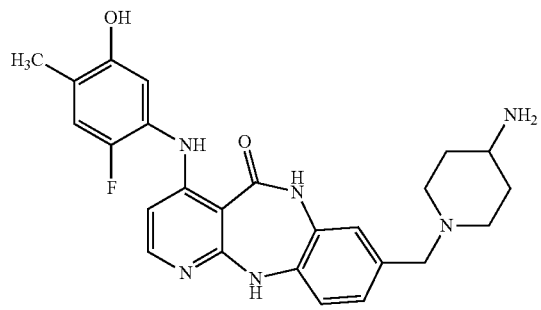 [SMILES: Cc1cc(F)c(Nc2ccnc3c2C(=O)Nc2cc(CN4CCC(N)CC4)ccc2N3)cc1O]

In analogy to Example 203, tert-butyl [1-({4-[(5-{[tert-butyl(dimethyl)silyl]oxy}-2-fluoro-4-methylphenyl)amino]-5-oxo-6,11-dihydro-5H-pyrido[2,3-b][1,5]benzodiazepin-8-yl}methyl)piperidin-4-yl]carbamate (Intermediate 39A; 46 mg, 0.068 mmol) was reacted with a 4N solution of hydrogen chloride in 1,4-dioxane/water (1:1). 32 mg of the title compound were obtained.

LC/MS (Method 26): $R_t$=1.24 min; MS (ESIneg): m/z=461 [M−H]⁻

$^1$H-NMR (400 MHz, DMSO-d$_6$): δ [ppm]=1.36-1.50 (m, 2H), 1.72-1.84 (m, 2H), 1.88-1.98 (m, 2H), 2.10 (s, 3H), 2.72-2.81 (m, 2H), 2.81-2.91 (m, 1H), 3.45-3.53 (m, 1H), 3.64-3.74 (m, 1H), 6.38 (dd, 1H), 6.73 (d, 1H), 6.88-6.94 (m, 2H), 7.04 (m, 2H), 7.79 (d, 1H), 8.15 (s, 1H), 9.44 (br. s, 1H), 9.87 (s, 1H), 10.11 (br. s, 1H).

Example 219

8-{[(3S)-3-Aminopiperidin-1-yl]methyl}-4-[(2-fluoro-5-hydroxy-4-methylphenyl)amino]-6,11-dihydro-5H-pyrido[2,3-b][1,5]benzodiazepin-5-one

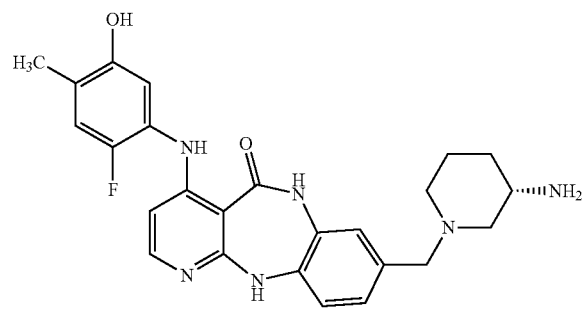 [SMILES: Cc1cc(F)c(Nc2ccnc3c2C(=O)Nc2cc(CN4CCC[C@H](N)C4)ccc2N3)cc1O]

In analogy to Example 197, tert-butyl [(3S)-1-({4-[(5-{[tert-butyl(dimethyl)silyl]oxy}-2-fluoro-4-methylphenyl)amino]-5-oxo-6,11-dihydro-5H-pyrido[2,3-b][1,5]benzodiazepin-8-yl}methyl)piperidin-3-yl]carbamate (trifluoroacetic acid salt, Intermediate 40A; 81 mg, 0.102 mmol) was reacted with a 4 N solution of hydrogen chloride in 1,4-dioxane/water (1:1). 26 mg (47% of theory) of the title compound were obtained.

LC/MS (Method 5): $R_t$=0.45 min; MS (ESIneg): m/z=461 [M−H]⁻

$^1$H-NMR (500 MHz, DMSO-d$_6$): δ [ppm]=0.90-1.01 (m, 1H), 1.37-1.46 (m, 1H), 1.53-1.65 (m, 2H), 1.70 (d, 1H), 1.84-1.92 (m, 1H), 2.10 (s, 3H), 2.54-2.74 (m, 3H), 6.37 (dd, 1H), 6.72 (d, 1H), 6.86-6.95 (m, 2H), 6.99-7.08 (m, 2H), 7.79 (d, 1H), 8.13 (s, 1H), 9.43 (br. s, 1H), 9.86 (s, 1H), 10.08 (br. s, 1H).

Example 220

8-{[(3S)-3-(Dimethylamino)pyrrolidin-1-yl]methyl}-4-[(2-fluoro-5-hydroxy-4-methylphenyl)amino]-6,11-dihydro-5H-pyrido[2,3-b][1,5]benzodiazepin-5-one

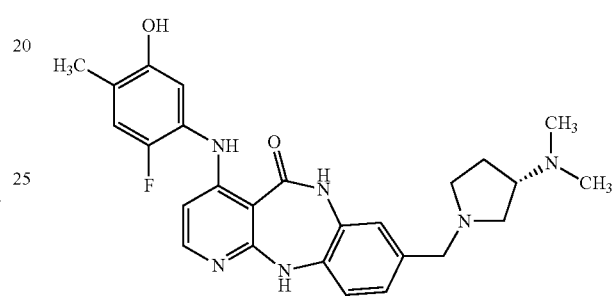

In analogy to Example 197, 4-[(5-{[tert-butyl(dimethyl)silyl]oxy}-2-fluoro-4-methylphenyl)amino]-8-{[(3S)-3-(dimethylamino)pyrrolidin-1-yl]methyl}-6,11-dihydro-5H-pyrido[2,3-b][1,5]benzodiazepin-5-one (Intermediate 41A; 82 mg, 0.139 mmol) was reacted with a 4 N solution of hydrogen chloride in 1,4-dioxane/water (1:1). 35 mg of the title compound were obtained.

LC/MS (Method 26): $R_t$=1.28 min; MS (ESIneg): m/z=475 [M−H]⁻

$^1$H-NMR (400 MHz, DMSO-d$_6$): δ [ppm]=1.54-1.66 (m, 1H), 1.76-1.90 (m, 1H), 2.10 (br. s, 9H), 2.24 (t, 1H), 2.35-2.45 (m, 1H), 2.59-2.78 (m, 2H), 3.43 (q, 2H), 6.38 (dd, 1H), 6.72 (d, 1H), 6.87-6.96 (m, 2H), 6.99-7.07 (m, 2H), 7.79 (d, 1H), 8.13 (s, 1H), 9.42 (s, 1H), 9.87 (s, 1H), 10.09 (s, 1H).

Example 221

4-[(2-Fluoro-5-hydroxy-4-methylphenyl)amino]-8-{[(3-hydroxypropyl)(methyl)amino]methyl}-6,11-dihydro-5H-pyrido[2,3-b][1,5]benzodiazepin-5-one

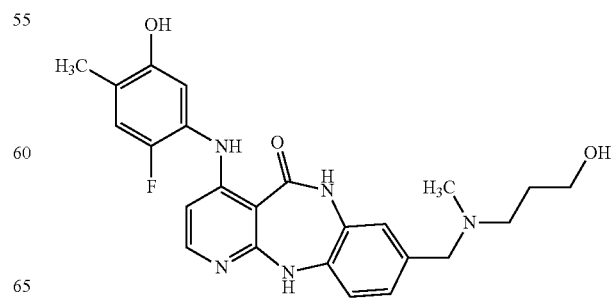

In analogy to Example 197, 4-[(5-{[tert-butyl(dimethyl)silyl]oxy}-2-fluoro-4-methylphenyl)amino]-8-{[(3-hydroxypropyl)(methyl)amino]methyl}-6,11-dihydro-5H-pyrido[2,3-b][1,5]benzodiazepin-5-one (Intermediate 42A; 90 mg, 0.111 mmol) was reacted with a 4 N solution of hydrogen chloride in 1,4-dioxane/water (1:1). 31 mg of the title compound were obtained.

LC/MS (Method 26): R$_t$=1.26 min; MS (ESIneg): m/z=450 [M−H]$^-$ $^1$H-NMR (500 MHz, DMSO-d$_6$): δ [ppm]=1.59 (quin, 2H), 2.07 (s, 3H), 2.10 (s, 3H), 2.36 (t, 2H), 3.43 (t, 2H), 4.39 (br. s, 1H), 6.38 (dd, 1H), 6.72 (d, 1H), 6.88-6.96 (m, 2H), 7.00-7.07 (m, 2H), 7.79 (d, 1H), 8.13 (s, 1H), 9.42 (s, 1H), 9.88 (s, 1H), 10.09 (s, 1H).

Example 222

8-{[Ethyl(3-hydroxypropyl)amino]methyl}-4-[(2-fluoro-5-hydroxy-4-methylphenyl)amino]-6,11-dihydro-5H-pyrido[2,3-b][1,5]benzodiazepin-5-one

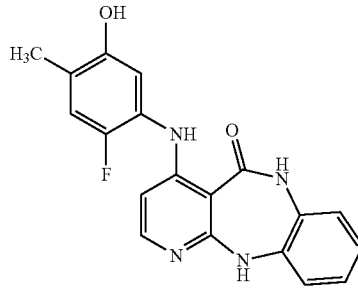

In analogy to Example 197, 4-[(5-{[tert-butyl(dimethyl)silyl]oxy}-2-fluoro-4-methylphenyl)amino]-8-{[ethyl(3-hydroxypropyl)amino]methyl}-6,11-dihydro-5H-pyrido[2,3-b][1,5]benzodiazepin-5-one (Intermediate 43A; 68 mg, 0.088 mmol) was reacted with a 4 N solution of hydrogen chloride in 1,4-dioxane/water (1:1). 24.3 mg (59% of theory) of the title compound were obtained.

LC/MS (Method 26): R$_t$=1.29 min; MS (ESIneg): m/z=464 [M−H]$^-$ $^1$H-NMR (400 MHz, DMSO-d$_6$): δ [ppm]=0.95 (t, 3H), 1.56 (quin, 2H), 2.10 (s, 3H), 2.35-2.45 (m, 4H), 3.35-3.45 (m, 4H), 4.37 (br. s, 1H), 6.38 (dd, 1H), 6.72 (d, 1H), 6.89-6.97 (m, 2H), 7.03 (m, 2H), 7.79 (d, 1H), 8.11 (s, 1H), 9.42 (s, 1H), 9.88 (s, 1H), 10.09 (s, 1H).

Example 223

4-[(2-Fluoro-5-hydroxy-4-methylphenyl)amino]-8-{[(3S)-3-hydroxypiperidin-1-yl]methyl}-6,11-dihydro-5H-pyrido[2,3-b][1,5]benzodiazepin-5-one

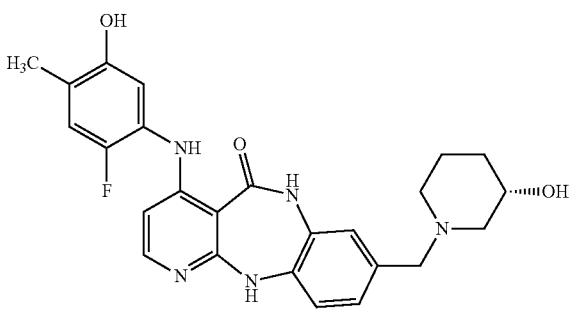 [SMILES: Cc1cc(F)c(Nc2ccnc3c2C(=O)Nc2cc(CN4CCC[C@H](O)C4)ccc2N3)cc1O]

In analogy to Example 197, 4-[(5-{[tert-butyl(dimethyl)silyl]oxy}-2-fluoro-4-methylphenyl)amino]-8-{[(3S)-3-hydroxypiperidin-1-yl]methyl}-6,11-dihydro-5H-pyrido[2,3-b][1,5]benzodiazepin-5-one (Intermediate 44A; 796 mg, 1.38 mmol) was reacted with a 4 N solution of hydrogen chloride in 1,4-dioxane/water (1:1). 301 mg (47% of theory) of the title compound were obtained.

LC/MS (Method 7): R$_t$=0.73 min; MS (ESIneg): m/z=462 [M−H]$^-$ $^1$H-NMR (400 MHz, DMSO-d$_6$): δ [ppm]=0.96-1.11 (m, 1H), 1.32-1.49 (m, 1H), 1.53-1.70 (m, 2H), 1.73-1.86 (m, 2H), 2.10 (s, 3H), 2.57-2.66 (m, 1H), 2.71-2.80 (m, 1H), 3.33-3.49 (m, 2H), 4.51 (d, 1H), 6.37 (dd, 1H), 6.72 (d, 1H), 6.87-6.97 (m, 2H), 7.04 (m, 2H), 7.79 (d, 1H), 8.13 (s, 1H), 9.42 (s, 1H), 9.86 (s, 1H), 10.09 (s, 1H).

Example 224

4-[(2-Fluoro-5-hydroxy-4-methylphenyl)amino]-8-{[(3R)-3-hydroxypiperidin-1-yl]methyl}-6,11-dihydro-5H-pyrido[2,3-b][1,5]benzodiazepin-5-one

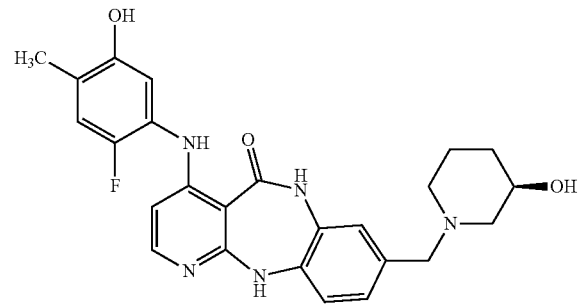 [SMILES: Cc1cc(F)c(Nc2ccnc3c2C(=O)Nc2cc(CN4CCC[C@@H](O)C4)ccc2N3)cc1O]

In analogy to Example 197, 4-[(5-{[tert-butyl(dimethyl)silyl]oxy}-2-fluoro-4-methylphenyl)amino]-8-{[(3R)-3-hydroxypiperidin-1-yl]methyl}-6,11-dihydro-5H-pyrido[2,3-b][1,5]benzodiazepin-5-one (Intermediate 45A; 16.9 mg, 0.029 mmol) was reacted with a 4 N solution of hydrogen chloride in 1,4-dioxane/water (1:1). 8 mg (59% of theory) of the title compound were obtained.

LC/MS (Method 7): R$_t$=0.71 min; MS (ESIneg): m/z=462 [M−H]$^-$ $^1$H-NMR (400 MHz, DMSO-d$_6$): δ [ppm]=0.97-1.11 (m, 1H), 1.31-1.47 (m, 1H), 1.53-1.69 (m, 2H), 1.73-1.87 (m, 2H), 2.10 (s, 3H), 2.57-2.65 (m, 1H), 2.72-2.79 (m, 1H), 3.34-3.49 (m, 2H), 4.51 (d, 1H), 6.37 (dd, 1H), 6.72 (d, 1H), 6.87-6.96 (m, 2H), 7.00-7.08 (m, 2H), 7.79 (d, 1H), 8.13 (s, 1H), 9.42 (s, 1H), 9.86 (s, 1H), 10.09 (s, 1H).

Example 225

N-(3-Chlorobenzyl)-4-[(5-hydroxy-2-methylphenyl)amino]-5-oxo-6,11-dihydro-5H-pyrido[2,3-b][1,5]benzodiazepine-8-carboxamide

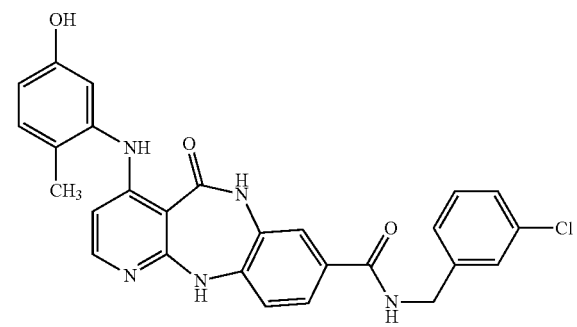 [SMILES: Cc1ccc(O)cc1Nc1ccnc2c1C(=O)Nc1cc(C(=O)NCc3cccc(Cl)c3)ccc1N2]

A solution of 4-{[5-(benzyloxy)-2-methylphenyl]amino}-N-(3-chlorobenzyl)-5-oxo-6,11-dihydro-5H-pyrido[2,3-b][1,5]benzodiazepine-8-carboxamide (Intermediate 48A; 151 mg, 0.256 mmol) and thioanisole (60 μl, 0.511 mmol) in trifluoroacetic acid (2.0 ml) was stirred at RT overnight. The volatile constituents were then removed under reduced pressure and the residue was purified by means of preparative HPLC (eluent A: 0.2% formic acid in water, eluent B: 0.2% formic acid in acetonitrile; gradient). 74.4 mg (55% of theory) of the title compound were obtained.

LC/MS (Method 9, ESIpos): $R_t$=1.00 min, m/z=500 [M+H]$^+$ $^1$H-NMR (400 MHz, DMSO-d$_6$): δ [ppm]=2.06 (s, 3H), 4.45 (d, 2H), 6.30 (d, 1H), 6.56 (dd, 1H), 6.61 (d, 1H), 7.09 (d, 1H), 7.17 (d, 1H), 7.25-7.32 (m, 2H), 7.32-7.39 (m, 2H), 7.53-7.58 (m, 2H), 7.77 (d, 1H), 8.49 (s, 1H), 8.92 (t, 1H), 9.34 (s, 1H), 9.91 (s, 1H), 10.18 (s, 1H).

Example 226

8-[(Cyclopentylamino)methyl]-4-[(2-fluoro-5-hydroxy-4-methylphenyl)amino]-6,11-dihydro-5H-pyrido[2,3-b][1,5]benzodiazepin-5-one

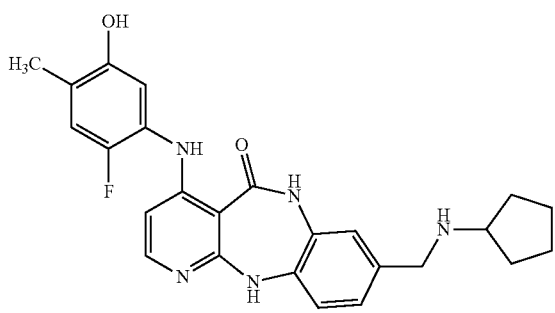 [SMILES: Cc1cc(F)c(Nc2ccnc3c2C(=O)Nc2cc(CNC4CCCC4)ccc2N3)cc1O]

To a suspension of 4-[(2-fluoro-5-hydroxy-4-methylphenyl)amino]-5-oxo-6,11-dihydro-5H-pyrido[2,3-b][1,5]benzodiazepine-8-carbaldehyde (Intermediate 11A; 80.0 mg, 211 μmol) in methanol (8.0 ml) were added acetic acid (100 μl, 1.7 mmol) and sodium cyanoborohydride (66.4 mg, 1.06 mmol). The mixture was stirred at room temperature for 16 h. The mixture was then concentrated under reduced pressure, and the residue was taken up in DMSO and purified by means of preparative HPLC. Yield: 19 mg (20% of theory).

LC/MS (Method 5): $R_t$=0.67 min; MS (ESIneg): m/z=446 [M−H]$^−$ $^1$H-NMR (400 MHz, DMSO-d$_6$): δ [ppm]=1.23-1.75 (m, 8H), 2.08 (s, 3H), 2.96 (s, 1H), 3.57 (m, 2H), 6.37 (d, 1H), 6.72 (d, 1H), 6.96-7.06 (m, 4H), 7.79 (d, 1H), 8.11 (s, 1H), 9.44 (s, 1H), 9.85 (s, 1H), 10.11 (s, 1H).

Example 227

8-{[4-(2,2-Difluoroethyl)piperazin-1-yl]methyl}-4-[(2-fluoro-5-hydroxy-4-methylphenyl)amino]-6,11-dihydro-5H-pyrido[2,3-b][1,5]benzodiazepin-5-one

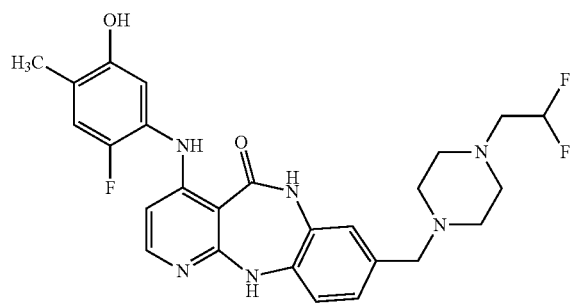 [SMILES: Cc1cc(F)c(Nc2ccnc3c2C(=O)Nc2cc(CN4CCN(CC(F)F)CC4)ccc2N3)cc1O]

4-[(2-Fluoro-5-hydroxy-4-methylphenyl)amino]-5-oxo-6,11-dihydro-5H-pyrido[2,3-b][1,5]benzodiazepine-8-carbaldehyde (Intermediate 11A; 150 mg, 54% purity, 0.21 mmol) was initially charged in 2.5 ml of NMP. 1-(2,2-Difluoroethyl)piperazine dihydrochloride (191 mg, 0.86 mmol) and trimethyl orthoformate (454 mg, 4.28 mmol) were added and the mixture was stirred at RT overnight. Then sodium triacetoxyborohydride (181 mg, 0.86 mmol) was added and the mixture was stirred once again at RT overnight. The reaction mixture was then poured into saturated aqueous sodium hydrogencarbonate solution and stirred for 30 min. The precipitate formed was filtered off, washed with water and dried. This crude product was purified by means of preparative HPLC [column: Sunfire C18; eluent A: water, eluent B: acetonitrile, eluent C: 1% formic acid in water; gradient: 90% A, 5% B, 5% C→0% A, 95% B, 5% C]. The product-containing fractions were concentrated to dryness. The residue was dissolved in a mixture of dichloromethane and methanol (1:1) and applied to a StratoSpheres™ PL-HCO$_3$ MP cartridge. After reconcentration and drying of the residue, 5 mg (5% of theory) of the title compound were obtained.

LC/MS (Method 5, ESIpos): $R_t$=0.59 min, m/z=513 [M+H]$^+$ $^1$H-NMR (400 MHz, DMSO-d$_6$): δ [ppm]=10.07 (br. s, 1H), 9.86 (s, 1H), 9.36 (br. s, 1H), 8.12 (s, 1H), 7.77 (d, 1H), 7.04 (d, 1H), 7.01 (d, 1H), 6.94-6.88 (m, 2H), 6.70 (d, 1H), 6.41-6.33 (m, 1H), 6.10 (tt, 1H), 2.73-2.65 (m, 2H), 2.40-2.25 (m, 4H), 2.09 (s, 3H).

B. Assessment of Pharmacological Efficacy

The pharmacological activity of the inventive compounds can be demonstrated by in vitro and in vivo studies, as known to the person skilled in the art. The application examples which follow describe the biological action of the inventive compounds, without restricting the invention to these examples.

ABBREVIATIONS AND ACRONYMS

Ahx 6-aminohexanoic acid
ATP adenosine triphosphate
AUC area beneath the curve of the concentration-time plot
BSA bovine serum albumin
DMSO dimethyl sulphoxide
EDTA ethylenediaminetetraacetic acid
FBS or FCS foetal calf serum GST glutathione S-transferase
HEPES 2-[4-(2-hydroxyethyl)piperazin-1-yl]ethanesulphonic acid
HTRF homogeneous time-resolved fluorescence
HUVEC human umbilical vein endothelial cells
IC inhibition concentration
KDR kinase insert domain receptor
MTP microtitre plate
PDGF platelet-derived growth factor
PDGFR platelet-derived growth factor receptor
PEG polyethylene glycol
pPDGFR phospho-PDGFR
Tris tris(hydroxymethyl)aminomethane
VEGF vascular endothelial growth factor
VEGFR vascular endothelial growth factor receptor
v/v volume to volume ratio (of a solution)
w/v weight to volume ratio (of a solution)
w/w weight to weight ratio (of a solution)

B-1. KDR (VEGFR-2) Kinase Assay

The KDR-inhibitory activity of the inventive compounds was determined in the KDR-HTRF assay described hereinafter.

The kinase used was a recombinant fusion protein composed of N-terminal GST and a C-terminal fragment of human KDR (amino acids D807-V1356), expressed in baculovirus-infected insect cells (Sf9) and purified by affinity chromatography (from ProQinase GmbH, Freiburg, Germany). The substrate used for the kinase reaction was the biotinylated peptide biotin-Ahx-DFGLARDMYD-KEYYSVG (C terminus in acid form) (from Biosynthan GmbH, Berlin-Buch, Germany).

For the assay, 50 nl of a 100-fold concentrated solution of the test substance in DMSO was pipetted into a black "low-volume 384 well" microtitre plate (from Greiner Bio-One, Frickenhausen, Germany), then 2 µl of a solution of KDR in assay buffer [50 mM HEPES/HCl pH 7.0, 25 mM $MgCl_2$, 5 mM $MnCl_2$, 1.0 mM dithiothreitol, 0.1 mM sodium orthovanadate, 0.001% (v/v) Nonidet-P40 (from Sigma)] was added and the mixture was incubated for 15 min, in order to enable preliminary binding of the substance to the enzyme before the kinase reaction. Then the kinase reaction was started by adding 3 µl of a solution of ATP (16.7 µM, final concentration in assay volume 5 µl is 10 µM) and substrate (0.835 µM, final concentration in assay volume 5 µl is 0.5 µM) in assay buffer and the resulting mixture was incubated at 22° C. for 45 min. The KDR concentration was adjusted with respect to the respective activity of the enzyme in such a way that the assay proceeded in the linear range. The reaction was stopped by adding 5 µl of a solution of HTRF detection reagents [0.1 µM streptavidin-XL665 (from Cisbio Bioassays, Codolet, France) and 2 nM PT66-Eu chelate, a europium chelate-labelled anti-phosphotyrosine antibody (from PerkinElmer), in aqueous EDTA solution (125 mM EDTA, 0.2% (w/v) BSA in 50 mM HEPES/HCl pH 7.0)]. The resulting mixture was incubated at 22° C. for 1 h to allow formation of a complex of the biotinylated phosphorylated substrate and the detection reagents.

Subsequently, the amount of the phosphorylated substrate was evaluated by measuring the resonance energy transfer from the PT66-Eu chelate to the streptavidin-XL665. To this end, the fluorescence emissions at 620 nm and 665 nm after excitation at 350 nm were measured in an HTRF instrument [e.g. PHERAstar (from BMG Labtechnologies, Offenburg, Germany) or ViewLux (from PerkinElmer)]. The ratio of the emissions at 665 nm and 620 nm was taken as a measure of the amount of phosphorylated substrate. The data were normalized (enzyme reaction without inhibitor=0% inhibition; all other assay components except enzyme=100% inhibition). Typically, the test substances were tested on the same microtitre plate at 11 different concentrations in the range from 20 µM to 0.073 nM (20 µM, 5.7 µM, 1.6 µM, 0.47 µM, 0.13 µM, 38 nM, 11 nM, 3.1 nM, 0.89 nM, 0.25 nM and 0.073 nM) in twin values for each concentration. The dilution series were prepared by serial dilutions prior to the assay at the level of the 100-fold concentrated solution (i.e. 2 mM to 7.3 nM in 100% DMSO), although it was possible for the exact concentrations to be different depending on the pipettors used in each case. The $IC_{50}$ values were calculated by a 4-parameter fit.

B-2. PDGFRβ Kinase Assay

The PDGFRβ-inhibitory activity of the inventive compounds was determined in the PDGFRβ-HTRF assay described hereinafter.

The kinase used was a recombinant fusion protein composed of N-terminal GST and a C-terminal fragment of human PDGFRβ (amino acids R561-L1106), expressed in baculovirus-infected insect cells (Sf9) and purified by affinity chromatography (from ProQinase GmbH, Freiburg, Germany). The substrate used for the kinase reaction was biotinylated poly-Glu,Tyr (4:1) copolymer (from Cisbio Bioassays, Codolet, France).

For the assay, 50 nl of a 100-fold concentrated solution of the test substance in DMSO was pipetted into a black "low-volume 384 well" microtitre plate (from Greiner Bio-One, Frickenhausen, Germany), then 2 µl of a solution of PDGFRβ in assay buffer [50 mM HEPES/NaOH pH 7.5, 10 mM $MgCl_2$, 2.5 mM dithiothreitol, 0.01% (v/v) Triton-X100 (from Sigma)] was added and the mixture was incubated for 15 min, in order to enable preliminary binding of the substance to the enzyme before the kinase reaction. Then the kinase reaction was started by adding 3 µl of a solution of ATP (16.7 µM, final concentration in assay volume 5 µl is 10 µM) and substrate (2.27 µg/ml, final concentration in assay volume 5 µl is 1.36 µg/ml, ~30 nM) in assay buffer and the resulting mixture was incubated at 22° C. for 25 min. The PDGFRβ concentration was adjusted with respect to the respective activity of the enzyme in such a way that the assay proceeded in the linear range (typical enzyme concentration 125 pg/µl). The reaction was stopped by adding 5 µl of a solution of HTRF detection reagents [0.2 µM streptavidin-XL665 (from Cisbio Bioassays, Codolet, France) and 1.4 nM PT66-Eu chelate, a europium chelate-labelled anti-phosphotyrosine antibody (from PerkinElmer), in aqueous EDTA solution (100 mM EDTA, 0.2% (w/v) BSA in 50 mM HEPES/NaOH pH 7.5)]. The resulting mixture was incubated at 22° C. for 1 h to allow formation of a complex of the biotinylated phosphorylated substrate and the detection reagents.

Subsequently, the amount of the phosphorylated substrate was evaluated by measuring the resonance energy transfer from the PT66-Eu chelate to the streptavidin-XL665. To this end, the fluorescence emissions at 620 nm and 665 nm after excitation at 350 nm were measured in an HTRF instrument [e.g. PHERAstar (from BMG Labtechnologies, Offenburg, Germany) or ViewLux (from PerkinElmer)]. The ratio of the emissions at 665 nm and 620 nm was taken as a measure of the amount of phosphorylated substrate. The data were normalized (enzyme reaction without inhibitor=0% inhibition; all other assay components except enzyme=100% inhibition). Typically, the test substances were tested on the same microtitre plate at 11 different concentrations in the range from 20 µM to 0.073 nM (20 µM, 5.7 µM, 1.6 µM, 0.47 µM, 0.13 µM, 38 nM, 11 nM, 3.1 nM, 0.89 nM, 0.25 nM and 0.073 nM) in twin values for each concentration.

The dilution series were prepared by serial dilutions prior to the assay at the level of the 100-fold concentrated solution (i.e. 2 mM to 7.3 nM in 100% DMSO), although it was possible for the exact concentrations to be different depending on the pipettors used in each case. The $IC_{50}$ values were calculated by a 4-parameter fit.

Table 1 below collates the $IC_{50}$ values thus obtained from the KDR and PDGFRβ kinase assays for individual working examples of the invention (some as mean values from multiple independent individual determinations).

TABLE 1

| Example No. | KDR (VEGFR-2) $IC_{50}$ [mol/l] | PDGFRβ $IC_{50}$ [mol/l] |
| --- | --- | --- |
| 1 | 3.92E−09 | 5.43E−09 |
| 2 | 9.19E−08 | 8.62E−07 |
| 3 | 1.23E−09 | 3.82E−09 |
| 4 | 8.65E−08 | 3.52E−07 |
| 5 | 2.68E−09 | 5.10E−09 |
| 6 | 1.64E−07 | 6.89E−07 |
| 7 | 2.34E−09 | 9.47E−09 |
| 8 | 2.72E−09 | 4.76E−09 |
| 9 | 3.78E−08 | 3.83E−09 |
| 10 | 9.80E−09 | 6.59E−08 |
| 11 | 2.65E−09 | 4.03E−09 |
| 12 | 5.06E−08 | 8.44E−08 |
| 13 | 5.85E−09 | 2.19E−08 |
| 14 | 8.66E−09 | 9.14E−09 |
| 15 | 9.56E−09 | 5.77E−09 |
| 16 | 1.06E−08 | 7.05E−09 |
| 17 | 1.20E−08 | 5.63E−09 |
| 18 | 1.57E−08 | 5.19E−09 |
| 19 | 8.35E−09 | 2.02E−09 |
| 20 | 7.22E−09 | 2.89E−09 |
| 21 | 1.12E−08 | 2.99E−09 |
| 22 | 1.42E−08 | 2.84E−09 |
| 23 | 9.71E−09 | 2.98E−09 |
| 24 | 2.43E−08 | 4.74E−09 |
| 25 | 1.24E−08 | 3.25E−09 |
| 26 | 8.79E−08 | 6.03E−08 |
| 27 | 1.94E−09 | 1.53E−08 |
| 28 | 4.01E−10 | 9.53E−10 |
| 29 | 8.31E−10 | 2.89E−09 |
| 30 | 1.03E−09 | 2.17E−09 |
| 31 | 4.48E−10 | 1.22E−09 |
| 32 | 1.81E−09 | 3.25E−09 |
| 33 | 1.28E−09 | 4.30E−09 |
| 34 | 1.34E−09 | 5.06E−09 |
| 35 | 6.80E−09 | 1.26E−08 |
| 36 | 6.22E−09 | 2.01E−08 |
| 37 | 1.26E−09 | 4.60E−09 |
| 38 | 2.60E−09 | 7.03E−09 |
| 39 | 1.26E−08 | 1.86E−09 |
| 40 | 7.27E−09 | 1.80E−09 |
| 41 | 6.61E−09 | 3.72E−09 |
| 42 | 7.56E−09 | 2.44E−09 |
| 43 | 7.77E−09 | 2.30E−09 |
| 44 | 1.00E−08 | 1.98E−08 |
| 45 | 4.98E−10 | 9.28E−10 |
| 46 | 5.80E−10 | 1.52E−09 |
| 47 | 9.77E−10 | 3.67E−09 |
| 48 | 3.63E−10 | 1.01E−09 |
| 49 | 3.88E−10 | 4.87E−10 |
| 50 | 8.49E−10 | 1.13E−09 |
| 51 | 8.31E−10 | 1.15E−09 |
| 52 | 5.82E−10 | 1.10E−09 |
| 53 | 5.25E−10 | 9.62E−10 |
| 54 | 2.94E−09 | 6.51E−09 |
| 55 | 4.73E−10 | 9.05E−10 |
| 56 | 5.95E−10 | 1.49E−09 |
| 57 | 3.30E−10 | 1.66E−09 |
| 58 | 5.48E−10 | 2.05E−09 |
| 59 | 4.32E−10 | 1.82E−09 |
| 60 | 3.36E−09 | 3.83E−09 |
| 61 | 2.30E−09 | 4.55E−09 |
| 62 | 3.94E−10 | 1.39E−09 |
| 63 | 6.79E−10 | 1.05E−09 |
| 64 | 2.87E−10 | 6.80E−10 |
| 65 | 2.46E−10 | 1.05E−09 |
| 66 | 1.94E−09 | 3.75E−09 |
| 67 | 1.02E−09 | 2.23E−09 |
| 68 | 1.01E−09 | 1.85E−09 |
| 69 | 4.96E−10 | 9.85E−10 |
| 70 | 6.47E−10 | 1.38E−09 |
| 71 | 6.70E−10 | 1.16E−09 |
| 72 | 2.70E−09 | 9.59E−09 |
| 73 | 2.19E−09 | 1.98E−09 |
| 74 | 4.59E−10 | 4.75E−10 |
| 75 | 7.06E−10 | 8.26E−10 |
| 76 | 3.72E−10 | 1.58E−09 |
| 77 | 1.06E−09 | 4.90E−09 |
| 78 | 4.29E−10 | 9.74E−10 |
| 79 | 2.56E−08 | 2.13E−07 |
| 80 | 8.33E−10 | 7.44E−09 |
| 81 | 7.78E−10 | 1.31E−09 |
| 82 | 3.01E−09 | 1.01E−08 |
| 83 | 9.44E−10 | 2.78E−09 |
| 84 | 3.21E−09 | 1.46E−08 |
| 85 | 1.76E−09 | 1.39E−08 |
| 86 | 1.18E−09 | 8.61E−09 |
| 87 | 6.13E−10 | 1.41E−09 |
| 88 | 8.74E−10 | 1.70E−09 |
| 89 | 1.20E−09 | 3.51E−09 |
| 90 | 1.31E−09 | 7.93E−10 |
| 91 | 5.22E−10 | 1.66E−09 |
| 92 | 1.04E−08 | 5.27E−09 |
| 93 | 1.00E−08 | 4.98E−09 |
| 94 | 6.89E−09 | 3.52E−09 |
| 95 | 2.86E−09 | 1.95E−09 |
| 96 | 5.03E−09 | 2.10E−09 |
| 97 | 5.52E−09 | 2.45E−09 |
| 98 | 6.98E−09 | 5.17E−09 |
| 99 | 5.68E−09 | 2.97E−09 |
| 100 | 6.18E−09 | 1.66E−09 |
| 101 | 4.63E−09 | 2.98E−09 |
| 102 | 1.83E−09 | 1.57E−09 |
| 103 | 5.06E−09 | 3.46E−09 |
| 104 | 1.56E−08 | 1.22E−08 |
| 105 | 8.78E−09 | 1.46E−08 |
| 106 | 8.22E−09 | 3.86E−09 |
| 107 | 2.77E−08 | 1.84E−08 |
| 108 | 8.20E−09 | 2.87E−09 |
| 109 | 1.20E−08 | 3.55E−09 |
| 110 | 4.40E−09 | 3.29E−09 |
| 111 | 4.09E−09 | 4.03E−09 |
| 112 | 6.69E−09 | 2.34E−09 |
| 113 | 3.52E−09 | 3.60E−09 |
| 114 | 6.74E−09 | 1.83E−09 |
| 115 | 9.47E−09 | 3.93E−09 |
| 116 | 1.09E−08 | 4.75E−09 |
| 117 | 1.16E−08 | 3.46E−09 |
| 118 | 6.31E−09 | 4.02E−09 |
| 119 | 2.67E−09 | 1.92E−09 |
| 120 | 3.53E−09 | 1.49E−09 |
| 121 | 5.61E−09 | 5.74E−09 |
| 122 | 8.47E−09 | 3.24E−09 |
| 123 | 3.49E−09 | 7.14E−09 |
| 124 | 6.64E−09 | 3.02E−09 |
| 125 | 4.79E−09 | 1.97E−09 |
| 126 | 5.14E−09 | 2.24E−09 |
| 127 | 7.33E−09 | 3.52E−09 |
| 128 | 1.41E−08 | 3.60E−09 |
| 129 | 9.04E−09 | 3.99E−09 |
| 130 | 5.77E−09 | 2.31E−09 |
| 131 | 3.56E−09 | 2.05E−09 |
| 132 | 7.44E−09 | 2.89E−09 |
| 133 | 8.25E−09 | 7.53E−09 |
| 134 | 7.75E−09 | 2.82E−09 |
| 135 | 8.75E−09 | 5.74E−09 |
| 136 | 8.09E−09 | 2.05E−09 |
| 137 | 5.78E−09 | 1.68E−09 |
| 138 | 7.25E−09 | 2.41E−09 |
| 139 | 1.01E−08 | 3.58E−09 |
| 140 | 5.34E−09 | 1.64E−09 |

TABLE 1-continued

| Example No. | KDR (VEGFR-2) IC$_{50}$ [mol/l] | PDGFRβ IC$_{50}$ [mol/l] |
|---|---|---|
| 141 | 1.03E−08 | 3.48E−09 |
| 142 | 4.17E−09 | 2.11E−09 |
| 143 | 5.77E−09 | 5.55E−09 |
| 144 | 9.74E−09 | 7.72E−09 |
| 145 | 5.82E−09 | 5.82E−09 |
| 146 | 1.66E−08 | 7.56E−09 |
| 147 | 7.00E−08 | 5.29E−08 |
| 148 | 7.31E−09 | 1.52E−09 |
| 149 | 3.57E−09 | 1.74E−09 |
| 150 | 6.42E−09 | 1.18E−09 |
| 151 | 7.36E−09 | 3.71E−09 |
| 152 | 9.30E−09 | 4.42E−09 |
| 153 | 5.83E−09 | 3.61E−09 |
| 154 | 6.31E−09 | 2.10E−09 |
| 155 | 6.11E−09 | 2.33E−09 |
| 156 | 6.51E−09 | 3.31E−09 |
| 157 | 8.81E−09 | 3.40E−09 |
| 158 | 8.31E−09 | 1.16E−09 |
| 159 | 8.33E−10 | 1.28E−09 |
| 160 | 1.40E−09 | 7.25E−09 |
| 161 | 1.83E−09 | 1.07E−08 |
| 162 | 1.79E−09 | 1.21E−08 |
| 163 | 3.88E−10 | 3.03E−09 |
| 164 | 9.60E−10 | 3.71E−09 |
| 165 | 1.74E−09 | 4.61E−09 |
| 166 | 1.47E−09 | 5.02E−09 |
| 167 | 4.07E−10 | 1.31E−09 |
| 168 | 1.09E−09 | 1.90E−09 |
| 169 | 1.69E−09 | 2.08E−09 |
| 170 | 6.18E−10 | 1.05E−09 |
| 171 | 9.29E−10 | 2.56E−09 |
| 172 | 2.82E−09 | 4.11E−09 |
| 173 | 9.86E−10 | 4.41E−09 |
| 174 | 1.70E−09 | 1.25E−09 |
| 175 | 1.83E−09 | 1.26E−09 |
| 176 | 1.17E−09 | 3.45E−09 |
| 177 | 9.81E−10 | 1.71E−09 |
| 178 | 2.87E−09 | 1.48E−08 |
| 179 | 2.34E−09 | 1.46E−08 |
| 180 | 8.84E−10 | 2.43E−09 |
| 181 | 1.43E−09 | 8.91E−09 |
| 182 | 8.82E−10 | 1.62E−09 |
| 183 | 7.91E−10 | 1.20E−09 |
| 184 | 7.80E−10 | 1.62E−09 |
| 185 | 5.18E−09 | 2.50E−08 |
| 186 | 5.03E−10 | 5.14E−09 |
| 187 | 3.25E−10 | 1.51E−09 |
| 188 | 1.01E−09 | 1.75E−09 |
| 189 | 6.77E−10 | 2.01E−09 |
| 190 | 5.03E−10 | 1.22E−09 |
| 191 | 4.19E−10 | 6.26E−10 |
| 192 | 2.74E−10 | 1.61E−09 |
| 193 | 1.72E−09 | 3.22E−09 |
| 194 | 6.92E−10 | 1.92E−09 |
| 195 | 5.73E−10 | 1.56E−09 |
| 196 | 2.43E−09 | 9.38E−09 |
| 197 | 9.40E−10 | 8.61E−10 |
| 198 | 8.51E−10 | 9.62E−10 |
| 199 | 6.89E−10 | 1.31E−09 |
| 200 | 7.14E−10 | 7.27E−10 |
| 201 | 7.28E−10 | 1.35E−09 |
| 202 | 8.74E−10 | 1.55E−09 |
| 203 | 8.63E−10 | 1.87E−09 |
| 204 | 8.58E−10 | 1.71E−09 |
| 205 | 1.86E−09 | 1.76E−09 |
| 206 | 8.77E−10 | 1.55E−09 |
| 207 | 7.65E−10 | 9.95E−10 |
| 208 | 6.01E−10 | 1.03E−09 |
| 209 | 7.89E−10 | 7.39E−10 |
| 210 | 5.78E−10 | 1.03E−09 |
| 211 | 1.19E−9 | 1.94E−09 |
| 212 | 1.88E−9 | 8.29E−10 |
| 213 | 1.39E−9 | 1.58E−09 |
| 214 | 8.06E−10 | 1.37E−09 |
| 215 | 2.20E−9 | 2.06E−09 |
| 216 | 9.54E−10 | 1.12E−09 |
| 217 | 3.11E−9 | 3.39E−09 |
| 218 | 2.64E−9 | 1.06E−09 |
| 219 | 2.16E−9 | 1.48E−09 |
| 220 | 1.25E−9 | 2.15E−09 |
| 221 | 9.41E−10 | 1.74E−09 |
| 222 | 7.09E−10 | 1.01E−09 |
| 223 | 7.55E−10 | 1.01E−09 |
| 224 | 9.04E−10 | 1.63E−09 |
| 225 | 1.39E−8 | 1.41E−08 |
| 226 | 4.72E−10 | 1.09E−09 |
| 227 | 9.57E−10 | 6.38E−09 |

[Reading examples: 3.92E−09 mol/l = 3.92 × $10^{-9}$ M = 3.92 nM; 1.64E−07 mol/l = 1.64 × $10^{-7}$ M = 164 nM; 5.80E−10 mol/l = 5.80 × $10^{-10}$ M = 0.58 nM].

B-3. Cellular pPDGFRβ Inhibition Assay

Normal human dermal fibroblasts (NHDF; Promocell, Cat. No. C-12300; passage 2-7) were sown in a quantity of 7×10$^3$ cells/well in 48-well plates (Falcon™ MultiWell Cell Culture Plates, Falcon, Cat. No. B3668-3B) and incubated at 37° C., 5% CO$_2$ and 95% relative air humidity overnight in minimal medium supplemented with GlutaMAX™ (Minimum Essential Medium, Gibco, Cat. No. 41090-028), 10% heat-inactivated (30 min at 56° C.) foetal calf serum (FBS; BioWhittaker, Lonza, Cat. No. DE14-801F) and 5 µg/ml insulin (Insulin solution human, Sigma, Cat. No. 19278). The next day, the GlutaMAX™-supplemented minimal medium was replaced by the Opti-MEM® I Reduced Serum Medium (Gibco, Cat. No. 31985-047) and incubated again under the conditions described above for 3 h. Thereafter, 50 ng/ml recombinant human PDGF-BB (R&D Systems, Cat. No. 220-BB-050) and a dilution series of the test substances to be examined in DMSO were added to the cells. The total volume per well was 100 µl. After incubation under the abovementioned conditions for one hour, the Opti-MEM® I Reduced Serum Medium was tapped out and discarded. Subsequently, the lysis buffer [Phospho PDGFRβ (Tyr751) Assay Whole Cell Lysate Kit, MSD, Cat. No. K150DVD-2] was made up according to the manufacturer's instructions and 70 µl of this mixture per well were added. The lysed cell samples were either stored at −20° C. or analysed immediately after the lysis in a Meso Scale SECTOR® Imager 2400 according to the abovementioned manufacturer's instructions. The measurement data were presented as percentage pPDGFRβ stimulation compared to PDGF-BB-stimulated but substance-untreated cells. The IC$_{50}$ values were calculated by employing the nonlinear regression (curve fit) function of GraphPad Prism 6 (La Jolla, Calif., USA).

Table 2 below lists the IC$_{50}$ values from this assay for representative working examples of the invention (some as mean values from multiple independent individual determinations).

TABLE 2

| Example No. | pPDGFRβ IC$_{50}$ [mol/l] |
|---|---|
| 19 | 4.09E−08 |
| 28 | 2.16E−08 |
| 29 | 3.53E−08 |
| 30 | 1.11E−07 |
| 31 | 3.33E−08 |
| 32 | 2.28E−08 |
| 42 | 1.40E−07 |
| 49 | 4.11E−08 |
| 50 | 9.74E−08 |
| 51 | 2.21E−08 |
| 52 | 2.97E−08 |

TABLE 2-continued

| Example No. | pPDGFRβ IC$_{50}$ [mol/l] |
|---|---|
| 55 | 6.07E−08 |
| 58 | 2.87E−08 |
| 64 | 1.43E−08 |
| 75 | 4.39E−08 |
| 76 | 1.13E−08 |
| 78 | 3.26E−08 |
| 162 | 8.90E−07 |
| 174 | 1.06E−07 |
| 187 | 4.13E−08 |
| 198 | 4.98E−08 |
| 202 | 3.91E−08 |
| 209 | 2.15E−07 |
| 227 | 5.54E−07 |

[Reading example: 4.09E−08 mol/l = 4.09 × 10$^{-8}$ M = 40.9 nM].

B-4. Inhibition of the VEGF-Induced Proliferation of Endothelial Cells

For the testing of the substances, 3000 human venous endothelial cells from the umbilical cord (HUVEC; CellSystems, Cat. No. FC-0003) were cultivated in 100 µl of complete medium (VascuLife® basal medium with VEGF LifeFactors, CellSystems, LM-0002 and LS-1020) in 96-well plates (Greiner Bio-One, Cat. No. 655090) (Heraeus incubator, 37° C., 5% CO$_2$). After 6 hours, the complete medium was removed and replaced by starvation medium (VascuLife® Basalmedium, CellSystems, Cat. No. LM-0002) containing heparin (Heparin Sulfate LifeFactor, CellSystems, Cat. No. LS-1017), ascorbic acid (Ascorbic Acid LifeFactor, CellSystems, Cat. No. LS-1005), L-glutamine (L-Glutamine LifeFactor, CellSystems, Cat. No. LS-1013) and 0.2% FCS (FBS LifeFactor, CellSystems, Cat. No. LS-1005). The cells remained in the starvation medium for about 18 h. Thereafter, the substances to be tested were added in fresh starvation medium. For this purpose, the test substance (dissolved ad 10 mM in 100% DMSO) was diluted in starvation medium typically ad 10$^{-6}$ M, 10$^{-7}$ M, 10$^{-8}$ M, 10$^{-9}$ M, 10$^{-10}$ M and 10$^{-11}$ M, not exceeding the final concentration of 0.1% DMSO. Then the cells were stimulated with VEGF-A (20 ng/ml, R&D Systems, Cat. No. 293 VE). The controls used were cells which were kept in minimal medium and VEGF (positive control) and cells which were kept in minimal medium only (negative control). In this way, the cells were cultivated for 72 h. Then 5 µl of AlamarBlue® (CellTiter-Blue® Cell Viability Assay, Promega, Cat. No. G8080) per well were added. After incubation for a further 4 h, the fluorescence was measured in a microtitre reader (Infinite® M200, Tecan; settings: excitation wavelength 535 nm, emission wavelength 590 nm, amplification 70 V). The measurements were first normalized against the plate background and the IC$_{50}$ values were determined by employing a non-linear sigmoidal regression function (curve fit) in GraphPad Prism 6 (La Jolla, Calif., USA). The concentration-dependent inhibition was compared with the stimulated and unstimulated cells.

Table 3 below lists the IC$_{50}$ values from this assay for representative working examples of the invention (some as mean values from multiple independent individual determinations).

TABLE 3

| Example No. | VEGF-induced HUVEC proliferation, IC$_{50}$ [mol/l] |
|---|---|
| 19 | 4.27E−08 |
| 28 | 3.79E−09 |
| 29 | 3.39E−09 |
| 30 | 5.57E−09 |
| 31 | 1.94E−09 |
| 32 | 4.33E−08 |
| 42 | 1.41E−08 |
| 49 | 1.40E−08 |
| 50 | 3.33E−08 |
| 51 | 6.93E−09 |
| 52 | 4.39E−09 |
| 55 | 9.53E−09 |
| 58 | 8.40E−09 |
| 64 | 1.02E−08 |
| 75 | 2.33E−08 |
| 76 | 2.78E−08 |
| 78 | 2.50E−08 |
| 162 | 2.10E−08 |
| 174 | 5.08E−08 |
| 187 | 4.01E−09 |
| 198 | 4.89E−09 |
| 202 | 6.57E−09 |
| 209 | 2.62E−08 |
| 227 | 2.99E−08 |

[Reading example: 4.27E−08 mol/l = 4.27 × 10$^{-8}$ M = 42.7 nM].

B-5. Topical Efficacy in the Model of Laser-Induced Choroidal Neovascularization The test described hereinafter serves to investigate the efficacy of a test substance applied in the form of eye drops on the reduction of extravasation/ooedema formation and/or choroidal neovascularization in the rat model of laser-induced choroidal neovascularization.

To this end, pigmented rats of the Brown-Norway strain having no indications of ophthalmological disorders were selected and randomized into treatment groups. On day 0, the animals were anaesthetized by intraperitoneal injection (15 mg/kg xylazine and 80 mg/kg ketamine). Following instillation of a drop of a 0.5% tropicamide solution to dilate the pupils, choroidal neovascularization was triggered at six defined locations around the optic nerve using a 532 nm argon laser photocoagulator (diameter 50 µm, intensity 150 mW, duration 100 ms). The test substance and the appropriate vehicle were applied to the lasered eye twice daily as eye drops over the entire experimental duration of 23 days (interval between the applications: 10 to 14 h; volume: 10 µl). The test substance was suspended either in 100% liquid paraffin or in an aqueous vehicle (hydroxypropylmethyl cellulose 3.5%, polysorbate 80 0.5%, NaCl 0.9% in water).

On day 21, angiography was conducted using a fluorescence fundus camera (Kowe). Under anaesthesia and after another pupil dilation, a 10% sodium fluorescein dye was injected subcutaneously (s.c.). 2 min later, pictures of the eyeground were taken. The extent of extravasation/ooedema, represented by the leakage of fluorescein, was assessed by three blinded observers and classified into degrees of severity of 0 (no extravasation) to 3 (intense colour beyond the actual lesion).

After the animals had been sacrificed on day 23, the eyes were removed and fixated in 4% paraformaldehyde solution at room temperature for 1 h. After one washing, the retina was carefully peeled off and the sclera-choroidea complex was stained with an FITC isolectin B4 antibody and then applied flat to a microscope slide. The preparations thus obtained were evaluated using a fluorescence microscope (Keyence Biozero) at an excitation wavelength of 488 nm. The area of the choroidal neovascularization (in µm$^2$) was determined by morphometric analysis by means of ImageTool software.

B-6. Oxygen-Induced Retinopathy Model

It has been shown that oxygen-induced retinopathy is a valuable animal model for the study of pathological retinal angiogenesis [Connor et al., *Nature Protocols* 4, 1565-1573 (2009)]. This model is based on the observation that hyperoxia during early postnatal development in the retina causes arrest or delay of the growth of normal retinal blood vessels. If the animals are returned to normoxic room air after a 7-day hyperoxia phase, this is equivalent to relative hypoxia since the retina lacks the normal vessels required to ensure adequate supply of the neural tissue under normoxic conditions. The ischaemic situation caused in this manner results in an abnormal neovascularization which has some similarities with pathophysiological neovascularization in eye disorders such as wet AMD. In addition, the neovascularization caused is highly reproducible and quantifiable and is an important parameter for the study of the disease mechanisms and possible treatments for a wide variety of different forms of retinal disorders.

The purpose of the test described hereinafter was therefore to examine the efficacy of a test compound on the growth of the retinal vessels in the oxygen-induced retinopathy model in mice.

For this purpose, neonate C57BL/6 mice and their mothers were subjected to hyperoxia (70% oxygen) on postnatal day 7 (PD7) for 5 days. From PD12, the mice were kept under normoxic conditions (room air, 21% oxygen) until PD17. From day 12 to day 17, the mice were given daily intraperitoneal (i.p.) treatment with the test substance or the appropriate vehicle. On day 17, all mice were anaesthetized with isoflurane and then sacrificed. The eyes were removed and fixated in 4% formalin. After washing in phosphate-buffered saline, the retina was excised, a flat preparation thereof was produced and this was stained with isolectin B4 antibody. Quantification of neovascularization was conducted using a Zeiss ApoTome.

B-7. VEGF-Induced Hyperpermeability Model

In a number of eye disorders, the vessels in the eyes are damaged in such a way as to result in exudation of liquid from the vessel. The exuded liquid, which accumulates in the macula, leads to swelling of the tissue and considerably worsens the sight of the patient affected and hence makes a major contribution to loss of vision. This extravasation caused by increased vascular permeability can be efficiently induced and quantified in an animal model.

For this purpose, the substance to be tested, according to the kinetics of the substance, is administered once or more than once at intervals of days or several hours prior to induction of an increase in vascular permeability.

Induction is effected in rabbits by the intravitreal injection of 500 ng of $hVEGF_{165}$ into an eye posterior to the limbus, which leads to increased retinal extravasation. Two days after the induction of vascular permeability, fluorescein is administered systemically (50 mg/ml in physiological saline per kg of body weight). Shortly (about 50 min) after the administration of fluorescein, the animals are sedated by anaesthesia. The eye to be examined is then positioned before the lens of a fluorophotometer (Fluorotron, OcuMetrics Inc., CA) and the measurement is started. The relative fluorescein concentration in the eye is measured from posterior to anterior. To quantify the extravasation, the AUC of the fluorescein concentration is calculated for each eye and presented as the quotient between VEGF-treated eyes and the untreated contralateral eyes.

C. Working Examples for Pharmaceutical Compositions

The inventive compounds can be converted to pharmaceutical formulations as follows:

Tablet:

Composition:

100 mg of the inventive compound, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of inventive compound, lactose and starch is granulated with a 5% solution (w/w) of the PVP in water. The granules are dried and then mixed with the magnesium stearate for 5 minutes. This mixture is compressed in a conventional tabletting press (see above for format of the tablet). The guide value used for the pressing is a pressing force of 15 kN.

Suspension for Oral Administration:

Composition:

1000 mg of the inventive compound, 1000 mg of ethanol (96%), 400 mg of Rhodigel® (xanthan gum from FMC, Pennsylvania, USA) and 99 g of water.

10 ml of oral suspension correspond to a single dose of 100 mg of the inventive compound.

Production:

The Rhodigel is suspended in ethanol; the inventive compound is added to the suspension. The water is added while stirring. The mixture is stirred for about 6 h before swelling of the Rhodigel is complete.

Solution for Oral Administration:

Composition:

500 mg of the inventive compound, 2.5 g of polysorbate and 97 g of polyethylene glycol 400. 20 g of oral solution correspond to a single dose of 100 mg of the inventive compound.

Production:

The inventive compound is suspended in the mixture of polyethylene glycol and polysorbate with stirring. The stirring operation is continued until dissolution of the inventive compound is complete.

i.v. Solution:

The inventive compound is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

Solution or Suspension for Topical Administration to the Eye (Eye Drops):

A sterile pharmaceutical preparation for topical administration to the eye can be prepared by reconstituting a lyophilizate of the inventive compound in sterile saline. Suitable preservatives for such a solution or suspension are, for example, benzalkonium chloride, thiomersal or phenylmercury nitrate in a concentration range of from 0.001 to 1 percent by weight.

The invention claimed is:
1. A compound of formula (I)

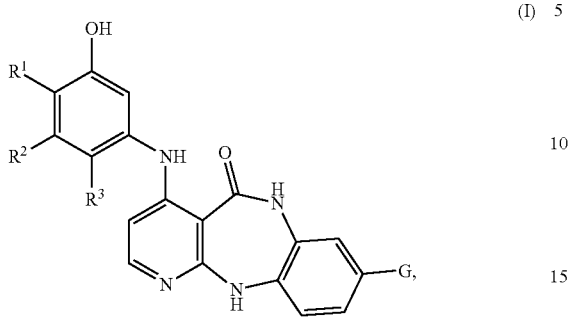

wherein:
R$^1$ is hydrogen, halogen, hydroxyl, (C$_1$-C$_4$)-alkyl, —NH—C(=O)—R$^4$, —NH—C(=O)—O—R$^5$ or —NH—SO$_2$—R$^6$,
wherein
R$^4$ is hydrogen or (C$_1$-C$_4$)-alkyl;
R$^5$ is (C$_1$-C$_4$)-alkyl; and
R$^6$ is (C$_1$-C$_4$)-alkyl or phenyl;
R$^2$ is hydrogen, fluorine, chlorine, methyl or methoxy;
R$^3$ is hydrogen, fluorine, chlorine or methyl;
and
G is cyano, hydroxycarbonyl, —C(=O)—NR$^{7A}$R$^{7B}$ or —CH$_2$—NR$^{8A}$R$^{8B}$,
wherein
R$^{7A}$ is hydrogen or (C$_1$-C$_4$)-alkyl optionally substituted by hydroxyl, (C$_1$-C$_4$)-alkoxy or up to trisubstituted by fluorine;
R$^{7B}$ is hydrogen, (C$_1$-C$_6$)-alkyl, (C$_3$-C$_6$)-cycloalkyl, phenyl, 4- to 7-membered heterocyclyl or 5- to 10-membered heteroaryl;
wherein (C$_1$-C$_6$)-alkyl is optionally up to hexasubstituted by fluorine and up to disubstituted, identically or differently, by a radical selected from the group consisting of —OR$^9$, —O—(CH$_2$CH$_2$O)$_n$—R$^{10}$, —SR$^{11}$, —NR$^{12A}$R$^{12B}$, —C(=O)—NR$^{13A}$R$^{13B}$, (C$_3$-C$_6$)-cycloalkyl, (C$_4$-C$_6$)-cycloalkenyl, phenyl, 4- to 7-membered heterocyclyl and 5- or 6-membered heteroaryl;
and wherein
(i) the cycloalkyl groups are optionally up to disubstituted, identically or differently, by a radical selected from the group consisting of fluorine, (C$_1$-C$_4$)-alkyl, hydroxyl, (C$_1$-C$_4$)-alkoxy, hydroxycarbonyl and (C$_1$-C$_4$)-alkoxy carbonyl;
(ii) the phenyl groups are optionally up to disubstituted, identically or differently, by a radical selected from the group consisting of fluorine, chlorine, (C$_1$-C$_4$)-alkyl and (C$_1$-C$_4$)-alkoxy;
(iii) the heterocyclyl groups are optionally up to trisubstituted, identically or differently, by a radical selected from the group consisting of fluorine, (C$_1$-C$_4$)-alkyl, hydroxyl, oxo, hydroxycarbonyl and (C$_1$-C$_4$)-alkoxycarbonyl; and
(iv) the heteroaryl groups are optionally up to disubstituted, identically or differently, by a radical selected from the group consisting of fluorine, chlorine, (C$_1$-C$_4$)-alkyl and (C$_1$-C$_4$)-alkoxy;
and wherein
R$^9$ is hydrogen or (C$_1$-C$_4$)-alkyl optionally substituted by 4- to 6-membered heterocyclyl;
R$^{10}$ is hydrogen or (C$_1$-C$_4$)-alkyl;
R$^{11}$ is (C$_1$-C$_4$)-alkyl;
R$^{12A}$, R$^{12B}$, R$^{13A}$ and R$^{13B}$ are independently hydrogen or (C$_1$-C$_4$)-alkyl optionally substituted by hydroxyl;
and
n is an integer from 1 to 10;
or
R$^{7A}$ and R$^{7B}$ are joined to one another and, together with the nitrogen atom to which they are bonded, form a 4- to 10-membered heterocycle which optionally contains up to 2 further ring heteroatoms selected from the group consisting of N, O and S, and which is optionally up to tetrasubstituted, identically or differently, by a radical selected from the group consisting of fluorine, (C$_1$-C$_4$)-alkyl, oxo, —OR$^{14}$, —NR$^{15A}$R$^{15B}$, —C(=O)—NR$^{16A}$R$^{16B}$ and phenyl;
wherein (C$_1$-C$_4$)-alkyl is optionally substituted by hydroxy or up to three times by fluorine;
and wherein
R$^{14}$ is hydrogen, (C$_1$-C$_4$)-alkyl or phenyl;
wherein (C$_1$-C$_4$)-alkyl is optionally substituted by hydroxyl, —C(=O)—NR$^{17A}$R$^{17B}$, (C$_3$-C$_6$)-cycloalkyl or up to trisubstituted by fluorine;
and
R$^{15A}$, R$^{15B}$, R$^{16A}$, R$^{16B}$, R$^{17A}$ and R$^{17B}$ are independently hydrogen or (C$_1$-C$_4$)-alkyl optionally substituted by hydroxyl;
R$^{8A}$ is hydrogen or (C$_1$-C$_4$)-alkyl optionally substituted by hydroxyl, (C$_1$-C$_4$)-alkoxy or up to trisubstituted by fluorine;
and
R$^{8B}$ is hydrogen, (C$_1$-C$_6$)-alkyl, (C$_3$-C$_6$)-cycloalkyl, phenyl, 4- to 7-membered heterocyclyl or 5- to 10-membered heteroaryl;
wherein (C$_1$-C$_6$)-alkyl is optionally up to hexasubstituted by fluorine and up to disubstituted, identically or differently, by a radical selected from the group consisting of —OR$^{18}$, —O—(CH$_2$CH$_2$O)$_p$—R$^{19}$, —SR$^{20}$, —NR$^{21A}$R$^{21B}$, —C(=O)—NR$^{22A}$R$^{22B}$, (C$_3$-C$_6$)-cycloalkyl, (C$_4$-C$_6$)-cycloalkenyl, phenyl, 4- to 7-membered heterocyclyl and 5- or 6-membered heteroaryl;
and wherein
(i) the cycloalkyl groups are optionally up to disubstituted, identically or differently, by a radical selected from the group consisting of fluorine, (C$_1$-C$_4$)-alkyl, hydroxyl, (C$_1$-C$_4$)-alkoxy, hydroxycarbonyl and (C$_1$-C$_4$)-alkoxycarbonyl;
(ii) the phenyl groups are optionally up to disubstituted, identically or differently, by a radical selected from the group consisting of fluorine, chlorine, (C$_1$-C$_4$)-alkyl and (C$_1$-C$_4$)-alkoxy;
(iii) the heterocyclyl groups are optionally up to trisubstituted, identically or differently, by a radical selected from the group consisting of fluorine, (C$_1$-C$_4$)-alkyl, hydroxyl, oxo, hydroxycarbonyl and (C$_1$-C$_4$)-alkoxycarbonyl; and
(iv) the heteroaryl groups are optionally up to disubstituted, identically or differently, by a radical selected from the group consisting of fluorine, chlorine, (C$_1$-C$_4$)-alkyl and (C$_1$-C$_4$)-alkoxy;
and wherein
R$^{18}$ is hydrogen or (C$_1$-C$_4$)-alky optionally substituted by 4- to 6-membered heterocyclyl;

$R^{19}$ is hydrogen or $(C_1-C_4)$-alkyl;

$R^{20}$ is $(C_1-C_4)$-alkyl;

$R^{21A}$, $R^{21B}$, $R^{22A}$ and $R^{22B}$ are independently hydrogen or $(C_1-C_4)$-alkyl optionally substituted by hydroxyl;

and p is an integer from 1 to 10;

or $R^{8A}$ and $R^{8B}$ are joined to one another and, together with the nitrogen atom to which they are bonded, form a 4- to 10-membered heterocycle which optionally contains up to 2 further ring heteroatoms selected from the group consisting of N, O and S, and which is optionally up to tetrasubstituted, identically or differently, by a radical selected from the group consisting of fluorine, $(C_1-C_4)$-alkyl, oxo, —$OR^{23}$, —$NR^{24A}R^{24B}$, —C(=O)—$NR^{25A}R^{25B}$ and phenyl;

wherein $(C_1-C_4)$-alkyl is optionally substituted by hydroxy or up to three times by fluorine;

and wherein $R^{23}$ is hydrogen, $(C_1-C_4)$-alkyl or phenyl;

wherein $(C_1-C_4)$-alkyl is optionally substituted by hydroxyl, —C(=O)—$NR^{26A}R^{26B}$, $(C_3-C_6)$-cycloalkyl or up to trisubstituted by fluorine;

and $R^{24A}$, $R^{24B}$, $R^{25A}$, $R^{25B}$, $R^{26A}$ and $R^{26B}$ are independently hydrogen or $(C_1-C_4)$-alkyl optionally substituted by hydroxyl, or a salt, a solvate or a solvate of a salt thereof.

2. The compound of formula (I) according to claim 1, wherein:

$R^1$ is hydrogen, fluorine, chlorine, $(C_1-C_4)$-alkyl or —NH—$SO_2$—$R^6$, wherein $R^6$ is $(C_1-C_4)$-alkyl or phenyl;

$R^2$ is hydrogen, fluorine, chlorine or methyl;

$R^3$ is hydrogen, fluorine, chlorine or methyl;

and

G is cyano, —C(=O)—$NR^{7A}R^{7B}$ or —$CH_2$—$NR^{8A}R^{8B}$, wherein $R^{7A}$ is hydrogen, methyl, ethyl, 2-hydroxyethyl, 2-methoxyethyl or 2-ethoxyethyl;

wherein methyl and ethyl are optionally up to trisubstituted by fluorine;

$R^{7B}$ is hydrogen, $(C_1-C_4)$-alkyl or $(C_3-C_6)$-cycloalkyl;

wherein $(C_1-C_4)$-alkyl is optionally up to trisubstituted by fluorine and up to disubstituted, identically or differently, by a radical selected from the group consisting of —$OR^9$, —$SR^{11}$, —$NR^{12A}R^{12B}$, $(C_3-C_6)$-cycloalkyl and phenyl;

and wherein (i) the cycloalkyl groups are optionally up to disubstituted, identically or differently, by a radical selected from the group consisting of fluorine, methyl, ethyl, hydroxyl, methoxy, ethoxy, hydroxycarbonyl, methoxycarbonyl and ethoxycarbonyl; and (ii) the phenyl groups are optionally up to disubstituted, identically or differently, by a radical selected from the group consisting of fluorine, chlorine, methyl, ethyl, methoxy and ethoxy;

and wherein $R^9$ is hydrogen, methyl or ethyl;

$R^{11}$ is methyl or ethyl;

and $R^{12A}$ and $R^{12B}$ are independently hydrogen, methyl, ethyl or 2-hydroxyethyl;

or $R^{7A}$ and $R^{7B}$ are joined to one another and, together with the nitrogen atom to which they are bonded, form a 5- to 7-membered heterocycle which optionally contains one further ring heteroatom selected from the group consisting of N, O and S, and which is optionally up to tetrasubstituted, identically or differently, by a radical selected from the group consisting of fluorine, $(C_1-C_3)$-alkyl, oxo, —$OR^{14}$, $NR^{15A}R^{15B}$, —C(=O)—$NR^{16A}R^{16B}$ and phenyl;

wherein $(C_1-C_3)$-alkyl is optionally substituted by hydroxy or up to three times by fluorine;

and wherein $R^{14}$ is hydrogen, methyl or ethyl;

and $R^{15A}$, $R^{15B}$, $R^{16A}$ and $R^{16B}$ are independently hydrogen, methyl or ethyl;

$R^{8A}$ is hydrogen or $(C_1-C_4)$-alkyl optionally substituted by hydroxyl, methoxy, ethoxy or up to trisubstituted by fluorine;

and $R^{8B}$ is hydrogen, $(C_1-C_6)$-alkyl, $(C_3-C_6)$-cycloalkyl, phenyl, 5- or 6-membered heterocyclyl or 5- or 6-membered heteroaryl;

wherein $(C_1-C_6)$-alkyl is optionally up to trisubstituted by fluorine and up to disubstituted, identically or differently, by a radical selected from the group consisting of —$OR^{18}$, —$SR^{20}$, —$NR^{21A}R^{21B}$, —C(=O)—$NR^{22A}R^{22B}$, (C3-C6)-cycloalkyl, phenyl, 5- or 6-membered heterocyclyl and 5- or 6-membered heteroaryl;

and wherein (i) the cycloalkyl groups are optionally up to disubstituted, identically or differently, by a radical selected from the group consisting of fluorine, $(C_1-C_3)$-alkyl, hydroxyl, $(C_1-C_3)$-alkoxy, hydroxycarbonyl, methoxycarbonyl and ethoxycarbonyl;

(ii) the phenyl groups are optionally up to disubstituted, identically or differently, by a radical selected from the group consisting of fluorine, chlorine, methyl, ethyl, methoxy and ethoxy;

(iii) the heterocyclyl groups are optionally up to trisubstituted, identically or differently, by a radical selected from the group consisting of fluorine, $(C_1-C_3)$-alkyl, hydroxyl, oxo, hydroxycarbonyl, methoxycarbonyl and ethoxycarbonyl; and (iv) the heteroaryl groups are optionally up to disubstituted, identically or differently, by a radical selected from the group consisting of fluorine, chlorine, $(C_1-C_3)$-alkyl and $(C_1-C_3)$-alkoxy;

and wherein $R^{18}$ is hydrogen or $(C_1-C_3)$-alkyl;

$R^{20}$ is $(C_1-C_3)$-alkyl;

and $R^{21A}$, $R^{21B}$, $R^{22A}$ and $R^{22B}$ are independently hydrogen or $(C_1-C_3)$-alkyl optionally substituted by hydroxyl;

or $R^{8A}$ and $R^{8B}$ are joined to one another and, together with the nitrogen atom to which they are bonded, form a 5- to 7-membered heterocycle which optionally contains one further ring heteroatom from the group of N, O and S, and which is optionally up to tetrasubstituted, identically or differently, by a radical selected from the group consisting of fluorine, ($C_1$-$C_4$)-alkyl, oxo, —$OR^{23}$, —$NR^{24A}R^{24B}$, —C(=O)—$NR^{25A}R^{25B}$ and phenyl;

wherein ($C_1$-$C_4$)-alkyl is optionally substituted by hydroxy or up to three times by fluorine;

and wherein $R^{23}$ is hydrogen or ($C_1$-$C_3$)-alkyl;

wherein ($C_1$-$C_3$)-alkyl is optionally substituted by hydroxyl, ($C_3$-$C_6$)-cycloalkyl or up to trisubstituted by fluorine;

and $R^{24A}$, $R^{24B}$, $R^{25A}$ and $R^{25B}$ are independently hydrogen or ($C_1$-$C_3$)-alkyl optionally substituted by hydroxyl, or a salt, a solvate or a solvate of a salt thereof.

3. The compound of formula (I) according to claim 1, wherein:

$R^1$ is hydrogen, fluorine, chlorine or ($C_1$-$C_4$)-alkyl;

$R^2$ is hydrogen or fluorine;

$R^3$ is hydrogen, fluorine, chlorine or methyl;

and

G is —C(=O)—$NR^{7A}R^{7B}$ or —$CH_2$—$NR^{8A}R^{8B}$, wherein $R^{7A}$ is hydrogen, methyl or ethyl;

$R^{7B}$ is methyl, ethyl, 2-hydroxyethyl or cyclohexyl;

wherein cyclohexyl is optionally up to disubstituted by hydroxyl;

or $R^{7A}$ and $R^{7B}$ are joined to one another and, together with the nitrogen atom to which they are bonded, form a 5- to 7-membered heterocycle which optionally contains one further ring heteroatom selected from the group consisting of N and O, and which is optionally up to disubstituted, identically or differently, by a radical selected from the group consisting of methyl, ethyl, oxo and hydroxyl;

wherein the methyl and ethyl are optionally substituted by hydroxyl;

$R^{8A}$ is hydrogen or ($C_1$-$C_4$)-alkyl;

and $R^{8B}$ is ($C_1$-$C_6$)-alkyl, ($C_3$-$C_6$)-cycloalkyl or 5- or 6-membered heterocyclyl;

wherein ($C_1$-$C_6$)-alkyl is optionally up to trisubstituted by fluorine and up to disubstituted, identically or differently, by a radical selected from the group consisting of —$OR^{18}$, —$SR^{20}$, —$NR^{21A}R^{21B}$, ($C_3$-$C_6$)-cycloalkyl, 5- or 6-membered heterocyclyl and 5- or 6-membered heteroaryl;

and wherein (i) the cycloalkyl groups are optionally up to disubstituted, identically or differently, by a radical selected from the group consisting of fluorine, ($C_1$-$C_3$)-alkyl, hydroxyl, ($C_1$-$C_3$)-alkoxy, hydroxycarbonyl, methoxycarbonyl and ethoxycarbonyl;

(ii) the heterocyclyl groups are optionally up to trisubstituted, identically or differently, by a radical selected from the group consisting of fluorine, ($C_1$-$C_3$)-alkyl, hydroxyl, oxo, hydroxycarbonyl, methoxycarbonyl and ethoxycarbonyl; and (iii) the heteroaryl group is optionally up to disubstituted, identically or differently, by a radical selected from the group consisting of fluorine, chlorine, ($C_1$-$C_3$)-alkyl and ($C_1$-$C_3$)-alkoxy;

and wherein $R^{18}$ is hydrogen, methyl or ethyl;

$R^{20}$ is methyl or ethyl;

and $R^{21A}$ and $R^{21B}$ are independently hydrogen, methyl or ethyl;

or $R^{8A}$ and $R^{8B}$ are joined to one another and, together with the nitrogen atom to which they are bonded, form a 5- to 7-membered heterocycle which optionally contains one further ring heteroatom selected from the group consisting of N and O, and which is optionally up to tetrasubstituted, identically or differently, by a radical selected from the group consisting of fluorine, ($C_1$-$C_3$)-alkyl, oxo, —$OR^{23}$, —$NR^{24A}R^{24B}$ and —C(=O)—$NR^{25A}R^{25B}$;

wherein ($C_1$-$C_3$)-alkyl is optionally substituted by hydroxy or up to three times by fluorine;

and wherein $R^{23}$ is hydrogen or ($C_1$-$C_3$)-alkyl;

wherein ($C_1$-$C_3$)-alkyl is optionally substituted by hydroxyl or up to trisubstituted by fluorine;

and $R^{24A}$, $R^{24B}$, $R^{25A}$ and $R^{25B}$ are independently hydrogen, methyl or ethyl, or a salt, a solvate or a solvate of a salt thereof.

4. The compound of formula (I) according to claim 1, wherein:

$R^1$ is methyl;

$R^2$ is hydrogen;

$R^3$ is fluorine;

and

G is —$CH_2$—$NR^{8A}R^{8B}$, wherein $R^{8A}$ is hydrogen, methyl or ethyl;

and $R^{8B}$ is ($C_1$-$C_6$)-alkyl or ($C_3$-$C_6$)-cycloalkyl;

wherein ($C_1$-$C_6$)-alkyl is optionally up to disubstituted, identically or differently, by a radical selected from the group consisting of hydroxyl, methoxy and ethoxy;

and ($C_3$-$C_6$)-cycloalkyl is optionally up to disubstituted, identically or differently, by a radical selected from the group consisting of hydroxyl, methoxy, ethoxy, isopropoxy, hydroxycarbonyl, methoxycarbonyl and ethoxycarbonyl;

or $R^{8A}$ and $R^{8B}$ are joined to one another and, together with the nitrogen atom to which they are bonded, form a 5- to 7-membered heterocycle which optionally contains one further ring heteroatom selected from the group consisting of N and O, and which is optionally up to disubstituted, identically or differently, by a radical selected from the group consisting of methyl, ethyl, hydroxyl, methoxy, ethoxy and n-propoxy;

wherein the methyl and ethyl are optionally substituted by hydroxyl, or a salt, a solvate or a solvate of a salt thereof.

5. A method for preparing the compound of formula (I) according to claim 1, wherein the compound of formula (I) is a compound of the formula (I-A), a compound of formula (I-B), a compound of formula (I-C) or a compound of formula (I-D), comprising:

[A] reacting a compound of formula (II)

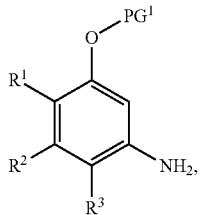

(II)

wherein R¹, R² and R³ are as defined in claim 1;
and
PG¹ is a suitable protecting group;
in the presence of a base with 2,4-dichloropyridine-3-carboxylic acid (III)

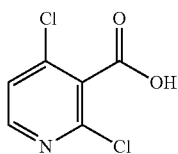

(III)

to give a compound of formula (IV)

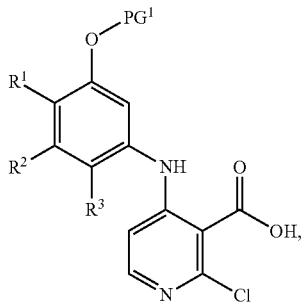

(IV)

wherein PG¹ is a suitable protecting group, and R¹, R² and R³ are as defined in claim 1;
coupling the compound of formula (IV) with 3,4-diaminobenzonitrile (V)

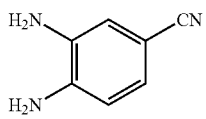

(V)

with activation of the carboxylic acid group in the compound of formula (IV) to give a compound of formula (VI)

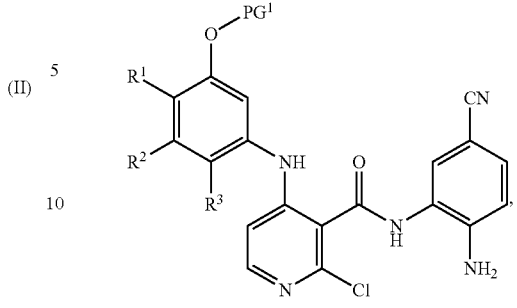

(VI)

wherein PG¹ is a suitable protecting group, and R¹, R² and R³ are as defined in claim 1;
cyclizing the compound of formula (VI) by heating in an inert solvent to give a compound of formula (VII)

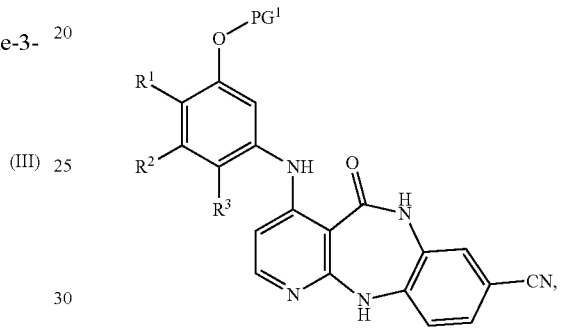

(VII)

wherein PG¹ is a suitable protecting group, and R¹, R² and R³ are as defined in claim 1;
and
detaching the protecting group PG¹ to obtain the compound of formula (I-A)

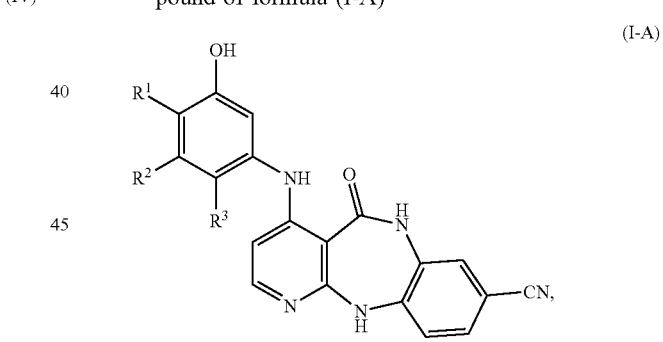

(I-A)

wherein R¹, R² and R³ are as defined in claim 1;
or
[B] reacting a compound of formula (VIII)

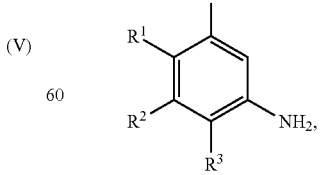

(VIII)

wherein R¹, R² and R³ are as defined in claim 1,
in the presence of an acid while heating with a compound of formula (IX)

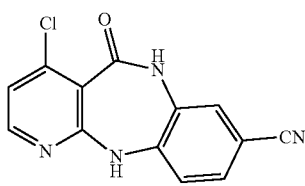

(IX)

to give the compound of formula (I-A)

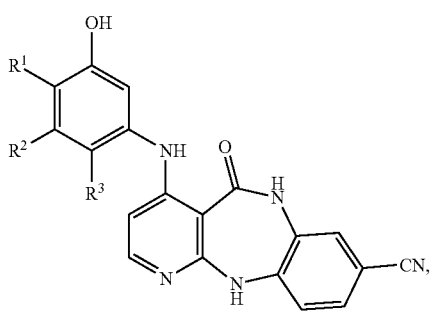

(I-A)

wherein $R^1$, $R^2$ and $R^3$ are as defined in claim 1;
and optionally

[C] treating the compound of formula (I-A) with an aqueous acid to give the compound of formula (I-B)

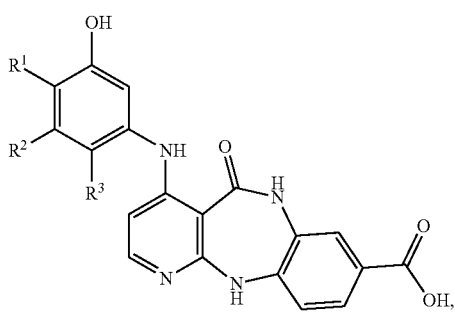

(I-B)

wherein $R^1$, $R^2$ and $R^3$ are as defined in claim 1;
and optionally coupling the compound of formula (I-B) with a compound of formula (X)

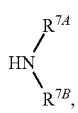

(X)

wherein $R^{7A}$ and $R^{7B}$ are as defined in claim 1;

with activation of the carboxylic acid function in the compound of formula (I-B) to give the compound of formula (I-C)

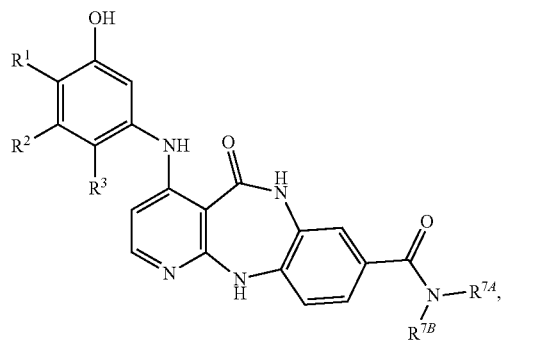

(I-C)

wherein $R^1$, $R^2$, $R^3$, $R^{7A}$ and $R^{7B}$ are as defined in claim 1;

or

[D] reacting the compound of formula (I-A) with diisobutylaluminium hydride to give a compound of formula (XI)

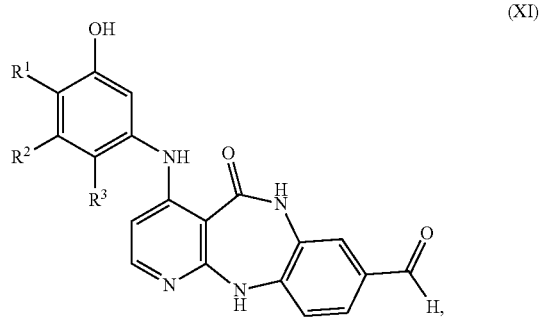

(XI)

wherein $R^1$, $R^2$ and $R^3$ are as defined in claim 1;
and reacting the compound of formula (XI) in the presence of a suitable reducing agent with a compound of formula (XII)

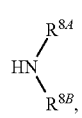

(XII)

wherein $R^{8A}$ and $R^{8B}$ are as defined in claim 1;
to give the compound of formula (I-D)

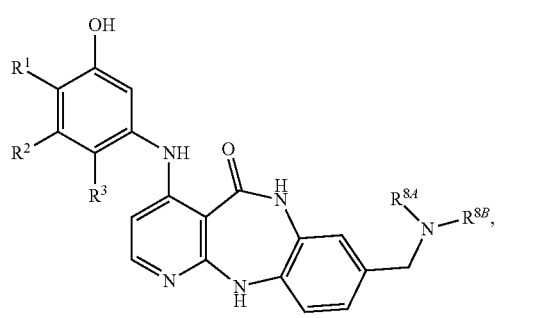

(I-D)

wherein $R^1$, $R^2$, $R^3$, $R^{8A}$ and $R^{8B}$ are as defined in claim 1;

and the compound of formula (I-A), the compound of formula (I-B), the compound of formula (I-C) or the compound of formula (I-D) is optionally separated into its enantiomers or diastereomers, or optionally converted with the appropriate (i) solvent and/or (ii) acid or base to a solvate, a salt, or a solvate of a salt thereof.

6. A pharmaceutical composition comprising the compound of claim 1, or a salt, a solvate, or a solvate of a salt thereof, in combination with one or more inert, nontoxic, pharmaceutically suitable excipients.

7. A pharmaceutical composition comprising the compound of claim 1, or a salt, a solvate, or a solvate of a salt thereof, in combination with one or more VEGF signalling pathway inhibitors selected from the group consisting of aflibercept, ranibizumab, bevacizumab, and pegaptanib.

8. The method of claim 5, wherein $PG^1$ is benzyl, 4-methoxybenzyl or 2,4-dimethoxybenzyl.

9. A pharmaceutical composition comprising the compound of claim 2, or a salt, a solvate, or a solvate of a salt thereof, in combination with one or more inert, nontoxic, pharmaceutically suitable excipients.

10. A pharmaceutical composition comprising the compound of claim 3, or a salt, a solvate, or a solvate of a salt thereof, in combination with one or more inert, nontoxic, pharmaceutically suitable excipients.

11. A pharmaceutical composition comprising the compound of claim 4, or a salt, a solvate, or a solvate of a salt thereof, in combination with one or more inert, nontoxic, pharmaceutically suitable excipients.

12. The compound of claim 1 or a salt thereof.

* * * * *

UNITED STATES PATENT AND TRADEMARK OFFICE
CERTIFICATE OF CORRECTION

PATENT NO. : 10,047,096 B2
APPLICATION NO. : 15/529043
DATED : August 14, 2018
INVENTOR(S) : Andreas Schall et al.

Page 1 of 1

It is certified that error appears in the above-identified patent and that said Letters Patent is hereby corrected as shown below:

On the Title Page

Please remove the following in item (71) Applicants:
"Petra Heinrich-Keldenich, Wuppertal (DE)"

Signed and Sealed this
Eleventh Day of December, 2018

Andrei Iancu
*Director of the United States Patent and Trademark Office*